(12) United States Patent
Gao et al.

(10) Patent No.: US 11,820,990 B2
(45) Date of Patent: Nov. 21, 2023

(54) METHOD FOR BASE EDITING IN PLANTS

(71) Applicant: INSTITUTE OF GENETICS AND DEVELOPMENTAL BIOLOGY, CHINESE ACADEMY OF SCIENCES, Beijing (CN)

(72) Inventors: Caixia Gao, Beijing (CN); Chao Li, Beijing (CN); Yuan Zong, Beijing (CN); Yanpeng Wang, Beijing (CN)

(73) Assignee: INSTITUTE OF GENETICS AND DEVELOPMENTAL BIOLOGY, CHINESE ACADEMY OF SCIENCES, Beijing (CN)

( * ) Notice: Subject to any disclaimer, the term of this patent is extended or adjusted under 35 U.S.C. 154(b) by 20 days.

(21) Appl. No.: 16/955,920

(22) PCT Filed: Dec. 21, 2018

(86) PCT No.: PCT/CN2018/122640
§ 371 (c)(1),
(2) Date: Jun. 19, 2020

(87) PCT Pub. No.: WO2019/120283
PCT Pub. Date: Jun. 27, 2019

(65) Prior Publication Data
US 2020/0340002 A1 Oct. 29, 2020

(30) Foreign Application Priority Data
Dec. 21, 2017 (CN) .......................... 201711393160.7
Apr. 28, 2018 (CN) .......................... 201810402244.0

(51) Int. Cl.
*C12N 15/82* (2006.01)
*C12N 9/22* (2006.01)
*C12N 9/78* (2006.01)
*C12N 15/11* (2006.01)

(52) U.S. Cl.
CPC ........... *C12N 15/8213* (2013.01); *C12N 9/22* (2013.01); *C12N 9/78* (2013.01); *C12N 15/11* (2013.01); *C12N 15/8216* (2013.01); *C12Y 305/04002* (2013.01); *C07K 2319/09* (2013.01); *C12N 2310/20* (2017.05); *C12N 2800/80* (2013.01)

(58) Field of Classification Search
CPC .................................................. C12N 2310/20
See application file for complete search history.

(56) References Cited

U.S. PATENT DOCUMENTS

| 2004/0169260 A1 | 9/2004 | Sylvester et al. |
| 2015/0166982 A1 | 6/2015 | Liu et al. |
| 2017/0114351 A1* | 4/2017 | Mahfouz ................ C12N 9/22 |
| 2017/0233762 A1* | 8/2017 | Zalatan ............... C12N 15/113 |
| | | 435/455 |
| 2017/0268022 A1 | 9/2017 | Liu et al. |
| 2018/0073012 A1* | 3/2018 | Liu .................... C12N 15/1024 |
| 2020/0190527 A1 | 6/2020 | Bundock |

FOREIGN PATENT DOCUMENTS

| CN | 105907785 A | 8/2016 |
| CN | 108070611 A | 5/2018 |
| CN | 108138176 A | 6/2018 |
| EP | 3382019 | 10/2018 |
| WO | 97/41228 | 11/1997 |
| WO | 2014/127287 A1 | 8/2014 |
| WO | 2016/022363 | 2/2016 |
| WO | 2017/090761 | 6/2017 |
| WO | 2018/027078 A1 | 2/2018 |
| WO | 2018/149915 A1 | 8/2018 |
| WO | 2018/213708 | 11/2018 |

OTHER PUBLICATIONS

Zetsche et al., "Cpf1 is a single RNA-guided endonuclease of a Class 2 CRISPR-Cas system", Cell, vol. 163, No. 3, 2015, pp. 759-771.
Kim et al., "Increasing the genome-targeting scope and precision of base editing with engineered Cas9-cytidine deaminase fusions", Nat. Biotechnol., vol. 35, No. 4, 371-376.
Gaudelli et al., "Programmable base editing of A•T to G•C in genomic DNA without DNA cleavage", Nature, vol. 551, No. 7681, 2017, pp. 464-471.
Shan et al., "Targeted genome modification of crop plants using a CRISPR-Cas system", Nature Biotechnology, 2013, vol. 31, No. 8, pp. 686-688.
Liang et al., "Targeted mutagenesis in *Zea mays* using TALENs and the CRISPR/Cas system", Journal of Genetics and Genomics, 2014, vol. 41, pp. 63-68.
Zhang et al., "Perfectly matched 20-nucleotide guide RNA sequences enable robust genome editing using high-fidelity SpCas9 nucleases", Genome Biology, 2017, vol. 18: 191.
Shan et al., "Genome editing in rice and wheat using the CRISPR /Cas system", Nature Protocols, 2014, vol. 9, No. 10, pp. 2395-2410.
Wang et al., "Simultaneous editing of three homoeoalleles in hexaploid bread wheat confers heritable resistance to powdery mildew", Nature Biotechnology, 2014, vol. 32, 947-951.

(Continued)

*Primary Examiner* — Weihua Fan
(74) *Attorney, Agent, or Firm* — Troutman Pepper Hamilton Sanders LLP

(57) ABSTRACT

Provided relates to the field of genetic engineering. In particular, a method for base editing in plant is provided. More specifically, a highly efficient A to G base editing method for a target sequence in a genome of a plant (e.g., a crop plant) by a guide RNA-directed CRISPR-adenine deaminase fusion protein and the plant and their progeny produced by the method are provided.

14 Claims, 16 Drawing Sheets

Specification includes a Sequence Listing.

(56) References Cited

OTHER PUBLICATIONS

Shan et al., "Rapid and efficient gene modification in rice and Brachypodium using TALENs", Molecular Plant, 2013, vol. 6, No. 4, pp. 1365-1368.

Zhang et al., "Efficient and transgene-free genome editing in wheat through transient expression of CRISPR/Cas9 DNA or RNA", Nature Communications, 2016, 7:12617.

International Search Report and Written Opinion issued in PCT/CN2018/122640 dated Mar. 20, 2019.

Li et al., "CRISPR/Cas9-Mediated Adenine Base Editing in Rice Genome", Rice Science, 2019, vol. 26, No. 2, pp. 125-128.

Li et al., "Targeted, random mutagenesis of plant genes with dual cytosine and adenine base editors", Nature Biotechnology, 2020, vol. 38, pp. 875-882.

Yuan et al., "Plant-Based Biosensors for Detecting CRISPR-Mediated Genome Engineering", ACS Synthetic Biology, 2021, vol. 10, pp. 3600-3603.

Monsur et al., "Base Editing: The Ever Expanding Clustered Regularly Interspaced Short Palindromic Repeats (CRISPR) Tool Kit for Precise Genome Editing in Plants", Genes, 2020, vol. 11, No. 466, 15 pages.

Lu et al., "Precise Editing of a Target Base in the Rice Genome Using a Modified CRISPR/Cas9 System", Molecular Plant, 2016, vol. 10, No. 3, pp. 523-525.

\* cited by examiner

A

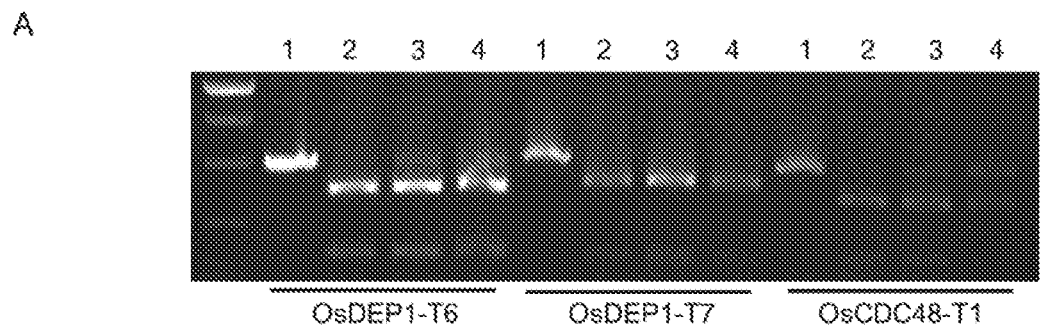

B

OsDEP1-T6

CATCAATCCGAGGCTGGCGAGACAAGCTTGGCCCTCTTTGGGCGTGGCGCCATGGCTG
CATCAATCCGAGGCTGGCGAGACGAGCTTGGCCCTCTTTGGGCGTGGCGCCATGGCTG
CATCAATCCGAGGCTGGCGAGGCGGCTTGGCCCTCTTTGGGCGTGGCGCCATGGCTG
CATCAATCCGAGGCTGGCGAGGCGGCTTGGCCCTCTTTGGGCGTGGCGCCATGGCTG
CATCAATCCGAGGCTGGCGAGACAGGCTTGGCCCTCTTTGGGCGTGGCGCCATGGCTG

OsDEP1-T7

ACAGAAAGAGAAGGAGGCACAGATCTTGCCGTCTTTTTCGGTGGATCGGGTATGTTTT
ACAGAAAGAGAAGGAGGCACGGATCTTGCCGTCTTTTTCGGTGGATCGGGTATGTTTT

OsCDC48-T1

TTACTCTCACTTTCTCCTGCTAGCTTTGACATAATCTCCGGGCCATTAATCAGAAAGA
TTACTCTCACTTTCTCCTGCTGGCTTTGACATAATCTCCGGGCCATTAATCAGAAAGA

Figure 3

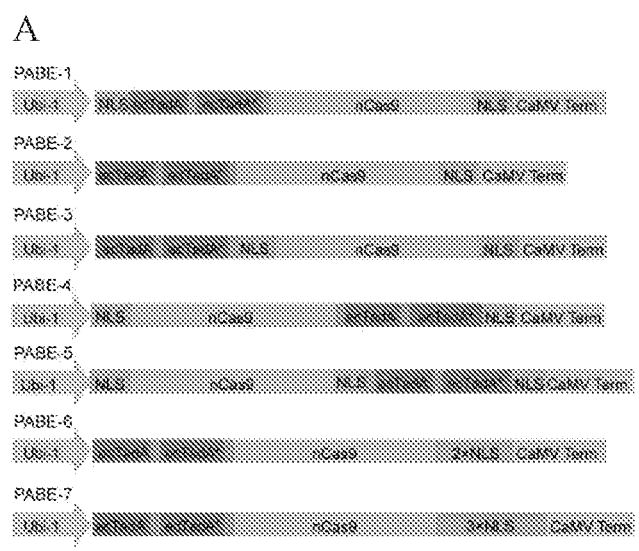
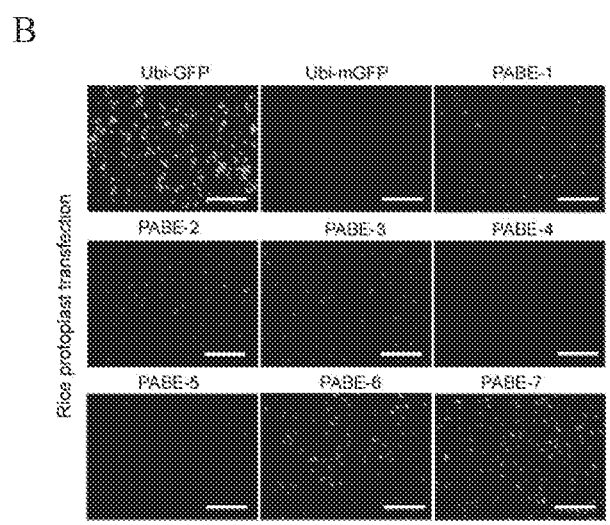
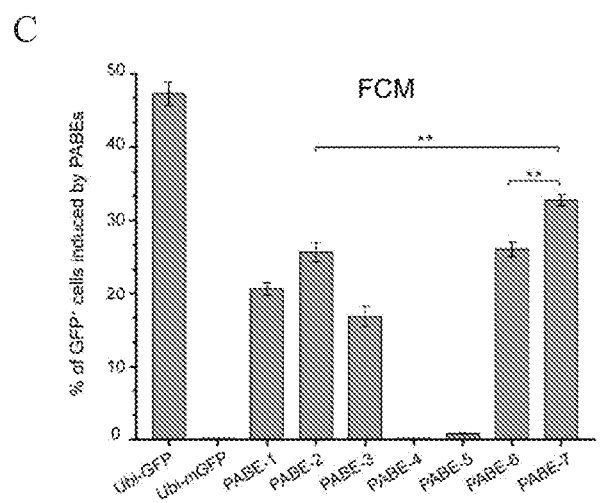
Figure 5 a
pOsU3-sgRNA

AGTAATTCATCCAGGTCACCAAGTTCTAGGATTTTCAGAACTGCAACTTATTTTATCAAGGAATCTTTA
AACATACGAACAGATCACTTAAAGTTCTTCTGAAGCAACTTAAAGTTATCAGGCATGCATGGATCTTGG
AGGAATCAGATGTGCAGTCAGGGACCATAGCACAAGACAGGCGTCTTCTACTGGTGCTACCAGCAAATG
CTGGAAGCCGGGAACACTGGGTACGTTGGAAACCACGTGATGTGAAGAAGTAAGATAAACTGTAGGAGA
AAAGCATTTCGTAGTGGGCCATGAAGCCTTTCAGGACATGTATTGCAGTATGGGCCGGCCCATTACGCA
ATTGGACGACAACAAAGACTAGTATTAGTACCACCTCGGCTATCCACATAGATCAAAGCTGATTTAAAA
GAGTTGTGCAGATGATCCGTGG█TGAGACCCTGCAGGGTCTCTGTTTTAGAGCTAGAAATAGCAAGTT
AAAATAAGGCTAGTCCGTTATCAACTTGAAAAAGTGGCACCGAGTCGGTGCTTTTTTTGTTTTTTATGT
CT b
pOsU3-esgRNA

AGTAATTCATCCAGGTCACCAAGTTCTAGGATTTTCAGAACTGCAACTTATTTTATCAAGGAATCTTTA
AACATACGAACAGATCACTTAAAGTTCTTCTGAAGCAACTTAAAGTTATCAGGCATGCATGGATCTTGG
AGGAATCAGATGTGCAGTCAGGGACCATAGCACAAGACAGGCGTCTTCTACTGGTGCTACCAGCAAATG
CTGGAAGCCGGGAACACTGGGTACGTTGGAAACCACGTGATGTGAAGAAGTAAGATAAACTGTAGGAGA
AAAGCATTTCGTAGTGGGCCATGAAGCCTTTCAGGACATGTATTGCAGTATGGGCCGGCCCATTACGCA
ATTGGACGACAACAAAGACTAGTATTAGTACCACCTCGGCTATCCACATAGATCAAAGCTGATTTAAAA
GAGTTGTGCAGATGATCCGTGG█TGAGACCCTGCAGGGTCTCTGTTTAaGCGCTAtgctgCAAAcagc
aTAGCAAGTTtAAATAAGGCTAGTCCGTTATCAACTTGAAAAAGTGGCACCGAGTCGGTGCTTTTTTTG
TTTTTTATGTCT c
pOsU3-tRNA-sgRNA

AAGGAATCTTTAAACATACGAACAGATCACTTAAAGTTCTTCTGAAGCAACTTAAAGTTATCAGG
CATGCATGGATCTTGGAGGAATCAGATGTGCAGTCAGGGACCATAGCACAAGACAGGCGTCTTCT
ACTGGTGCTACCAGCAAATGCTGGAAGCCGGGAACACTGGGTACGTTGGAAACCACGTGATGTGA
AGAAGTAAGATAAACTGTAGGAGAAAAGCATTTCGTAGTGGGCCATGAAGCCTTTCAGGACATGT
ATTGCAGTATGGGCCGGCCCATTACGCAATTGGACGACAACAAAGACTAGTATTAGTACCACCTC
GGCTATCCACATAGATCAAAGCTGATTTAAAAGAGTTGTGCAGATGATCCGTGG█GAAAACGAC
AGTGGTTCGTGGATAGTACCTGCAAGGTACAGACTCGGTTCGATTCCGGTCTGTCCTAGA
GACCGATATCCCATGGCTCGAGGGTCTCGGTTTTAGAGCTAGAAATAGCAAGTTAAAATAAGGCTAGTC
CGTTATCAACTTGAAAAAGTGGCACCGAGTCGGTGCTTTTTTTT d
pTaU6-sgRNA

GACCAAGCCCGTTATTCTGACAGTTCTGGTGCTCAACACATTTATATTTATCAAGGAGCACATTGTTAC
TCACTGCTAGGAGGGAATCGAACTAGGAATATTGATCAGAGGAACTACGAGAGAGCTGAAGATAACTGC
CCTCTAGCTCTCACTGATCTGGGCGCATAGTGAGATGCAGCCCACGTGAGTTCAGCAACGGTCTAGCGC
TGGGCTTTTAGGCCCGCATGATCGGGCTTTGTCGGGTGGTCGACGTGTTCACGATTGGGGAGAGCAACG
CAGCAGTTCCTCTTAGTTTAGTCCCACCTCGCCTGTCCAGCAGAGTTCTGACCGGTTTATAAACTGGCT
TGCTGCATCAGACTT█TGAGACCCTGCAGGGTCTCTGTTTTAGAGCTAGAAATAGCAAGTTAAAATAAG
GCTAGTCCGTTATCAACTTGAAAAAGTGGCACCGAGTCGGTGCTTTTTTTGTTTTTTATGTCT

Figure 7 e
pTaU6-esgRNA
GACCAAGCCCGTTATTCTGACAGTTCTGGTGCTCAACACATTTATATTTATCAAGGAGCACATTGTTAC
TCACTGCTAGGAGGGAATCGAACTAGGAATATTGATCAGAGGAACTACGAGAGAGCTGAAGATAACTGC
CCTCTAGCTCTCACTGATCTGGGCGCATAGTGAGATGCAGCCCACGTGAGTTCAGCAACGGTCTAGCGC
TGGGCTTTTAGGCCCGCATGATCGGGCTTTGTCGGGTGGTCGACGTGTTCACGATTGGGGAGAGCAACG
CAGCAGTTCCTCTTAGTTTAGTCCCACCTCGCCTGTCCAGCAGAGTTCTGACCGGTTTATAAACTCGCT
TGCTGCATCAGACTTGTGAGACCCTGCAGGGTCTCTGTTTaAGAGCTAtgctgAAAcagcaTAGCAAG
TTtAAATAAGGCTAGTCCGTTATCAACTTGAAAAAGTGGCACCGAGTCGGTGCTTTTTTGTTTTTTAT
GTCT f
pTaU6-tRNA-sgRNA
GACCAAGCCCGTTATTCTGACAGTTCTGGTGCTCAACACATTTATATTTATCAAGGAGCACATTGTTAC
TCACTGCTAGGAGGGAATCGAACTAGGAATATTGATCAGAGGAACTACGAGAGAGCTGAAGATAACTGC
CCTCTAGCTCTCACTGATCTGGGCGCATAGTGAGATGCAGCCCACGTGAGTTCAGCAACGGTCTAGCGC
TGGGCTTTTAGGCCCGCATGATCGGGCTTTGTCGGGTGGTCGACGTGTTCACGATTGGGGAGAGCAACG
CAGCAGTTCCTCTTAGTTTAGTCCCACCTCGCCTGTCCAGCAGAGTTCTGACCGGTTTATAAACTCGCT
TGCTGCATCAGACTT...
...AGAGACCGATATCCCATGGCTCGAGGGTCTCGGTTTTAGAGCTAG
AAATAGCAAGTTAAAATAAGGCTAGTCCGTTATCAACTTGAAAAAGTGGCACCGAGTCGGTGCTTTTTT
T

Figure 7 (Continued)

SEQUENCE LISTING

<160> NUMBER OF SEQ ID NOS: 212

<210> SEQ ID NO 1
<211> LENGTH: 166
<212> TYPE: PRT
<213> ORGANISM: Escherichia coli

<400> SEQUENCE: 1

```
Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp
                165
```

<210> SEQ ID NO 2
<211> LENGTH: 166
<212> TYPE: PRT

<213> ORGANISM: Artificial Sequence
<220> FEATURE:
<223> OTHER INFORMATION: Description of Artificial Sequence: Synthetic
      mu-ecTadA (7.10) polypeptide

<400> SEQUENCE: 2

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
                20                  25                  30

Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
                100                 105                 110

Ala Gly Ser Leu Met Asp Val Leu His Tyr Pro Gly Met Asn His Arg
            115                 120                 125

Val Glu Ile Thr Glu Gly Ile Leu Ala Asp Glu Cys Ala Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 3
<211> LENGTH: 1367
<212> TYPE: PRT
<213> ORGANISM: Artificial Sequence
<220> FEATURE:
<223> OTHER INFORMATION: Description of Artificial Sequence: Synthetic
      SPnCas9 polypeptide

<400> SEQUENCE: 3

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
                20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
                100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met

```
            145                 150                 155                 160
        Ile Lys Phe Arg Gly His Phe Leu Ile Glu Gly Asp Leu Asn Pro Asp
                        165                 170                 175

Asn Ser Asp Val Asp Lys Leu Phe Ile Gln Leu Val Gln Thr Tyr Asn
                        180                 185                 190

Gln Leu Phe Glu Glu Asn Pro Ile Asn Ala Ser Gly Val Asp Ala Lys
                        195                 200                 205

Ala Ile Leu Ser Ala Arg Leu Ser Lys Ser Arg Arg Leu Glu Asn Leu
        210                 215                 220

Ile Ala Gln Leu Pro Gly Glu Lys Lys Asn Gly Leu Phe Gly Asn Leu
        225                 230                 235                 240

Ile Ala Leu Ser Leu Gly Leu Thr Pro Asn Phe Lys Ser Asn Phe Asp
                        245                 250                 255

Leu Ala Glu Asp Ala Lys Leu Gln Leu Ser Lys Asp Thr Tyr Asp Asp
                        260                 265                 270

Asp Leu Asp Asn Leu Leu Ala Gln Ile Gly Asp Gln Tyr Ala Asp Leu
                        275                 280                 285

Phe Leu Ala Ala Lys Asn Leu Ser Asp Ala Ile Leu Leu Ser Asp Ile
        290                 295                 300

Leu Arg Val Asn Thr Glu Ile Thr Lys Ala Pro Leu Ser Ala Ser Met
        305                 310                 315                 320

Ile Lys Arg Tyr Asp Glu His His Gln Asp Leu Thr Leu Leu Lys Ala
                        325                 330                 335

Leu Val Arg Gln Gln Leu Pro Glu Lys Tyr Lys Glu Ile Phe Phe Asp
                        340                 345                 350

Gln Ser Lys Asn Gly Tyr Ala Gly Tyr Ile Asp Gly Gly Ala Ser Gln
                        355                 360                 365

Glu Glu Phe Tyr Lys Phe Ile Lys Pro Ile Leu Glu Lys Met Asp Gly
                        370                 375                 380

Thr Glu Glu Leu Leu Val Lys Leu Asn Arg Glu Asp Leu Leu Arg Lys
        385                 390                 395                 400

Gln Arg Thr Phe Asp Asn Gly Ser Ile Pro His Gln Ile His Leu Gly
                        405                 410                 415

Glu Leu His Ala Ile Leu Arg Arg Gln Glu Asp Phe Tyr Pro Phe Leu
                        420                 425                 430

Lys Asp Asn Arg Glu Lys Ile Glu Lys Ile Leu Thr Phe Arg Ile Pro
                        435                 440                 445

Tyr Tyr Val Gly Pro Leu Ala Arg Gly Asn Ser Arg Phe Ala Trp Met
                        450                 455                 460

Thr Arg Lys Ser Glu Glu Thr Ile Thr Pro Trp Asn Phe Glu Glu Val
        465                 470                 475                 480

Val Asp Lys Gly Ala Ser Ala Gln Ser Phe Ile Glu Arg Met Thr Asn
                        485                 490                 495

Phe Asp Lys Asn Leu Pro Asn Glu Lys Val Leu Pro Lys His Ser Leu
                        500                 505                 510

Leu Tyr Glu Tyr Phe Thr Val Tyr Asn Glu Leu Thr Lys Val Lys Tyr
                        515                 520                 525

Val Thr Glu Gly Met Arg Lys Pro Ala Phe Leu Ser Gly Glu Gln Lys
                        530                 535                 540

Lys Ala Ile Val Asp Leu Leu Phe Lys Thr Asn Arg Lys Val Thr Val
        545                 550                 555                 560

Lys Gln Leu Lys Glu Asp Tyr Phe Lys Lys Ile Glu Cys Phe Asp Ser
                        565                 570                 575
```

```
Val Glu Ile Ser Gly Val Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990
```

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 4
<211> LENGTH: 1792
<212> TYPE: PRT

```
<213> ORGANISM: Artificial Sequence
<220> FEATURE:
<223> OTHER INFORMATION: Description of Artificial Sequence: Synthetic
      SPnCas9-ABE polypeptide

<400> SEQUENCE: 4
```

| | | | | | | | | | | | | | | |
|---|---|---|---|---|---|---|---|---|---|---|---|---|---|---|
| Pro | Lys | Lys | Lys | Arg | Lys | Val | Ser | Gly | Gly | Ser | Ser | Glu | Val | Glu | Phe |
| 1 | | | | 5 | | | | | 10 | | | | | 15 | |
| Ser | His | Glu | Tyr | Trp | Met | Arg | His | Ala | Leu | Thr | Leu | Ala | Lys | Arg | Ala |
| | | | 20 | | | | | 25 | | | | | 30 | | |
| Trp | Asp | Glu | Arg | Glu | Val | Pro | Val | Gly | Ala | Val | Leu | Val | His | Asn | Asn |
| | | 35 | | | | | 40 | | | | | 45 | | | |
| Arg | Val | Ile | Gly | Glu | Gly | Trp | Asn | Arg | Pro | Ile | Gly | Arg | His | Asp | Pro |
| | 50 | | | | | 55 | | | | | 60 | | | | |
| Thr | Ala | His | Ala | Glu | Ile | Met | Ala | Leu | Arg | Gln | Gly | Gly | Leu | Val | Met |
| 65 | | | | | 70 | | | | | 75 | | | | | 80 |
| Gln | Asn | Tyr | Arg | Leu | Ile | Asp | Ala | Thr | Leu | Tyr | Val | Thr | Leu | Glu | Pro |
| | | | | 85 | | | | | 90 | | | | | 95 | |
| Cys | Val | Met | Cys | Ala | Gly | Ala | Met | Ile | His | Ser | Arg | Ile | Gly | Arg | Val |
| | | | 100 | | | | | 105 | | | | | 110 | | |
| Val | Phe | Gly | Ala | Arg | Asp | Ala | Lys | Thr | Gly | Ala | Ala | Gly | Ser | Leu | Met |
| | | 115 | | | | | 120 | | | | | 125 | | | |
| Asp | Val | Leu | His | His | Pro | Gly | Met | Asn | His | Arg | Val | Glu | Ile | Thr | Glu |
| | 130 | | | | | 135 | | | | | 140 | | | | |
| Gly | Ile | Leu | Ala | Asp | Glu | Cys | Ala | Ala | Leu | Leu | Ser | Asp | Phe | Phe | Arg |
| 145 | | | | | 150 | | | | | 155 | | | | | 160 |
| Met | Arg | Arg | Gln | Glu | Ile | Lys | Ala | Gln | Lys | Lys | Ala | Gln | Ser | Ser | Thr |
| | | | | 165 | | | | | 170 | | | | | 175 | |
| Asp | Ser | Gly | Gly | Ser | Ser | Gly | Gly | Ser | Ser | Gly | Ser | Glu | Thr | Pro | Gly |
| | | | 180 | | | | | 185 | | | | | 190 | | |
| Thr | Ser | Glu | Ser | Ala | Thr | Pro | Glu | Ser | Ser | Gly | Gly | Ser | Ser | Gly | Gly |
| | | 195 | | | | | 200 | | | | | 205 | | | |
| Ser | Ser | Glu | Val | Glu | Phe | Ser | His | Glu | Tyr | Trp | Met | Arg | His | Ala | Leu |
| | 210 | | | | | 215 | | | | | 220 | | | | |
| Thr | Leu | Ala | Lys | Arg | Ala | Arg | Asp | Glu | Arg | Glu | Val | Pro | Val | Gly | Ala |
| 225 | | | | | 230 | | | | | 235 | | | | | 240 |
| Val | Leu | Val | Leu | Asn | Asn | Arg | Val | Ile | Gly | Glu | Gly | Trp | Asn | Arg | Ala |
| | | | | 245 | | | | | 250 | | | | | 255 | |
| Ile | Gly | Leu | His | Asp | Pro | Thr | Ala | His | Ala | Glu | Ile | Met | Ala | Leu | Arg |
| | | | | 260 | | | | | 265 | | | | | 270 | |
| Gln | Gly | Gly | Leu | Val | Met | Gln | Asn | Tyr | Arg | Leu | Ile | Asp | Ala | Thr | Leu |
| | | | 275 | | | | | 280 | | | | | 285 | | |
| Tyr | Val | Thr | Phe | Glu | Pro | Cys | Val | Met | Cys | Ala | Gly | Ala | Met | Ile | His |
| | | 290 | | | | | 295 | | | | | 300 | | | |
| Ser | Arg | Ile | Gly | Arg | Val | Val | Phe | Gly | Val | Arg | Asn | Ala | Lys | Thr | Gly |
| 305 | | | | | 310 | | | | | 315 | | | | | 320 |
| Ala | Ala | Gly | Ser | Leu | Met | Asp | Val | Leu | His | Tyr | Pro | Gly | Met | Asn | His |
| | | | | 325 | | | | | 330 | | | | | 335 | |
| Arg | Val | Glu | Ile | Thr | Glu | Gly | Ile | Leu | Ala | Asp | Glu | Cys | Ala | Ala | Leu |
| | | | 340 | | | | | 345 | | | | | 350 | | |
| Leu | Cys | Tyr | Phe | Phe | Arg | Met | Pro | Arg | Gln | Val | Phe | Asn | Ala | Gln | Lys |
| | | | 355 | | | | | 360 | | | | | 365 | | |
| Lys | Ala | Gln | Ser | Ser | Thr | Asp | Ser | Gly | Gly | Ser | Ser | Gly | Gly | Ser | Ser |
| | | 370 | | | | | 375 | | | | | 380 | | | |

-continued

```
Gly Ser Glu Thr Pro Gly Thr Ser Glu Ser Ala Thr Pro Glu Ser Ser
385                 390                 395                 400

Gly Gly Ser Ser Gly Ser Leu Lys Asp Lys Lys Tyr Ser Ile Gly
            405                 410                 415

Leu Ala Ile Gly Thr Asn Ser Val Gly Trp Ala Val Ile Thr Asp Glu
            420                 425                 430

Tyr Lys Val Pro Ser Lys Lys Phe Lys Val Leu Gly Asn Thr Asp Arg
        435                 440                 445

His Ser Ile Lys Lys Asn Leu Ile Gly Ala Leu Leu Phe Asp Ser Gly
    450                 455                 460

Glu Thr Ala Glu Ala Thr Arg Leu Lys Arg Thr Ala Arg Arg Arg Tyr
465                 470                 475                 480

Thr Arg Arg Lys Asn Arg Ile Cys Tyr Leu Gln Glu Ile Phe Ser Asn
                485                 490                 495

Glu Met Ala Lys Val Asp Asp Ser Phe Phe His Arg Leu Glu Glu Ser
            500                 505                 510

Phe Leu Val Glu Glu Asp Lys Lys His Glu Arg His Pro Ile Phe Gly
        515                 520                 525

Asn Ile Val Asp Glu Val Ala Tyr His Glu Lys Tyr Pro Thr Ile Tyr
    530                 535                 540

His Leu Arg Lys Lys Leu Val Asp Ser Thr Asp Lys Ala Asp Leu Arg
545                 550                 555                 560

Leu Ile Tyr Leu Ala Leu Ala His Met Ile Lys Phe Arg Gly His Phe
                565                 570                 575

Leu Ile Glu Gly Asp Leu Asn Pro Asp Asn Ser Asp Val Asp Lys Leu
            580                 585                 590

Phe Ile Gln Leu Val Gln Thr Tyr Asn Gln Leu Phe Glu Glu Asn Pro
        595                 600                 605

Ile Asn Ala Ser Gly Val Asp Ala Lys Ala Ile Leu Ser Ala Arg Leu
    610                 615                 620

Ser Lys Ser Arg Arg Leu Glu Asn Leu Ile Ala Gln Leu Pro Gly Glu
625                 630                 635                 640

Lys Lys Asn Gly Leu Phe Gly Asn Leu Ile Ala Leu Ser Leu Gly Leu
                645                 650                 655

Thr Pro Asn Phe Lys Ser Asn Phe Asp Leu Ala Glu Asp Ala Lys Leu
            660                 665                 670

Gln Leu Ser Lys Asp Thr Tyr Asp Asp Asp Leu Asp Asn Leu Leu Ala
        675                 680                 685

Gln Ile Gly Asp Gln Tyr Ala Asp Leu Phe Leu Ala Ala Lys Asn Leu
    690                 695                 700

Ser Asp Ala Ile Leu Leu Ser Asp Ile Leu Arg Val Asn Thr Glu Ile
705                 710                 715                 720

Thr Lys Ala Pro Leu Ser Ala Ser Met Ile Lys Arg Tyr Asp Glu His
                725                 730                 735

His Gln Asp Leu Thr Leu Leu Lys Ala Leu Val Arg Gln Gln Leu Pro
            740                 745                 750

Glu Lys Tyr Lys Glu Ile Phe Phe Asp Gln Ser Lys Asn Gly Tyr Ala
        755                 760                 765

Gly Tyr Ile Asp Gly Gly Ala Ser Gln Glu Glu Phe Tyr Lys Phe Ile
    770                 775                 780

Lys Pro Ile Leu Glu Lys Met Asp Gly Thr Glu Glu Leu Leu Val Lys
785                 790                 795                 800

Leu Asn Arg Glu Asp Leu Leu Arg Lys Gln Arg Thr Phe Asp Asn Gly
```

-continued

```
            805                 810                 815
Ser Ile Pro His Gln Ile His Leu Gly Glu Leu His Ala Ile Leu Arg
            820                 825                 830

Arg Gln Glu Asp Phe Tyr Pro Phe Leu Lys Asp Asn Arg Glu Lys Ile
            835                 840                 845

Glu Lys Ile Leu Thr Phe Arg Ile Pro Tyr Tyr Val Gly Pro Leu Ala
            850                 855                 860

Arg Gly Asn Ser Arg Phe Ala Trp Met Thr Arg Lys Ser Glu Glu Thr
865                 870                 875                 880

Ile Thr Pro Trp Asn Phe Glu Glu Val Val Asp Lys Gly Ala Ser Ala
                    885                 890                 895

Gln Ser Phe Ile Glu Arg Met Thr Asn Phe Asp Lys Asn Leu Pro Asn
                    900                 905                 910

Glu Lys Val Leu Pro Lys His Ser Leu Leu Tyr Glu Tyr Phe Thr Val
                    915                 920                 925

Tyr Asn Glu Leu Thr Lys Val Lys Tyr Val Thr Glu Gly Met Arg Lys
            930                 935                 940

Pro Ala Phe Leu Ser Gly Glu Gln Lys Lys Ala Ile Val Asp Leu Leu
945                 950                 955                 960

Phe Lys Thr Asn Arg Lys Val Thr Val Lys Gln Leu Lys Glu Asp Tyr
                    965                 970                 975

Phe Lys Lys Ile Glu Cys Phe Asp Ser Val Glu Ile Ser Gly Val Glu
                    980                 985                 990

Asp Arg Phe Asn Ala Ser Leu Gly Thr Tyr His Asp Leu Leu Lys Ile
                    995                 1000                1005

Ile Lys Asp Lys Asp Phe Leu Asp Asn Glu Glu Asn Glu Asp Ile
            1010                1015                1020

Leu Glu Asp Ile Val Leu Thr Leu Thr Leu Phe Glu Asp Arg Glu
            1025                1030                1035

Met Ile Glu Glu Arg Leu Lys Thr Tyr Ala His Leu Phe Asp Asp
            1040                1045                1050

Lys Val Met Lys Gln Leu Lys Arg Arg Arg Tyr Thr Gly Trp Gly
            1055                1060                1065

Arg Leu Ser Arg Lys Leu Ile Asn Gly Ile Arg Asp Lys Gln Ser
            1070                1075                1080

Gly Lys Thr Ile Leu Asp Phe Leu Lys Ser Asp Gly Phe Ala Asn
            1085                1090                1095

Arg Asn Phe Met Gln Leu Ile His Asp Asp Ser Leu Thr Phe Lys
            1100                1105                1110

Glu Asp Ile Gln Lys Ala Gln Val Ser Gly Gln Gly Asp Ser Leu
            1115                1120                1125

His Glu His Ile Ala Asn Leu Ala Gly Ser Pro Ala Ile Lys Lys
            1130                1135                1140

Gly Ile Leu Gln Thr Val Lys Val Val Asp Glu Leu Val Lys Val
            1145                1150                1155

Met Gly Arg His Lys Pro Glu Asn Ile Val Ile Glu Met Ala Arg
            1160                1165                1170

Glu Asn Gln Thr Thr Gln Lys Gly Gln Lys Asn Ser Arg Glu Arg
            1175                1180                1185

Met Lys Arg Ile Glu Glu Gly Ile Lys Glu Leu Gly Ser Gln Ile
            1190                1195                1200

Leu Lys Glu His Pro Val Glu Asn Thr Gln Leu Gln Asn Glu Lys
            1205                1210                1215
```

```
Leu Tyr Leu Tyr Tyr Leu Gln Asn Gly Arg Asp Met Tyr Val Asp
    1220            1225                1230

Gln Glu Leu Asp Ile Asn Arg Leu Ser Asp Tyr Asp Val Asp His
    1235            1240                1245

Ile Val Pro Gln Ser Phe Leu Lys Asp Asp Ser Ile Asp Asn Lys
    1250            1255                1260

Val Leu Thr Arg Ser Asp Lys Asn Arg Gly Lys Ser Asp Asn Val
    1265            1270                1275

Pro Ser Glu Glu Val Val Lys Lys Met Lys Asn Tyr Trp Arg Gln
    1280            1285                1290

Leu Leu Asn Ala Lys Leu Ile Thr Gln Arg Lys Phe Asp Asn Leu
    1295            1300                1305

Thr Lys Ala Glu Arg Gly Gly Leu Ser Glu Leu Asp Lys Ala Gly
    1310            1315                1320

Phe Ile Lys Arg Gln Leu Val Glu Thr Arg Gln Ile Thr Lys His
    1325            1330                1335

Val Ala Gln Ile Leu Asp Ser Arg Met Asn Thr Lys Tyr Asp Glu
    1340            1345                1350

Asn Asp Lys Leu Ile Arg Glu Val Lys Val Ile Thr Leu Lys Ser
    1355            1360                1365

Lys Leu Val Ser Asp Phe Arg Lys Asp Phe Gln Phe Tyr Lys Val
    1370            1375                1380

Arg Glu Ile Asn Asn Tyr His His Ala His Asp Ala Tyr Leu Asn
    1385            1390                1395

Ala Val Val Gly Thr Ala Leu Ile Lys Lys Tyr Pro Lys Leu Glu
    1400            1405                1410

Ser Glu Phe Val Tyr Gly Asp Tyr Lys Val Tyr Asp Val Arg Lys
    1415            1420                1425

Met Ile Ala Lys Ser Glu Gln Glu Ile Gly Lys Ala Thr Ala Lys
    1430            1435                1440

Tyr Phe Phe Tyr Ser Asn Ile Met Asn Phe Phe Lys Thr Glu Ile
    1445            1450                1455

Thr Leu Ala Asn Gly Glu Ile Arg Lys Arg Pro Leu Ile Glu Thr
    1460            1465                1470

Asn Gly Glu Thr Gly Glu Ile Val Trp Asp Lys Gly Arg Asp Phe
    1475            1480                1485

Ala Thr Val Arg Lys Val Leu Ser Met Pro Gln Val Asn Ile Val
    1490            1495                1500

Lys Lys Thr Glu Val Gln Thr Gly Gly Phe Ser Lys Glu Ser Ile
    1505            1510                1515

Leu Pro Lys Arg Asn Ser Asp Lys Leu Ile Ala Arg Lys Lys Asp
    1520            1525                1530

Trp Asp Pro Lys Lys Tyr Gly Gly Phe Asp Ser Pro Thr Val Ala
    1535            1540                1545

Tyr Ser Val Leu Val Val Ala Lys Val Glu Lys Gly Lys Ser Lys
    1550            1555                1560

Lys Leu Lys Ser Val Lys Glu Leu Leu Gly Ile Thr Ile Met Glu
    1565            1570                1575

Arg Ser Ser Phe Glu Lys Asn Pro Ile Asp Phe Leu Glu Ala Lys
    1580            1585                1590

Gly Tyr Lys Glu Val Lys Lys Asp Leu Ile Ile Lys Leu Pro Lys
    1595            1600                1605
```

-continued

Tyr Ser Leu Phe Glu Leu Glu Asn Gly Arg Lys Arg Met Leu Ala
    1610                1615                1620

Ser Ala Gly Glu Leu Gln Lys Gly Asn Glu Leu Ala Leu Pro Ser
    1625                1630                1635

Lys Tyr Val Asn Phe Leu Tyr Leu Ala Ser His Tyr Glu Lys Leu
    1640                1645                1650

Lys Gly Ser Pro Glu Asp Asn Glu Gln Lys Gln Leu Phe Val Glu
    1655                1660                1665

Gln His Lys His Tyr Leu Asp Glu Ile Ile Glu Gln Ile Ser Glu
    1670                1675                1680

Phe Ser Lys Arg Val Ile Leu Ala Asp Ala Asn Leu Asp Lys Val
    1685                1690                1695

Leu Ser Ala Tyr Asn Lys His Arg Asp Lys Pro Ile Arg Glu Gln
    1700                1705                1710

Ala Glu Asn Ile Ile His Leu Phe Thr Leu Thr Asn Leu Gly Ala
    1715                1720                1725

Pro Ala Ala Phe Lys Tyr Phe Asp Thr Thr Ile Asp Arg Lys Arg
    1730                1735                1740

Tyr Thr Ser Thr Lys Glu Val Leu Asp Ala Thr Leu Ile His Gln
    1745                1750                1755

Ser Ile Thr Gly Leu Tyr Glu Thr Arg Ile Asp Leu Ser Gln Leu
    1760                1765                1770

Gly Gly Asp Lys Arg Pro Ala Ala Thr Lys Lys Ala Gly Gln Ala
    1775                1780                1785

Lys Lys Lys Lys
    1790

<210> SEQ ID NO 5
<211> LENGTH: 1777
<212> TYPE: PRT
<213> ORGANISM: Artificial Sequence
<220> FEATURE:
<223> OTHER INFORMATION: Description of Artificial Sequence: Synthetic
      SPnCas9-ABE-1 polypeptide

<400> SEQUENCE: 5

Met Ser Glu Val Glu Phe Ser His Glu Tyr Trp Met Arg His Ala Leu
1                   5                   10                  15

Thr Leu Ala Lys Arg Ala Trp Asp Glu Arg Glu Val Pro Val Gly Ala
                20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

```
Lys Ala Gln Ser Ser Thr Asp Ser Gly Gly Ser Ser Gly Gly Ser Ser
                165                 170                 175
Gly Ser Glu Thr Pro Gly Thr Ser Glu Ser Ala Thr Pro Glu Ser Ser
            180                 185                 190
Gly Gly Ser Ser Gly Ser Ser Glu Val Glu Phe Ser His Glu Tyr
        195                 200                 205
Trp Met Arg His Ala Leu Thr Leu Ala Lys Arg Ala Arg Asp Glu Arg
    210                 215                 220
Glu Val Pro Val Gly Ala Val Leu Val Leu Asn Asn Arg Val Ile Gly
225                 230                 235                 240
Glu Gly Trp Asn Arg Ala Ile Gly Leu His Asp Pro Thr Ala His Ala
                245                 250                 255
Glu Ile Met Ala Leu Arg Gln Gly Gly Leu Val Met Gln Asn Tyr Arg
            260                 265                 270
Leu Ile Asp Ala Thr Leu Tyr Val Thr Phe Glu Pro Cys Val Met Cys
        275                 280                 285
Ala Gly Ala Met Ile His Ser Arg Ile Gly Arg Val Val Phe Gly Val
    290                 295                 300
Arg Asn Ala Lys Thr Gly Ala Ala Gly Ser Leu Met Asp Val Leu His
305                 310                 315                 320
Tyr Pro Gly Met Asn His Arg Val Glu Ile Thr Glu Gly Ile Leu Ala
                325                 330                 335
Asp Glu Cys Ala Ala Leu Leu Cys Tyr Phe Phe Arg Met Pro Arg Gln
            340                 345                 350
Val Phe Asn Ala Gln Lys Lys Ala Gln Ser Ser Thr Asp Ser Gly Gly
        355                 360                 365
Ser Ser Gly Gly Ser Ser Gly Ser Glu Thr Pro Gly Thr Ser Glu Ser
    370                 375                 380
Ala Thr Pro Glu Ser Ser Gly Gly Ser Ser Gly Gly Ser Leu Lys Asp
385                 390                 395                 400
Lys Lys Tyr Ser Ile Gly Leu Ala Ile Gly Thr Asn Ser Val Gly Trp
                405                 410                 415
Ala Val Ile Thr Asp Glu Tyr Lys Val Pro Ser Lys Lys Phe Lys Val
            420                 425                 430
Leu Gly Asn Thr Asp Arg His Ser Ile Lys Lys Asn Leu Ile Gly Ala
        435                 440                 445
Leu Leu Phe Asp Ser Gly Glu Thr Ala Glu Ala Thr Arg Leu Lys Arg
    450                 455                 460
Thr Ala Arg Arg Arg Tyr Thr Arg Arg Lys Asn Arg Ile Cys Tyr Leu
465                 470                 475                 480
Gln Glu Ile Phe Ser Asn Glu Met Ala Lys Val Asp Asp Ser Phe Phe
                485                 490                 495
His Arg Leu Glu Glu Ser Phe Leu Val Glu Glu Asp Lys Lys His Glu
            500                 505                 510
Arg His Pro Ile Phe Gly Asn Ile Val Asp Glu Val Ala Tyr His Glu
        515                 520                 525
Lys Tyr Pro Thr Ile Tyr His Leu Arg Lys Lys Leu Val Asp Ser Thr
    530                 535                 540
Asp Lys Ala Asp Leu Arg Leu Ile Tyr Leu Ala Leu Ala His Met Ile
545                 550                 555                 560
Lys Phe Arg Gly His Phe Leu Ile Glu Gly Asp Leu Asn Pro Asp Asn
                565                 570                 575
```

```
Ser Asp Val Asp Lys Leu Phe Ile Gln Leu Val Gln Thr Tyr Asn Gln
            580                 585                 590

Leu Phe Glu Glu Asn Pro Ile Asn Ala Ser Gly Val Asp Ala Lys Ala
        595                 600                 605

Ile Leu Ser Ala Arg Leu Ser Lys Ser Arg Arg Leu Glu Asn Leu Ile
        610                 615                 620

Ala Gln Leu Pro Gly Glu Lys Lys Asn Gly Leu Phe Gly Asn Leu Ile
625                 630                 635                 640

Ala Leu Ser Leu Gly Leu Thr Pro Asn Phe Lys Ser Asn Phe Asp Leu
                645                 650                 655

Ala Glu Asp Ala Lys Leu Gln Leu Ser Lys Asp Thr Tyr Asp Asp Asp
            660                 665                 670

Leu Asp Asn Leu Leu Ala Gln Ile Gly Asp Gln Tyr Ala Asp Leu Phe
        675                 680                 685

Leu Ala Ala Lys Asn Leu Ser Asp Ala Ile Leu Leu Ser Asp Ile Leu
690                 695                 700

Arg Val Asn Thr Glu Ile Thr Lys Ala Pro Leu Ser Ala Ser Met Ile
705                 710                 715                 720

Lys Arg Tyr Asp Glu His His Gln Asp Leu Thr Leu Leu Lys Ala Leu
                725                 730                 735

Val Arg Gln Gln Leu Pro Glu Lys Tyr Lys Glu Ile Phe Phe Asp Gln
            740                 745                 750

Ser Lys Asn Gly Tyr Ala Gly Tyr Ile Asp Gly Gly Ala Ser Gln Glu
        755                 760                 765

Glu Phe Tyr Lys Phe Ile Lys Pro Ile Leu Glu Lys Met Asp Gly Thr
770                 775                 780

Glu Glu Leu Leu Val Lys Leu Asn Arg Glu Asp Leu Leu Arg Lys Gln
785                 790                 795                 800

Arg Thr Phe Asp Asn Gly Ser Ile Pro His Gln Ile His Leu Gly Glu
                805                 810                 815

Leu His Ala Ile Leu Arg Arg Gln Glu Asp Phe Tyr Pro Phe Leu Lys
            820                 825                 830

Asp Asn Arg Glu Lys Ile Glu Lys Ile Leu Thr Phe Arg Ile Pro Tyr
        835                 840                 845

Tyr Val Gly Pro Leu Ala Arg Gly Asn Ser Arg Phe Ala Trp Met Thr
850                 855                 860

Arg Lys Ser Glu Glu Thr Ile Thr Pro Trp Asn Phe Glu Glu Val Val
865                 870                 875                 880

Asp Lys Gly Ala Ser Ala Gln Ser Phe Ile Glu Arg Met Thr Asn Phe
                885                 890                 895

Asp Lys Asn Leu Pro Asn Glu Lys Val Leu Pro Lys His Ser Leu Leu
            900                 905                 910

Tyr Glu Tyr Phe Thr Val Tyr Asn Glu Leu Thr Lys Val Lys Tyr Val
        915                 920                 925

Thr Glu Gly Met Arg Lys Pro Ala Phe Leu Ser Gly Glu Gln Lys Lys
930                 935                 940

Ala Ile Val Asp Leu Leu Phe Lys Thr Asn Arg Lys Val Thr Val Lys
945                 950                 955                 960

Gln Leu Lys Glu Asp Tyr Phe Lys Lys Ile Glu Cys Phe Asp Ser Val
                965                 970                 975

Glu Ile Ser Gly Val Glu Asp Arg Phe Asn Ala Ser Leu Gly Thr Tyr
            980                 985                 990

His Asp Leu Leu Lys Ile Ile Lys  Asp Lys Asp Phe Leu  Asp Asn Glu
```

```
            995                 1000                1005
    Glu Asn Glu Asp Ile Leu Glu Asp Ile Val Leu Thr Leu Thr Leu
            1010                1015                1020

Phe Glu Asp Arg Glu Met Ile Glu Glu Arg Leu Lys Thr Tyr Ala
            1025                1030                1035

His Leu Phe Asp Asp Lys Val Met Lys Gln Leu Lys Arg Arg Arg
            1040                1045                1050

Tyr Thr Gly Trp Gly Arg Leu Ser Arg Lys Leu Ile Asn Gly Ile
            1055                1060                1065

Arg Asp Lys Gln Ser Gly Lys Thr Ile Leu Asp Phe Leu Lys Ser
            1070                1075                1080

Asp Gly Phe Ala Asn Arg Asn Phe Met Gln Leu Ile His Asp Asp
            1085                1090                1095

Ser Leu Thr Phe Lys Glu Asp Ile Gln Lys Ala Gln Val Ser Gly
            1100                1105                1110

Gln Gly Asp Ser Leu His Glu His Ile Ala Asn Leu Ala Gly Ser
            1115                1120                1125

Pro Ala Ile Lys Lys Gly Ile Leu Gln Thr Val Lys Val Val Asp
            1130                1135                1140

Glu Leu Val Lys Val Met Gly Arg His Lys Pro Glu Asn Ile Val
            1145                1150                1155

Ile Glu Met Ala Arg Glu Asn Gln Thr Thr Gln Lys Gly Gln Lys
            1160                1165                1170

Asn Ser Arg Glu Arg Met Lys Arg Ile Glu Glu Gly Ile Lys Glu
            1175                1180                1185

Leu Gly Ser Gln Ile Leu Lys Glu His Pro Val Glu Asn Thr Gln
            1190                1195                1200

Leu Gln Asn Glu Lys Leu Tyr Leu Tyr Tyr Leu Gln Asn Gly Arg
            1205                1210                1215

Asp Met Tyr Val Asp Gln Glu Leu Asp Ile Asn Arg Leu Ser Asp
            1220                1225                1230

Tyr Asp Val Asp His Ile Val Pro Gln Ser Phe Leu Lys Asp Asp
            1235                1240                1245

Ser Ile Asp Asn Lys Val Leu Thr Arg Ser Asp Lys Asn Arg Gly
            1250                1255                1260

Lys Ser Asp Asn Val Pro Ser Glu Glu Val Val Lys Lys Met Lys
            1265                1270                1275

Asn Tyr Trp Arg Gln Leu Leu Asn Ala Lys Leu Ile Thr Gln Arg
            1280                1285                1290

Lys Phe Asp Asn Leu Thr Lys Ala Glu Arg Gly Gly Leu Ser Glu
            1295                1300                1305

Leu Asp Lys Ala Gly Phe Ile Lys Arg Gln Leu Val Glu Thr Arg
            1310                1315                1320

Gln Ile Thr Lys His Val Ala Gln Ile Leu Asp Ser Arg Met Asn
            1325                1330                1335

Thr Lys Tyr Asp Glu Asn Asp Lys Leu Ile Arg Glu Val Lys Val
            1340                1345                1350

Ile Thr Leu Lys Ser Lys Leu Val Ser Asp Phe Arg Lys Asp Phe
            1355                1360                1365

Gln Phe Tyr Lys Val Arg Glu Ile Asn Asn Tyr His His Ala His
            1370                1375                1380

Asp Ala Tyr Leu Asn Ala Val Val Gly Thr Ala Leu Ile Lys Lys
            1385                1390                1395
```

```
Tyr Pro Lys Leu Glu Ser Glu Phe Val Tyr Gly Asp Tyr Lys Val
    1400            1405            1410

Tyr Asp Val Arg Lys Met Ile Ala Lys Ser Glu Gln Glu Ile Gly
    1415            1420            1425

Lys Ala Thr Ala Lys Tyr Phe Phe Tyr Ser Asn Ile Met Asn Phe
    1430            1435            1440

Phe Lys Thr Glu Ile Thr Leu Ala Asn Gly Glu Ile Arg Lys Arg
    1445            1450            1455

Pro Leu Ile Glu Thr Asn Gly Glu Thr Gly Glu Ile Val Trp Asp
    1460            1465            1470

Lys Gly Arg Asp Phe Ala Thr Val Arg Lys Val Leu Ser Met Pro
    1475            1480            1485

Gln Val Asn Ile Val Lys Lys Thr Glu Val Gln Thr Gly Gly Phe
    1490            1495            1500

Ser Lys Glu Ser Ile Leu Pro Lys Arg Asn Ser Asp Lys Leu Ile
    1505            1510            1515

Ala Arg Lys Lys Asp Trp Asp Pro Lys Lys Tyr Gly Gly Phe Asp
    1520            1525            1530

Ser Pro Thr Val Ala Tyr Ser Val Leu Val Val Ala Lys Val Glu
    1535            1540            1545

Lys Gly Lys Ser Lys Lys Leu Lys Ser Val Lys Glu Leu Leu Gly
    1550            1555            1560

Ile Thr Ile Met Glu Arg Ser Ser Phe Glu Lys Asn Pro Ile Asp
    1565            1570            1575

Phe Leu Glu Ala Lys Gly Tyr Lys Glu Val Lys Lys Asp Leu Ile
    1580            1585            1590

Ile Lys Leu Pro Lys Tyr Ser Leu Phe Glu Leu Glu Asn Gly Arg
    1595            1600            1605

Lys Arg Met Leu Ala Ser Ala Gly Glu Leu Gln Lys Gly Asn Glu
    1610            1615            1620

Leu Ala Leu Pro Ser Lys Tyr Val Asn Phe Leu Tyr Leu Ala Ser
    1625            1630            1635

His Tyr Glu Lys Leu Lys Gly Ser Pro Glu Asp Asn Glu Gln Lys
    1640            1645            1650

Gln Leu Phe Val Glu Gln His Lys His Tyr Leu Asp Glu Ile Ile
    1655            1660            1665

Glu Gln Ile Ser Glu Phe Ser Lys Arg Val Ile Leu Ala Asp Ala
    1670            1675            1680

Asn Leu Asp Lys Val Leu Ser Ala Tyr Asn Lys His Arg Asp Lys
    1685            1690            1695

Pro Ile Arg Glu Gln Ala Glu Asn Ile Ile His Leu Phe Thr Leu
    1700            1705            1710

Thr Asn Leu Gly Ala Pro Ala Ala Phe Lys Tyr Phe Asp Thr Thr
    1715            1720            1725

Ile Asp Arg Lys Arg Tyr Thr Ser Thr Lys Glu Val Leu Asp Ala
    1730            1735            1740

Thr Leu Ile His Gln Ser Ile Thr Gly Leu Tyr Glu Thr Arg Ile
    1745            1750            1755

Asp Leu Ser Gln Leu Gly Gly Asp Ser Gly Gly Ser Pro Lys Lys
    1760            1765            1770

Lys Arg Lys Val
    1775
```

<210> SEQ ID NO 6
<211> LENGTH: 5379
<212> TYPE: DNA
<213> ORGANISM: Artificial Sequence
<220> FEATURE:
<223> OTHER INFORMATION: Description of Artificial Sequence: Synthetic nCas9-ABE polynucleotide

<400> SEQUENCE: 6

| | |
|---|---|
| atgccaaaaa agaagagaaa ggtttcaggc ggctcctccg aggtggagtt ctctcacgag | 60 |
| tattggatga ggcacgctct tacacttgct aagagagctt gggacgaaag agaagtgcca | 120 |
| gttggcgccg ttcttgtgca taataatagg gtgatcggcg agggttggaa tagaccaatt | 180 |
| ggaaggcatg atccaacagc tcacgcagag attatggctc tcagacaagg cggcctcgtt | 240 |
| atgcagaact acaggctcat tgacgctaca ctctacgtga cactcgaacc ttgcgttatg | 300 |
| tgcgccggag ctatgattca ttctaggatt ggcagggtcg tgtttggagc tagggacgct | 360 |
| aaaacaggag ccgccggatc tcttatggac gtgttgcatc atccaggcat gaaccatagg | 420 |
| gtggagatta cagagggcat tcttgcagac gagtgcgctg ctcttctttc cgatttcttc | 480 |
| aggatgagaa ggcaggagat taaggcccag aagaaggctc agtcttctac agatagcgga | 540 |
| ggatcttccg gaggatctag cggctccgag acaccaggaa catccgaaag cgctacacca | 600 |
| gaatctagcg gaggctcttc cggaggatct tctgaagtgg agttctccca cgagtattgg | 660 |
| atgaggcacg ctcttacact tgctaaaagg gctagggacg aaagggaagt tccagttgga | 720 |
| gctgttctcg tgctcaataa cagggtgatt ggcgagggtt ggaatagagc cattggactc | 780 |
| catgatccaa cagctcacgc agagattatg gctcttagac aaggcggcct cgttatgcag | 840 |
| aattacagac tcatcgacgc cacactctac gttaccttcg aaccttgcgt tatgtgcgcc | 900 |
| ggagctatga tccattctag gattggcagg gtcgtgttcg gcgttagaaa cgctaagaca | 960 |
| ggagctgcag gctctcttat ggacgttctt cattacccag gcatgaatca tagagtggag | 1020 |
| atcacagaag gcattcttgc agacgagtgc gcagctctcc tttgctattt cttcaggatg | 1080 |
| ccgaggcaag ttttcaacgc tcagaagaag gcccagtctt ctacagattc cggcggatct | 1140 |
| tctggaggat ctagcggctc cgagacacca ggaacatccg aatccgctac accagagtct | 1200 |
| tctggaggat ctagcggagg atctcttaag acaagaagt actcgatcgg cctcgccatt | 1260 |
| gggactaact ctgttggctg ggccgtgatc accgacgagt acaaggtgcc ctcaaagaag | 1320 |
| ttcaaggtcc tgggcaacac cgatcggcat tccatcaaga agaatctcat tggcgctctc | 1380 |
| ctgttcgaca gcggcgagac ggctgaggct acgcggctca gcgcaccgc ccgcaggcgg | 1440 |
| tacacgcgca ggaagaatcg catctgctac ctgcaggaga ttttctccaa cgagatggcg | 1500 |
| aaggttgacg attctttctt ccacaggctg gaggagtcat tcctcgtgga ggaggataag | 1560 |
| aagcacgagc ggcatccaat cttcggcaac attgtcgacg aggttgccta ccacgagaag | 1620 |
| taccctacga tctaccatct gcggaagaag ctcgtggact ccacagataa gcggacctc | 1680 |
| cgcctgatct acctcgctct ggcccacatg attaagttca ggggccattt cctgatcgag | 1740 |
| ggggatctca acccggacaa tagcgatgtt gacaagctgt tcatccagct cgtgcagacg | 1800 |
| tacaaccagc tcttcgagga acccccatt aatgcgtcag gcgtcgacgc gaaggctatc | 1860 |
| ctgtccgcta ggctctcgaa gtctcggcgc ctcgagaacc tgatcgccca gctgccgggc | 1920 |
| gagaagaaga acgccctgtt cgggaatctc attgcgctca gcctgggct cacgcccaac | 1980 |
| ttcaagtcga atttcgatct cgctgaggac gccaagctgc agctctccaa ggacacatac | 2040 |

```
gacgatgacc tggataacct cctggcccag atcggcgatc agtacgcgga cctgttcctc    2100
gctgccaaga atctgtcgga cgccatcctc ctgtctgata ttctcagggt gaacaccgag    2160
attacgaagg ctccgctctc agcctccatg atcaagcgct acgacgagca ccatcaggat    2220
ctgaccctcc tgaaggcgct ggtcaggcag cagctcccg agaagtacaa ggagatcttc     2280
ttcgatcagt cgaagaacgg ctacgctggg tacattgacg gcggggcctc tcaggaggag    2340
ttctacaagt tcatcaagcc gattctggag aagatggacg gcacggagga gctgctggtg    2400
aagctcaatc gcgaggacct cctgaggaag cagcggacat tcgataacgg cagcatccca    2460
caccagattc atctcgggga gctgcacgct atcctgagga ggcaggagga cttctaccct    2520
ttcctcaagg ataaccgcga agatcgagaa gattctga ctttcaggat cccgtactac      2580
gtcggcccac tcgctagggg caactcccgc ttcgcttgga tgacccgcaa gtcagaggag    2640
acgatcacgc cgtggaactt cgaggaggtg gtcgacaagg gcgctagcgc tcagtcgttc    2700
atcgagagga tgacgaattt cgacaagaac ctgccaaatg agaaggtgct ccctaagcac    2760
tcgctcctgt acgagtactt cacagtctac aacgagctga ctaaggtgaa gtatgtgacc    2820
gagggcatga ggaagccggc tttcctgtct ggggagcaga agaaggccat cgtggacctc    2880
ctgttcaaga ccaaccggaa ggtcacggtt aagcagctca aggaggacta cttcaagaag    2940
attgagtgct tcgattcggt cgagatctct ggcgttgagg accgcttcaa cgcctccctg    3000
gggacctacc acgatctcct gaagatcatt aaggataagg acttcctgga caacgaggag    3060
aatgaggata tcctcgagga cattgtgctg acactcactc tgttcgagga ccgggagatg    3120
atcgaggagc gcctgaagac ttacgcccat ctcttcgatg acaaggtcat gaagcagctc    3180
aagaggagga ggtacaccgg ctgggggagg ctgagcagga agctcatcaa cggcattcgg    3240
gacaagcagt ccgggaagac gatcctcgac ttcctgaaga gcgatggctt cgcgaaccgc    3300
aatttcatgc agctgattca cgatgacagc ctcacattca aggaggatat ccagaaggct    3360
caggtgagcg gccaggggga ctcgctgcac gagcatatcg cgaacctcgc tggctcgcca    3420
gctatcaaga aggggattct gcagaccgtg aaggttgtgg acgagctggt gaaggtcatg    3480
ggcaggcaca agcctgagaa catcgtcatt gagatggccc gggagaatca gaccacgcag    3540
aagggccaga agaactcacg cgagaggatg aagaggatcg aggagggcat taaggagctg    3600
gggtcccaga tcctcaagga gcacccggtg gagaacacgc agctgcagaa tgagaagctc    3660
tacctgtact acctccagaa tggccgcgat atgtatgtgg accaggagct ggatattaac    3720
aggctcagcg attacgacgt cgatcatatc gttccacagt cattcctgaa ggatgactcc    3780
attgacaaca aggtcctcac caggtcggac aagaaccggg gcaagtctga taatgttcct    3840
tcagaggagg tcgttaagaa gatgaagaac tactggcgcc agctcctgaa tgccaagctg    3900
atcacgcagc ggaagttcga taacctcaca aaggctgaga ggggcgggct ctctgagctg    3960
gacaaggcgg gcttcatcaa gaggcagctg gtcgagacac ggcagatcac taagcacgtt    4020
gcgcagattc tcgactcacg gatgaacact aagtacgatg agaatgacaa gctgatccgc    4080
gaggtgaagg tcatcaccct gaagtcaaag ctcgtctccg acttcaggaa ggatttccag    4140
ttctacaagg ttcgggagat caacaattac caccatgccc atgacgcgta cctgaacgcg    4200
gtggtcggca cagctctgat caagaagtac ccaaagctcg agagcgagtt cgtgtacggg    4260
gactacaagg tttacgatgt gaggaagatg atcgccaagt cggagcagga gattggcaag    4320
gctaccgcca agtacttctt ctactctaac attatgaatt tcttcaagac agagatcact    4380
ctggccaatg gcgagatccg gaagcgcccc ctcatcgaga cgaacggcga gacggggggag  4440
```

```
atcgtgtggg acaagggcag ggatttcgcg accgtcagga aggttctctc catgccacaa    4500
gtgaatatcg tcaagaagac agaggtccag actggcgggt tctctaagga gtcaattctg    4560
cctaagcgga acagcgacaa gctcatcgcc cgcaagaagg actgggatcc gaagaagtac    4620
ggcgggttcg acagccccac tgtggcctac tcggtcctgg ttgtggcgaa ggttgagaag    4680
ggcaagtcca agaagctcaa gagcgtgaag gagctgctgg ggatcacgat tatggagcgc    4740
tccagcttcg agaagaaccc gatcgatttc ctggaggcga agggctacaa ggaggtgaag    4800
aaggacctga tcattaagct ccccaagtac tcactcttcg agctggagaa cggcaggaag    4860
cggatgctgg cttccgctgg cgagctgcag aaggggaacg agctggctct gccgtccaag    4920
tatgtgaact tcctctacct ggcctcccac tacgagaagc tcaagggcag ccccgaggac    4980
aacgagcaga gcagctgtt cgtcgagcag cacaagcatt acctcgacga gatcattgag    5040
cagatttccg agttctccaa gcgcgtgatc ctggccgacg cgaatctgga taaggtcctc    5100
tccgcgtaca acaagcaccg cgacaagcca atcagggagc aggctgagaa tatcattcat    5160
ctcttcaccc tgacgaacct cggcgcccct gctgctttca gtacttcga cacaactatc    5220 gatcgcaaga ggtacacaag cactaaggag gtcctggacg cgaccctcat ccaccagtcg    5280
attaccggcc tctacgagac gcgcatcgac ctgtctcagc tcggggggcga caagcggcca    5340 gcggcgacga agaaggcggg gcaggcgaag aagaagaag    5379

<210> SEQ ID NO 7
<211> LENGTH: 5334
<212> TYPE: DNA
<213> ORGANISM: Artificial Sequence
<220> FEATURE:
<223> OTHER INFORMATION: Description of Artificial Sequence: Synthetic
      SpnCas9-ABE-1 polynucleotide

<400> SEQUENCE: 7
atgtccgagg tggagttctc tcacgagtat tggatgaggc acgctcttac acttgctaag      60
agagcttggg acgaaagaga agtgccagtt ggcgccgttc ttgtgcataa taatagggtg     120
atcggcgagg gttggaatag accaattgga aggcatgatc caacagctca cgcagagatt     180
atggctctca gacaaggcgg cctcgttatg cagaactaca ggctcattga cgctacactc     240
tacgtgacac tcgaaccttg cgttatgtgc gccggagcta tgattcattc taggattggc     300
agggtcgtgt ttggagctag ggacgctaaa acaggagccg ccggatctct tatggacgtg     360
ttgcatcatc caggcatgaa ccataggggt gagattacag agggcattct tgcagacgag     420
tgcgctgctc ttctttccga tttcttcagg atgagaaggc aggagattaa ggcccagaag     480
aaggctcagt cttctacaga tagcggagga tcttccggag atctagcgg ctccgagaca     540 ccaggaacat ccgaaagcgc tacaccagaa tctagcggag gctcttccgg aggatcttct     600
gaagtggagt ctcccacga gtattggatg aggcacgctc ttacacttgc taaaagggct     660
agggacgaaa gggaagttcc agttggagct gttctcgtgc tcaataacag ggtgattggc     720
gagggttgga ataagagccat ggactccat gatccaacag ctcacgcaga gattatggct     780
cttagacaag gcgcctcgt tatgcagaat tacagactca tcgacgccac actctacgtt     840
accttcgaac cttgcgttat gtgcgccgga gctatgatcc attctaggat tggcagggtc     900
gtgttcggcg ttagaaacgc taagacagga gctgcaggct ctcttatgga cgttcttcat     960
tacccaggca tgaatcatag agtggagatc acagaaggca ttcttgcaga cgagtgcgca    1020
gctctccttt gctatttctt caggatgccg aggcaagttt tcaacgctca gaagaaggcc    1080
```

```
cagtcttcta cagattccgg cggatcttct ggaggatcta gcggctccga gacaccagga    1140
acatccgaat ccgctacacc agagtcttct ggaggatcta gcggaggatc tcttaaggac    1200
aagaagtact cgatcggcct cgccattggg actaactctg ttggctgggc cgtgatcacc    1260
gacgagtaca aggtgccctc aaagaagttc aaggtcctgg gcaacaccga tcggcattcc    1320
atcaagaaga atctcattgg cgctctcctg ttcgacagcg gcgagacggc tgaggctacg    1380
cggctcaagc gcaccgcccg caggcggtac acgcgcagga agaatcgcat ctgctacctg    1440
caggagattt tctccaacga gatggcgaag gttgacgatt ctttcttcca caggctggag    1500
gagtcattcc tcgtggagga ggataagaag cacgagcggc atccaatctt cggcaacatt    1560
gtcgacgagg ttgcctacca cgagaagtac cctacgatct accatctgcg gaagaagctc    1620
gtggactcca cagataaggc ggacctccgc ctgatctacc tcgctctggc ccacatgatt    1680
aagttcaggg gccatttcct gatcgagggg gatctcaacc cggacaatag cgatgttgac    1740
aagctgttca tccagctcgt gcagacgtac aaccagctct cgaggagaa ccccattaat    1800
gcgtcaggcg tcgacgcgaa ggctatcctg tccgctaggc tctcgaagtc tcggcgcctc    1860
gagaacctga tcgcccagct gccgggcgag aagaagaacg gcctgttcgg gaatctcatt    1920
gcgctcagcc tggggctcac gcccaacttc aagtcgaatt tcgatctcgc tgaggacgcc    1980
aagctgcagc tctccaagga cacatacgac gatgacctgg ataacctcct ggcccagatc    2040
ggcgatcagt acgcggacct gttcctcgct gccaagaatc tgtcggacgc catcctcctg    2100
tctgatattc tcagggtgaa caccgagatt acgaaggctc cgctctcagc ctccatgatc    2160
aagcgctacg acgagcacca tcaggatctg accctcctga aggcgctggt caggcagcag    2220
ctccccgaga agtacaagga gatcttcttc gatcagtcga agaacggcta cgctgggtac    2280
attgacggcg gggcctctca ggaggagttc tacaagttca tcaagccgat tctggagaag    2340
atggacggca cggaggagct gctggtgaag ctcaatcgcg aggacctcct gaggaagcag    2400
cggacattcg ataacggcag catcccacac cagattcatc tcggggagct gcacgctatc    2460
ctgaggaggc aggaggactt ctacccttc ctcaaggata accgcgagaa gatcgagaag    2520
attctgactt tcaggatccc gtactacgtc ggcccactcg ctaggggcaa ctcccgcttc    2580
gcttggatga cccgcaagtc agaggagacg atcacgccgt ggaacttcga ggaggtggtc    2640
gacaagggcg ctagcgctca gtcgttcatc gagaggatga cgaatttcga caagaacctg    2700
ccaaatgaga aggtgctccc taagcactcg ctcctgtacg agtacttcac agtctacaac    2760
gagctgacta aggtgaagta tgtgaccgag gcatgagga agccggcttt cctgtctggg    2820
gagcagaaga aggccatcgt ggacctcctg ttcaagacca accggaaggt cacggttaag    2880
cagctcaagg aggactactt caagaagatt gagtgcttcg attcggtcga gatctctggc    2940
gttgaggacc gcttcaacgc ctccctgggg acctaccacg atctcctgaa gatcattaag    3000
gataaggact tcctggacaa cgaggagaat gaggatatcc tcgaggacat tgtgctgaca    3060
ctcactctgt tcgaggaccg ggagatgatc gaggagcgcc tgaagactta cgcccatctc    3120
ttcgatgaca aggtcatgaa gcagctcaag aggaggaggt acaccggctg ggggaggctg    3180
agcaggaagc tcatcaacgg cattcgggac aagcagtccg ggaagacgat cctcgacttc    3240
ctgaagagcg atggcttcgc gaaccgcaat ttcatgcagc tgattcacga tgacagcctc    3300
acattcaagg aggatatcca gaaggctcag gtgagcggcc aggggactc gctgcacgag    3360
catatcgcga acctcgctgg ctcgccagct atcaagaagg ggattctgca gaccgtgaag    3420
```

```
gttgtggacg agctggtgaa ggtcatgggc aggcacaagc ctgagaacat cgtcattgag   3480
atggcccggg agaatcagac cacgcagaag ggccagaaga actcacgcga gaggatgaag   3540
aggatcgagg agggcattaa ggagctgggg tcccagatcc tcaaggagca cccggtggag   3600
aacacgcagc tgcagaatga gaagctctac ctgtactacc tccagaatgg ccgcgatatg   3660
tatgtggacc aggagctgga tattaacagg ctcagcgatt acgacgtcga tcatatcgtt   3720
ccacagtcat tcctgaagga tgactccatt gacaacaagg tcctcaccag gtcggacaag   3780
aaccggggca gtctgataat gttccttca gaggaggtcg ttaagaagat gaagaactac   3840
tggcgccagc tcctgaatgc caagctgatc acgcagcgga agttcgataa cctcacaaag   3900
gctgagaggg gcgggctctc tgagctggac aaggcgggct tcatcaagag gcagctggtc   3960
gagacacggc agatcactaa gcacgttgcg cagattctcg actcacggat gaacactaag   4020
tacgatgaga atgacaagct gatccgcgag gtgaaggtca tcaccctgaa gtcaaagctc   4080
gtctccgact tcaggaagga tttccagttc tacaaggttc gggagatcaa caattaccac   4140
catgcccatg acgcgtacct gaacgcggtg gtcggcacag ctctgatcaa gaagtaccca   4200
aagctcgaga gcgagttcgt gtacggggac tacaaggttt acgatgtgag gaagatgatc   4260
gccaagtcgg agcaggagat tggcaaggct accgccaagt acttcttcta ctctaacatt   4320
atgaatttct tcaagacaga gatcactctg gccaatggcg agatccggaa gcgcccctc   4380
atcgagacga acgcgagac gggggagatc gtgtgggaca agggcaggga tttcgcgacc   4440
gtcaggaagg ttctctccat gccacaagtg aatatcgtca agaagacaga ggtccagact   4500
ggcgggttct ctaaggagtc aattctgcct aagcggaaca gcgacaagct catcgcccgc   4560
aagaaggact gggatccgaa gaagtacggc gggttcgaca gccccactgt ggcctactcg   4620
gtcctggttg tggcgaaggt tgagaagggc aagtccaaga agctcaagag cgtgaaggag   4680
ctgctgggga tcacgattat ggagcgctcc agcttcgaga agaacccgat cgatttcctg   4740
gaggcgaagg gctacaagga ggtgaagaag gacctgatca ttaagctccc caagtactca   4800
ctcttcgagc tggagaacgg caggaagcgg atgctggctt ccgctggcga gctgcagaag   4860
gggaacgagc tggctctgcc gtccaagtat gtgaacttcc tctacctggc ctcccactac   4920
gagaagctca agggcagccc cgaggacaac gagcagaagc agctgttcgt cgagcagcac   4980
aagcattacc tcgacgagat cattgagcag atttccgagt tctccaagcg cgtgatcctg   5040
gccgacgcga atctggataa ggtcctctcc gcgtacaaca agcaccgcga caagccaatc   5100
agggagcagg ctgagaatat cattcatctc ttcaccctga cgaacctcgg cgcccctgct   5160
gctttcaagt acttcgacac aactatcgat cgcaagaggt acacaagcac taaggaggtc   5220
ctggacgcga ccctcatcca ccagtcgatt accggcctct acgagacgcg catcgacctg   5280
tctcagctcg ggggcgactc cggcggcagc ccaaagaaga agcggaaggt gtag         5334
```

<210> SEQ ID NO 8
<211> LENGTH: 5686
<212> TYPE: DNA
<213> ORGANISM: Artificial Sequence
<220> FEATURE:
<223> OTHER INFORMATION: Description of Artificial Sequence: Synthetic
      pJIT163-GFP polynucleotide

<400> SEQUENCE: 8

```
gagctcggta cctgacccgg tcgtgcccct ctctagagat aatgagcatt gcatgtctaa     60
gttataaaaa attaccacat atttttttg tcacacttgt ttgaagtgca gtttatctat    120
```

```
ctttatacat atatttaaac tttactctac gaataatata atctatagta ctacaataat        180
atcagtgttt tagagaatca tataaatgaa cagttagaca tggtctaaag gacaattgag        240
tattttgaca acaggactct acagttttat cttttagtg tgcatgtgtt ctcctttttt         300
tttgcaaata gcttcaccta tataatactt catccatttt attagtacat ccatttaggg        360 tttaggggtta atggttttta tagactaatt tttttagtac atctatttta ttctatttta      420
gcctctaaat taagaaaact aaaactctat tttagttttt ttatttaata atttagatat        480
aaaatagaat aaaataaagt gactaaaaat taaacaaata cccttttaaga aattaaaaaa       540 actaaggaaa cattttttctt gtttcgagta gataatgcca gcctgttaaa cgccgtcgac       600
gagtctaacg gacaccaacc agcgaaccag cagcgtcgcg tcgggccaag cgaagcagac       660
ggcacggcat ctctgtcgct gcctctggac ccctctcgat cgagagttcc gctccaccgt       720
tggacttgct ccgctgtcgg catccagaaa ttgcgtggcg gagcggcaga cgtgagccgg      780
cacggcaggc ggcctcctcc tcctctcacg gcaccggcag ctacggggga ttccttttccc     840 accgctcctt cgctttccct cctcgcccg ccgtaataaa tagacacccc ctccacaccc       900
tctttcccca acctcgtgtt gttcggagcg cacacacaca caaccagatc tcccccaaat      960
ccacccgtcg gcacctccgc ttcaaggtac gccgctcgtc ctcccccccc cccctctct       1020 accttctcta gatcggcgtt ccggtccatg gttagggccc ggtagttcta cttctgttca      1080
tgtttgtgtt agatccgtgt ttgtgttaga tccgtgctgc tagcgttcgt acacggatgc      1140
gacctgtacg tcagacacgt tctgattgct aacttgccag tgtttctctt tggggaatcc     1200
tgggatggct ctagccgttc cgcagacggg atcgatttca tgatttttt tgtttcgttg      1260 catagggttt ggtttgccct tttcctttat ttcaatatat gccgtgcact tgtttgtcgg     1320
gtcatctttt catgcttttt tttgtcttgg ttgtgatgat gtggtctggt tgggcggtcg      1380
ttctagatcg gagtagaatt aattctgttt caaactacct ggtggattta ttaattttgg     1440
atctgtatgt gtgtgccata catattcata gttacgaatt gaagatgatg gatgaaata      1500 tcgatctagg ataggtatac atgttgatgc gggttttact gatgcatata cagagatgct     1560
ttttgttcgc ttggttgtga tgatgtggtg tggttgggcg tcgttcatt cgttctagat      1620 cggagtagaa tactgtttca aactacctgg tgtatttatt aattttggaa ctgtatgtgt     1680
gtgtcataca tcttcatagt tacgagttta agatggatgg aaatatcgat ctaggatagg     1740
tatacatgtt gatgtgggtt ttactgatgc atatacatga tggcatatgc agcatctatt     1800
catatgctct aaccttgagt acctatctat tataataaac aagtatgttt tataattatt     1860
ttgatcttga tatacttgga tgatggcata tgcagcagct atatgtggat tttttttagcc    1920 ctgccttcat acgctattta tttgcttggt actgtttctt ttgtcgatgc tcaccctgtt     1980
gtttggtgtt acttctgcaa agcttgtcga cggatccatg gtgagcaagg gcgaggagct    2040
gttcaccggg gtggtgccca tcctggtcga gctggacggc gacgtaaacg gccacaagtt    2100
cagcgtgtcc ggcgagggcg agggcgatgc cacctacggc aagctgaccc tgaagttcat   2160
ctgcaccacc ggcaagctgc ccgtgccctg gcccaccctc gtgaccacct tcacctacgg   2220
cgtgcagtgc ttcagccgct accccgacca catgaagcag cacgacttct tcaagtccgc   2280
catgcccgaa ggctacgtcc aggagcgcac catcttcttc aaggacgacg gcaactacaa   2340
gacccgcgcc gaggtgaagt tcgagggcga caccctggtg aaccgcatcg agctgaaggg   2400
catcgacttc aaggaggacg gcaacatcct ggggcacaag ctggagtaca actacaacag   2460
ccacaacgtc tatatcatgg ccgacaagca gaagaacggc atcaaggtga acttcaagat   2520
```

```
ccgccacaac atcgaggacg gcagcgtgca gctcgccgac cactaccagc agaacacccc    2580
catcggcgac ggccccgtgc tgctgcccga caaccactac ctgagcaccc agtccgccct    2640
gagcaaagac cccaacgaga agcgcgatca catggtcctg ctggagttcg tgaccgccgc    2700
cgggatcact cacggcatgg acgagctgta caagtaaccc gggaattcgg tacgctgaaa    2760
tcaccagtct ctctctacaa atctatctct ctctattttc tccataaata atgtgtgagt    2820
agtttcccga taagggaaat tagggttctt atagggtttc gctcatgtgt tgagcatata    2880
agaaaccctt agtatgtatt tgtatttgta aaatacttct atcaataaaa tttctaattc    2940
ctaaaaccaa aatccagtac taaaatccag atctcctaaa gtccctatag atctttgtcg    3000
tgaatataaa ccagacacga gacgactaaa cctggagccc agacgccgtt cgaagctaga    3060
agtaccgctt aggcaggagg ccgttaggga aagatgctaa aggcagggtt ggttacgttg    3120 actccccgt aggtttggtt taaatatgat gaagtggacg gaaggaagga ggaagacaag     3180
gaaggataag gttgcaggcc ctgtgcaagg taagaagatg gaaatttgat agaggtacgc    3240
tactatactt atactatacg ctaagggaat gcttgtattt ataccctata cccctaata    3300 accccttatc aatttaagaa ataatccgca taagcccccg cttaaaaatt ggtatcagag    3360
ccatgaatag gtctatgacc aaaactcaag aggataaaac ctcaccaaaa tacgaaagag    3420
ttcttaactc taaagataaa agatctttca agatcaaaac tagttccctc acccggagc    3480 atgcgatatc ctcgagagat ctaggcgtaa tcatggtcat agctgtttcc tgtgtgaaat    3540
tgttatccgc tcacaattcc acacaacata cgagccggaa gcataaagtg taaagcctgg    3600
ggtgcctaat gagtgagcta actcacatta attgcgttgc gctcactgcc cgctttccag    3660
tcgggaaacc tgtcgtgcca gctgcattaa tgaatcggcc aacgcgcggg gagaggcggt    3720
ttgcgtattg ggcgctcttc cgcttcctcg ctcactgact cgctgcgctc ggtcgttcgg    3780
ctgcggcgag cggtatcagc tcactcaaag gcggtaatac ggttatccac agaatcaggg    3840
gataacgcag gaaagaacat gtgagcaaaa ggccagcaaa aggccaggaa ccgtaaaaag    3900
gccgcgttgc tggcgttttt ccataggctc cgcccccctg acgagcatca caaaaatcga    3960
cgctcaagtc agaggtggcg aaacccgaca ggactataaa gataccaggc gtttccccct    4020
ggaagctccc tcgtgcgctc tcctgttccg accctgccgc ttaccggata cctgtccgcc    4080
tttctccctt cgggaagcgt ggcgctttct caatgctcac gctgtaggta tctcagttcg    4140
gtgtaggtcg ttcgctccaa gctgggctgt gtgcacgaac cccccgttca gcccgaccgc    4200
tgcgccttat ccggtaacta tcgtcttgag tccaacccgg taagacacga cttatcgcca    4260
ctggcagcag ccactggtaa caggattagc agagcgaggt atgtaggcgg tgctacagag    4320
ttcttgaagt ggtggcctaa ctacggctac actagaagga cagtatttgg tatctgcgct    4380
ctgctgaagc cagttacctt cggaaaaaga gttggtagct cttgatccgg caaacaaacc    4440
accgctggta gcggtggttt ttttgtttgc aagcagcaga ttacgcgcag aaaaaaagga    4500
tctcaagaag atcctttgat cttttctacg ggtctgacg ctcagtggaa cgaaaactca    4560
cgttaaggga ttttggtcat gagattatca aaaaggatct tcacctagat ccttttaaat    4620
taaaaatgaa gttttaaatc aatctaaagt atatatgagt aaacttggtc tgacagttac    4680
caatgcttaa tcagtgaggc acctatctca gcgatctgtc tatttcgttc atccatagtt    4740
gcctgactcc ccgtcgtgta gataactacg atacgggagg gcttaccatc tggccccagt    4800
gctgcaatga taccgcgaga cccacgctca ccggctccag atttatcagc aataaaccag    4860
```

| | |
|---|---:|
| ccagccggaa gggccgagcg cagaagtggt cctgcaactt tatccgcctc catccagtct | 4920 |
| attaattgtt gccgggaagc tagagtaagt agttcgccag ttaatagttt gcgcaacgtt | 4980 |
| gttgccattg ctacaggcat cgtggtgtca cgctcgtcgt ttggtatggc ttcattcagc | 5040 |
| tccggttccc aacgatcaag gcgagttaca tgatccccca tgttgtgcaa aaaagcggtt | 5100 |
| agctccttcg gtcctccgat cgttgtcaga agtaagttgg ccgcagtgtt atcactcatg | 5160 |
| gttatggcag cactgcataa ttctcttact gtcatgccat ccgtaagatg cttttctgtg | 5220 |
| actggtgagt actcaaccaa gtcattctga aatagtgta tgcggcgacc gagttgctct | 5280 |
| tgcccggcgt caatacggga taataccgcg ccacatagca gaactttaaa agtgctcatc | 5340 |
| attggaaaac gttcttcggg gcgaaaactc tcaaggatct taccgctgtt gagatccagt | 5400 |
| tcgatgtaac ccactcgtgc acccaactga tcttcagcat cttttacttt caccagcgtt | 5460 |
| tctgggtgag caaaaacagg aaggcaaaat gccgcaaaaa agggaataag ggcgacacgg | 5520 |
| aaatgttgaa tactcatact cttcctttt caatattatt gaagcattta tcagggttat | 5580 |
| tgtctcatga gcggatacat atttgaatgt atttagaaaa ataaacaaat aggggttccg | 5640 |
| cgcacatttc cccgaaaagt gccacctgcc agtgccaagc taattc | 5686 |

```
<210> SEQ ID NO 9
<211> LENGTH: 720
<212> TYPE: DNA
<213> ORGANISM: Artificial Sequence
<220> FEATURE:
<223> OTHER INFORMATION: Description of Artificial Sequence: Synthetic
      pBUI-mGFP polynucleotide

<400> SEQUENCE: 9
```

| | |
|---|---:|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcaccta cggcgtgtag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actcacggca tggacgagct gtacaagtaa | 720 |

```
<210> SEQ ID NO 10
<211> LENGTH: 5406
<212> TYPE: DNA
<213> ORGANISM: Artificial Sequence
<220> FEATURE:
<223> OTHER INFORMATION: Description of Artificial Sequence: Synthetic
      SpnCas9-VQR-ABE polynucleotide

<400> SEQUENCE: 10
```

| | |
|---|---:|
| atgccaaaaa agaagagaaa ggtttcaggc ggctcctccg aggtggagtt ctctcacgag | 60 |
| tattggatga ggcacgctct tacacttgct aagagagctt gggacgaaag agaagtgcca | 120 |
| gttggcgccg ttcttgtgca taataatagg gtgatcggcg agggttggaa tagaccaatt | 180 |

| | |
|---|---|
| ggaaggcatg atccaacagc tcacgcagag attatggctc tcagacaagg cggcctcgtt | 240 |
| atgcagaact acaggctcat tgacgctaca ctctacgtga cactcgaacc ttgcgttatg | 300 |
| tgcgccggag ctatgattca ttctaggatt ggcagggtcg tgtttggagc tagggacgct | 360 |
| aaaacaggag ccgccggatc tcttatggac gtgttgcatc atccaggcat gaaccatagg | 420 |
| gtggagatta cagagggcat tcttgcagac gagtgcgctg ctcttctttc cgatttcttc | 480 |
| aggatgagaa ggcaggagat taaggcccag aagaaggctc agtcttctac agatagcgga | 540 |
| ggatcttccg gaggatctag cggctccgag acaccaggaa catccgaaag cgctacacca | 600 |
| gaatctagcg gaggctcttc cggaggatct tctgaagtgg agttctccca cgagtattgg | 660 |
| atgaggcacg ctcttacact tgctaaaagg gctagggacg aaagggaagt tccagttgga | 720 |
| gctgttctcg tgctcaataa cagggtgatt ggcgagggtt ggaatagagc cattggactc | 780 |
| catgatccaa cagctcacgc agagattatg gctcttagac aaggcggcct cgttatgcag | 840 |
| aattacagac tcatcgacgc cacactctac gttaccttcg aaccttgcgt tatgtgcgcc | 900 |
| ggagctatga tccattctag gattggcagg gtcgtgttcg gcgttagaaa cgctaagaca | 960 |
| ggagctgcag gctctcttat ggacgttctt cattacccag gcatgaatca tagagtggag | 1020 |
| atcacagaag gcattcttgc agacgagtgc gcagctctcc tttgctattt cttcaggatg | 1080 |
| ccgaggcaag ttttcaacgc tcagaagaag gcccagtctt ctacagattc cggcggatct | 1140 |
| tctggaggat ctagcggctc cgagacacca ggaacatccg aatccgctac accagagtct | 1200 |
| tctggaggat ctagcggagg atctcttaag ggcatccacg gggtgccagc tgctgacaag | 1260 |
| aagtactcga tcggcctcga tattgggact aactctgttg gctggccgt gatcaccgac | 1320 |
| gagtacaagg tgccctcaaa gaagttcaag gtcctgggca caccgatcg gcattccatc | 1380 |
| aagaagaatc tcattggcgc tctcctgttc gacagcggcg agacggctga ggctacgcgg | 1440 |
| ctcaagcgca ccgcccgcag gcggtacacg cgcaggaaga tcgcatctg ctacctgcag | 1500 |
| gagattttct ccaacgagat ggcgaaggtt gacgattctt cttccacag gctggaggag | 1560 |
| tcattcctcg tggaggagga taagaagcac gagcggcatc caatcttcgg caacattgtc | 1620 |
| gacgaggttg cctaccacga gaagtaccct acgatctacc atctgcggaa gaagctcgtg | 1680 |
| gactccacag ataaggcgga cctccgcctg atctacctcg ctctggccca catgattaag | 1740 |
| ttcagggggcc atttcctgat cgagggggat ctcaacccgg acaatagcga tgttgacaag | 1800 |
| ctgttcatcc agctcgtgca gacgtacaac cagctcttcg aggagaaccc cattaatgcg | 1860 |
| tcaggcgtcg acgcgaaggc tatcctgtcc gctaggctct cgaagtctcg gcgcctcgag | 1920 |
| aacctgatcg cccagctgcc gggcgagaag aagaacggcc tgttcgggaa tctcattgcg | 1980 |
| ctcagcctgg ggctcacgcc caacttcaag tcgaatttcg atctcgctga ggacgccaag | 2040 |
| ctgcagctct ccaaggacac atacgacgat gacctggata acctcctggc ccagatcggc | 2100 |
| gatcagtacg cggacctgtt cctcgctgcc aagaatctgt cggacgccat cctcctgtct | 2160 |
| gatattctca gggtgaacac cgagattacg aaggctccgc tctcagcctc catgatcaag | 2220 |
| cgctacgacg agcaccatca ggatctgacc ctcctgaagg cgctggtcag gcagcagctc | 2280 |
| cccgagaagt acaaggagat cttcttcgat cagtcgaaga acggctacgc tgggtacatt | 2340 |
| gacggcgggg cctctcagga ggagttctac aagttcatca agccgattct ggagaagatg | 2400 |
| gacggcacgg aggagctgct ggtgaagctc aatcgcgagg acctcctgag gaagcagcgg | 2460 |
| acattcgata acggcagcat cccacaccag attcatctcg gggagctgca cgctatcctg | 2520 |

```
aggaggcagg aggacttcta cccctttcctc aaggataacc gcgagaagat cgagaagatt   2580
ctgactttca ggatcccgta ctacgtcggc ccactcgcta ggggcaactc ccgcttcgct    2640
tggatgaccc gcaagtcaga ggagacgatc acgccgtgga acttcgagga ggtggtcgac    2700
aagggcgcta gcgctcagtc gttcatcgag aggatgacga atttcgacaa gaacctgcca    2760
aatgagaagg tgctccctaa gcactcgctc ctgtacgagt acttcacagt ctacaacgag    2820
ctgactaagt tgaagtatgt gaccgagggc atgaggaagc cggcttttcct gtctggggag   2880 cagaagaagg ccatcgtgga cctcctgttc aagaccaacc ggaaggtcac ggttaagcag    2940
ctcaaggagg actacttcaa gaagattgag tgcttcgatt cggtcgagat ctctggcgtt    3000
gaggaccgct tcaacgcctc cctggggacc taccacgatc tcctgaagat cattaaggat    3060
aaggacttcc tggacaacga ggagaatgag gatatcctcg aggacattgt gctgacactc    3120
actctgttcg aggaccggga gatgatcgag gagcgcctga agacttacgc ccatctcttc    3180
gatgacaagg tcatgaagca gctcaagagg aggaggtaca ccggctgggg gaggctgagc    3240
aggaagctca tcaacggcat tcgggacaag cagtccggga gacgatcct cgacttcctg    3300 aagagcgatg gcttcgcgaa ccgcaatttc atgcagctga ttcacgatga cagcctcaca    3360
ttcaaggagg atatccagaa ggctcaggtg agcggccagg gggactcgct gcacgagcat    3420
atcgcgaacc tcgctggctc gccagctatc aagaagggga ttctgcagac cgtgaaggtt    3480
gtggacgagc tggtgaaggt catgggcagg cacaagcctg agaacatcgt cattgagatg    3540
gcccgggaga atcagaccac gcagaagggc cagaagaact cacgcgagag gatgaagagg    3600
atcgaggagg gcattaagga gctggggtcc cagatcctca aggagcaccc ggtggagaac    3660
acgcagctgc agaatgagaa gctctacctg tactacctcc agaatggccg cgatatgtat    3720
gtggaccagg agctggatat taacaggctc agcgattacg acgtcgatca tatcgttcca    3780
cagtcattcc tgaaggatga ctccattgac aacaaggtcc tcaccaggtc ggacaagaac    3840
cggggcaagt ctgataatgt tccttcagag gaggtcgtta agaagatgaa gaactactgg    3900
cgccagctcc tgaatgccaa gctgatcacg cagcggaagt tcgataacct cacaaaggct    3960
gagaggggcg ggctctctga gctggacaag gcgggcttca tcaagaggca gctggtcgag    4020
acacggcaga tcactaagca cgttgcgcag attctcgact cacggatgaa cactaagtac    4080
gatgagaatg acaagctgat ccgcgaggtg aaggtcatca ccctgaagtc aaagctcgtc    4140
tccgacttca ggaaggattt ccagttctac aaggttcggg agatcaacaa ttaccaccat    4200
gcccatgacg cgtacctgaa cgcggtggtc ggcacagctc tgatcaagaa gtacccaaag    4260
ctcgagagcg agttcgtgta cggggactac aaggtttacg atgtgaggaa gatgatcgcc    4320
aagtcggagc aggagattgg caaggctacc gccaagtact tcttctactc taacattatg    4380
aatttcttca agacagagat cactctggcc aatggcgaga tccggaagcg ccccctcatc    4440
gagacgaacg gcgagacggg ggagatcgtg tgggacaagg gcagggattt cgcgaccgtc    4500
aggaaggttc tctccatgcc acaagtgaat atcgtcaaga gacagaggt ccagactggc    4560 gggttctcta aggagtcaat tctgcctaag cggaacagcg acaagctcat cgcccgcaag    4620
aaggactggg atccgaagaa gtacggcggg ttcgtcagcc ccactgtggc ctactcggtc    4680
ctggttgtgg cgaaggttga agggcaag tccaagaagc tcaagagcgt gaaggagctg    4740
ctggggatca cgattatgga gcgctccagc ttcgagaaga acccgatcga tttcctggag    4800
gcgaagggct acaaggaggt gaagaaggac ctgatcatta agctccccaa gtactcactc    4860
ttcgagctgg agaacggcag gaagcggatg ctggcttccg ctggcgagct gcagaagggg    4920
```

| | |
|---|---|
| aacgagctgg ctctgccgtc caagtatgtg aacttcctct acctggcctc ccactacgag | 4980 |
| aagctcaagg gcagccccga ggacaacgag cagaagcagc tgttcgtcga gcagcacaag | 5040 |
| cattacctcg acgagatcat tgagcagatt ccgagttct ccaagcgcgt gatcctggcc | 5100 |
| gacgcgaatc tggataaggt cctctccgcg tacaacaagc accgcgacaa gccaatcagg | 5160 |
| gagcaggctg agaatatcat tcatctcttc accctgacga acctcggcgc ccctgctgct | 5220 |
| ttcaagtact cgacacaac tatcgatcgc aagcagtaca gaagcactaa ggaggtcctg | 5280 |
| gacgcgaccc tcatccacca gtcgattacc ggcctctacg agacgcgcat cgacctgtct | 5340 |
| cagctcgggg gcgacaagcg gccagcggcg acgaagaagg cggggcaggc gaagaagaag | 5400 |
| aagtag | 5406 |

<210> SEQ ID NO 11
<211> LENGTH: 5406
<212> TYPE: DNA
<213> ORGANISM: Artificial Sequence
<220> FEATURE:
<223> OTHER INFORMATION: Description of Artificial Sequence: Synthetic
      SpnCas9-VRER-ABE polynucleotide

<400> SEQUENCE: 11

| | |
|---|---|
| atgccaaaaa agaagagaaa ggtttcaggc ggctcctccg aggtggagtt ctctcacgag | 60 |
| tattggatga ggcacgctct tacacttgct aagagagctt gggacgaaag agaagtgcca | 120 |
| gttggcgccg ttcttgtgca taataatagg gtgatcggcg agggttggaa tagaccaatt | 180 |
| ggaaggcatg atccaacagc tcacgcagag attatggctc tcagacaagg cggcctcgtt | 240 |
| atgcagaact acaggctcat tgacgctaca ctctacgtga cactcgaacc ttgcgttatg | 300 |
| tgcgccggac ctatgattca ttctaggatt ggcagggtc tgtttggagc tagggacgct | 360 |
| aaaacaggag ccgccggatc tcttatggac gtgttgcatc atccaggcat gaaccatagg | 420 |
| gtggagatta cagagggcat tcttgcagac gagtgcgctg ctcttctttc cgatttcttc | 480 |
| aggatgagaa ggcaggagat taaggcccag aagaaggctc agtcttctac agatagcgga | 540 |
| ggatcttccg gaggatctag cggctccgag acaccaggaa catccgaaag cgctacacca | 600 |
| gaatctagcg gaggctcttc cggaggatct tctgaagtgg agttctccca cgagtattgg | 660 |
| atgaggcacg ctcttacact tgctaaaagg gctagggacg aaagggaagt tccagttgga | 720 |
| gctgttctcg tgctcaataa cagggtgatt ggcgagggtt ggaatagagc cattggactc | 780 |
| catgatccaa cagctcacgc agagattatg gctcttagac aaggcggcct cgttatgcag | 840 |
| aattacagac tcatcgacgc cacactctac gttaccttcg aaccttgcgt tatgtgcgcc | 900 |
| ggagctatga tccattctag gattggcagg tcgtgttcg cgttagaaa cgctaagaca | 960 |
| ggagctgcag gctctcttat ggacgttctt cattacccag gcatgaatca tagagtggag | 1020 |
| atcacagaag gcattcttgc agacgagtgc gcagctctcc tttgctattt cttcaggatg | 1080 |
| ccgaggcaag ttttcaacgc tcagaagaag gcccagtctt ctacagattc cggcggatct | 1140 |
| tctggaggat ctagcggctc cgagacacca ggaacatccg aatccgctac accagagtct | 1200 |
| tctggaggat ctagcggagg atctcttaag ggcatccacg ggtgccagc tgctgacaag | 1260 |
| aagtactcga tcggcctcga tattgggact aactctgttg gctgggccgt gatcaccgac | 1320 |
| gagtacaagg tgccctcaaa gaagttcaag gtcctgggca acaccgatcg gcattccatc | 1380 |
| aagaagaatc tcattggcgc tctcctgttc gacagcggcg agacggctga ggctacgcgg | 1440 |
| ctcaagcgca ccgcccgcag gcggtacacg cgcaggaaga tcgcatctg ctacctgcag | 1500 |

```
gagattttct ccaacgagat ggcgaaggtt gacgattctt tcttccacag gctggaggag    1560
tcattcctcg tggaggagga taagaagcac gagcggcatc caatcttcgg caacattgtc    1620
gacgaggttg cctaccacga gaagtaccct acgatctacc atctgcggaa gaagctcgtg    1680
gactccacag ataaggcgga cctccgcctg atctacctcg ctctggccca catgattaag    1740
ttcaggggcc atttcctgat cgaggggat ctcaacccgg acaatagcga tgttgacaag    1800
ctgttcatcc agctcgtgca gacgtacaac cagctcttcg aggagaaccc cattaatgcg    1860
tcaggcgtcg acgcgaaggc tatcctgtcc gctaggctct cgaagtctcg gcgcctcgag    1920
aacctgatcg cccagctgcc gggcgagaag aagaacggcc tgttcgggaa tctcattgcg    1980
ctcagcctgg ggctcacgcc caacttcaag tcgaatttcg atctcgctga ggacgccaag    2040
ctgcagctct ccaaggacac atacgacgat gacctggata acctcctggc ccagatcggc    2100
gatcagtacg cggacctgtt cctcgctgcc aagaatctgt cggacgccat cctcctgtct    2160
gatattctca gggtgaacac cgagattacg aaggctccgc tctcagcctc catgatcaag    2220
cgctacgacg agcaccatca ggatctgacc ctcctgaagg cgctggtcag gcagcagctc    2280
cccgagaagt acaaggagat cttcttcgat cagtcgaaga acggctacgc tgggtacatt    2340
gacggcgggg cctctcagga ggagttctac aagttcatca agccgattct ggagaagatg    2400
gacggcacgg aggagctgct ggtgaagctc aatcgcgagg acctcctgag gaagcagcgg    2460
acattcgata acggcagcat cccacaccag attcatctcg gggagctgca cgctatcctg    2520
aggaggcagg aggacttcta ccctttcctc aaggataacc gcgagaagat cgagaagatt    2580
ctgactttca ggatcccgta ctacgtcggc ccactcgcta ggggcaactc ccgcttcgct    2640
tggatgaccc gcaagtcaga ggagacgatc acgccgtgga acttcgagga ggtggtcgac    2700
aagggcgcta gcgctcagtc gttcatcgag aggatgacga atttcgacaa gaacctgcca    2760
aatgagaagg tgctccctaa gcactcgctc ctgtacgagt acttcacagt ctacaacgag    2820
ctgactaagg tgaagtatgt gaccgagggc atgaggaagc cggctttcct gtctggggag    2880
cagaagaagg ccatcgtgga cctcctgttc aagaccaacc ggaaggtcac ggttaagcag    2940
ctcaaggagg actacttcaa gaagattgag tgcttcgatt cggtcgagat ctctggcgtt    3000
gaggaccgct tcaacgcctc cctggggacc taccacgatc tcctgaagat cattaaggat    3060
aaggacttcc tggacaacga ggagaatgag gatatcctcg aggacattgt gctgacactc    3120
actctgttcg aggaccggga gatgatcgag gagcgcctga agacttacgc ccatctcttc    3180
gatgacaagg tcatgaagca gctcaagagg aggaggtaca ccggctgggg gaggctgagc    3240
aggaagctca tcaacggcat tcgggacaag cagtccggga agacgatcct cgacttcctg    3300
aagagcgatg gcttcgcgaa ccgcaatttc atgcagctga ttcacgatga cagcctcaca    3360
ttcaaggagg atatccagaa ggctcaggtg agcggccagg gggactcgct gcacgagcat    3420
atcgcgaacc tcgctggctc gccagctatc aagaagggga ttctgcagac cgtgaaggtt    3480
gtggacgagc tggtgaaggt catgggcagg cacaagcctg agaacatcgt cattgagatg    3540
gcccgggaga atcagaccac gcagaagggc cagaagaact cacgcgagag gatgaagagg    3600
atcgaggagg gcattaagga gctggggtcc cagatcctca aggagcaccc ggtggagaac    3660
acgcagctgc agaatgagaa gctctacctg tactacctcc agaatggccg cgatatgtat    3720
gtggaccagg agctggatat taacaggctc agcgattacg acgtcgatca tatcgttcca    3780
cagtcattcc tgaaggatga ctccattgac aacaaggtcc tcaccaggtc ggacaagaac    3840
```

```
cggggcaagt ctgataatgt tccttcagag gaggtcgtta agaagatgaa gaactactgg    3900
cgccagctcc tgaatgccaa gctgatcacg cagcggaagt tcgataacct cacaaaggct    3960
gagaggggcg ggctctctga gctggacaag gcgggcttca tcaagaggca gctggtcgag    4020
acacggcaga tcactaagca cgttgcgcag attctcgact cacgatgaa cactaagtac     4080 gatgagaatg acaagctgat ccgcgaggtg aaggtcatca ccctgaagtc aaagctcgtc    4140
tccgacttca ggaaggattt ccagttctac aaggttcggg agatcaacaa ttaccaccat    4200
gcccatgacg cgtacctgaa cgcggtggtc ggcacagctc tgatcaagaa gtacccaaag    4260
ctcgagagcg agttcgtgta cggggactac aaggtttacg atgtgaggaa gatgatcgcc    4320
aagtcggagc aggagattgg caaggctacc gccaagtact tcttctactc taacattatg    4380
aatttcttca agacagagat cactctggcc aatggcgaga tccggaagcg cccccctcatc   4440 gagacgaacg gcgagacggg ggagatcgtg tgggacaagg gcagggattt cgcgaccgtc    4500
aggaaggttc tctccatgcc acaagtgaat atcgtcaaga agacagaggt ccagactggc    4560
gggttctcta aggagtcaat tctgcctaag cggaacagcc acaagctcat cgcccgcaag    4620
aaggactggg atccgaagaa gtacggcggg ttcgtcagcc ccactgtggc ctactcggtc    4680
ctggttgtgg cgaaggttga aagggcaag tccaagaagc tcaagagcgt gaaggagctg     4740
ctggggatca cgattatgga gcgctccagc ttcgagaaga cccgatcga tttcctggag     4800 gcgaagggct acaaggaggt gaagaaggac ctgatcatta gctcccaa gtactcactc      4860 ttcgagctgg agaacggcag gaagcggatg ctggcttccg ctcgcgagct gcagaagggg   4920
aacgagctgg ctctgccgtc caagtatgtg aacttcctct acctggcctc ccactacgag    4980
aagctcaagg gcagccccga ggacaacgag cagaagcagc tgttcgtcga gcagcacaag    5040
cattacctcg acgagatcat tgagcagatt tccgagttct ccaagcgcgt gatcctggcc    5100
gacgcgaatc tggataaggt cctctccgcg tacaacaagc accgcgacaa gccaatcagg    5160
gagcaggctg agaatatcat tcatctcttc accctgacga acctcggcgc ccctgctgct   5220
ttcaagtact cgacacaac tatcgatcgc aaggagtaca aagcactaa ggaggtcctg      5280 gacgcgaccc tcatccacca gtcgattacc ggcctctacg agacgcgcat cgacctgtct    5340
cagctcgggg cgacaagcg gccagcggcg acgaagaagg cggggcaggc gaagaagaag    5400
aagtag                                                              5406
```

<210> SEQ ID NO 12
<211> LENGTH: 4437
<212> TYPE: DNA
<213> ORGANISM: Artificial Sequence
<220> FEATURE:
<223> OTHER INFORMATION: Description of Artificial Sequence: Synthetic
      SanCas9-ABE polynucleotide

<400> SEQUENCE: 12

```
atgccaaaaa agaagagaaa ggtttcaggc ggctcctccg aggtggagtt ctctcacgag      60
tattggatga ggcacgctct tacacttgct aagagagctt gggacgaaag agaagtgcca    120
gttggcgccg ttcttgtgca ataataagg gtgatcggcg agggttggaa tagaccaatt     180
ggaaggcatg atccaacagc tcacgcagag attatggctc tcagacaagg cggcctcgtt    240
atgcagaact acaggctcat tgacgctaca ctctacgtga cactcgaacc ttgcgttatg    300
tgcgccggag ctatgattca ttctaggatt ggcagggtcg tgtttggagc tagggacgct    360
aaaacaggag ccgccggatc tcttatggac gtgttgcatc atccaggcat gaaccatagg    420
```

```
gtggagatta cagagggcat tcttgcagac gagtgcgctg ctcttctttc cgatttcttc    480
aggatgagaa ggcaggagat taaggcccag aagaaggctc agtcttctac agatagcgga    540
ggatcttccg gaggatctag cggctccgag acaccaggaa catccgaaag cgctacacca    600
gaatctagcg gaggctcttc cggaggatct tctgaagtgg agttctccca cgagtattgg    660
atgaggcacg ctcttacact tgctaaaagg gctagggacg aaagggaagt tccagttgga    720
gctgttctcg tgctcaataa cagggtgatt ggcgagggtt ggaatagagc cattggactc    780
catgatccaa cagctcacgc agagattatg gctcttagac aaggcggcct cgttatgcag    840
aattacagac tcatcgacgc cacactctac gttaccttcg aaccttgcgt tatgtgcgcc    900
ggagctatga tccattctag gattggcagg gtcgtgttcg gcgttagaaa cgctaagaca    960
ggagctgcag gctctcttat ggacgttctt cattacccag gcatgaatca tagagtggag   1020
atcacagaag gcattcttgc agacgagtgc gcagctctcc tttgctattt cttcaggatg   1080
ccgaggcaag ttttcaacgc tcagaagaag gcccagtctt ctacagattc cggcggatct   1140
tctggaggat ctagcggctc cgagacacca ggaacatccg aatccgctac accagagtct   1200
tctggaggat ctagcggagg atctcttaag aagaggaact acatcctcgg ctggatatt    1260
ggcatcacct ctgtgggcta cgggatcatt gactacgaga cgcgggatgt catcgacgct   1320
ggcgttcgcc tgttcaagga ggccaacgtc gagaacaatg aggggaggag gtccaagagg   1380
ggcgcccgca ggctcaagag gaggaggagg cacaggatcc agagggtgaa gaagctcctg   1440
ttcgattaca acctcctgac cgaccattcg gagctgtctg ggatcaatcc gtacgaggcc   1500
cgcgtcaagg gcctgtctca gaagctctca gaggaggagt tcagcgctgc cctcctgcac   1560
ctcgctaagc gcaggggcgt ccataacgtt aatgaggtgg aggaggacac aggcaacgag   1620
ctgtcgacta aggagcagat ctcccgcaac tccaaggcgc tggaggagaa gtatgtggct   1680
gagctgcagc tggagcgcct caagaaggat ggggaggtcc ggggctcaat caaccgcttc   1740
aagacatccg actacgtcaa ggaggccaag cagctcctga aggttcagaa ggcgtaccac   1800
cagctggacc agtcattcat tgatacttac atcgacctcc tcgagacgag gcggacgtac   1860
tacgagggcc caggggaggg ctccccttc gggtggaagg acatcaagga gtggtacgag    1920
atgctgatgg gccattgcac gtacttcccg gaggagctga ggagcgttaa gtacgcttac   1980
aacgccgatc tgtacaacgc gctcaatgac ctgaacaatc tcgtcatcac ccgggacgag   2040
aacgagaagc tcgagtacta cgagaagttc cagatcattg agaatgtgtt caagcagaag   2100
aagaagccaa cgctgaagca gattgcgaag gagatcctcg ttaacgagga ggacatcaag   2160
gggtacaggg tgacctcgac gggcaagcct gagttcacaa acctgaaggt ctaccacgat   2220
attaaggaca tcactgccag gaaggagatc attgagaacg ccgagctgct cgaccagatt   2280
gcgaagatcc tcacgatcta ccagtccagc gaggacatcc aggaggagct gaccaacctc   2340
aattcggagc tgacgcagga ggagatcgag cagatttcta acctgaaggg gtacacaggc   2400
actcacaacc tcagcctgaa ggcgatcaat ctcattctgg atgagctgtg gcatacaaac   2460
gacaatcaga ttgctatctt caacaggctc aagctggtgc aaagaaggt cgacctctct    2520
cagcagaagg agatcccgac cacgctggtg gacgatttca ttctctcacc cgtggtcaag   2580
aggtccttca tccagagcat taaggtcatc aacgccatca ttaagaagta cggcctgccc   2640
aatgatatca ttatcgagct ggcgcgcgag aagaactcca aggacgctca gaagatgatc   2700
aatgagatgc agaagcggaa ccgccagacc aatgagagga tcgaggagat tatccggaca   2760
actggcaagg agaacgctaa gtacctgatt gagaagatca agctccacga tatgcaggag   2820
```

```
ggcaagtgcc tgtactccct cgaggccatc ccactggagg acctcctgaa caatcctttc   2880
aactacgagg ttgatcatat tatcccgagg tccgtgagct tcgacaatag cttcaacaat   2940
aaggtcctgg ttaagcaaga ggagaactcg aagaagggca atcgcacccc cttccagtac   3000
ctctcgtctt cagacagcaa gatctcgtac gagacgttca agaagcacat tctcaacctg   3060
gcgaagggga agggcaggat ctccaagacc aagaaggagt acctcctgga ggagcgggac   3120
atcaaccgct tcagcgtcca gaaggatttc attaaccgga atctggttga cacacgctac   3180
gccactcggg gcctcatgaa cctcctgcgc tcctacttca gggtgaacaa tctggacgtg   3240
aaggtcaaga gcatcaacgg cgggttcacg tcgttcctcc gcaggaagtg gaagttcaag   3300
aaggagagga acaagggcta caagcaccat gcggaggatg ctctgattat cgccaatgcg   3360
gacttcatct tcaaggagtg gaagaagctc gacaaggcca agaaggtcat ggagaaccag   3420
atgttcgagg agaagcaggc cgagagcatg ccagagatcg agacagagca ggagtacaag   3480 gagatttttca tcactcctca ccagattaag catatcaagg attttcaagga ctacaagtac   3540 tcgcaccgcg tggataagaa gccgaacagg gagctgatca tgacaccct ctactctacg   3600 cgcaaggacg ataaggggaa cacactcatc gtcaacaatc tgaacggcct ctacgacaag   3660
gataatgaca agctgaagaa gctcatcaac aagagcccag agaagctcct gatgtaccac   3720
catgatcctc agacttacca gaagctcaag ctgatcatgg agcagtacgg cgacgagaag   3780
aacccgctct acaagtacta cgaggagaca ggcaactacc tgactaagta ctcgaagaag   3840
gataatgggc ccgtgattaa gagatcaag tactacggca caagctgaa tgcgcatctc   3900 gacatcaccg acgattaccc gaactctcgc aataaggttg tgaagctctc actgaagccc   3960
tacaggttcg atgtgtacct ggacaacggc gtctacaagt tcgttacggt gaagaatctc   4020
gacgtgatca agaaggagaa ctactacgag gtcaattcca agtgctacga ggaggccaag   4080
aagctgaaga gatttccaa ccaggctgag ttcatcgcca gcttctacaa caatgacctg   4140
attaagatca acggggagct gtacagggtc atcggcgtta acaatgatct cctgaaccgg   4200
attgaagtga atatgattga catcacctac cgcgagtacc tcgagaacat gaatgataag   4260 cgccccgccca ggattatcaa gaccattgcc tcgaagacgc agtctatcaa gaagtactca   4320
acagacattc tgggcaacct ctacgaggtc aagtccaaga agcacccgca gattatcaag   4380
aagggcaagc gcccggccgc cactaagaag gctgggcagg ccaagaagaa gaagtag     4437
```

<210> SEQ ID NO 13
<211> LENGTH: 4431
<212> TYPE: DNA
<213> ORGANISM: Artificial Sequence
<220> FEATURE:
<223> OTHER INFORMATION: Description of Artificial Sequence: Synthetic
      SanCas9-KKH-ABE polynucleotide

<400> SEQUENCE: 13

```
atgccaaaaa agaagagaaa ggtttcaggc ggctcctccg aggtggagtt ctctcacgag    60
tattggatga ggcacgctct tacacttgct aagagagctt gggacgaaag agaagtgcca   120
gttggcgccg ttcttgtgca taataatagg gtgatcggcg agggttggaa tagaccaatt   180
ggaaggcatg atccaacagc tcacgcagag attatggctc tcagacaagg cggcctcgtt   240
atgcagaact acaggctcat tgacgctaca ctctacgtga cactcgaacc ttgcgttatg   300
tgcgccggag ctatgattca ttctaggatt ggcagggtca tgtttggagc tagggacgct   360
aaaacaggag ccgccggatc tcttatggac gtgttgcatc atccaggcat gaaccatagg   420
```

```
gtggagatta cagagggcat tcttgcagac gagtgcgctg ctcttctttc cgatttcttc        480
aggatgagaa ggcaggagat taaggcccag aagaaggctc agtcttctac agatagcgga        540
ggatcttccg gaggatctag cggctccgag acaccaggaa catccgaaag cgctacacca        600
gaatctagcg gaggctcttc cggaggatct tctgaagtgg agttctccca cgagtattgg        660
atgaggcacg ctcttacact tgctaaaagg gctagggacg aaagggaagt tccagttgga        720
gctgttctcg tgctcaataa cagggtgatt ggcgagggtt ggaatagagc cattggactc        780
catgatccaa cagctcacgc agagattatg gctcttagac aaggcggcct cgttatgcag        840
aattacagac tcatcgacgc cacactctac gttaccttcg aaccttgcgt tatgtgcgcc        900
ggagctatga tccattctag gattggcagg gtcgtgttcg gcgttagaaa cgctaagaca        960
ggagctgcag gctctcttat ggacgttctt cattacccag gcatgaatca tagagtggag       1020
atcacagaag gcattcttgc agacgagtgc gcagctctcc tttgctattt cttcaggatg       1080
ccgaggcaag ttttcaacgc tcagaagaag gcccagtctt ctacagattc cggcggatct       1140
tctggaggat ctagcggctc cgagacacca ggaacatccg aatccgctac accagagtct       1200
tctggaggat ctagcggagg atctaagagg aactacatcc tcgggctgga tattggcatc       1260
acctctgtgg gctacgggat cattgactac gagacgcggg atgtcatcga cgctggcgtt       1320
cgcctgttca aggaggccaa cgtcgagaac aatgagggga ggaggtccaa gaggggcgcc       1380
cgcaggctca agaggaggag gaggcacagg atccagaggg tgaagaagct cctgttcgat       1440
tacaacctcc tgaccgacca ttcggagctg tctgggatca atccgtacga ggcccgcgtc       1500
aagggcctgt ctcagaagct ctcagaggag gagttcagcg ctgccctcct gcacctcgct       1560
aagcgcaggg gcgtccataa cgttaatgag gtggaggagg acacaggcaa cgagctgtcg       1620
actaaggagc agatctcccg caactccaag gcgctggagg agaagtatgt ggctgagctg       1680
cagctggagc gcctcaagaa ggatggggag gtccgggggct caatcaaccg cttcaagaca       1740
tccgactacg tcaaggaggc caagcagctc ctgaaggttc agaaggcgta ccaccagctg       1800
gaccagtcat tcattgatac ttacatcgac ctcctcgaga cgaggcggac gtactacgag       1860
ggcccagggg agggctcccc cttcgggtgg aaggacatca aggagtggta cgagatgctg       1920
atgggccatt gcacgtactt cccggaggag ctgaggagcg ttaagtacgc ttacaacgcc       1980
gatctgtaca acgcgctcaa tgacctgaac aatctcgtca tcacccggga cgagaacgag       2040
aagctcgagt actacgagaa gttccagatc attgagaatg tgttcaagca gaagaagaag       2100
ccaacgctga gcagattgc gaaggagatc ctcgttaacg aggaggacat caaggggtac       2160
agggtgacct cgacgggcaa gcctgagttc acaaacctga aggtctacca cgatattaag       2220
gacatcactg ccaggaagga gatcattgag aacgccgagc tgctcgacca gattgcgaag       2280
atcctcacga tctaccagtc cagcgaggac atccaggagg agctgaccaa cctcaattcg       2340
gagctgacgc aggaggagat cgagcagatt tctaacctga aggggtacac aggcactcac       2400
aacctcagcc tgaaggcgat caatctcatt ctggatgagc tgtggcatac aaacgacaat       2460
cagattgcta tcttcaacag gctcaagctg gtgccaaaga aggtcgacct ctctcagcag       2520
aaggagatcc cgaccacgct ggtggacgat ttcattctct cacccgtggt caagaggtcc       2580
ttcatccaga gcattaaggt catcaacgcc atcattaaga agtacggcct gcccaatgat       2640
atcattatcg agctggcgcg cgagaagaac tccaaggacg ctcagaagat gatcaatgag       2700
atgcagaagc ggaaccgcca gaccaatgag aggatcgagg agattatccg gacaactggc       2760
```

```
aaggagaacg ctaagtacct gattgagaag atcaagctcc acgatatgca ggagggcaag    2820
tgcctgtact ccctcgaggc catcccactg gaggacctcc tgaacaatcc tttcaactac    2880
gaggttgatc atattatccc gaggtccgtg agcttcgaca atagcttcaa caataaggtc    2940
ctggttaagc aagaggagaa ctcgaagaag ggcaatcgca ccccttcca gtacctctcg     3000 tcttcagaca gcaagatctc gtacgagacg ttcaagaagc acattctcaa cctggcgaag    3060
gggaagggca ggatctccaa gaccaagaag gagtacctcc tggaggagcg ggacatcaac    3120
cgcttcagcg tccagaagga tttcattaac cggaatctgg ttgacacacg ctacgccact    3180
cggggcctca tgaacctcct cgctcctac ttcagggtga acaatctgga cgtgaaggtc     3240
aagagcatca acggcgggtt cacgtcgttc ctccgcagga agtggaagtt caagaaggag    3300
aggaacaagg gctacaagca ccatgcggag gatgctctga ttatcgccaa tgcggacttc    3360
atcttcaagg agtggaagaa gctcgacaag gccaagaagg tcatggagaa ccagatgttc    3420
gaggagaagc aggccgagag catgccagag atcgagacag agcaggagta caaggagatt    3480
ttcatcactc ctcaccagat taagcatatc aaggatttca aggactacaa gtactcgcac    3540
cgcgtggata gaagccgaa caggaagctg atcaatgaca ccctctactc tacgcgcaag    3600
gacgataagg ggaacacact catcgtcaac aatctgaacg cctctacga caaggataat    3660 gacaagctga agaagctcat caacaagagc ccagagaagc tcctgatgta ccaccatgat    3720
cctcagactt accagaagct caagctgatc atggagcagt acggcgacga gaagaacccg    3780
ctctacaagt actacgagga gacaggcaac tacctgacta gtactcgaa gaaggataat     3840 gggcccgtga ttaagaagat caagtactac ggcaacaagc tgaatgcgca tctcgacatc    3900
accgacgatt acccgaactc tcgcaataag gttgtgaagc tctcactgaa gccctacagg    3960
ttcgatgtgt acctggacaa cggcgtctac aagttcgtta cggtgaagaa tctcgacgtg    4020
atcaagaagg agaactacta cgaggtcaat tccaagtgct acgaggaggc caagaagctg    4080
aagaagattt ccaaccaggc tgagttcatc gccagcttct acaagaatga cctgattaag    4140
atcaacgggg agctgtacag ggtcatcggc gttaacaatg atctcctgaa ccggattgaa    4200
gtgaatatga ttgacatcac ctaccgcgag tacctcgaga acatgaatga taagcgcccg    4260
ccccacatta tcaagaccat tgcctcgaag acgcagtcta tcaagaagta ctcaacagac    4320
attctgggca acctctacga ggtcaagtcc aagaagcacc cgcagattat caagaagggc    4380
aagcgcccgg ccgccactaa gaaggctggg caggccaaga agaagaagta g            4431
```

<210> SEQ ID NO 14
<211> LENGTH: 5373
<212> TYPE: DNA
<213> ORGANISM: Artificial Sequence
<220> FEATURE:
<223> OTHER INFORMATION: Description of Artificial Sequence: Synthetic
      SpnCas9-VQR-ABE-1 polynucleotide

<400> SEQUENCE: 14

```
atgtccgagg tggagttctc tcacgagtat tggatgaggc acgctcttac acttgctaag      60
agagcttggg acgaaagaga agtgccagtt ggcgccgttc ttgtgcataa taatagggtg     120
atcggcgagg gttggaatag accaattgga aggcatgatc caacagctca cgcagagatt     180
atggctctca gacaaggcgg cctcgttatg cagaactaca ggctcattga cgctacactc     240
tacgtgacac tcgaaccttg cgttatgtgc gccggagcta tgattcattc taggattggc     300
agggtcgtgt ttgagctag gacgctaaa acaggagccg ccggatctct tatggacgtg      360
```

```
ttgcatcatc caggcatgaa ccatagggtg gagattacag agggcattct tgcagacgag    420
tgcgctgctc ttctttccga tttcttcagg atgagaaggc aggagattaa ggcccagaag    480
aaggctcagt cttctacaga tagcggagga tcttccggag gatctagcgg ctccgagaca    540
ccaggaacat ccgaaagcgc taccagaaa tctagcggag gctcttccgg aggatcttct    600
gaagtggagt tctcccacga gtattggatg aggcacgctc ttacacttgc taaaagggct    660
agggacgaaa gggaagttcc agttggagct gttctcgtgc tcaataacag ggtgattggc    720
gagggttgga atagagccat tggactccat gatccaacag ctcacgcaga gattatggct    780
cttagacaag gcggcctcgt tatgcagaat tacagactca tcgacgccac actctacgtt    840
accttcgaac cttgcgttat gtgcgccgga gctatgatcc attctaggat tggcagggtc    900
gtgttcggcg ttagaaacgc taagacagga gctgcaggct ctcttatgga cgttcttcat    960
tacccaggca tgaatcatag agtggagatc acagaaggca ttcttgcaga cgagtgcgca   1020
gctctccttt gctatttctt caggatgccg aggcaagttt tcaacgctca gaagaaggcc   1080
cagtcttcta cagattccgg cggatcttct ggaggatcta gcggctccga caccagga    1140 acatccgaat ccgctacacc agagtcttct ggaggatcta gcggaggatc tcttaagggc   1200
atccacgggg tgccagctgc tgacaagaag tactcgatcg gcctcgatat tgggactaac   1260
tctgttggct gggccgtgat caccgacgag tacaaggtgc cctcaaagaa gttcaaggtc   1320
ctgggcaaca ccgatcggca ttccatcaag aagaatctca ttggcgctct cctgttcgac   1380
agcggcgaga cggctgaggc tacgcggctc aagcgcaccg cccgcaggcg gtacacgcgc   1440
aggaagaatc gcatctgcta cctgcaggag attttctcca acgagatggc gaaggttgac   1500
gattctttct ccacaggct ggaggagtca ttcctcgtgg aggaggataa gaagcacgag    1560
cggcatccaa tcttcggcaa cattgtcgac gaggttgcct accacgagaa gtaccctacg   1620
atctaccatc tgcggaagaa gctcgtggac tccacagata aggcggacct ccgcctgatc   1680
tacctcgctc tggcccacat gattaagttc aggggccatt tcctgatcga gggggatctc   1740
aacccggaca atagcgatgt tgacaagctg ttcatccagc tcgtgcagac gtacaaccag   1800
ctcttcgagg agaaccccat taatgcgtca ggcgtcgacg cgaaggctat cctgtccgct   1860
aggctctcga gtctcggcg cctcgagaac ctgatcgccc agctgccggg cgagaagaag   1920
aacggcctgt cgggaatct cattgcgctc agcctgggc tcacgcccaa cttcaagtcg   1980
aatttcgatc tcgctgagga cgccaagctg cagctctcca aggacacata cgacgatgac   2040
ctggataacc tcctggccca gatcggcgat cagtacgcgg acctgttcct cgctgccaag   2100
aatctgtcgg acgccatcct cctgtctgat attctcaggg tgaacaccga gattacgaag   2160
gctccgctct cagcctccat gatcaagcgc tacgacgagc accatcagga tctgaccctc   2220
ctgaaggcgc tggtcaggca gcagctcccc gagaagtaca aggagatctt cttcgatcag   2280
tcgaagaacg gctacgctgg gtacattgac ggcggggcct tcaggagga gttctacaag   2340 ttcatcaagc cgattctgga gaagatggac ggcacggagg agctgctggt gaagctcaat   2400
cgcgaggacc tcctgaggaa gcagcggaca ttcgataacg gcagcatccc acaccagatt   2460
catctcgggg agctgcacgc tatcctgagg aggcaggagg acttctaccc tttccctcaag   2520 gataaccgcg agaagatcga gaagattctg actttcagga tcccgtacta cgtcggccca   2580
ctcgctaggg gcaactcccg cttcgcttgg atgaccgca agtcagagga gacgatcacg   2640
ccgtggaact cgaggaggt ggtcgacaag ggcgctagcg ctcagtcgtt catcgagagg    2700
atgacgaatt tcgacaagaa cctgccaaat gagaaggtgc tccctaagca ctcgctcctg   2760
```

```
tacgagtact tcacagtcta caacgagctg actaaggtga agtatgtgac cgagggcatg    2820
aggaagccgg ctttcctgtc tggggagcag aagaaggcca tcgtggacct cctgttcaag    2880
accaaccgga aggtcacggt taagcagctc aaggaggact acttcaagaa gattgagtgc    2940
ttcgattcgg tcgagatctc tggcgttgag gaccgcttca acgcctccct ggggacctac    3000
cacgatctcc tgaagatcat taaggataag gacttcctgg acaacgagga gaatgaggat    3060
atcctcgagg acattgtgct gacactcact ctgttcgagg accggagat  gatcgaggag    3120 cgcctgaaga cttacgccca tctcttcgat gacaaggtca tgaagcagct caagaggagg    3180
aggtacaccg gctgggggag gctgagcagg aagctcatca acggcattcg ggacaagcag    3240
tccgggaaga cgatcctcga cttcctgaag agcgatggct tcgcgaaccg caatttcatg    3300
cagctgattc acgatgacag cctcacattc aaggaggata tccagaaggc tcaggtgagc    3360
ggccaggggg actcgctgca cgagcatatc gcgaacctcg ctggctcgcc agctatcaag    3420 aagggggattc tgcagaccgt gaaggttgtg gacgagctgg tgaaggtcat gggcaggcac    3480
aagcctgaga acatcgtcat tgagatggcc cgggagaatc agaccacgca gaagggccag    3540
aagaactcac gcgagaggat gaagaggatc gaggagggca ttaaggagct ggggtcccag    3600
atcctcaagg agcacccggt ggagaacacg cagctgcaga tgagaagct  ctacctgtac    3660 tacctccaga tggccgcga  tatgtatgtg gaccaggagc tggatattaa caggctcagc    3720
gattacgacg tcgatcatat cgttccacag tcattcctga aggatgactc cattgacaac    3780
aaggtcctca ccaggtcgga caagaaccgg ggcaagtctg ataatgttcc ttcagaggag    3840
gtcgttaaga agatgaagaa ctactggcgc cagctcctga atgccaagct gatcacgcag    3900
cggaagttcg ataacctcac aaaggctgag aggggcgggc tctctgagct ggacaaggcg    3960
ggcttcatca agaggcagct ggtcgagaca cggcagatca ctaagcacgt tgcgcagatt    4020
ctcgactcac ggatgaacac taagtacgat gagaatgaca agctgatccg cgaggtgaag    4080
gtcatcaccc tgaagtcaaa gctcgtctcc gacttcagga aggatttcca gttctacaag    4140
gttcgggaga tcaacaatta ccaccatgcc catgacgcgt acctgaacgc ggtggtcggc    4200
acagctctga tcaagaagta cccaaagctc gagagcgagt tcgtgtacgg ggactacaag    4260
gtttacgatg tgaggaagat gatcgccaag tcggagcagg agattggcaa ggctaccgcc    4320
aagtacttct tctactctaa cattatgaat ttcttcaaga cagagatcac tctggccaat    4380
ggcgagatcc ggaagcgccc cctcatcgag acgaacggcg agacggggga gatcgtgtgg    4440
gacaagggca gggatttcgc gaccgtcagg aaggttctct ccatgccaca agtgaatatc    4500
gtcaagaaga cagaggtcca gactggcggg ttctctaagg agtcaattct gcctaagcgg    4560
aacagcgaca agctcatcgc ccgcaagaag gactgggatc cgaagaagta cggcgggttc    4620
gtcagcccca ctgtggccta ctcggtcctg gttgtggcga aggttgagaa gggcaagtcc    4680
aagaagctca gagcgtgaa  ggagctgctg ggatcacga  ttatggagcg ctccagcttc    4740
gagaagaacc cgatcgattt cctggaggcg aagggctaca aggaggtgaa gaaggacctg    4800
atcattaagc tccccaagta ctcactcttc gagctggaga acggcaggaa gcggatgctg    4860
gcttccgctg gcgagctgca gaagggaac  gagctggctc tgccgtccaa gtatgtgaac    4920
ttcctctacc tggcctccca ctacgagaag ctcaagggca gccccgagga caacgagcag    4980
aagcagctgt tcgtcgagca gcacaagcat tacctgacg  agatcattga gcagatttcc    5040
gagttctcca agcgcgtgat cctggccgac gcgaatctgg ataaggtcct ctccgcgtac    5100
```

| | |
|---|---|
| aacaagcacc gcgacaagcc aatcagggag caggctgaga atatcattca tctcttcacc | 5160 |
| ctgacgaacc tcggcgcccc tgctgctttc aagtacttcg acacaactat cgatcgcaag | 5220 |
| cagtacagaa gcactaagga ggtcctggac gcgaccctca tccaccagtc gattaccggc | 5280 |
| ctctacgaga cgcgcatcga cctgtctcag ctcgggggcg acaagcggcc agcggcgacg | 5340 |
| aagaaggcgg ggcaggcgaa gaagaagaag tag | 5373 |

<210> SEQ ID NO 15
<211> LENGTH: 5373
<212> TYPE: DNA
<213> ORGANISM: Artificial Sequence
<220> FEATURE:
<223> OTHER INFORMATION: Description of Artificial Sequence: Synthetic
      SpnCas9-VRER-ABE-1 polynucleotide

<400> SEQUENCE: 15

| | |
|---|---|
| atgtccgagg tggagttctc tcacgagtat tggatgaggc acgctcttac acttgctaag | 60 |
| agagcttggg acgaaagaga agtgccagtt ggcgccgttc ttgtgcataa taatagggtg | 120 |
| atcggcgagg gttggaatag accaattgga aggcatgatc caacagctca cgcagagatt | 180 |
| atggctctca gacaaggcgg cctcgttatg cagaactaca ggctcattga cgctacactc | 240 |
| tacgtgacac tcgaaccttg cgttatgtgc gccggagcta tgattcattc taggattggc | 300 |
| agggtcgtgt ttggagctag ggacgctaaa acaggagccg ccggatctct tatggacgtg | 360 |
| ttgcatcatc caggcatgaa ccatagggtg gagattacag agggcattct tgcagacgag | 420 |
| tgcgctgctc ttctttccga tttcttcagg atgagaaggc aggagattaa ggcccagaag | 480 |
| aaggctcagt cttctacaga tagcggagga tcttccggag gatctagcgg ctccgagaca | 540 |
| ccaggaacat ccgaaagcgc taccagaa tctagcggag gctcttccgg aggatcttct | 600 |
| gaagtggagt ctcccacga gtattggatg aggcacgctc ttacacttgc taaaagggct | 660 |
| agggacgaaa gggaagttcc agttggagct gttctcgtgc tcaataacag ggtgattggc | 720 |
| gagggttgga atagagccat ggactccat gatccaacag ctcacgcaga gattatggct | 780 |
| cttagacaag gcggcctcgt tatgcagaat tacagactca tcgacgccac actctacgtt | 840 |
| accttcgaac cttgcgttat gtgcgccgga gctatgatcc attctaggat tggcagggtc | 900 |
| gtgttcggcg ttagaaacgc taagacagga gctgcaggct ctcttatgga cgttcttcat | 960 |
| tacccaggca tgaatcatag agtggagatc acagaaggca ttcttgcaga cgagtgcgca | 1020 |
| gctctcctt gctatttctt caggatgccg aggcaagttt tcaacgctca gaagaaggcc | 1080 |
| cagtcttcta cagattccgg cggatcttct ggaggatcta gcggctccga gacaccagga | 1140 |
| acatccgaat ccgctacacc agagtcttct ggaggatcta gcggaggatc tcttaagggc | 1200 |
| atccacgggt gccagctgc tgacaagaag tactcgatcg gcctcgatat tgggactaac | 1260 |
| tctgttggct gggccgtgat caccgacgag tacaaggtgc cctcaaagaa gttcaaggtc | 1320 |
| ctgggcaaca ccgatcggca ttccatcaag aagaatctca ttggcgctct cctgttcgac | 1380 |
| agcggcgaga cggctgaggc tacgcggctc aagcgcaccg cccgcaggcg gtacacgcgc | 1440 |
| aggaagaatc gcatctgcta cctgcaggag attttctcca acgagatggc gaaggttgac | 1500 |
| gattctttct ccacaggct ggaggagtca ttcctcgtgg aggaggataa gaagcacgag | 1560 |
| cggcatccaa tcttcggcaa cattgtcgac gaggttgcct accacgagaa gtaccctacg | 1620 |
| atctaccatc tgcggaagaa gctcgtggac tccacagata ggcggacct ccgcctgatc | 1680 |
| tacctcgctc tggcccacat gattaagttc aggggccatt tcctgatcga gggggatctc | 1740 |

```
aacccggaca atagcgatgt tgacaagctg ttcatccagc tcgtgcagac gtacaaccag    1800
ctcttcgagg agaaccccat taatgcgtca ggcgtcgacg cgaaggctat cctgtccgct    1860
aggctctcga agtctcggcg cctcgagaac ctgatcgccc agctgccggg cgagaagaag    1920
aacggcctgt tcgggaatct cattgcgctc agcctgggc tcacgcccaa cttcaagtcg     1980
aatttcgatc tcgctgagga cgccaagctg cagctctcca aggacacata cgacgatgac    2040
ctggataacc tcctggccca gatcggcgat cagtacgcgg acctgttcct cgctgccaag    2100
aatctgtcgg acgccatcct cctgtctgat attctcaggg tgaacaccga gattacgaag    2160
gctccgctct cagcctccat gatcaagcgc tacgacgagc accatcagga tctgaccctc    2220
ctgaaggcgc tggtcaggca gcagctcccc gagaagtaca aggagatctt cttcgatcag    2280
tcgaagaacg gctacgctgg gtacattgac ggcggggcct ctcaggagga gttctacaag    2340
ttcatcaagc cgattctgga gaagatggac ggcacggagg agctgctggt gaagctcaat    2400
cgcgaggacc tcctgaggaa gcagcggaca ttcgataacg gcagcatccc acaccagatt    2460
catctcgggg agctgcacgc tatcctgagg aggcaggagg acttctaccc tttcctcaag    2520
gataaccgcg agaagatcga gaagattctg actttcagga tcccgtacta cgtcggccca    2580
ctcgctaggg gcaactcccg cttcgcttgg atgacccgca agtcagagga gacgatcacg    2640
ccgtggaact tcgaggaggt ggtcgacaag ggcgctagcg ctcagtcgtt catcgagagg    2700
atgacgaatt tcgacaagaa cctgccaaat gagaaggtgc tccctaagca ctcgctcctg    2760
tacgagtact tcacagtcta caacgagctg actaaggtga agtatgtgac cgagggcatg    2820
aggaagccgc ctttcctgtc tggggagcag aagaaggcca tcgtggacct cctgttcaag    2880
accaaccgga aggtcacggt taagcagctc aaggaggact acttcaagaa gattgagtgc    2940
ttcgattcgg tcgagatctc tggcgttgag gaccgcttca acgcctccct ggggacctac    3000
cacgatctcc tgaagatcat taaggataag gacttcctgg acaacgagga gaatgaggat    3060
atcctcgagg acattgtgct gacactcact ctgttcgagg accgggagat gatcgaggag    3120
cgcctgaaga cttacgccca tctcttcgat gacaaggtca tgaagcagct caagaggagg    3180
aggtacaccg gctgggggag gctgagcagg aagctcatca acggcattcg ggacaagcag    3240
tccgggaaga cgatcctcga cttcctgaag agcgatggct tcgcgaaccg caatttcatg    3300
cagctgattc acgatgacag cctcacattc aaggaggata tccagaaggc tcaggtgagc    3360
ggccaggggg actcgctgca cgagcatatc gcgaacctcg ctggctcgcc agctatcaag    3420 aagggggattc tgcagaccgt gaaggttgtg gacgagctgg tgaaggtcat gggcaggcac    3480
aagcctgaga acatcgtcat tgagatggcc cgggagaatc agaccacgca gaagggccag    3540
aagaactcac gcgagaggat gaagaggatc gaggagggca ttaaggagct gggtgcccag    3600
atcctcaagg agcacccggt ggagaacacg cagctgcaga atgagaagct ctacctgtac    3660
tacctccaga atggccgcga tatgtatgtg gaccaggagc tggatattaa caggctcagc    3720
gattacgacg tcgatcatat cgttccacag tcattcctga aggatgactc cattgacaac    3780
aaggtcctca ccaggtcgga caagaaccgg ggcaagtctg ataatgttcc ttcagaggag    3840
gtcgttaaga agatgaagaa ctactggcgc cagctcctga atgccaagct gatcacgcag    3900
cggaagttcg ataacctcac aaaggctgag aggggcgggc tctctgagct ggacaaggcg    3960
ggcttcatca gaggcagct ggtcgagaca cggcagatca ctaagcacgt tgcgcagatt    4020
ctcgactcac ggatgaacac taagtacgat gagaatgaca agctgatccg cgaggtgaag    4080
gtcatcaccc tgaagtcaaa gctcgtctcc gacttcagga aggatttcca gttctacaag    4140
```

```
gttcgggaga tcaacaatta ccaccatgcc catgacgcgt acctgaacgc ggtggtcggc    4200
acagctctga tcaagaagta cccaaagctc gagagcgagt cgtgtacgg ggactacaag     4260 gtttacgatg tgaggaagat gatcgccaag tcggagcagg agattggcaa ggctaccgcc    4320
aagtacttct tctactctaa cattatgaat ttcttcaaga cagagatcac tctggccaat    4380
ggcgagatcc ggaagcgccc cctcatcgag acgaacggcg agacgggga gatcgtgtgg      4440 gacaagggca gggatttcgc gaccgtcagg aaggttctct ccatgccaca agtgaatatc    4500
gtcaagaaga cagaggtcca gactggcggg ttctctaagg agtcaattct gcctaagcgg    4560
aacagcgaca agctcatcgc ccgcaagaag gactgggatc cgaagaagta cggcgggttc    4620
gtcagcccca ctgtggccta ctcggtcctg gttgtggcga aggttgagaa gggcaagtcc    4680
aagaagctca gagcgtgaa ggagctgctg ggatcacga ttatggagcg ctccagcttc       4740
gagaagaacc cgatcgattt cctggaggcg aagggctaca aggaggtgaa gaaggacctg    4800
atcattaagc tccccaagta ctcactcttc gagctggaga cggcaggaa gcggatgctg      4860 gcttccgctc gcgagctgca gaaggggaac gagctggctc tgccgtccaa gtatgtgaac    4920
ttcctctacc tggcctccca ctacgagaag ctcaagggca gccccgagga caacgagcag    4980
aagcagctgt tcgtcgagca gcacaagcat tacctcgacg agatcattga gcagatttcc    5040
gagttctcca agcgcgtgat cctggccgac gcgaatctgg ataaggtcct ctccgcgtac    5100
aacaagcacc gcgacaagcc aatcagggag caggctgaga atatcattca tctcttcacc    5160
ctgacgaacc tcggcgcccc tgctgctttc aagtacttcg acacaactat cgatcgcaag    5220
gagtacagaa gcactaagga ggtcctggac gcgaccctca tccaccagtc gattaccggc    5280
ctctacgaga cgcgcatcga cctgtctcag ctcggggcg acaagcggcc agcggcgacg      5340
aagaaggcgg ggcaggcgaa gaagaagaag tag                                 5373
```

<210> SEQ ID NO 16
<211> LENGTH: 2427
<212> TYPE: DNA
<213> ORGANISM: Artificial Sequence
<220> FEATURE:
<223> OTHER INFORMATION: Description of Artificial Sequence: Synthetic SanCas9-ABE-1 polynucleotide

<400> SEQUENCE: 16

```
atgtccgagg tggagttctc tcacgagtat tggatgaggc acgctcttac acttgctaag    60
agagcttggg acgaaagaga agtgccagtt ggcgccgttc ttgtgcataa taatagggtg    120
atcggcgagg gttggaatag accaattgga aggcatgatc aacagctcca cgcagagatt    180
atggctctca gacaaggcgg cctcgttatg cagaactaca ggctcattga cgctacactc    240
tacgtgacac tcgaaccttg cgttatgtgc gccggagcta tgattcattc taggattggc    300
agggtcgtgt ttggagctag ggacgctaaa acaggagccg ccggatctct tatgacgtg     360 ttgcatcatc aggcatgaa ccataggtg gagattacag agggcattct gcagacgag       420 tgcgctgctc ttcttttccga tttcttcagg atgagaaggc aggagattaa ggcccagaag    480
aaggctcagt cttctacaga tagcggagga tcttccggag atctagcgg ctccgagaca      540 ccaggaacat ccgaaagcgc tacaccagaa tctagcggag gctcttccgg aggatcttct    600
gaagtggagt ctcccacga gtattggatg aggcacgctc ttacacttgc taaaagggct    660
agggacgaaa gggaagttcc agttggagct gttctcgtgc tcaataacag ggtgattggc    720
gagggttgga atagagccat ggactccat gatccaacag ctcacgcaga gattatggct    780
```

```
cttagacaag gcggcctcgt tatgcagaat tacagactca tcgacgccac actctacgtt    840
accttcgaac cttgcgttat gtgcgccgga gctatgatcc attctaggat tggcagggtc    900
gtgttcggcg ttagaaacgc taagacagga gctgcaggct ctcttatgga cgttcttcat    960
tacccaggca tgaatcatag agtggagatc acagaaggca ttcttgcaga cgagtgcgca   1020
gctctccttt gctatttctt caggatgccg aggcaagttt tcaacgctca gaagaaggcc   1080
cagtcttcta cagattccgg cggatcttct ggaggatcta gcggctccga gacaccagga   1140
acatccgaat ccgctacacc agagtcttct ggaggatcta gcggaggatc tcttaagatg   1200
ccaaaaaaga agagaaaggt tcaggcggc tcctccgagg tggagttctc tcacgagtat   1260
tggatgaggc acgctcttac acttgctaag agagcttggg acgaaagaga agtgccagtt   1320
ggcgccgttc ttgtgcataa taatagggtg atcggcgagg gttggaatag accaattgga   1380
aggcatgatc aacagctca cgcagagatt atggctctca gacaaggcgg cctcgttatg   1440
cagaactaca ggctcattga cgctacactc tacgtgacac tcgaaccttg cgttatgtgc   1500
gccggagcta tgattcattc taggattggc agggtcgtgt ttggagctag ggacgctaaa   1560
acaggagccg ccggatctct tatggacgtg ttgcatcatc caggcatgaa ccataggggtg   1620 gagattacag agggcattct tgcagacgag tgcgctgctc ttcttttccga tttcttcagg   1680 atgaaaggc aggagattaa ggcccagaag aaggctcagt cttctacaga tagcggagga   1740
tcttccggag gatctagcgg ctccgagaca ccaggaacat ccgaaagcgc tacaccagaa   1800
tctagcggag gctcttccgg aggatcttct gaagtggagt tctcccacga gtattggatg   1860
aggcacgctc ttacacttgc taaaagggct agggacgaaa gggaagttcc agttggagct   1920
gttctcgtgc tcaataacag ggtgattggc gagggttgga atagagccat tggactccat   1980
gatccaacag ctcacgcaga gattatggct cttagacaag gcggcctcgt tatgcagaat   2040
tacagactca tcgacgccac actctacgtt accttcgaac cttgcgttat gtgcgccgga   2100
gctatgatcc attctaggat tggcagggtc gtgttcggcg ttagaaacgc taagacagga   2160
gctgcaggct ctcttatgga cgttcttcat tacccaggca tgaatcatag agtggagatc   2220
acagaaggca ttcttgcaga cgagtgcgca gctctccttt gctatttctt caggatgccg   2280
aggcaagttt tcaacgctca gaagaaggcc cagtcttcta cagattccgg cggatcttct   2340
ggaggatcta gcggctccga gacaccagga acatccgaat ccgctacacc agagtcttct   2400
ggaggatcta gcggaggatc tcttaag                                       2427

<210> SEQ ID NO 17
<211> LENGTH: 4398
<212> TYPE: DNA
<213> ORGANISM: Artificial Sequence
<220> FEATURE:
<223> OTHER INFORMATION: Description of Artificial Sequence: Synthetic
      SanCas9-KKH-ABE -1 polynucleotide

<400> SEQUENCE: 17
atgtccgagg tggagttctc tcacgagtat tggatgaggc acgctcttac acttgctaag     60
agagcttggg acgaaagaga agtgccagtt ggcgccgttc ttgtgcataa taatagggtg    120
atcggcgagg gttggaatag accaattgga aggcatgatc aacagctca cgcagagatt    180 atggctctca gacaaggcgg cctcgttatg cagaactaca ggctcattga cgctacactc    240
tacgtgacac tcgaaccttg cgttatgtgc gccggagcta tgattcattc taggattggc    300
agggtcgtgt ttggagctag ggacgctaaa acaggagccg ccggatctct tatggacgtg    360
```

```
ttgcatcatc caggcatgaa ccatagggtg gagattacag agggcattct tgcagacgag      420
tgcgctgctc ttctttccga tttcttcagg atgagaaggc aggagattaa ggcccagaag      480
aaggctcagt cttctacaga tagcggagga tcttccggag gatctagcgg ctccgagaca      540
ccaggaacat ccgaaagcgc tacaccagaa tctagcggag gctcttccgg aggatcttct      600
gaagtggagt ctcccacga gtattggatg aggcacgctc ttacacttgc taaaagggct      660
agggacgaaa gggaagttcc agttggagct gttctcgtgc tcaataacag ggtgattggc      720
gagggttgga atagagccat tggactccat gatccaacag ctcacgcaga gattatggct      780
cttagacaag gcggcctcgt tatgcagaat tacagactca tcgacgccac actctacgtt      840
accttcgaac cttgcgttat gtgcgccgga gctatgatcc attctaggat tggcagggtc      900
gtgttcggcg ttagaaacgc taagacagga gctgcaggct ctcttatgga cgttcttcat      960
tacccaggca tgaatcatag agtggagatc acagaaggca ttcttgcaga cgagtgcgca     1020
gctctccttt gctatttctt caggatgccg aggcaagttt tcaacgctca gaagaaggcc     1080
cagtcttcta cagattccgg cggatcttct ggaggatcta gcggctccga gacaccagga     1140
acatccgaat ccgctacacc agagtcttct ggaggatcta gcggaggatc taagaggaac     1200
tacatcctcg ggctggatat tggcatcacc tctgtgggct acgggatcat tgactacgag     1260
acgcgggatg tcatcgacgc tggcgttcgc ctgttcaagg aggccaacgt cgagaacaat     1320
gaggggagga ggtccaagag gggcgcccgc aggctcaaga ggaggaggag gcacaggatc     1380
cagagggtga agaagctcct gttcgattac aacctcctga ccgaccattc ggagctgtct     1440
gggatcaatc cgtacgaggc ccgcgtcaag ggcctgtctc agaagctctc agaggaggag     1500
ttcagcgctg ccctcctgca cctgctaagc gcaggggcg tccataacgt taatgaggtg     1560
gaggaggaca caggcaacga gctgtcgact aaggagcaga tctcccgcaa ctccaaggcg     1620
ctggaggaga gtatgtggc tgagctgcag ctggagcgcc tcaagaagga tggggaggtc     1680
cggggctcaa tcaaccgctt caagacatcc gactacgtca aggaggccaa gcagctcctg     1740
aaggttcaga aggcgtacca ccagctggac cagtcattca ttgatactta catcgacctc     1800
ctcgagacga ggcggacgta ctacgagggc ccaggggagg gctcccccctt cgggtggaag     1860 gacatcaagg agtggtacga gatgctgatg ggccattgca cgtacttccc ggaggagctg     1920
aggagcgtta agtacgctta caacgccgat ctgtacaacg cgctcaatga cctgaacaat     1980
ctcgtcatca cccgggacga gaacgagaag ctcgagtact acgagaagtt ccagatcatt     2040
gagaatgtgt tcaagcagaa gaagaagcca acgctgaagc agattgcgaa ggagatcctc     2100
gttaacgagg aggacatcaa ggggtacagg gtgacctcga cgggcaagcc tgagttcaca     2160
aacctgaagg tctaccacga tattaaggac atcactgcca ggaaggagat cattgagaac     2220
gccgagctgc tcgaccagat tgcgaagatc ctcacgatct accagtccag cgaggacatc     2280
caggaggagc tgaccaacct caattcggag ctgacgcagg aggagatcga gcagatttct     2340
aacctgaagg ggtacacagg cactcacaac ctcagcctga aggcgatcaa tctcattctg     2400
gatgagctgt ggcatacaaa cgacaatcag attgctatct tcaacaggct caagctggtg     2460
ccaaagaagg tcgacctctc tcagcagaag gagatcccga ccacgctggt ggacgatttc     2520
attctctcac ccgtggtcaa gaggtccttc atccagagca ttaaggtcat caacgccatc     2580
attaagaagt acgcctgcc caatgatatc attatcgagc tggcgcgcga gaagaactcc     2640
aaggacgctc agaagatgat caatgagatg cagaagcgga accgccagac caatgagagg     2700
```

```
atcgaggaga ttatccggac aactggcaag gagaacgcta agtacctgat tgagaagatc   2760
aagctccacg atatgcagga gggcaagtgc ctgtactccc tcgaggccat cccactggag   2820
gacctcctga caatcctttt caactacgag gttgatcata ttatcccgag gtccgtgagc   2880
ttcgacaata gcttcaacaa taaggtcctg gttaagcaag aggagaactc gaagaagggc   2940
aatcgcaccc ccttccagta cctctcgtct tcagacagca agatctcgta cgagacgttc   3000
aagaagcaca ttctcaacct ggcgaagggg aagggcagga tctccaagac caagaaggag   3060
tacctcctgg aggagcggga catcaaccgc ttcagcgtcc agaaggattt cattaaccgg   3120
aatctggttg acacacgcta cgccactcgg ggcctcatga acctcctgcg ctcctacttc   3180
agggtgaaca atctggacgt gaaggtcaag agcatcaacg gcgggttcac gtcgttcctc   3240
cgcaggaagt ggaagttcaa gaaggagagg aacaagggct acaagcacca tgcggaggat   3300
gctctgatta tcgccaatgc ggacttcatc ttcaaggagt ggaagaagct cgacaaggcc   3360
aagaaggtca tggagaacca gatgttcgag gagaagcagg ccgagagcat gccagagatc   3420
gagacagagc aggagtacaa ggagattttc atcactcctc accagattaa gcatatcaag   3480
gatttcaagg actacaagta ctcgcaccgc gtggataaga gccgaacag gaagctgatc   3540 aatgacaccc tctactctac gcgcaaggac gataagggga acacactcat cgtcaacaat   3600
ctgaacggcc tctacgacaa ggataatgac aagctgaaga gctcatcaa caagagccca   3660 gagaagctcc tgatgtacca ccatgatcct cagacttacc agaagctcaa gctgatcatg   3720
gagcagtacg gcgacgagaa gaacccgctc tacaagtact acgaggagac aggcaactac   3780
ctgactaagt actcgaagaa ggataatggg cccgtgatta gaagatcaa gtactacggc   3840 aacaagctga atgcgcatct cgacatcacc gacgattacc gaactctcg caataaggtt   3900 gtgaagctct cactgaagcc ctacaggttc gatgtgtacc tggacaacgg cgtctacaag   3960
ttcgttacgg tgaagaatct cgacgtgatc aagaaggaga actactacga ggtcaattcc   4020
aagtgctacg aggaggccaa gaagctgaag aagatttcca accaggctga gttcatcgcc   4080
agcttctaca gaatgaccct gattaagatc aacggggagc tgtacagggt catcggcgtt   4140
aacaatgatc tcctgaaccg gattgaagtg aatatgattg acatcaccta ccgcgagtac   4200
ctcgagaaca tgaatgataa gcgcccgccc cacattatca gaccattgc ctcgaagacg   4260 cagtctatca agaagtactc aacagacatt ctgggcaacc tctacgaggt caagtccaag   4320
aagcacccgc agattatcaa gaagggcaag cgcccggccg ccactaagaa ggctgggcag   4380
gccaagaaga agaagtag                                                  4398
```

<210> SEQ ID NO 18
<211> LENGTH: 1801
<212> TYPE: PRT
<213> ORGANISM: Artificial Sequence
<220> FEATURE:
<223> OTHER INFORMATION: Description of Artificial Sequence: Synthetic
      SpnCas9-VQR-ABE polypeptide

<400> SEQUENCE: 18

```
Met Pro Lys Lys Lys Arg Lys Val Ser Gly Gly Ser Ser Glu Val Glu
1               5                   10                  15

Phe Ser His Glu Tyr Trp Met Arg His Ala Leu Thr Leu Ala Lys Arg
            20                  25                  30

Ala Trp Asp Glu Arg Glu Val Pro Val Gly Ala Val Leu Val His Asn
        35                  40                  45

Asn Arg Val Ile Gly Glu Gly Trp Asn Arg Pro Ile Gly Arg His Asp
```

-continued

```
                 50                  55                  60
Pro Thr Ala His Ala Glu Ile Met Ala Leu Arg Gln Gly Gly Leu Val
 65                  70                  75                  80

Met Gln Asn Tyr Arg Leu Ile Asp Ala Thr Leu Tyr Val Thr Leu Glu
                     85                  90                  95

Pro Cys Val Met Cys Ala Gly Ala Met Ile His Ser Arg Ile Gly Arg
                100                 105                 110

Val Val Phe Gly Ala Arg Asp Ala Lys Thr Gly Ala Ala Gly Ser Leu
            115                 120                 125

Met Asp Val Leu His His Pro Gly Met Asn His Arg Val Glu Ile Thr
130                 135                 140

Glu Gly Ile Leu Ala Asp Glu Cys Ala Ala Leu Leu Ser Asp Phe Phe
145                 150                 155                 160

Arg Met Arg Arg Gln Glu Ile Lys Ala Gln Lys Lys Ala Gln Ser Ser
                165                 170                 175

Thr Asp Ser Gly Gly Ser Ser Gly Gly Ser Gly Ser Glu Thr Pro
            180                 185                 190

Gly Thr Ser Glu Ser Ala Thr Pro Glu Ser Ser Gly Ser Ser Gly
        195                 200                 205

Gly Ser Ser Glu Val Glu Phe Ser His Glu Tyr Trp Met Arg His Ala
        210                 215                 220

Leu Thr Leu Ala Lys Arg Ala Arg Asp Glu Arg Glu Val Pro Val Gly
225                 230                 235                 240

Ala Val Leu Val Leu Asn Asn Arg Val Ile Gly Glu Gly Trp Asn Arg
                245                 250                 255

Ala Ile Gly Leu His Asp Pro Thr Ala His Ala Glu Ile Met Ala Leu
                260                 265                 270

Arg Gln Gly Gly Leu Val Met Gln Asn Tyr Arg Leu Ile Asp Ala Thr
                275                 280                 285

Leu Tyr Val Thr Phe Glu Pro Cys Val Met Cys Ala Gly Ala Met Ile
                290                 295                 300

His Ser Arg Ile Gly Arg Val Val Phe Gly Val Arg Asn Ala Lys Thr
305                 310                 315                 320

Gly Ala Ala Gly Ser Leu Met Asp Val Leu His Tyr Pro Gly Met Asn
                325                 330                 335

His Arg Val Glu Ile Thr Glu Gly Ile Leu Ala Asp Glu Cys Ala Ala
                340                 345                 350

Leu Leu Cys Tyr Phe Phe Arg Met Pro Arg Gln Val Phe Asn Ala Gln
                355                 360                 365

Lys Lys Ala Gln Ser Ser Thr Asp Ser Gly Gly Ser Ser Gly Gly Ser
                370                 375                 380

Ser Gly Ser Glu Thr Pro Gly Thr Ser Glu Ser Ala Thr Pro Glu Ser
385                 390                 395                 400

Ser Gly Gly Ser Ser Gly Gly Ser Leu Lys Gly Ile His Gly Val Pro
                405                 410                 415

Ala Ala Asp Lys Lys Tyr Ser Ile Gly Leu Asp Ile Gly Thr Asn Ser
                420                 425                 430

Val Gly Trp Ala Val Ile Thr Asp Glu Tyr Lys Val Pro Ser Lys Lys
                435                 440                 445

Phe Lys Val Leu Gly Asn Thr Asp Arg His Ser Ile Lys Lys Asn Leu
                450                 455                 460

Ile Gly Ala Leu Leu Phe Asp Ser Gly Glu Thr Ala Glu Ala Thr Arg
465                 470                 475                 480
```

```
Leu Lys Arg Thr Ala Arg Arg Tyr Thr Arg Arg Lys Asn Arg Ile
            485                 490                 495

Cys Tyr Leu Gln Glu Ile Phe Ser Asn Glu Met Ala Lys Val Asp Asp
                500                 505                 510

Ser Phe Phe His Arg Leu Glu Glu Ser Phe Leu Val Glu Glu Asp Lys
            515                 520                 525

Lys His Glu Arg His Pro Ile Phe Gly Asn Ile Val Asp Glu Val Ala
            530                 535                 540

Tyr His Glu Lys Tyr Pro Thr Ile Tyr His Leu Arg Lys Lys Leu Val
545                 550                 555                 560

Asp Ser Thr Asp Lys Ala Asp Leu Arg Leu Ile Tyr Leu Ala Leu Ala
                565                 570                 575

His Met Ile Lys Phe Arg Gly His Phe Leu Ile Glu Gly Asp Leu Asn
                580                 585                 590

Pro Asp Asn Ser Asp Val Asp Lys Leu Phe Ile Gln Leu Val Gln Thr
                595                 600                 605

Tyr Asn Gln Leu Phe Glu Glu Asn Pro Ile Asn Ala Ser Gly Val Asp
                610                 615                 620

Ala Lys Ala Ile Leu Ser Ala Arg Leu Ser Lys Ser Arg Arg Leu Glu
625                 630                 635                 640

Asn Leu Ile Ala Gln Leu Pro Gly Glu Lys Lys Asn Gly Leu Phe Gly
                645                 650                 655

Asn Leu Ile Ala Leu Ser Leu Gly Leu Thr Pro Asn Phe Lys Ser Asn
                660                 665                 670

Phe Asp Leu Ala Glu Asp Ala Lys Leu Gln Leu Ser Lys Asp Thr Tyr
                675                 680                 685

Asp Asp Asp Leu Asp Asn Leu Leu Ala Gln Ile Gly Asp Gln Tyr Ala
                690                 695                 700

Asp Leu Phe Leu Ala Ala Lys Asn Leu Ser Asp Ala Ile Leu Leu Ser
705                 710                 715                 720

Asp Ile Leu Arg Val Asn Thr Glu Ile Thr Lys Ala Pro Leu Ser Ala
                725                 730                 735

Ser Met Ile Lys Arg Tyr Asp Glu His His Gln Asp Leu Thr Leu Leu
                740                 745                 750

Lys Ala Leu Val Arg Gln Gln Leu Pro Glu Lys Tyr Lys Glu Ile Phe
                755                 760                 765

Phe Asp Gln Ser Lys Asn Gly Tyr Ala Gly Tyr Ile Asp Gly Gly Ala
                770                 775                 780

Ser Gln Glu Glu Phe Tyr Lys Phe Ile Lys Pro Ile Leu Glu Lys Met
785                 790                 795                 800

Asp Gly Thr Glu Glu Leu Leu Val Lys Leu Asn Arg Glu Asp Leu Leu
                805                 810                 815

Arg Lys Gln Arg Thr Phe Asp Asn Gly Ser Ile Pro His Gln Ile His
                820                 825                 830

Leu Gly Glu Leu His Ala Ile Leu Arg Arg Gln Glu Asp Phe Tyr Pro
                835                 840                 845

Phe Leu Lys Asp Asn Arg Glu Lys Ile Glu Lys Ile Leu Thr Phe Arg
                850                 855                 860

Ile Pro Tyr Tyr Val Gly Pro Leu Ala Arg Gly Asn Ser Arg Phe Ala
865                 870                 875                 880

Trp Met Thr Arg Lys Ser Glu Glu Thr Ile Thr Pro Trp Asn Phe Glu
                885                 890                 895
```

```
Glu Val Val Asp Lys Gly Ala Ser Ala Gln Ser Phe Ile Glu Arg Met
            900                 905                 910

Thr Asn Phe Asp Lys Asn Leu Pro Asn Glu Lys Val Leu Pro Lys His
        915                 920                 925

Ser Leu Leu Tyr Glu Tyr Phe Thr Val Tyr Asn Glu Leu Thr Lys Val
        930                 935                 940

Lys Tyr Val Thr Glu Gly Met Arg Lys Pro Ala Phe Leu Ser Gly Glu
945                 950                 955                 960

Gln Lys Lys Ala Ile Val Asp Leu Leu Phe Lys Thr Asn Arg Lys Val
                965                 970                 975

Thr Val Lys Gln Leu Lys Glu Asp Tyr Phe Lys Lys Ile Glu Cys Phe
        980                 985                 990

Asp Ser Val Glu Ile Ser Gly Val Glu Asp Arg Phe Asn Ala Ser Leu
        995                 1000                1005

Gly Thr Tyr His Asp Leu Leu Lys Ile Ile Lys Asp Lys Asp Phe
        1010                1015                1020

Leu Asp Asn Glu Glu Asn Glu Asp Ile Leu Glu Asp Ile Val Leu
        1025                1030                1035

Thr Leu Thr Leu Phe Glu Asp Arg Glu Met Ile Glu Glu Arg Leu
        1040                1045                1050

Lys Thr Tyr Ala His Leu Phe Asp Asp Lys Val Met Lys Gln Leu
        1055                1060                1065

Lys Arg Arg Arg Tyr Thr Gly Trp Gly Arg Leu Ser Arg Lys Leu
        1070                1075                1080

Ile Asn Gly Ile Arg Asp Lys Gln Ser Gly Lys Thr Ile Leu Asp
        1085                1090                1095

Phe Leu Lys Ser Asp Gly Phe Ala Asn Arg Asn Phe Met Gln Leu
        1100                1105                1110

Ile His Asp Asp Ser Leu Thr Phe Lys Glu Asp Ile Gln Lys Ala
        1115                1120                1125

Gln Val Ser Gly Gln Gly Asp Ser Leu His Glu His Ile Ala Asn
        1130                1135                1140

Leu Ala Gly Ser Pro Ala Ile Lys Lys Gly Ile Leu Gln Thr Val
        1145                1150                1155

Lys Val Val Asp Glu Leu Val Lys Val Met Gly Arg His Lys Pro
        1160                1165                1170

Glu Asn Ile Val Ile Glu Met Ala Arg Glu Asn Gln Thr Thr Gln
        1175                1180                1185

Lys Gly Gln Lys Asn Ser Arg Glu Arg Met Lys Arg Ile Glu Glu
        1190                1195                1200

Gly Ile Lys Glu Leu Gly Ser Gln Ile Leu Lys Glu His Pro Val
        1205                1210                1215

Glu Asn Thr Gln Leu Gln Asn Glu Lys Leu Tyr Leu Tyr Tyr Leu
        1220                1225                1230

Gln Asn Gly Arg Asp Met Tyr Val Asp Gln Glu Leu Asp Ile Asn
        1235                1240                1245

Arg Leu Ser Asp Tyr Asp Val Asp His Ile Val Pro Gln Ser Phe
        1250                1255                1260

Leu Lys Asp Asp Ser Ile Asp Asn Lys Val Leu Thr Arg Ser Asp
        1265                1270                1275

Lys Asn Arg Gly Lys Ser Asp Asn Val Pro Ser Glu Glu Val Val
        1280                1285                1290

Lys Lys Met Lys Asn Tyr Trp Arg Gln Leu Leu Asn Ala Lys Leu
```

-continued

```
            1295                1300                1305
Ile Thr Gln Arg Lys Phe Asp Asn Leu Thr Lys Ala Glu Arg Gly
    1310                1315                1320
Gly Leu Ser Glu Leu Asp Lys Ala Gly Phe Ile Lys Arg Gln Leu
    1325                1330                1335
Val Glu Thr Arg Gln Ile Thr Lys His Val Ala Gln Ile Leu Asp
    1340                1345                1350
Ser Arg Met Asn Thr Lys Tyr Asp Glu Asn Asp Lys Leu Ile Arg
    1355                1360                1365
Glu Val Lys Val Ile Thr Leu Lys Ser Lys Leu Val Ser Asp Phe
    1370                1375                1380
Arg Lys Asp Phe Gln Phe Tyr Lys Val Arg Glu Ile Asn Asn Tyr
    1385                1390                1395
His His Ala His Asp Ala Tyr Leu Asn Ala Val Val Gly Thr Ala
    1400                1405                1410
Leu Ile Lys Lys Tyr Pro Lys Leu Glu Ser Glu Phe Val Tyr Gly
    1415                1420                1425
Asp Tyr Lys Val Tyr Asp Val Arg Lys Met Ile Ala Lys Ser Glu
    1430                1435                1440
Gln Glu Ile Gly Lys Ala Thr Ala Lys Tyr Phe Phe Tyr Ser Asn
    1445                1450                1455
Ile Met Asn Phe Phe Lys Thr Glu Ile Thr Leu Ala Asn Gly Glu
    1460                1465                1470
Ile Arg Lys Arg Pro Leu Ile Glu Thr Asn Gly Glu Thr Gly Glu
    1475                1480                1485
Ile Val Trp Asp Lys Gly Arg Asp Phe Ala Thr Val Arg Lys Val
    1490                1495                1500
Leu Ser Met Pro Gln Val Asn Ile Val Lys Lys Thr Glu Val Gln
    1505                1510                1515
Thr Gly Gly Phe Ser Lys Glu Ser Ile Leu Pro Lys Arg Asn Ser
    1520                1525                1530
Asp Lys Leu Ile Ala Arg Lys Lys Asp Trp Asp Pro Lys Lys Tyr
    1535                1540                1545
Gly Gly Phe Val Ser Pro Thr Val Ala Tyr Ser Val Leu Val Val
    1550                1555                1560
Ala Lys Val Glu Lys Gly Lys Ser Lys Lys Leu Lys Ser Val Lys
    1565                1570                1575
Glu Leu Leu Gly Ile Thr Ile Met Glu Arg Ser Ser Phe Glu Lys
    1580                1585                1590
Asn Pro Ile Asp Phe Leu Glu Ala Lys Gly Tyr Lys Glu Val Lys
    1595                1600                1605
Lys Asp Leu Ile Ile Lys Leu Pro Lys Tyr Ser Leu Phe Glu Leu
    1610                1615                1620
Glu Asn Gly Arg Lys Arg Met Leu Ala Ser Ala Gly Glu Leu Gln
    1625                1630                1635
Lys Gly Asn Glu Leu Ala Leu Pro Ser Lys Tyr Val Asn Phe Leu
    1640                1645                1650
Tyr Leu Ala Ser His Tyr Glu Lys Leu Lys Gly Ser Pro Glu Asp
    1655                1660                1665
Asn Glu Gln Lys Gln Leu Phe Val Glu Gln His Lys His Tyr Leu
    1670                1675                1680
Asp Glu Ile Ile Glu Gln Ile Ser Glu Phe Ser Lys Arg Val Ile
    1685                1690                1695
```

-continued

```
Leu Ala Asp Ala Asn Leu Asp Lys Val Leu Ser Ala Tyr Asn Lys
    1700                1705                1710

His Arg Asp Lys Pro Ile Arg Glu Gln Ala Glu Asn Ile Ile His
    1715                1720                1725

Leu Phe Thr Leu Thr Asn Leu Gly Ala Pro Ala Ala Phe Lys Tyr
    1730                1735                1740

Phe Asp Thr Thr Ile Asp Arg Lys Gln Tyr Arg Ser Thr Lys Glu
    1745                1750                1755

Val Leu Asp Ala Thr Leu Ile His Gln Ser Ile Thr Gly Leu Tyr
    1760                1765                1770

Glu Thr Arg Ile Asp Leu Ser Gln Leu Gly Gly Asp Lys Arg Pro
    1775                1780                1785

Ala Ala Thr Lys Lys Ala Gly Gln Ala Lys Lys Lys Lys
    1790                1795                1800

<210> SEQ ID NO 19
<211> LENGTH: 1801
<212> TYPE: PRT
<213> ORGANISM: Artificial Sequence
<220> FEATURE:
<223> OTHER INFORMATION: Description of Artificial Sequence: Synthetic
      SpnCas9-VRER-ABE polypeptide

<400> SEQUENCE: 19

Met Pro Lys Lys Lys Arg Lys Val Ser Gly Gly Ser Glu Val Glu
1               5                   10                  15

Phe Ser His Glu Tyr Trp Met Arg His Ala Leu Thr Leu Ala Lys Arg
            20                  25                  30

Ala Trp Asp Glu Arg Glu Val Pro Val Gly Ala Val Leu Val His Asn
        35                  40                  45

Asn Arg Val Ile Gly Glu Gly Trp Asn Arg Pro Ile Gly Arg His Asp
    50                  55                  60

Pro Thr Ala His Ala Glu Ile Met Ala Leu Arg Gln Gly Gly Leu Val
65                  70                  75                  80

Met Gln Asn Tyr Arg Leu Ile Asp Ala Thr Leu Tyr Val Thr Leu Glu
                85                  90                  95

Pro Cys Val Met Cys Ala Gly Ala Met Ile His Ser Arg Ile Gly Arg
            100                 105                 110

Val Val Phe Gly Ala Arg Asp Ala Lys Thr Gly Ala Ala Gly Ser Leu
        115                 120                 125

Met Asp Val Leu His His Pro Gly Met Asn His Arg Val Glu Ile Thr
    130                 135                 140

Glu Gly Ile Leu Ala Asp Glu Cys Ala Ala Leu Leu Ser Asp Phe Phe
145                 150                 155                 160

Arg Met Arg Arg Gln Glu Ile Lys Ala Gln Lys Lys Ala Gln Ser Ser
                165                 170                 175

Thr Asp Ser Gly Gly Ser Ser Gly Gly Ser Ser Gly Ser Glu Thr Pro
            180                 185                 190

Gly Thr Ser Glu Ser Ala Thr Pro Glu Ser Ser Gly Gly Ser Ser Gly
        195                 200                 205

Gly Ser Ser Glu Val Glu Phe Ser His Glu Tyr Trp Met Arg His Ala
    210                 215                 220

Leu Thr Leu Ala Lys Arg Ala Arg Asp Glu Arg Glu Val Pro Val Gly
225                 230                 235                 240

Ala Val Leu Val Leu Asn Asn Arg Val Ile Gly Glu Gly Trp Asn Arg
```

-continued

```
               245                 250                 255
Ala Ile Gly Leu His Asp Pro Thr Ala His Ala Glu Ile Met Ala Leu
            260                 265                 270
Arg Gln Gly Gly Leu Val Met Gln Asn Tyr Arg Leu Ile Asp Ala Thr
        275                 280                 285
Leu Tyr Val Thr Phe Glu Pro Cys Val Met Cys Ala Gly Ala Met Ile
    290                 295                 300
His Ser Arg Ile Gly Arg Val Val Phe Gly Val Arg Asn Ala Lys Thr
305                 310                 315                 320
Gly Ala Ala Gly Ser Leu Met Asp Val Leu His Tyr Pro Gly Met Asn
                325                 330                 335
His Arg Val Glu Ile Thr Glu Gly Ile Leu Ala Asp Glu Cys Ala Ala
            340                 345                 350
Leu Leu Cys Tyr Phe Phe Arg Met Pro Arg Gln Val Phe Asn Ala Gln
        355                 360                 365
Lys Lys Ala Gln Ser Ser Thr Asp Ser Gly Gly Ser Ser Gly Gly Ser
    370                 375                 380
Ser Gly Ser Glu Thr Pro Gly Thr Ser Glu Ser Ala Thr Pro Glu Ser
385                 390                 395                 400
Ser Gly Gly Ser Ser Gly Gly Ser Leu Lys Gly Ile His Gly Val Pro
                405                 410                 415
Ala Ala Asp Lys Lys Tyr Ser Ile Gly Leu Asp Ile Gly Thr Asn Ser
            420                 425                 430
Val Gly Trp Ala Val Ile Thr Asp Glu Tyr Lys Val Pro Ser Lys Lys
        435                 440                 445
Phe Lys Val Leu Gly Asn Thr Asp Arg His Ser Ile Lys Lys Asn Leu
    450                 455                 460
Ile Gly Ala Leu Leu Phe Asp Ser Gly Glu Thr Ala Glu Ala Thr Arg
465                 470                 475                 480
Leu Lys Arg Thr Ala Arg Arg Arg Tyr Thr Arg Arg Lys Asn Arg Ile
                485                 490                 495
Cys Tyr Leu Gln Glu Ile Phe Ser Asn Glu Met Ala Lys Val Asp Asp
            500                 505                 510
Ser Phe Phe His Arg Leu Glu Glu Ser Phe Leu Val Glu Glu Asp Lys
        515                 520                 525
Lys His Glu Arg His Pro Ile Phe Gly Asn Ile Val Asp Glu Val Ala
    530                 535                 540
Tyr His Glu Lys Tyr Pro Thr Ile Tyr His Leu Arg Lys Lys Leu Val
545                 550                 555                 560
Asp Ser Thr Asp Lys Ala Asp Leu Arg Leu Ile Tyr Leu Ala Leu Ala
                565                 570                 575
His Met Ile Lys Phe Arg Gly His Phe Leu Ile Glu Gly Asp Leu Asn
            580                 585                 590
Pro Asp Asn Ser Asp Val Asp Lys Leu Phe Ile Gln Leu Val Gln Thr
        595                 600                 605
Tyr Asn Gln Leu Phe Glu Glu Asn Pro Ile Asn Ala Ser Gly Val Asp
    610                 615                 620
Ala Lys Ala Ile Leu Ser Ala Arg Leu Ser Lys Ser Arg Arg Leu Glu
625                 630                 635                 640
Asn Leu Ile Ala Gln Leu Pro Gly Glu Lys Lys Asn Gly Leu Phe Gly
                645                 650                 655
Asn Leu Ile Ala Leu Ser Leu Gly Leu Thr Pro Asn Phe Lys Ser Asn
            660                 665                 670
```

```
Phe Asp Leu Ala Glu Asp Ala Lys Leu Gln Leu Ser Lys Asp Thr Tyr
        675                 680                 685

Asp Asp Asp Leu Asp Asn Leu Ala Gln Ile Gly Asp Gln Tyr Ala
    690                 695                 700

Asp Leu Phe Leu Ala Ala Lys Asn Leu Ser Asp Ala Ile Leu Leu Ser
705                 710                 715                 720

Asp Ile Leu Arg Val Asn Thr Glu Ile Thr Lys Ala Pro Leu Ser Ala
            725                 730                 735

Ser Met Ile Lys Arg Tyr Asp Glu His His Gln Asp Leu Thr Leu Leu
        740                 745                 750

Lys Ala Leu Val Arg Gln Leu Pro Glu Lys Tyr Lys Glu Ile Phe
            755                 760                 765

Phe Asp Gln Ser Lys Asn Gly Tyr Ala Gly Tyr Ile Asp Gly Gly Ala
    770                 775                 780

Ser Gln Glu Glu Phe Tyr Lys Phe Ile Lys Pro Ile Leu Glu Lys Met
785                 790                 795                 800

Asp Gly Thr Glu Glu Leu Leu Val Lys Leu Asn Arg Glu Asp Leu Leu
            805                 810                 815

Arg Lys Gln Arg Thr Phe Asp Asn Gly Ser Ile Pro His Gln Ile His
        820                 825                 830

Leu Gly Glu Leu His Ala Ile Leu Arg Arg Gln Glu Asp Phe Tyr Pro
        835                 840                 845

Phe Leu Lys Asp Asn Arg Glu Lys Ile Glu Lys Ile Leu Thr Phe Arg
850                 855                 860

Ile Pro Tyr Tyr Val Gly Pro Leu Ala Arg Gly Asn Ser Arg Phe Ala
865                 870                 875                 880

Trp Met Thr Arg Lys Ser Glu Glu Thr Ile Thr Pro Trp Asn Phe Glu
            885                 890                 895

Glu Val Val Asp Lys Gly Ala Ser Ala Gln Ser Phe Ile Glu Arg Met
            900                 905                 910

Thr Asn Phe Asp Lys Asn Leu Pro Asn Glu Lys Val Leu Pro Lys His
        915                 920                 925

Ser Leu Leu Tyr Glu Tyr Phe Thr Val Tyr Asn Glu Leu Thr Lys Val
    930                 935                 940

Lys Tyr Val Thr Glu Gly Met Arg Lys Pro Ala Phe Leu Ser Gly Glu
945                 950                 955                 960

Gln Lys Lys Ala Ile Val Asp Leu Leu Phe Lys Thr Asn Arg Lys Val
            965                 970                 975

Thr Val Lys Gln Leu Lys Glu Asp Tyr Phe Lys Lys Ile Glu Cys Phe
        980                 985                 990

Asp Ser Val Glu Ile Ser Gly Val Glu Asp Arg Phe Asn Ala Ser Leu
    995                 1000                1005

Gly Thr Tyr His Asp Leu Leu Lys Ile Ile Lys Asp Lys Asp Phe
    1010                1015                1020

Leu Asp Asn Glu Glu Asn Glu Asp Ile Leu Glu Asp Ile Val Leu
    1025                1030                1035

Thr Leu Thr Leu Phe Glu Asp Arg Glu Met Ile Glu Glu Arg Leu
    1040                1045                1050

Lys Thr Tyr Ala His Leu Phe Asp Asp Lys Val Met Lys Gln Leu
    1055                1060                1065

Lys Arg Arg Arg Tyr Thr Gly Trp Gly Arg Leu Ser Arg Lys Leu
    1070                1075                1080
```

```
Ile Asn Gly Ile Arg Asp Lys Gln Ser Gly Lys Thr Ile Leu Asp
1085                1090                1095

Phe Leu Lys Ser Asp Gly Phe Ala Asn Arg Asn Phe Met Gln Leu
1100                1105                1110

Ile His Asp Asp Ser Leu Thr Phe Lys Glu Asp Ile Gln Lys Ala
1115                1120                1125

Gln Val Ser Gly Gln Gly Asp Ser Leu His Glu His Ile Ala Asn
1130                1135                1140

Leu Ala Gly Ser Pro Ala Ile Lys Lys Gly Ile Leu Gln Thr Val
1145                1150                1155

Lys Val Val Asp Glu Leu Val Lys Val Met Gly Arg His Lys Pro
1160                1165                1170

Glu Asn Ile Val Ile Glu Met Ala Arg Glu Asn Gln Thr Thr Gln
1175                1180                1185

Lys Gly Gln Lys Asn Ser Arg Glu Arg Met Lys Arg Ile Glu Glu
1190                1195                1200

Gly Ile Lys Glu Leu Gly Ser Gln Ile Leu Lys Glu His Pro Val
1205                1210                1215

Glu Asn Thr Gln Leu Gln Asn Glu Lys Leu Tyr Leu Tyr Tyr Leu
1220                1225                1230

Gln Asn Gly Arg Asp Met Tyr Val Asp Gln Glu Leu Asp Ile Asn
1235                1240                1245

Arg Leu Ser Asp Tyr Asp Val Asp His Ile Val Pro Gln Ser Phe
1250                1255                1260

Leu Lys Asp Asp Ser Ile Asp Asn Lys Val Leu Thr Arg Ser Asp
1265                1270                1275

Lys Asn Arg Gly Lys Ser Asp Asn Val Pro Ser Glu Glu Val Val
1280                1285                1290

Lys Lys Met Lys Asn Tyr Trp Arg Gln Leu Leu Asn Ala Lys Leu
1295                1300                1305

Ile Thr Gln Arg Lys Phe Asp Asn Leu Thr Lys Ala Glu Arg Gly
1310                1315                1320

Gly Leu Ser Glu Leu Asp Lys Ala Gly Phe Ile Lys Arg Gln Leu
1325                1330                1335

Val Glu Thr Arg Gln Ile Thr Lys His Val Ala Gln Ile Leu Asp
1340                1345                1350

Ser Arg Met Asn Thr Lys Tyr Asp Glu Asn Asp Lys Leu Ile Arg
1355                1360                1365

Glu Val Lys Val Ile Thr Leu Lys Ser Lys Leu Val Ser Asp Phe
1370                1375                1380

Arg Lys Asp Phe Gln Phe Tyr Lys Val Arg Glu Ile Asn Asn Tyr
1385                1390                1395

His His Ala His Asp Ala Tyr Leu Asn Ala Val Val Gly Thr Ala
1400                1405                1410

Leu Ile Lys Lys Tyr Pro Lys Leu Glu Ser Glu Phe Val Tyr Gly
1415                1420                1425

Asp Tyr Lys Val Tyr Asp Val Arg Lys Met Ile Ala Lys Ser Glu
1430                1435                1440

Gln Glu Ile Gly Lys Ala Thr Ala Lys Tyr Phe Phe Tyr Ser Asn
1445                1450                1455

Ile Met Asn Phe Phe Lys Thr Glu Ile Thr Leu Ala Asn Gly Glu
1460                1465                1470

Ile Arg Lys Arg Pro Leu Ile Glu Thr Asn Gly Glu Thr Gly Glu
```

```
            1475                1480                1485

Ile Val Trp Asp Lys Gly Arg Asp Phe Ala Thr Val Arg Lys Val
        1490                1495                1500

Leu Ser Met Pro Gln Val Asn Ile Val Lys Lys Thr Glu Val Gln
        1505                1510                1515

Thr Gly Gly Phe Ser Lys Glu Ser Ile Leu Pro Lys Arg Asn Ser
        1520                1525                1530

Asp Lys Leu Ile Ala Arg Lys Lys Asp Trp Asp Pro Lys Lys Tyr
        1535                1540                1545

Gly Gly Phe Val Ser Pro Thr Val Ala Tyr Ser Val Leu Val Val
        1550                1555                1560

Ala Lys Val Glu Lys Gly Lys Ser Lys Lys Leu Lys Ser Val Lys
        1565                1570                1575

Glu Leu Leu Gly Ile Thr Ile Met Glu Arg Ser Ser Phe Glu Lys
        1580                1585                1590

Asn Pro Ile Asp Phe Leu Glu Ala Lys Gly Tyr Lys Glu Val Lys
        1595                1600                1605

Lys Asp Leu Ile Ile Lys Leu Pro Lys Tyr Ser Leu Phe Glu Leu
        1610                1615                1620

Glu Asn Gly Arg Lys Arg Met Leu Ala Ser Ala Arg Glu Leu Gln
        1625                1630                1635

Lys Gly Asn Glu Leu Ala Leu Pro Ser Lys Tyr Val Asn Phe Leu
        1640                1645                1650

Tyr Leu Ala Ser His Tyr Glu Lys Leu Lys Gly Ser Pro Glu Asp
        1655                1660                1665

Asn Glu Gln Lys Gln Leu Phe Val Glu Gln His Lys His Tyr Leu
        1670                1675                1680

Asp Glu Ile Ile Glu Gln Ile Ser Glu Phe Ser Lys Arg Val Ile
        1685                1690                1695

Leu Ala Asp Ala Asn Leu Asp Lys Val Leu Ser Ala Tyr Asn Lys
        1700                1705                1710

His Arg Asp Lys Pro Ile Arg Glu Gln Ala Glu Asn Ile Ile His
        1715                1720                1725

Leu Phe Thr Leu Thr Asn Leu Gly Ala Pro Ala Ala Phe Lys Tyr
        1730                1735                1740

Phe Asp Thr Thr Ile Asp Arg Lys Glu Tyr Arg Ser Thr Lys Glu
        1745                1750                1755

Val Leu Asp Ala Thr Leu Ile His Gln Ser Ile Thr Gly Leu Tyr
        1760                1765                1770

Glu Thr Arg Ile Asp Leu Ser Gln Leu Gly Gly Asp Lys Arg Pro
        1775                1780                1785

Ala Ala Thr Lys Lys Ala Gly Gln Ala Lys Lys Lys Lys
        1790                1795                1800

<210> SEQ ID NO 20
<211> LENGTH: 1478
<212> TYPE: PRT
<213> ORGANISM: Artificial Sequence
<220> FEATURE:
<223> OTHER INFORMATION: Description of Artificial Sequence: Synthetic
      SanCas9-ABE polypeptide

<400> SEQUENCE: 20

Met Pro Lys Lys Lys Arg Lys Val Ser Gly Gly Ser Ser Glu Val Glu
1               5                   10                  15
```

-continued

```
Phe Ser His Glu Tyr Trp Met Arg His Ala Leu Thr Leu Ala Lys Arg
            20                  25                  30

Ala Trp Asp Glu Arg Glu Val Pro Val Gly Ala Val Leu Val His Asn
        35                  40                  45

Asn Arg Val Ile Gly Glu Gly Trp Asn Arg Pro Ile Gly Arg His Asp
    50                  55                  60

Pro Thr Ala His Ala Glu Ile Met Ala Leu Arg Gln Gly Gly Leu Val
65                  70                  75                  80

Met Gln Asn Tyr Arg Leu Ile Asp Ala Thr Leu Tyr Val Thr Leu Glu
                85                  90                  95

Pro Cys Val Met Cys Ala Gly Ala Met Ile His Ser Arg Ile Gly Arg
            100                 105                 110

Val Val Phe Gly Ala Arg Asp Ala Lys Thr Gly Ala Ala Gly Ser Leu
        115                 120                 125

Met Asp Val Leu His His Pro Gly Met Asn His Arg Val Glu Ile Thr
    130                 135                 140

Glu Gly Ile Leu Ala Asp Glu Cys Ala Ala Leu Leu Ser Asp Phe Phe
145                 150                 155                 160

Arg Met Arg Arg Gln Glu Ile Lys Ala Gln Lys Lys Ala Gln Ser Ser
                165                 170                 175

Thr Asp Ser Gly Gly Ser Ser Gly Gly Ser Gly Ser Glu Thr Pro
            180                 185                 190

Gly Thr Ser Glu Ser Ala Thr Pro Glu Ser Ser Gly Ser Ser Gly
        195                 200                 205

Gly Ser Ser Glu Val Glu Phe Ser His Glu Tyr Trp Met Arg His Ala
    210                 215                 220

Leu Thr Leu Ala Lys Arg Ala Arg Asp Glu Arg Glu Val Pro Val Gly
225                 230                 235                 240

Ala Val Leu Val Leu Asn Asn Arg Val Ile Gly Glu Gly Trp Asn Arg
                245                 250                 255

Ala Ile Gly Leu His Asp Pro Thr Ala His Ala Glu Ile Met Ala Leu
            260                 265                 270

Arg Gln Gly Gly Leu Val Met Gln Asn Tyr Arg Leu Ile Asp Ala Thr
        275                 280                 285

Leu Tyr Val Thr Phe Glu Pro Cys Val Met Cys Ala Gly Ala Met Ile
    290                 295                 300

His Ser Arg Ile Gly Arg Val Val Phe Gly Val Arg Asn Ala Lys Thr
305                 310                 315                 320

Gly Ala Ala Gly Ser Leu Met Asp Val Leu His Tyr Pro Gly Met Asn
                325                 330                 335

His Arg Val Glu Ile Thr Glu Gly Ile Leu Ala Asp Glu Cys Ala Ala
            340                 345                 350

Leu Leu Cys Tyr Phe Phe Arg Met Pro Arg Gln Val Phe Asn Ala Gln
        355                 360                 365

Lys Lys Ala Gln Ser Ser Thr Asp Ser Gly Gly Ser Ser Gly Gly Ser
    370                 375                 380

Ser Gly Ser Glu Thr Pro Gly Thr Ser Glu Ser Ala Thr Pro Glu Ser
385                 390                 395                 400

Ser Gly Gly Ser Ser Gly Gly Ser Leu Lys Lys Arg Asn Tyr Ile Leu
                405                 410                 415

Gly Leu Asp Ile Gly Ile Thr Ser Val Gly Tyr Gly Ile Ile Asp Tyr
            420                 425                 430

Glu Thr Arg Asp Val Ile Asp Ala Gly Val Arg Leu Phe Lys Glu Ala
```

```
                435                 440                 445
Asn Val Glu Asn Asn Glu Gly Arg Arg Ser Lys Arg Gly Ala Arg Arg
450                 455                 460

Leu Lys Arg Arg Arg His Arg Ile Gln Arg Val Lys Lys Leu Leu
465                 470                 475                 480

Phe Asp Tyr Asn Leu Leu Thr Asp His Ser Glu Leu Ser Gly Ile Asn
                485                 490                 495

Pro Tyr Glu Ala Arg Val Lys Gly Leu Ser Gln Lys Leu Ser Glu Glu
                500                 505                 510

Glu Phe Ser Ala Ala Leu Leu His Leu Ala Lys Arg Arg Gly Val His
                515                 520                 525

Asn Val Asn Glu Val Glu Glu Asp Thr Gly Asn Glu Leu Ser Thr Lys
530                 535                 540

Glu Gln Ile Ser Arg Asn Ser Lys Ala Leu Glu Lys Tyr Val Ala
545                 550                 555                 560

Glu Leu Gln Leu Glu Arg Leu Lys Lys Asp Gly Glu Val Arg Gly Ser
                565                 570                 575

Ile Asn Arg Phe Lys Thr Ser Asp Tyr Val Lys Glu Ala Lys Gln Leu
                580                 585                 590

Leu Lys Val Gln Lys Ala Tyr His Gln Leu Asp Gln Ser Phe Ile Asp
                595                 600                 605

Thr Tyr Ile Asp Leu Leu Glu Thr Arg Arg Thr Tyr Tyr Glu Gly Pro
610                 615                 620

Gly Glu Gly Ser Pro Phe Gly Trp Lys Asp Ile Lys Glu Trp Tyr Glu
625                 630                 635                 640

Met Leu Met Gly His Cys Thr Tyr Phe Pro Glu Glu Leu Arg Ser Val
                645                 650                 655

Lys Tyr Ala Tyr Asn Ala Asp Leu Tyr Asn Ala Leu Asn Asp Leu Asn
                660                 665                 670

Asn Leu Val Ile Thr Arg Asp Glu Asn Glu Lys Leu Glu Tyr Tyr Glu
                675                 680                 685

Lys Phe Gln Ile Ile Glu Asn Val Phe Lys Gln Lys Lys Pro Thr
                690                 695                 700

Leu Lys Gln Ile Ala Lys Glu Ile Leu Val Asn Glu Glu Asp Ile Lys
705                 710                 715                 720

Gly Tyr Arg Val Thr Ser Thr Gly Lys Pro Glu Phe Thr Asn Leu Lys
                725                 730                 735

Val Tyr His Asp Ile Lys Asp Ile Thr Ala Arg Lys Glu Ile Ile Glu
                740                 745                 750

Asn Ala Glu Leu Leu Asp Gln Ile Ala Lys Ile Leu Thr Ile Tyr Gln
                755                 760                 765

Ser Ser Glu Asp Ile Gln Glu Glu Leu Thr Asn Leu Asn Ser Glu Leu
                770                 775                 780

Thr Gln Glu Glu Ile Glu Gln Ile Ser Asn Leu Lys Gly Tyr Thr Gly
785                 790                 795                 800

Thr His Asn Leu Ser Leu Lys Ala Ile Asn Leu Ile Leu Asp Glu Leu
                805                 810                 815

Trp His Thr Asn Asp Asn Gln Ile Ala Ile Phe Asn Arg Leu Lys Leu
                820                 825                 830

Val Pro Lys Lys Val Asp Leu Ser Gln Gln Lys Glu Ile Pro Thr Thr
                835                 840                 845

Leu Val Asp Asp Phe Ile Leu Ser Pro Val Val Lys Arg Ser Phe Ile
850                 855                 860
```

Gln Ser Ile Lys Val Ile Asn Ala Ile Ile Lys Lys Tyr Gly Leu Pro
865                 870                 875                 880

Asn Asp Ile Ile Ile Glu Leu Ala Arg Glu Lys Asn Ser Lys Asp Ala
            885                 890                 895

Gln Lys Met Ile Asn Glu Met Gln Lys Arg Asn Arg Gln Thr Asn Glu
        900                 905                 910

Arg Ile Glu Glu Ile Ile Arg Thr Thr Gly Lys Glu Asn Ala Lys Tyr
    915                 920                 925

Leu Ile Glu Lys Ile Lys Leu His Asp Met Gln Glu Gly Lys Cys Leu
930                 935                 940

Tyr Ser Leu Glu Ala Ile Pro Leu Glu Asp Leu Asn Asn Pro Phe
945                 950                 955                 960

Asn Tyr Glu Val Asp His Ile Ile Pro Arg Ser Val Ser Phe Asp Asn
            965                 970                 975

Ser Phe Asn Asn Lys Val Leu Val Lys Gln Glu Glu Asn Ser Lys Lys
        980                 985                 990

Gly Asn Arg Thr Pro Phe Gln Tyr Leu Ser Ser Ser Asp Ser Lys Ile
    995                 1000                1005

Ser Tyr Glu Thr Phe Lys Lys His Ile Leu Asn Leu Ala Lys Gly
1010                1015                1020

Lys Gly Arg Ile Ser Lys Thr Lys Lys Glu Tyr Leu Leu Glu Glu
1025                1030                1035

Arg Asp Ile Asn Arg Phe Ser Val Gln Lys Asp Phe Ile Asn Arg
1040                1045                1050

Asn Leu Val Asp Thr Arg Tyr Ala Thr Arg Gly Leu Met Asn Leu
1055                1060                1065

Leu Arg Ser Tyr Phe Arg Val Asn Asn Leu Asp Val Lys Val Lys
1070                1075                1080

Ser Ile Asn Gly Gly Phe Thr Ser Phe Leu Arg Arg Lys Trp Lys
1085                1090                1095

Phe Lys Lys Glu Arg Asn Lys Gly Tyr Lys His His Ala Glu Asp
1100                1105                1110

Ala Leu Ile Ile Ala Asn Ala Asp Phe Ile Phe Lys Glu Trp Lys
1115                1120                1125

Lys Leu Asp Lys Ala Lys Lys Val Met Glu Asn Gln Met Phe Glu
1130                1135                1140

Glu Lys Gln Ala Glu Ser Met Pro Glu Ile Glu Thr Glu Gln Glu
1145                1150                1155

Tyr Lys Glu Ile Phe Ile Thr Pro His Gln Ile Lys His Ile Lys
1160                1165                1170

Asp Phe Lys Asp Tyr Lys Tyr Ser His Arg Val Asp Lys Lys Pro
1175                1180                1185

Asn Arg Glu Leu Ile Asn Asp Thr Leu Tyr Ser Thr Arg Lys Asp
1190                1195                1200

Asp Lys Gly Asn Thr Leu Ile Val Asn Asn Leu Asn Gly Leu Tyr
1205                1210                1215

Asp Lys Asp Asn Asp Lys Leu Lys Lys Leu Ile Asn Lys Ser Pro
1220                1225                1230

Glu Lys Leu Leu Met Tyr His His Asp Pro Gln Thr Tyr Gln Lys
1235                1240                1245

Leu Lys Leu Ile Met Glu Gln Tyr Gly Asp Glu Lys Asn Pro Leu
1250                1255                1260

-continued

```
Tyr Lys Tyr Tyr Glu Glu Thr Gly Asn Tyr Leu Thr Lys Tyr Ser
    1265                1270                1275

Lys Lys Asp Asn Gly Pro Val Ile Lys Lys Ile Lys Tyr Tyr Gly
    1280                1285                1290

Asn Lys Leu Asn Ala His Leu Asp Ile Thr Asp Tyr Pro Asn
    1295                1300                1305

Ser Arg Asn Lys Val Val Lys Leu Ser Leu Lys Pro Tyr Arg Phe
    1310                1315                1320

Asp Val Tyr Leu Asp Asn Gly Val Tyr Lys Phe Val Thr Val Lys
    1325                1330                1335

Asn Leu Asp Val Ile Lys Lys Glu Asn Tyr Tyr Glu Val Asn Ser
    1340                1345                1350

Lys Cys Tyr Glu Glu Ala Lys Lys Leu Lys Lys Ile Ser Asn Gln
    1355                1360                1365

Ala Glu Phe Ile Ala Ser Phe Tyr Asn Asn Asp Leu Ile Lys Ile
    1370                1375                1380

Asn Gly Glu Leu Tyr Arg Val Ile Gly Val Asn Asn Asp Leu Leu
    1385                1390                1395

Asn Arg Ile Glu Val Asn Met Ile Asp Ile Thr Tyr Arg Glu Tyr
    1400                1405                1410

Leu Glu Asn Met Asn Asp Lys Arg Pro Pro Arg Ile Ile Lys Thr
    1415                1420                1425

Ile Ala Ser Lys Thr Gln Ser Ile Lys Lys Tyr Ser Thr Asp Ile
    1430                1435                1440

Leu Gly Asn Leu Tyr Glu Val Lys Ser Lys Lys His Pro Gln Ile
    1445                1450                1455

Ile Lys Lys Gly Lys Arg Pro Ala Ala Thr Lys Lys Ala Gly Gln
    1460                1465                1470

Ala Lys Lys Lys Lys
    1475

<210> SEQ ID NO 21
<211> LENGTH: 1476
<212> TYPE: PRT
<213> ORGANISM: Artificial Sequence
<220> FEATURE:
<223> OTHER INFORMATION: Description of Artificial Sequence: Synthetic
      SanCas9-KKH-ABE polypeptide

<400> SEQUENCE: 21

Met Pro Lys Lys Lys Arg Lys Val Ser Gly Gly Ser Ser Glu Val Glu
1               5                   10                  15

Phe Ser His Glu Tyr Trp Met Arg His Ala Leu Thr Leu Ala Lys Arg
                20                  25                  30

Ala Trp Asp Glu Arg Glu Val Pro Val Gly Ala Val Leu Val His Asn
            35                  40                  45

Asn Arg Val Ile Gly Glu Gly Trp Asn Arg Pro Ile Gly Arg His Asp
        50                  55                  60

Pro Thr Ala His Ala Glu Ile Met Ala Leu Arg Gln Gly Gly Leu Val
65                  70                  75                  80

Met Gln Asn Tyr Arg Leu Ile Asp Ala Thr Leu Tyr Val Thr Leu Glu
                85                  90                  95

Pro Cys Val Met Cys Ala Gly Ala Met Ile His Ser Arg Ile Gly Arg
                100                 105                 110

Val Val Phe Gly Ala Arg Asp Ala Lys Thr Gly Ala Ala Gly Ser Leu
            115                 120                 125
```

```
Met Asp Val Leu His His Pro Gly Met Asn His Arg Val Glu Ile Thr
    130                 135                 140
Glu Gly Ile Leu Ala Asp Glu Cys Ala Ala Leu Leu Ser Asp Phe Phe
145                 150                 155                 160
Arg Met Arg Arg Gln Glu Ile Lys Ala Gln Lys Lys Ala Gln Ser Ser
                165                 170                 175
Thr Asp Ser Gly Gly Ser Ser Gly Ser Ser Gly Ser Glu Thr Pro
                180                 185                 190
Gly Thr Ser Glu Ser Ala Thr Pro Glu Ser Ser Gly Gly Ser Ser Gly
                195                 200                 205
Gly Ser Ser Glu Val Glu Phe Ser His Glu Tyr Trp Met Arg His Ala
    210                 215                 220
Leu Thr Leu Ala Lys Arg Ala Arg Asp Glu Arg Glu Val Pro Val Gly
225                 230                 235                 240
Ala Val Leu Val Leu Asn Asn Arg Val Ile Gly Glu Gly Trp Asn Arg
                245                 250                 255
Ala Ile Gly Leu His Asp Pro Thr Ala His Ala Glu Ile Met Ala Leu
                260                 265                 270
Arg Gln Gly Gly Leu Val Met Gln Asn Tyr Arg Leu Ile Asp Ala Thr
            275                 280                 285
Leu Tyr Val Thr Phe Glu Pro Cys Val Met Cys Ala Gly Ala Met Ile
    290                 295                 300
His Ser Arg Ile Gly Arg Val Val Phe Gly Val Arg Asn Ala Lys Thr
305                 310                 315                 320
Gly Ala Ala Gly Ser Leu Met Asp Val Leu His Tyr Pro Gly Met Asn
                325                 330                 335
His Arg Val Glu Ile Thr Glu Gly Ile Leu Ala Asp Glu Cys Ala Ala
                340                 345                 350
Leu Leu Cys Tyr Phe Phe Arg Met Pro Arg Gln Val Phe Asn Ala Gln
            355                 360                 365
Lys Lys Ala Gln Ser Ser Thr Asp Ser Gly Gly Ser Ser Gly Gly Ser
    370                 375                 380
Ser Gly Ser Glu Thr Pro Gly Thr Ser Glu Ser Ala Thr Pro Glu Ser
385                 390                 395                 400
Ser Gly Gly Ser Ser Gly Gly Ser Lys Arg Asn Tyr Ile Leu Gly Leu
                405                 410                 415
Asp Ile Gly Ile Thr Ser Val Gly Tyr Gly Ile Ile Asp Tyr Glu Thr
                420                 425                 430
Arg Asp Val Ile Asp Ala Gly Val Arg Leu Phe Lys Glu Ala Asn Val
            435                 440                 445
Glu Asn Asn Glu Gly Arg Arg Ser Lys Arg Gly Ala Arg Arg Leu Lys
    450                 455                 460
Arg Arg Arg Arg His Arg Ile Gln Arg Val Lys Lys Leu Leu Phe Asp
465                 470                 475                 480
Tyr Asn Leu Leu Thr Asp His Ser Glu Leu Ser Gly Ile Asn Pro Tyr
                485                 490                 495
Glu Ala Arg Val Lys Gly Leu Ser Gln Lys Leu Ser Glu Glu Glu Phe
                500                 505                 510
Ser Ala Ala Leu Leu His Leu Ala Lys Arg Arg Gly Val His Asn Val
            515                 520                 525
Asn Glu Val Glu Glu Asp Thr Gly Asn Glu Leu Ser Thr Lys Glu Gln
    530                 535                 540
```

-continued

```
Ile Ser Arg Asn Ser Lys Ala Leu Glu Glu Lys Tyr Val Ala Glu Leu
545                 550                 555                 560

Gln Leu Glu Arg Leu Lys Lys Asp Gly Glu Val Arg Gly Ser Ile Asn
                565                 570                 575

Arg Phe Lys Thr Ser Asp Tyr Val Lys Glu Ala Lys Gln Leu Leu Lys
            580                 585                 590

Val Gln Lys Ala Tyr His Gln Leu Asp Gln Ser Phe Ile Asp Thr Tyr
        595                 600                 605

Ile Asp Leu Leu Glu Thr Arg Arg Thr Tyr Tyr Glu Gly Pro Gly Glu
    610                 615                 620

Gly Ser Pro Phe Gly Trp Lys Asp Ile Lys Glu Trp Tyr Glu Met Leu
625                 630                 635                 640

Met Gly His Cys Thr Tyr Phe Pro Glu Glu Leu Arg Ser Val Lys Tyr
                645                 650                 655

Ala Tyr Asn Ala Asp Leu Tyr Asn Ala Leu Asn Asp Leu Asn Asn Leu
                660                 665                 670

Val Ile Thr Arg Asp Glu Asn Glu Lys Leu Glu Tyr Tyr Glu Lys Phe
            675                 680                 685

Gln Ile Ile Glu Asn Val Phe Lys Gln Lys Lys Pro Thr Leu Lys
        690                 695                 700

Gln Ile Ala Lys Glu Ile Leu Val Asn Glu Glu Asp Ile Lys Gly Tyr
705                 710                 715                 720

Arg Val Thr Ser Thr Gly Lys Pro Glu Phe Thr Asn Leu Lys Val Tyr
                725                 730                 735

His Asp Ile Lys Asp Ile Thr Ala Arg Lys Glu Ile Ile Glu Asn Ala
                740                 745                 750

Glu Leu Leu Asp Gln Ile Ala Lys Ile Leu Thr Ile Tyr Gln Ser Ser
            755                 760                 765

Glu Asp Ile Gln Glu Glu Leu Thr Asn Leu Asn Ser Glu Leu Thr Gln
        770                 775                 780

Glu Glu Ile Glu Gln Ile Ser Asn Leu Lys Gly Tyr Thr Gly Thr His
785                 790                 795                 800

Asn Leu Ser Leu Lys Ala Ile Asn Leu Ile Leu Asp Glu Leu Trp His
                805                 810                 815

Thr Asn Asp Asn Gln Ile Ala Ile Phe Asn Arg Leu Lys Leu Val Pro
            820                 825                 830

Lys Lys Val Asp Leu Ser Gln Gln Lys Glu Ile Pro Thr Thr Leu Val
        835                 840                 845

Asp Asp Phe Ile Leu Ser Pro Val Val Lys Arg Ser Phe Ile Gln Ser
850                 855                 860

Ile Lys Val Ile Asn Ala Ile Ile Lys Lys Tyr Gly Leu Pro Asn Asp
865                 870                 875                 880

Ile Ile Ile Glu Leu Ala Arg Glu Lys Asn Ser Lys Asp Ala Gln Lys
                885                 890                 895

Met Ile Asn Glu Met Gln Lys Arg Asn Arg Gln Thr Asn Glu Arg Ile
            900                 905                 910

Glu Glu Ile Ile Arg Thr Thr Gly Lys Glu Asn Ala Lys Tyr Leu Ile
        915                 920                 925

Glu Lys Ile Lys Leu His Asp Met Gln Glu Gly Lys Cys Leu Tyr Ser
    930                 935                 940

Leu Glu Ala Ile Pro Leu Glu Asp Leu Leu Asn Asn Pro Phe Asn Tyr
945                 950                 955                 960

Glu Val Asp His Ile Ile Pro Arg Ser Val Ser Phe Asp Asn Ser Phe
```

-continued

```
                965                 970                 975
Asn Asn Lys Val Leu Val Lys Gln Glu Glu Asn Ser Lys Lys Gly Asn
            980                 985                 990
Arg Thr Pro Phe Gln Tyr Leu Ser Ser Ser Asp Ser Lys Ile Ser Tyr
            995                1000                1005
Glu Thr Phe Lys Lys His Ile Leu Asn Leu Ala Lys Gly Lys Gly
           1010                1015                1020
Arg Ile Ser Lys Thr Lys Lys Glu Tyr Leu Leu Glu Glu Arg Asp
           1025                1030                1035
Ile Asn Arg Phe Ser Val Gln Lys Asp Phe Ile Asn Arg Asn Leu
           1040                1045                1050
Val Asp Thr Arg Tyr Ala Thr Arg Gly Leu Met Asn Leu Leu Arg
           1055                1060                1065
Ser Tyr Phe Arg Val Asn Asn Leu Asp Val Lys Val Lys Ser Ile
           1070                1075                1080
Asn Gly Gly Phe Thr Ser Phe Leu Arg Arg Lys Trp Lys Phe Lys
           1085                1090                1095
Lys Glu Arg Asn Lys Gly Tyr Lys His His Ala Glu Asp Ala Leu
           1100                1105                1110
Ile Ile Ala Asn Ala Asp Phe Ile Phe Lys Glu Trp Lys Lys Leu
           1115                1120                1125
Asp Lys Ala Lys Lys Val Met Glu Asn Gln Met Phe Glu Glu Lys
           1130                1135                1140
Gln Ala Glu Ser Met Pro Glu Ile Glu Thr Glu Gln Glu Tyr Lys
           1145                1150                1155
Glu Ile Phe Ile Thr Pro His Gln Ile Lys His Ile Lys Asp Phe
           1160                1165                1170
Lys Asp Tyr Lys Tyr Ser His Arg Val Asp Lys Lys Pro Asn Arg
           1175                1180                1185
Lys Leu Ile Asn Asp Thr Leu Tyr Ser Thr Arg Lys Asp Asp Lys
           1190                1195                1200
Gly Asn Thr Leu Ile Val Asn Asn Leu Asn Gly Leu Tyr Asp Lys
           1205                1210                1215
Asp Asn Asp Lys Leu Lys Lys Leu Ile Asn Lys Ser Pro Glu Lys
           1220                1225                1230
Leu Leu Met Tyr His His Asp Pro Gln Thr Tyr Gln Lys Leu Lys
           1235                1240                1245
Leu Ile Met Glu Gln Tyr Gly Asp Glu Lys Asn Pro Leu Tyr Lys
           1250                1255                1260
Tyr Tyr Glu Glu Thr Gly Asn Tyr Leu Thr Lys Tyr Ser Lys Lys
           1265                1270                1275
Asp Asn Gly Pro Val Ile Lys Lys Ile Lys Tyr Tyr Gly Asn Lys
           1280                1285                1290
Leu Asn Ala His Leu Asp Ile Thr Asp Asp Tyr Pro Asn Ser Arg
           1295                1300                1305
Asn Lys Val Val Lys Leu Ser Leu Lys Pro Tyr Arg Phe Asp Val
           1310                1315                1320
Tyr Leu Asp Asn Gly Val Tyr Lys Phe Val Thr Val Lys Asn Leu
           1325                1330                1335
Asp Val Ile Lys Lys Glu Asn Tyr Tyr Glu Val Asn Ser Lys Cys
           1340                1345                1350
Tyr Glu Glu Ala Lys Lys Leu Lys Lys Ile Ser Asn Gln Ala Glu
           1355                1360                1365
```

```
Phe Ile Ala Ser Phe Tyr Lys Asn Asp Leu Ile Lys Ile Asn Gly
        1370                1375                1380

Glu Leu Tyr Arg Val Ile Gly Val Asn Asn Asp Leu Leu Asn Arg
        1385                1390                1395

Ile Glu Val Asn Met Ile Asp Ile Thr Tyr Arg Glu Tyr Leu Glu
        1400                1405                1410

Asn Met Asn Asp Lys Arg Pro Pro His Ile Ile Lys Thr Ile Ala
        1415                1420                1425

Ser Lys Thr Gln Ser Ile Lys Lys Tyr Ser Thr Asp Ile Leu Gly
        1430                1435                1440

Asn Leu Tyr Glu Val Lys Ser Lys Lys His Pro Gln Ile Ile Lys
        1445                1450                1455

Lys Gly Lys Arg Pro Ala Ala Thr Lys Lys Ala Gly Gln Ala Lys
        1460                1465                1470

Lys Lys Lys
        1475

<210> SEQ ID NO 22
<211> LENGTH: 1790
<212> TYPE: PRT
<213> ORGANISM: Artificial Sequence
<220> FEATURE:
<223> OTHER INFORMATION: Description of Artificial Sequence: Synthetic
      SpnCas9-VQR-ABE-1 polypeptide

<400> SEQUENCE: 22

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
        195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
```

```
                225                 230                 235                 240

Glu Gly Trp Asn Arg Ala Ile Gly Leu His Asp Pro Thr Ala His Ala
                        245                 250                 255

Glu Ile Met Ala Leu Arg Gln Gly Gly Leu Val Met Gln Asn Tyr Arg
                        260                 265                 270

Leu Ile Asp Ala Thr Leu Tyr Val Thr Phe Glu Pro Cys Val Met Cys
                        275                 280                 285

Ala Gly Ala Met Ile His Ser Arg Ile Gly Arg Val Val Phe Gly Val
                        290                 295                 300

Arg Asn Ala Lys Thr Gly Ala Ala Gly Ser Leu Met Asp Val Leu His
        305                 310                 315                 320

Tyr Pro Gly Met Asn His Arg Val Glu Ile Thr Glu Gly Ile Leu Ala
                        325                 330                 335

Asp Glu Cys Ala Ala Leu Leu Cys Tyr Phe Phe Arg Met Pro Arg Gln
                        340                 345                 350

Val Phe Asn Ala Gln Lys Lys Ala Gln Ser Ser Thr Asp Ser Gly Gly
                        355                 360                 365

Ser Ser Gly Gly Ser Gly Ser Glu Thr Pro Gly Thr Ser Glu Ser
                        370                 375                 380

Ala Thr Pro Glu Ser Ser Gly Gly Ser Ser Gly Gly Ser Leu Lys Gly
        385                 390                 395                 400

Ile His Gly Val Pro Ala Ala Asp Lys Lys Tyr Ser Ile Gly Leu Asp
                        405                 410                 415

Ile Gly Thr Asn Ser Val Gly Trp Ala Val Ile Thr Asp Glu Tyr Lys
                        420                 425                 430

Val Pro Ser Lys Lys Phe Lys Val Leu Gly Asn Thr Asp Arg His Ser
                        435                 440                 445

Ile Lys Lys Asn Leu Ile Gly Ala Leu Leu Phe Asp Ser Gly Glu Thr
                        450                 455                 460

Ala Glu Ala Thr Arg Leu Lys Arg Thr Ala Arg Arg Arg Tyr Thr Arg
        465                 470                 475                 480

Arg Lys Asn Arg Ile Cys Tyr Leu Gln Glu Ile Phe Ser Asn Glu Met
                        485                 490                 495

Ala Lys Val Asp Asp Ser Phe Phe His Arg Leu Glu Glu Ser Phe Leu
                        500                 505                 510

Val Glu Glu Asp Lys Lys His Glu Arg His Pro Ile Phe Gly Asn Ile
                        515                 520                 525

Val Asp Glu Val Ala Tyr His Glu Lys Tyr Pro Thr Ile Tyr His Leu
                        530                 535                 540

Arg Lys Lys Leu Val Asp Ser Thr Asp Lys Ala Asp Leu Arg Leu Ile
        545                 550                 555                 560

Tyr Leu Ala Leu Ala His Met Ile Lys Phe Arg Gly His Phe Leu Ile
                        565                 570                 575

Glu Gly Asp Leu Asn Pro Asp Asn Ser Asp Val Asp Lys Leu Phe Ile
                        580                 585                 590

Gln Leu Val Gln Thr Tyr Asn Gln Leu Phe Glu Glu Asn Pro Ile Asn
                        595                 600                 605

Ala Ser Gly Val Asp Ala Lys Ala Ile Leu Ser Ala Arg Leu Ser Lys
                        610                 615                 620

Ser Arg Arg Leu Glu Asn Leu Ile Ala Gln Leu Pro Gly Glu Lys Lys
        625                 630                 635                 640

Asn Gly Leu Phe Gly Asn Leu Ile Ala Leu Ser Leu Gly Leu Thr Pro
                        645                 650                 655
```

```
Asn Phe Lys Ser Asn Phe Asp Leu Ala Glu Asp Ala Lys Leu Gln Leu
            660                 665                 670

Ser Lys Asp Thr Tyr Asp Asp Leu Asp Asn Leu Leu Ala Gln Ile
    675                 680                 685

Gly Asp Gln Tyr Ala Asp Leu Phe Leu Ala Ala Lys Asn Leu Ser Asp
690                 695                 700

Ala Ile Leu Leu Ser Asp Ile Leu Arg Val Asn Thr Glu Ile Thr Lys
705                 710                 715                 720

Ala Pro Leu Ser Ala Ser Met Ile Lys Arg Tyr Asp Glu His His Gln
                725                 730                 735

Asp Leu Thr Leu Leu Lys Ala Leu Val Arg Gln Gln Leu Pro Glu Lys
            740                 745                 750

Tyr Lys Glu Ile Phe Phe Asp Gln Ser Lys Asn Gly Tyr Ala Gly Tyr
        755                 760                 765

Ile Asp Gly Gly Ala Ser Gln Glu Glu Phe Tyr Lys Phe Ile Lys Pro
    770                 775                 780

Ile Leu Glu Lys Met Asp Gly Thr Glu Glu Leu Leu Val Lys Leu Asn
785                 790                 795                 800

Arg Glu Asp Leu Leu Arg Lys Gln Arg Thr Phe Asp Asn Gly Ser Ile
                805                 810                 815

Pro His Gln Ile His Leu Gly Glu Leu His Ala Ile Leu Arg Arg Gln
            820                 825                 830

Glu Asp Phe Tyr Pro Phe Leu Lys Asp Asn Arg Glu Lys Ile Glu Lys
        835                 840                 845

Ile Leu Thr Phe Arg Ile Pro Tyr Tyr Val Gly Pro Leu Ala Arg Gly
    850                 855                 860

Asn Ser Arg Phe Ala Trp Met Thr Arg Lys Ser Glu Glu Thr Ile Thr
865                 870                 875                 880

Pro Trp Asn Phe Glu Glu Val Val Asp Lys Gly Ala Ser Ala Gln Ser
                885                 890                 895

Phe Ile Glu Arg Met Thr Asn Phe Asp Lys Asn Leu Pro Asn Glu Lys
            900                 905                 910

Val Leu Pro Lys His Ser Leu Leu Tyr Glu Tyr Phe Thr Val Tyr Asn
        915                 920                 925

Glu Leu Thr Lys Val Lys Tyr Val Thr Glu Gly Met Arg Lys Pro Ala
    930                 935                 940

Phe Leu Ser Gly Glu Gln Lys Lys Ala Ile Val Asp Leu Leu Phe Lys
945                 950                 955                 960

Thr Asn Arg Lys Val Thr Val Lys Gln Leu Lys Glu Asp Tyr Phe Lys
                965                 970                 975

Lys Ile Glu Cys Phe Asp Ser Val Glu Ile Ser Gly Val Glu Asp Arg
            980                 985                 990

Phe Asn Ala Ser Leu Gly Thr Tyr His Asp Leu Leu Lys Ile Ile Lys
        995                 1000                1005

Asp Lys Asp Phe Leu Asp Asn Glu Glu Asn Glu Asp Ile Leu Glu
    1010                1015                1020

Asp Ile Val Leu Thr Leu Thr Leu Phe Glu Asp Arg Glu Met Ile
    1025                1030                1035

Glu Glu Arg Leu Lys Thr Tyr Ala His Leu Phe Asp Asp Lys Val
    1040                1045                1050

Met Lys Gln Leu Lys Arg Arg Arg Tyr Thr Gly Trp Gly Arg Leu
    1055                1060                1065
```

```
Ser Arg Lys Leu Ile Asn Gly Ile Arg Asp Lys Gln Ser Gly Lys
    1070            1075            1080

Thr Ile Leu Asp Phe Leu Lys Ser Asp Gly Phe Ala Asn Arg Asn
    1085            1090            1095

Phe Met Gln Leu Ile His Asp Asp Ser Leu Thr Phe Lys Glu Asp
    1100            1105            1110

Ile Gln Lys Ala Gln Val Ser Gly Gln Gly Asp Ser Leu His Glu
    1115            1120            1125

His Ile Ala Asn Leu Ala Gly Ser Pro Ala Ile Lys Lys Gly Ile
    1130            1135            1140

Leu Gln Thr Val Lys Val Val Asp Glu Leu Val Lys Val Met Gly
    1145            1150            1155

Arg His Lys Pro Glu Asn Ile Val Ile Glu Met Ala Arg Glu Asn
    1160            1165            1170

Gln Thr Thr Gln Lys Gly Gln Lys Asn Ser Arg Glu Arg Met Lys
    1175            1180            1185

Arg Ile Glu Glu Gly Ile Lys Glu Leu Gly Ser Gln Ile Leu Lys
    1190            1195            1200

Glu His Pro Val Glu Asn Thr Gln Leu Gln Asn Glu Lys Leu Tyr
    1205            1210            1215

Leu Tyr Tyr Leu Gln Asn Gly Arg Asp Met Tyr Val Asp Gln Glu
    1220            1225            1230

Leu Asp Ile Asn Arg Leu Ser Asp Tyr Asp Val Asp His Ile Val
    1235            1240            1245

Pro Gln Ser Phe Leu Lys Asp Asp Ser Ile Asp Asn Lys Val Leu
    1250            1255            1260

Thr Arg Ser Asp Lys Asn Arg Gly Lys Ser Asp Asn Val Pro Ser
    1265            1270            1275

Glu Glu Val Val Lys Lys Met Lys Asn Tyr Trp Arg Gln Leu Leu
    1280            1285            1290

Asn Ala Lys Leu Ile Thr Gln Arg Lys Phe Asp Asn Leu Thr Lys
    1295            1300            1305

Ala Glu Arg Gly Gly Leu Ser Glu Leu Asp Lys Ala Gly Phe Ile
    1310            1315            1320

Lys Arg Gln Leu Val Glu Thr Arg Gln Ile Thr Lys His Val Ala
    1325            1330            1335

Gln Ile Leu Asp Ser Arg Met Asn Thr Lys Tyr Asp Glu Asn Asp
    1340            1345            1350

Lys Leu Ile Arg Glu Val Lys Val Ile Thr Leu Lys Ser Lys Leu
    1355            1360            1365

Val Ser Asp Phe Arg Lys Asp Phe Gln Phe Tyr Lys Val Arg Glu
    1370            1375            1380

Ile Asn Asn Tyr His His Ala His Asp Ala Tyr Leu Asn Ala Val
    1385            1390            1395

Val Gly Thr Ala Leu Ile Lys Lys Tyr Pro Lys Leu Glu Ser Glu
    1400            1405            1410

Phe Val Tyr Gly Asp Tyr Lys Val Tyr Asp Val Arg Lys Met Ile
    1415            1420            1425

Ala Lys Ser Glu Gln Glu Ile Gly Lys Ala Thr Ala Lys Tyr Phe
    1430            1435            1440

Phe Tyr Ser Asn Ile Met Asn Phe Phe Lys Thr Glu Ile Thr Leu
    1445            1450            1455

Ala Asn Gly Glu Ile Arg Lys Arg Pro Leu Ile Glu Thr Asn Gly
```

```
            1460                1465                1470

Glu Thr Gly Glu Ile Val Trp Asp Lys Gly Arg Asp Phe Ala Thr
    1475                1480                1485

Val Arg Lys Val Leu Ser Met Pro Gln Val Asn Ile Val Lys Lys
    1490                1495                1500

Thr Glu Val Gln Thr Gly Gly Phe Ser Lys Glu Ser Ile Leu Pro
    1505                1510                1515

Lys Arg Asn Ser Asp Lys Leu Ile Ala Arg Lys Lys Asp Trp Asp
    1520                1525                1530

Pro Lys Lys Tyr Gly Gly Phe Val Ser Pro Thr Val Ala Tyr Ser
    1535                1540                1545

Val Leu Val Val Ala Lys Val Glu Lys Gly Lys Ser Lys Lys Leu
    1550                1555                1560

Lys Ser Val Lys Glu Leu Leu Gly Ile Thr Ile Met Glu Arg Ser
    1565                1570                1575

Ser Phe Glu Lys Asn Pro Ile Asp Phe Leu Glu Ala Lys Gly Tyr
    1580                1585                1590

Lys Glu Val Lys Lys Asp Leu Ile Ile Lys Leu Pro Lys Tyr Ser
    1595                1600                1605

Leu Phe Glu Leu Glu Asn Gly Arg Lys Arg Met Leu Ala Ser Ala
    1610                1615                1620

Gly Glu Leu Gln Lys Gly Asn Glu Leu Ala Leu Pro Ser Lys Tyr
    1625                1630                1635

Val Asn Phe Leu Tyr Leu Ala Ser His Tyr Glu Lys Leu Lys Gly
    1640                1645                1650

Ser Pro Glu Asp Asn Glu Gln Lys Gln Leu Phe Val Glu Gln His
    1655                1660                1665

Lys His Tyr Leu Asp Glu Ile Ile Glu Gln Ile Ser Glu Phe Ser
    1670                1675                1680

Lys Arg Val Ile Leu Ala Asp Ala Asn Leu Asp Lys Val Leu Ser
    1685                1690                1695

Ala Tyr Asn Lys His Arg Asp Lys Pro Ile Arg Glu Gln Ala Glu
    1700                1705                1710

Asn Ile Ile His Leu Phe Thr Leu Thr Asn Leu Gly Ala Pro Ala
    1715                1720                1725

Ala Phe Lys Tyr Phe Asp Thr Thr Ile Asp Arg Lys Gln Tyr Arg
    1730                1735                1740

Ser Thr Lys Glu Val Leu Asp Ala Thr Leu Ile His Gln Ser Ile
    1745                1750                1755

Thr Gly Leu Tyr Glu Thr Arg Ile Asp Leu Ser Gln Leu Gly Gly
    1760                1765                1770

Asp Lys Arg Pro Ala Ala Thr Lys Lys Ala Gly Gln Ala Lys Lys
    1775                1780                1785

Lys Lys
    1790

<210> SEQ ID NO 23
<211> LENGTH: 1790
<212> TYPE: PRT
<213> ORGANISM: Artificial Sequence
<220> FEATURE:
<223> OTHER INFORMATION: Description of Artificial Sequence: Synthetic
      SpnCas9-VRER-ABE-1 polypeptide

<400> SEQUENCE: 23
```

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
50                      55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
                100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
                195                 200                 205

Trp Met Arg His Ala Leu Thr Leu Ala Lys Arg Ala Arg Asp Glu Arg
210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
            290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ser Gly Gly
            355                 360                 365

Ser Ser Gly Gly Ser Ser Gly Ser Glu Thr Pro Gly Thr Ser Glu Ser
    370                 375                 380

Ala Thr Pro Glu Ser Ser Gly Gly Ser Ser Gly Gly Ser Leu Lys Gly
385                 390                 395                 400

Ile His Gly Val Pro Ala Ala Asp Lys Lys Tyr Ser Ile Gly Leu Asp
                405                 410                 415

Ile Gly Thr Asn Ser Val Gly Trp Ala Val Ile Thr Asp Glu Tyr Lys
```

```
                420             425             430
Val Pro Ser Lys Lys Phe Lys Val Leu Gly Asn Thr Asp Arg His Ser
            435             440             445

Ile Lys Lys Asn Leu Ile Gly Ala Leu Leu Phe Asp Ser Gly Glu Thr
            450             455             460

Ala Glu Ala Thr Arg Leu Lys Arg Thr Ala Arg Arg Arg Tyr Thr Arg
465             470             475             480

Arg Lys Asn Arg Ile Cys Tyr Leu Gln Glu Ile Phe Ser Asn Glu Met
            485             490             495

Ala Lys Val Asp Asp Ser Phe Phe His Arg Leu Glu Glu Ser Phe Leu
            500             505             510

Val Glu Glu Asp Lys Lys His Glu Arg His Pro Ile Phe Gly Asn Ile
            515             520             525

Val Asp Glu Val Ala Tyr His Glu Lys Tyr Pro Thr Ile Tyr His Leu
            530             535             540

Arg Lys Lys Leu Val Asp Ser Thr Asp Lys Ala Asp Leu Arg Leu Ile
545             550             555             560

Tyr Leu Ala Leu Ala His Met Ile Lys Phe Arg Gly His Phe Leu Ile
            565             570             575

Glu Gly Asp Leu Asn Pro Asp Asn Ser Asp Val Asp Lys Leu Phe Ile
            580             585             590

Gln Leu Val Gln Thr Tyr Asn Gln Leu Phe Glu Glu Asn Pro Ile Asn
            595             600             605

Ala Ser Gly Val Asp Ala Lys Ala Ile Leu Ser Ala Arg Leu Ser Lys
            610             615             620

Ser Arg Arg Leu Glu Asn Leu Ile Ala Gln Leu Pro Gly Glu Lys Lys
625             630             635             640

Asn Gly Leu Phe Gly Asn Leu Ile Ala Leu Ser Leu Gly Leu Thr Pro
            645             650             655

Asn Phe Lys Ser Asn Phe Asp Leu Ala Glu Asp Ala Lys Leu Gln Leu
            660             665             670

Ser Lys Asp Thr Tyr Asp Asp Asp Leu Asp Asn Leu Leu Ala Gln Ile
            675             680             685

Gly Asp Gln Tyr Ala Asp Leu Phe Leu Ala Ala Lys Asn Leu Ser Asp
            690             695             700

Ala Ile Leu Leu Ser Asp Ile Leu Arg Val Asn Thr Glu Ile Thr Lys
705             710             715             720

Ala Pro Leu Ser Ala Ser Met Ile Lys Arg Tyr Asp Glu His His Gln
            725             730             735

Asp Leu Thr Leu Leu Lys Ala Leu Val Arg Gln Gln Leu Pro Glu Lys
            740             745             750

Tyr Lys Glu Ile Phe Phe Asp Gln Ser Lys Asn Gly Tyr Ala Gly Tyr
            755             760             765

Ile Asp Gly Gly Ala Ser Gln Glu Glu Phe Tyr Lys Phe Ile Lys Pro
            770             775             780

Ile Leu Glu Lys Met Asp Gly Thr Glu Glu Leu Leu Val Lys Leu Asn
785             790             795             800

Arg Glu Asp Leu Leu Arg Lys Gln Arg Thr Phe Asp Asn Gly Ser Ile
            805             810             815

Pro His Gln Ile His Leu Gly Glu Leu His Ala Ile Leu Arg Arg Gln
            820             825             830

Glu Asp Phe Tyr Pro Phe Leu Lys Asp Asn Arg Glu Lys Ile Glu Lys
            835             840             845
```

-continued

```
Ile Leu Thr Phe Arg Ile Pro Tyr Tyr Val Gly Pro Leu Ala Arg Gly
    850                 855                 860

Asn Ser Arg Phe Ala Trp Met Thr Arg Lys Ser Glu Glu Thr Ile Thr
865                 870                 875                 880

Pro Trp Asn Phe Glu Glu Val Val Asp Lys Gly Ala Ser Ala Gln Ser
                885                 890                 895

Phe Ile Glu Arg Met Thr Asn Phe Asp Lys Asn Leu Pro Asn Glu Lys
                900                 905                 910

Val Leu Pro Lys His Ser Leu Leu Tyr Glu Tyr Phe Thr Val Tyr Asn
            915                 920                 925

Glu Leu Thr Lys Val Lys Tyr Val Thr Glu Gly Met Arg Lys Pro Ala
        930                 935                 940

Phe Leu Ser Gly Glu Gln Lys Lys Ala Ile Val Asp Leu Leu Phe Lys
945                 950                 955                 960

Thr Asn Arg Lys Val Thr Val Lys Gln Leu Lys Glu Asp Tyr Phe Lys
                965                 970                 975

Lys Ile Glu Cys Phe Asp Ser Val Glu Ile Ser Gly Val Glu Asp Arg
                980                 985                 990

Phe Asn Ala Ser Leu Gly Thr Tyr His Asp Leu Leu Lys Ile Ile Lys
            995                1000                1005

Asp Lys Asp Phe Leu Asp Asn Glu Glu Asn Glu Asp Ile Leu Glu
    1010                1015                1020

Asp Ile Val Leu Thr Leu Thr Leu Phe Glu Asp Arg Glu Met Ile
    1025                1030                1035

Glu Glu Arg Leu Lys Thr Tyr Ala His Leu Phe Asp Asp Lys Val
    1040                1045                1050

Met Lys Gln Leu Lys Arg Arg Arg Tyr Thr Gly Trp Gly Arg Leu
    1055                1060                1065

Ser Arg Lys Leu Ile Asn Gly Ile Arg Asp Lys Gln Ser Gly Lys
    1070                1075                1080

Thr Ile Leu Asp Phe Leu Lys Ser Asp Gly Phe Ala Asn Arg Asn
    1085                1090                1095

Phe Met Gln Leu Ile His Asp Asp Ser Leu Thr Phe Lys Glu Asp
    1100                1105                1110

Ile Gln Lys Ala Gln Val Ser Gly Gln Gly Asp Ser Leu His Glu
    1115                1120                1125

His Ile Ala Asn Leu Ala Gly Ser Pro Ala Ile Lys Lys Gly Ile
    1130                1135                1140

Leu Gln Thr Val Lys Val Val Asp Glu Leu Val Lys Val Met Gly
    1145                1150                1155

Arg His Lys Pro Glu Asn Ile Val Ile Glu Met Ala Arg Glu Asn
    1160                1165                1170

Gln Thr Thr Gln Lys Gly Gln Lys Asn Ser Arg Glu Arg Met Lys
    1175                1180                1185

Arg Ile Glu Glu Gly Ile Lys Glu Leu Gly Ser Gln Ile Leu Lys
    1190                1195                1200

Glu His Pro Val Glu Asn Thr Gln Leu Gln Asn Glu Lys Leu Tyr
    1205                1210                1215

Leu Tyr Tyr Leu Gln Asn Gly Arg Asp Met Tyr Val Asp Gln Glu
    1220                1225                1230

Leu Asp Ile Asn Arg Leu Ser Asp Tyr Asp Val Asp His Ile Val
    1235                1240                1245
```

-continued

| | | | | | | | | | | | | | | |
|---|---|---|---|---|---|---|---|---|---|---|---|---|---|---|
| Pro | Gln | Ser | Phe | Leu | Lys | Asp | Asp | Ser | Ile | Asp | Asn | Lys | Val | Leu |
| 1250 | | | | | 1255 | | | | 1260 | | | | | |
| Thr | Arg | Ser | Asp | Lys | Asn | Arg | Gly | Lys | Ser | Asp | Asn | Val | Pro | Ser |
| 1265 | | | | | 1270 | | | | 1275 | | | | | |
| Glu | Glu | Val | Val | Lys | Lys | Met | Lys | Asn | Tyr | Trp | Arg | Gln | Leu | Leu |
| 1280 | | | | | 1285 | | | | 1290 | | | | | |
| Asn | Ala | Lys | Leu | Ile | Thr | Gln | Arg | Lys | Phe | Asp | Asn | Leu | Thr | Lys |
| 1295 | | | | | 1300 | | | | 1305 | | | | | |
| Ala | Glu | Arg | Gly | Gly | Leu | Ser | Glu | Leu | Asp | Lys | Ala | Gly | Phe | Ile |
| 1310 | | | | | 1315 | | | | 1320 | | | | | |
| Lys | Arg | Gln | Leu | Val | Glu | Thr | Arg | Gln | Ile | Thr | Lys | His | Val | Ala |
| 1325 | | | | | 1330 | | | | 1335 | | | | | |
| Gln | Ile | Leu | Asp | Ser | Arg | Met | Asn | Thr | Lys | Tyr | Asp | Glu | Asn | Asp |
| 1340 | | | | | 1345 | | | | 1350 | | | | | |
| Lys | Leu | Ile | Arg | Glu | Val | Lys | Val | Ile | Thr | Leu | Lys | Ser | Lys | Leu |
| 1355 | | | | | 1360 | | | | 1365 | | | | | |
| Val | Ser | Asp | Phe | Arg | Lys | Asp | Phe | Gln | Phe | Tyr | Lys | Val | Arg | Glu |
| 1370 | | | | | 1375 | | | | 1380 | | | | | |
| Ile | Asn | Asn | Tyr | His | His | Ala | His | Asp | Ala | Tyr | Leu | Asn | Ala | Val |
| 1385 | | | | | 1390 | | | | 1395 | | | | | |
| Val | Gly | Thr | Ala | Leu | Ile | Lys | Lys | Tyr | Pro | Lys | Leu | Glu | Ser | Glu |
| 1400 | | | | | 1405 | | | | 1410 | | | | | |
| Phe | Val | Tyr | Gly | Asp | Tyr | Lys | Val | Tyr | Asp | Val | Arg | Lys | Met | Ile |
| 1415 | | | | | 1420 | | | | 1425 | | | | | |
| Ala | Lys | Ser | Glu | Gln | Glu | Ile | Gly | Lys | Ala | Thr | Ala | Lys | Tyr | Phe |
| 1430 | | | | | 1435 | | | | 1440 | | | | | |
| Phe | Tyr | Ser | Asn | Ile | Met | Asn | Phe | Phe | Lys | Thr | Glu | Ile | Thr | Leu |
| 1445 | | | | | 1450 | | | | 1455 | | | | | |
| Ala | Asn | Gly | Glu | Ile | Arg | Lys | Arg | Pro | Leu | Ile | Glu | Thr | Asn | Gly |
| 1460 | | | | | 1465 | | | | 1470 | | | | | |
| Glu | Thr | Gly | Glu | Ile | Val | Trp | Asp | Lys | Gly | Arg | Asp | Phe | Ala | Thr |
| 1475 | | | | | 1480 | | | | 1485 | | | | | |
| Val | Arg | Lys | Val | Leu | Ser | Met | Pro | Gln | Val | Asn | Ile | Val | Lys | Lys |
| 1490 | | | | | 1495 | | | | 1500 | | | | | |
| Thr | Glu | Val | Gln | Thr | Gly | Gly | Phe | Ser | Lys | Glu | Ser | Ile | Leu | Pro |
| 1505 | | | | | 1510 | | | | 1515 | | | | | |
| Lys | Arg | Asn | Ser | Asp | Lys | Leu | Ile | Ala | Arg | Lys | Lys | Asp | Trp | Asp |
| 1520 | | | | | 1525 | | | | 1530 | | | | | |
| Pro | Lys | Lys | Tyr | Gly | Gly | Phe | Val | Ser | Pro | Thr | Val | Ala | Tyr | Ser |
| 1535 | | | | | 1540 | | | | 1545 | | | | | |
| Val | Leu | Val | Val | Ala | Lys | Val | Glu | Lys | Gly | Lys | Ser | Lys | Lys | Leu |
| 1550 | | | | | 1555 | | | | 1560 | | | | | |
| Lys | Ser | Val | Lys | Glu | Leu | Leu | Gly | Ile | Thr | Ile | Met | Glu | Arg | Ser |
| 1565 | | | | | 1570 | | | | 1575 | | | | | |
| Ser | Phe | Glu | Lys | Asn | Pro | Ile | Asp | Phe | Leu | Glu | Ala | Lys | Gly | Tyr |
| 1580 | | | | | 1585 | | | | 1590 | | | | | |
| Lys | Glu | Val | Lys | Lys | Asp | Leu | Ile | Ile | Lys | Leu | Pro | Lys | Tyr | Ser |
| 1595 | | | | | 1600 | | | | 1605 | | | | | |
| Leu | Phe | Glu | Leu | Glu | Asn | Gly | Arg | Lys | Arg | Met | Leu | Ala | Ser | Ala |
| 1610 | | | | | 1615 | | | | 1620 | | | | | |
| Arg | Glu | Leu | Gln | Lys | Gly | Asn | Glu | Leu | Ala | Leu | Pro | Ser | Lys | Tyr |
| 1625 | | | | | 1630 | | | | 1635 | | | | | |
| Val | Asn | Phe | Leu | Tyr | Leu | Ala | Ser | His | Tyr | Glu | Lys | Leu | Lys | Gly |

1640                1645                1650

Ser Pro Glu Asp Asn Glu Gln Lys Gln Leu Phe Val Glu Gln His
    1655                1660                1665

Lys His Tyr Leu Asp Glu Ile Ile Glu Gln Ile Ser Glu Phe Ser
    1670                1675                1680

Lys Arg Val Ile Leu Ala Asp Ala Asn Leu Asp Lys Val Leu Ser
    1685                1690                1695

Ala Tyr Asn Lys His Arg Asp Lys Pro Ile Arg Glu Gln Ala Glu
    1700                1705                1710

Asn Ile Ile His Leu Phe Thr Leu Thr Asn Leu Gly Ala Pro Ala
    1715                1720                1725

Ala Phe Lys Tyr Phe Asp Thr Thr Ile Asp Arg Lys Glu Tyr Arg
    1730                1735                1740

Ser Thr Lys Glu Val Leu Asp Ala Thr Leu Ile His Gln Ser Ile
    1745                1750                1755

Thr Gly Leu Tyr Glu Thr Arg Ile Asp Leu Ser Gln Leu Gly Gly
    1760                1765                1770

Asp Lys Arg Pro Ala Ala Thr Lys Lys Ala Gly Gln Ala Lys Lys
    1775                1780                1785

Lys Lys
    1790

<210> SEQ ID NO 24
<211> LENGTH: 809
<212> TYPE: PRT
<213> ORGANISM: Artificial Sequence
<220> FEATURE:
<223> OTHER INFORMATION: Description of Artificial Sequence: Synthetic
      SanCas9-ABE-1 polypeptide

<400> SEQUENCE: 24

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

-continued

Gly Gly Ser Ser Gly Gly Ser Ser Glu Val Glu Phe Ser His Glu Tyr
        195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Leu Val Met Gln Asn Tyr Arg
                260                 265                 270

Leu Ile Asp Ala Thr Leu Tyr Val Thr Phe Glu Pro Cys Val Met Cys
        275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
                340                 345                 350

Val Phe Asn Ala Gln Lys Lys Ala Gln Ser Ser Thr Asp Ser Gly Gly
        355                 360                 365

Ser Ser Gly Gly Ser Ser Gly Ser Glu Thr Pro Gly Thr Ser Glu Ser
    370                 375                 380

Ala Thr Pro Glu Ser Ser Gly Gly Ser Ser Gly Gly Ser Leu Lys Met
385                 390                 395                 400

Pro Lys Lys Lys Arg Lys Val Ser Gly Gly Ser Ser Glu Val Glu Phe
            405                 410                 415

Ser His Glu Tyr Trp Met Arg His Ala Leu Thr Leu Ala Lys Arg Ala
                420                 425                 430

Trp Asp Glu Arg Glu Val Pro Val Gly Ala Val Leu Val His Asn Asn
        435                 440                 445

Arg Val Ile Gly Glu Gly Trp Asn Arg Pro Ile Gly Arg His Asp Pro
450                 455                 460

Thr Ala His Ala Glu Ile Met Ala Leu Arg Gln Gly Gly Leu Val Met
465                 470                 475                 480

Gln Asn Tyr Arg Leu Ile Asp Ala Thr Leu Tyr Val Thr Leu Glu Pro
            485                 490                 495

Cys Val Met Cys Ala Gly Ala Met Ile His Ser Arg Ile Gly Arg Val
                500                 505                 510

Val Phe Gly Ala Arg Asp Ala Lys Thr Gly Ala Ala Gly Ser Leu Met
        515                 520                 525

Asp Val Leu His His Pro Gly Met Asn His Arg Val Glu Ile Thr Glu
530                 535                 540

Gly Ile Leu Ala Asp Glu Cys Ala Ala Leu Leu Ser Asp Phe Phe Arg
545                 550                 555                 560

Met Arg Arg Gln Glu Ile Lys Ala Gln Lys Lys Ala Gln Ser Ser Thr
            565                 570                 575

Asp Ser Gly Gly Ser Ser Gly Gly Ser Ser Gly Ser Glu Thr Pro Gly
                580                 585                 590

Thr Ser Glu Ser Ala Thr Pro Glu Ser Ser Gly Gly Ser Ser Gly Gly
        595                 600                 605

Ser Ser Glu Val Glu Phe Ser His Glu Tyr Trp Met Arg His Ala Leu

```
                610                 615                 620
Thr Leu Ala Lys Arg Ala Arg Asp Glu Arg Glu Val Pro Val Gly Ala
625                 630                 635                 640

Val Leu Val Leu Asn Asn Arg Val Ile Gly Glu Gly Trp Asn Arg Ala
                645                 650                 655

Ile Gly Leu His Asp Pro Thr Ala His Ala Glu Ile Met Ala Leu Arg
            660                 665                 670

Gln Gly Gly Leu Val Met Gln Asn Tyr Arg Leu Ile Asp Ala Thr Leu
            675                 680                 685

Tyr Val Thr Phe Glu Pro Cys Val Met Cys Ala Gly Ala Met Ile His
690                 695                 700

Ser Arg Ile Gly Arg Val Val Phe Gly Val Arg Asn Ala Lys Thr Gly
705                 710                 715                 720

Ala Ala Gly Ser Leu Met Asp Val Leu His Tyr Pro Gly Met Asn His
            725                 730                 735

Arg Val Glu Ile Thr Glu Gly Ile Leu Ala Asp Glu Cys Ala Ala Leu
            740                 745                 750

Leu Cys Tyr Phe Phe Arg Met Pro Arg Gln Val Phe Asn Ala Gln Lys
        755                 760                 765

Lys Ala Gln Ser Ser Thr Asp Ser Gly Ser Ser Gly Gly Ser Ser
770                 775                 780

Gly Ser Glu Thr Pro Gly Thr Ser Glu Ser Ala Thr Pro Glu Ser Ser
785                 790                 795                 800

Gly Gly Ser Ser Gly Gly Ser Leu Lys
            805
```

<210> SEQ ID NO 25
<211> LENGTH: 1465
<212> TYPE: PRT
<213> ORGANISM: Artificial Sequence
<220> FEATURE:
<223> OTHER INFORMATION: Description of Artificial Sequence: Synthetic
    SanCas9-KKH-ABE-1 polypeptide

<400> SEQUENCE: 25

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
                20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160
```

-continued

```
Lys Ala Gln Ser Ser Thr Asp Ser Gly Gly Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
            290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ser Gly Gly
            355                 360                 365

Ser Ser Gly Gly Ser Ser Gly Ser Glu Thr Pro Gly Thr Ser Glu Ser
370                 375                 380

Ala Thr Pro Glu Ser Ser Gly Gly Ser Ser Gly Gly Ser Lys Arg Asn
385                 390                 395                 400

Tyr Ile Leu Gly Leu Asp Ile Gly Ile Thr Ser Val Gly Tyr Gly Ile
                405                 410                 415

Ile Asp Tyr Glu Thr Arg Asp Val Ile Asp Ala Gly Val Arg Leu Phe
            420                 425                 430

Lys Glu Ala Asn Val Glu Asn Asn Glu Gly Arg Arg Ser Lys Arg Gly
            435                 440                 445

Ala Arg Arg Leu Lys Arg Arg Arg Arg His Arg Ile Gln Arg Val Lys
            450                 455                 460

Lys Leu Leu Phe Asp Tyr Asn Leu Leu Thr Asp His Ser Glu Leu Ser
465                 470                 475                 480

Gly Ile Asn Pro Tyr Glu Ala Arg Val Lys Gly Leu Ser Gln Lys Leu
                485                 490                 495

Ser Glu Glu Glu Phe Ser Ala Ala Leu Leu His Leu Ala Lys Arg Arg
            500                 505                 510

Gly Val His Asn Val Asn Glu Val Glu Glu Asp Thr Gly Asn Glu Leu
            515                 520                 525

Ser Thr Lys Glu Gln Ile Ser Arg Asn Ser Lys Ala Leu Glu Glu Lys
530                 535                 540

Tyr Val Ala Glu Leu Gln Leu Glu Arg Leu Lys Lys Asp Gly Glu Val
545                 550                 555                 560

Arg Gly Ser Ile Asn Arg Phe Lys Thr Ser Asp Tyr Val Lys Glu Ala
                565                 570                 575

Lys Gln Leu Leu Lys Val Gln Lys Ala Tyr His Gln Leu Asp Gln Ser
```

```
                580                 585                 590
Phe Ile Asp Thr Tyr Ile Asp Leu Leu Glu Thr Arg Arg Thr Tyr Tyr
            595                 600                 605
Glu Gly Pro Gly Glu Gly Ser Pro Phe Gly Trp Lys Asp Ile Lys Glu
            610                 615                 620
Trp Tyr Glu Met Leu Met Gly His Cys Thr Tyr Phe Pro Glu Glu Leu
625                 630                 635                 640
Arg Ser Val Lys Tyr Ala Tyr Asn Ala Asp Leu Tyr Asn Ala Leu Asn
                645                 650                 655
Asp Leu Asn Asn Leu Val Ile Thr Arg Asp Glu Asn Glu Lys Leu Glu
                660                 665                 670
Tyr Tyr Glu Lys Phe Gln Ile Ile Glu Asn Val Phe Lys Gln Lys Lys
                675                 680                 685
Lys Pro Thr Leu Lys Gln Ile Ala Lys Glu Ile Leu Val Asn Glu Glu
            690                 695                 700
Asp Ile Lys Gly Tyr Arg Val Thr Ser Thr Gly Lys Pro Glu Phe Thr
705                 710                 715                 720
Asn Leu Lys Val Tyr His Asp Ile Lys Asp Ile Thr Ala Arg Lys Glu
                725                 730                 735
Ile Ile Glu Asn Ala Glu Leu Leu Asp Gln Ile Ala Lys Ile Leu Thr
                740                 745                 750
Ile Tyr Gln Ser Ser Glu Asp Ile Gln Glu Glu Leu Thr Asn Leu Asn
            755                 760                 765
Ser Glu Leu Thr Gln Glu Glu Ile Glu Gln Ile Ser Asn Leu Lys Gly
        770                 775                 780
Tyr Thr Gly Thr His Asn Leu Ser Leu Lys Ala Ile Asn Leu Ile Leu
785                 790                 795                 800
Asp Glu Leu Trp His Thr Asn Asp Asn Gln Ile Ala Ile Phe Asn Arg
                805                 810                 815
Leu Lys Leu Val Pro Lys Lys Val Asp Leu Ser Gln Gln Lys Glu Ile
                820                 825                 830
Pro Thr Thr Leu Val Asp Asp Phe Ile Leu Ser Pro Val Val Lys Arg
            835                 840                 845
Ser Phe Ile Gln Ser Ile Lys Val Ile Asn Ala Ile Ile Lys Lys Tyr
            850                 855                 860
Gly Leu Pro Asn Asp Ile Ile Ile Glu Leu Ala Arg Glu Lys Asn Ser
865                 870                 875                 880
Lys Asp Ala Gln Lys Met Ile Asn Glu Met Gln Lys Arg Asn Arg Gln
                885                 890                 895
Thr Asn Glu Arg Ile Glu Glu Ile Ile Arg Thr Thr Gly Lys Glu Asn
            900                 905                 910
Ala Lys Tyr Leu Ile Glu Lys Ile Lys Leu His Asp Met Gln Glu Gly
            915                 920                 925
Lys Cys Leu Tyr Ser Leu Glu Ala Ile Pro Leu Glu Asp Leu Leu Asn
        930                 935                 940
Asn Pro Phe Asn Tyr Glu Val Asp His Ile Ile Pro Arg Ser Val Ser
945                 950                 955                 960
Phe Asp Asn Ser Phe Asn Asn Lys Val Leu Val Lys Gln Glu Glu Asn
                965                 970                 975
Ser Lys Lys Gly Asn Arg Thr Pro Phe Gln Tyr Leu Ser Ser Ser Asp
            980                 985                 990
Ser Lys Ile Ser Tyr Glu Thr Phe Lys Lys His Ile Leu Asn Leu Ala
            995                 1000                1005
```

```
Lys Gly Lys Gly Arg Ile Ser Lys Thr Lys Lys Glu Tyr Leu Leu
    1010                1015                1020

Glu Glu Arg Asp Ile Asn Arg Phe Ser Val Gln Lys Asp Phe Ile
    1025                1030                1035

Asn Arg Asn Leu Val Asp Thr Arg Tyr Ala Thr Arg Gly Leu Met
    1040                1045                1050

Asn Leu Leu Arg Ser Tyr Phe Arg Val Asn Asn Leu Asp Val Lys
    1055                1060                1065

Val Lys Ser Ile Asn Gly Gly Phe Thr Ser Phe Leu Arg Arg Lys
    1070                1075                1080

Trp Lys Phe Lys Lys Glu Arg Asn Lys Gly Tyr Lys His His Ala
    1085                1090                1095

Glu Asp Ala Leu Ile Ile Ala Asn Ala Asp Phe Ile Phe Lys Glu
    1100                1105                1110

Trp Lys Lys Leu Asp Lys Ala Lys Lys Val Met Glu Asn Gln Met
    1115                1120                1125

Phe Glu Glu Lys Gln Ala Glu Ser Met Pro Glu Ile Glu Thr Glu
    1130                1135                1140

Gln Glu Tyr Lys Glu Ile Phe Ile Thr Pro His Gln Ile Lys His
    1145                1150                1155

Ile Lys Asp Phe Lys Asp Tyr Lys Tyr Ser His Arg Val Asp Lys
    1160                1165                1170

Lys Pro Asn Arg Lys Leu Ile Asn Asp Thr Leu Tyr Ser Thr Arg
    1175                1180                1185

Lys Asp Asp Lys Gly Asn Thr Leu Ile Val Asn Asn Leu Asn Gly
    1190                1195                1200

Leu Tyr Asp Lys Asp Asn Asp Lys Leu Lys Lys Leu Ile Asn Lys
    1205                1210                1215

Ser Pro Glu Lys Leu Leu Met Tyr His His Asp Pro Gln Thr Tyr
    1220                1225                1230

Gln Lys Leu Lys Leu Ile Met Glu Gln Tyr Gly Asp Glu Lys Asn
    1235                1240                1245

Pro Leu Tyr Lys Tyr Tyr Glu Glu Thr Gly Asn Tyr Leu Thr Lys
    1250                1255                1260

Tyr Ser Lys Lys Asp Asn Gly Pro Val Ile Lys Lys Ile Lys Tyr
    1265                1270                1275

Tyr Gly Asn Lys Leu Asn Ala His Leu Asp Ile Thr Asp Asp Tyr
    1280                1285                1290

Pro Asn Ser Arg Asn Lys Val Val Lys Leu Ser Leu Lys Pro Tyr
    1295                1300                1305

Arg Phe Asp Val Tyr Leu Asp Asn Gly Val Tyr Lys Phe Val Thr
    1310                1315                1320

Val Lys Asn Leu Asp Val Ile Lys Lys Glu Asn Tyr Tyr Glu Val
    1325                1330                1335

Asn Ser Lys Cys Tyr Glu Glu Ala Lys Lys Leu Lys Lys Ile Ser
    1340                1345                1350

Asn Gln Ala Glu Phe Ile Ala Ser Phe Tyr Lys Asn Asp Leu Ile
    1355                1360                1365

Lys Ile Asn Gly Glu Leu Tyr Arg Val Ile Gly Val Asn Asn Asp
    1370                1375                1380

Leu Leu Asn Arg Ile Glu Val Asn Met Ile Asp Ile Thr Tyr Arg
    1385                1390                1395
```

-continued

```
Glu Tyr Leu Glu Asn Met Asn Asp Lys Arg Pro Pro His Ile Ile
    1400                1405                1410

Lys Thr Ile Ala Ser Lys Thr Gln Ser Ile Lys Lys Tyr Ser Thr
1415                1420                1425

Asp Ile Leu Gly Asn Leu Tyr Glu Val Lys Ser Lys Lys His Pro
    1430                1435                1440

Gln Ile Ile Lys Lys Gly Lys Arg Pro Ala Ala Thr Lys Lys Ala
    1445                1450                1455

Gly Gln Ala Lys Lys Lys Lys
    1460                1465

<210> SEQ ID NO 26
<211> LENGTH: 5382
<212> TYPE: DNA
<213> ORGANISM: Artificial Sequence
<220> FEATURE:
<223> OTHER INFORMATION: Description of Artificial Sequence: Synthetic
      PABE-1 DNA polynucleotide

<400> SEQUENCE: 26
atgccaaaaa agaagagaaa ggtttcaggc ggctcctccg aggtggagtt ctctcacgag      60
tattggatga ggcacgctct tacacttgct aagagagctt gggacgaaag agaagtgcca     120
gttggcgccg ttcttgtgca taataatagg gtgatcggcg agggttggaa tagaccaatt     180
ggaaggcatg atccaacagc tcacgcagag attatggctc tcagacaagg cggcctcgtt     240
atgcagaact acaggctcat tgacgctaca ctctacgtga cactcgaacc ttgcgttatg     300
tgcgccggag ctatgattca ttctaggatt ggcagggtcg tgtttggagc tagggacgct     360
aaaacaggag ccgccggatc tcttatggac gtgttgcatc atccaggcat gaaccatagg     420
gtggagatta cagagggcat tcttgcagac gagtgcgctg ctcttctttc cgatttcttc     480
aggatgagaa ggcaggagat taaggcccag aagaaggctc agtcttctac agatagcgga     540
ggatcttccg aggatctag cggctccgag acaccaggaa catccgaaag cgctacacca     600
gaatctagcg gaggctcttc cggaggatct tctgaagtgg agttctccca cgagtattgg     660
atgaggcacg ctcttacact tgctaaaagg cctaggacg aaagggaagt tccagttgga     720
gctgttctcg tgctcaataa cagggtgatt ggcgacggtt ggaatagagc cattggactc     780
catgatccaa cagctcacgc agagattatg gctcttagac aaggcggcct cgttatgcag     840
aattacagac tcatcgacgc cacactctac gttaccttcg aaccttgcgt tatgtgcgcc     900
ggagctatga tccattctag gattggcagg gtcgtgttcg gcgttagaaa cgctaagaca     960
ggagctgcag gctctcttat ggacgttctt cattacccag gcatgaatca tagagtggag    1020
atcacagaag gcattcttgc agacgagtgc gcagctctcc tttgctattt cttcaggatg    1080
ccgaggcaag ttttcaacgc tcagaagaag gcccagtctt ctacagattc cggcggatct    1140
tctggaggat ctagcggctc cgagacacca ggaacatccg aatccgctac accagagtct    1200
tctggaggat ctagcggagg atctcttaag gacaagaagt actcgatcgg cctcgccatt    1260
gggactaact ctgttggctg ggccgtgatc accgacgagt acaaggtgcc ctcaaagaag    1320
ttcaaggtcc tgggcaacac cgatcggcat tccatcaaga agaatctcat tggcgctctc    1380
ctgttcgaca gcggcgagac ggctgaggct acgcggctca agcgcaccgc ccgcaggcgg    1440
tacacgcgca ggaagaatcg catctgctac ctgcaggaga ttttctccaa cgagatggcg    1500
aaggttgacg attctttctt ccacaggctg gaggagtcat tcctcgtgga ggaggataag    1560
aagcacgagc ggcatccaat cttcggcaac attgtcgacg aggttgccta ccacgagaag    1620
```

```
taccctacga tctaccatct gcggaagaag ctcgtggact ccacagataa ggcggacctc    1680
cgcctgatct acctcgctct ggcccacatg attaagttca ggggccattt cctgatcgag    1740
ggggatctca acccggacaa tagcgatgtt gacaagctgt tcatccagct cgtgcagacg    1800
tacaaccagc tcttcgagga gaaccccatt aatgcgtcag cgtcgacgc gaaggctatc     1860 ctgtccgcta ggctctcgaa gtctcggcgc ctcgagaacc tgatcgccca gctgccgggc    1920
gagaagaaga acggcctgtt cgggaatctc attgcgctca gcctggggct cacgcccaac    1980
ttcaagtcga atttcgatct cgctgaggac gccaagctgc agctctccaa ggacacatac    2040
gacgatgacc tggataacct cctggcccag atcggcgatc agtacgcgga cctgttcctc    2100
gctgccaaga atctgtcgga cgccatcctc ctgtctgata ttctcagggt gaacaccgag    2160
attacgaagg ctccgctctc agcctccatg atcaagcgct acgacgagca ccatcaggat    2220
ctgaccctcc tgaaggcgct ggtcaggcag cagctccccg agaagtacaa ggagatcttc    2280
ttcgatcagt cgaagaacgg ctacgctggg tacattgacg gcggggcctc tcaggaggag    2340
ttctacaagt tcatcaagcc gattctggag aagatggacg gcacggagga gctgctggtg    2400
aagctcaatc gcgaggacct cctgaggaag cagcggacat tcgataacgg cagcatccca    2460
caccagattc atctcgggga gctgcacgct atcctgagga ggcaggagga cttctaccct    2520
ttcctcaagg ataaccgcga gaagatcgag aagattctga cttttcaggat cccgtactac    2580 gtcggcccac tcgctagggg caactcccgc ttcgcttgga tgacccgcaa gtcagaggag    2640
acgatcacgc cgtggaactt cgaggaggtg gtcgacaagg cgctagcgc tcagtcgttc     2700 atcgagagga tgacgaattt cgacaagaac ctgccaaatg agaaggtgct ccctaagcac    2760
tcgctcctgt acgagtactt cacagtctac aacgagctga ctaaggtgaa gtatgtgacc    2820
gagggcatga ggaagccggc tttcctgtct ggggagcaga agaaggccat cgtggacctc    2880
ctgttcaaga ccaaccggaa ggtcacggtt aagcagctca aggaggacta cttcaagaag    2940
attgagtgct tcgattcggt cgagatctct ggcgttgagg accgcttcaa cgcctccctg    3000
gggacctacc acgatctcct gaagatcatt aaggataagg acttcctgga caacgaggag    3060
aatgaggata tcctcgagga cattgtgctg acactcactc tgttcgagga ccgggagatg    3120
atcgaggagc gcctgaagac ttacgcccat ctcttcgatg acaaggtcat gaagcagctc    3180
aagaggagga ggtacaccgg ctgggggagg ctgagcagga agctcatcaa cggcattcgg    3240
gacaagcagt ccgggaagac gatcctcgac ttcctgaaga gcgatggctt cgcgaaccgc    3300
aatttcatgc agctgattca cgatgacagc ctcacattca aggaggatat ccagaaggct    3360
caggtgagcg ccaggggga ctcgctgcac gagcatatcg cgaacctcgc tggctcgcca    3420
gctatcaaga agggattct gcagaccgtg aaggttgtgg acgagctggt gaaggtcatg    3480
ggcaggcaca agcctgagaa catcgtcatt gagatggccc gggagaatca gaccacgcag    3540
aagggccaga agaactcacg cgagaggatg aagaggatcg aggagggcat taaggagctg    3600
gggtcccaga tcctcaagga gcacccggtg agaacacgc agctgcagaa tgagaagctc     3660
tacctgtact acctccagaa tggccgcgat atgtatgtgg accaggagct ggatattaac    3720
aggctcagcg attacgacgt cgatcatatc gttccacagt cattcctgaa ggatgactcc    3780
attgacaaca aggtcctcac caggtcggac aagaaccggg gcaagtctga taatgttcct    3840
tcagaggagg tcgttaagaa gatgaagaac tactggcgcc agctcctgaa tgccaagctg    3900
atcacgcagc ggaagttcga taacctcaca aaggctgaga ggggcgggct ctctgagctg    3960
```

| | |
|---|---|
| gacaaggcgg gcttcatcaa gaggcagctg gtcgagacac ggcagatcac taagcacgtt | 4020 |
| gcgcagattc tcgactcacg gatgaacact aagtacgatg agaatgacaa gctgatccgc | 4080 |
| gaggtgaagg tcatcaccct gaagtcaaag ctcgtctccg acttcaggaa ggatttccag | 4140 |
| ttctacaagg ttcgggagat caacaattac caccatgccc atgacgcgta cctgaacgcg | 4200 |
| gtggtcggca cagctctgat caagaagtac ccaaagctcg agagcgagtt cgtgtacggg | 4260 |
| gactacaagg tttacgatgt gaggaagatg atcgccaagt cggagcagga gattggcaag | 4320 |
| gctaccgcca agtacttctt ctactctaac attatgaatt tcttcaagac agagatcact | 4380 |
| ctggccaatg cgagatccg gaagcgcccc ctcatcgaga cgaacggcga gacggggag | 4440 |
| atcgtgtggg acaagggcag ggatttcgcg accgtcagga aggttctctc catgccacaa | 4500 |
| gtgaatatcg tcaagaagac agaggtccag actggcgggt tctctaagga gtcaattctg | 4560 |
| cctaagcgga acagcgacaa gctcatcgcc cgcaagaagg actgggatcc gaagaagtac | 4620 |
| ggcgggttcg acagccccac tgtggcctac tcggtcctgg ttgtggcgaa ggttgagaag | 4680 |
| ggcaagtcca agaagctcaa gagcgtgaag gagctgctgg ggatcacgat tatggagcgc | 4740 |
| tccagcttcg agaagaaccc gatcgatttc ctggaggcga agggctacaa ggaggtgaag | 4800 |
| aaggacctga tcattaagct ccccaagtac tcactcttcg agctggagaa cggcaggaag | 4860 |
| cggatgctgg cttccgctgg cgagctgcag aaggggaacg agctggctct gccgtccaag | 4920 |
| tatgtgaact tcctctacct ggcctcccac tacgagaagc tcaagggcag ccccgaggac | 4980 |
| aacgagcaga agcagctgtt cgtcgagcag cacaagcatt acctcgacga gatcattgag | 5040 |
| cagatttccg agttctccaa gcgcgtgatc ctggccgacg cgaatctgga taaggtcctc | 5100 |
| tccgcgtaca acaagcaccg cgacaagcca atcagggagc aggctgagaa tatcattcat | 5160 |
| ctcttcaccc tgacgaacct cggcgcccct gctgctttca agtacttcga cacaactatc | 5220 |
| gatcgcaaga ggtacacaag cactaaggag gtcctggacg cgaccctcat ccaccagtcg | 5280 |
| attaccggcc tctacgagac gcgcatcgac ctgtctcagc tcggggcga caagcggcca | 5340 |
| gcggcgacga agaaggcggg gcaggcgaag aagaagaagt ag | 5382 |

<210> SEQ ID NO 27
<211> LENGTH: 5349
<212> TYPE: DNA
<213> ORGANISM: Artificial Sequence
<220> FEATURE:
<223> OTHER INFORMATION: Description of Artificial Sequence: Synthetic PABE-2 polynucleotide

<400> SEQUENCE: 27

| | |
|---|---|
| atgtccgagg tggagttctc tcacgagtat tggatgaggc acgctcttac acttgctaag | 60 |
| agagcttggg acgaaagaga agtcccagtt ggcgccgttc ttgtgcataa taatagggtg | 120 |
| atcggcgagg gttggaatag accaattgga aggcatgatc caacagctca cgcagacatt | 180 |
| atggctctca gacaaggcgg cctcgttatg cagaactaca ggctcattga cgctacactc | 240 |
| tacgtgacac tcgaaccttg cgttatgtgc gccggagcta tgattcattc taggattggc | 300 |
| agggtcgtgt ttggagctag ggacgctaaa acaggagccg ccggatctct tatgacgtg | 360 |
| ttgcatcatc caggcatgaa ccataggtg cagattacag agggcattct tgcagacgag | 420 |
| tgcgctcctc ttctttccga tttcttcagg atgagaaggc aggagattaa ggcccagaag | 480 |
| aaggctcagt cttctacaga tagcggagca tcttccggag catctagcgg ctccgagaca | 540 |
| ccaggaacat ccgaaagcgc tacaccagaa tctagccgag gctcttccgg aggatcttct | 600 |

```
gaagtggagt tctcccacga gtattggatg acgcaccctc ttacacttgc taaaagggct    660
agggacgaaa gggaagttcc agttggagct gttctcgtgc tcaataacag ggtgattggc    720
gagggttgga atagagccat tggactccat gatccaacag ctcacgcaga gattatggct    780
cttagacaag gcggcctcgt tatgcagaat tacagactca tcgacgccac actctacgtt    840
accttcgaac cttgcgttat gtgcgccgga gctatgatcc attctaggat tggcagggtc    900
gtgttcggcg ttagaaacgc taagacagga gctgcaggct ctcttatgga cgttcttcat    960
tacccaggca tgaatcatag agtggagatc acagaaggca ttcttgcaga cgagtgcgca   1020
gctctccttt gctatttctt caggatgccg aggcaagttt tcaacgctca gaagaaggcc   1080
cagtcttcta cagattccgg cggatcttct ggaggatcta gcggctccga gacaccagga   1140 acatcgaat ccgctacacc agagtcttct ggaggatcta gcggaggatc tcttaaggac   1200
aagaagtact cgatcggcct cgccattggg actaactctg ttggctgggc cgtgatcacc   1260
gacgagtaca aggtgccctc aaagaagttc aaggtcctgg gcaacaccga tcggcattcc   1320
atcaagaaga atctcattgg cgctctcctg ttcgacagcg gcgagacggc tgaggctacg   1380
cggctcaagc gcaccgcccg caggcggtac acgcgcagga gaatcgcat ctgctacctg   1440 caggagtttt ctccaacga gatggcgaag gttgacgatt ctttcttcca caggctggag   1500
gagtcattcc tcgtggagga ggataagaag cacgagcggc atccaatctt cggcaacatt   1560
gtcgacgagg ttgcctacca cgagaagtac cctacgatct accatctgcg gaagaagctc   1620
gtggactcca cagataaggc ggacctccgc ctgatctacc tcgctctggc ccacatgatt   1680
aagttcaggg gccatttcct gatcgagggg gatctcaacc cggacaatag cgatgttgac   1740
aagctgttca tccagctcgt gcagacgtac aaccagctct tcgaggagaa ccccattaat   1800
gcgtcaggcg tcgacgcgaa ggctatcctg tccgctaggc tctcgaagtc tcggcgcctc   1860
gagaacctga tcgcccagct gccgggcgag aagaagaacg gcctgttcgg gaatctcatt   1920
gcgctcagcc tggggctcac gcccaacttc aagtcgaatt tcgatctcgc tgaggacgcc   1980
aagctgcagc tctccaagga cacatacgac gatgacctgg ataacctcct ggcccagatc   2040
ggcgatcagt acgcggacct gttcctcgct gccaagaatc tgtcggacgc catcctcctg   2100
tctgatattc tcagggtgaa caccgagatt acgaaggctc cgctctcagc ctccatgatc   2160
aagcgctacg acgagcacca tcaggatctg accctcctga aggcgctggt caggcagcag   2220
ctccccgaga agtacaagga gatcttcttc gatcagtcga agaacggcta cgctgggtac   2280
attgacggcg gggcctctca ggaggagttc tacaagttca tcaagccgat tctggagaag   2340
atggacggca cggaggagct gctggtgaag ctcaatcgcg aggacctcct gaggaagcag   2400
cggacattcg ataacggcag catcccacac cagattcatc tcggggagct gcacgctatc   2460
ctgaggaggc aggaggactt ctacccttc ctcaaggata ccgcgagaa gatcgagaag   2520 attctgactt tcaggatccc gtactacgtc ggcccactcg ctaggggcaa ctcccgcttc   2580
gcttggatga cccgcaagtc agaggagacg atcacgccgt ggaacttcga ggaggtggtc   2640
gacaagggcg ctagcgctca gtcgttcatc gagaggatga cgaatttcga caagaacctg   2700
ccaaatgaga aggtgctccc taagcactcg ctcctgtacg agtacttcac agtctacaac   2760
gagctgacta aggtgaagta tgtgaccgag ggcatgagga agccggcttt cctgtctggg   2820
gagcagaaga aggccatcgt ggacctcctg ttcaagacca accggaaggt cacggttaag   2880
cagctcaagg aggactactt caagaagatt gagtgcttcg attcggtcga gatctctggc   2940
gttgaggacc gcttcaacgc ctccctgggg acctaccacg atctcctgaa gatcattaag   3000
```

-continued

| | |
|---|---|
| gataaggact tcctggacaa cgaggagaat gaggatatcc tcgaggacat tgtgctgaca | 3060 |
| ctcactctgt tcgaggaccg ggagatgatc gaggagcgcc tgaagactta cgcccatctc | 3120 |
| ttcgatgaca aggtcatgaa gcagctcaag aggaggaggt acaccggctg ggggaggctg | 3180 |
| agcaggaagc tcatcaacgg cattcgggac aagcagtccg ggaagacgat cctcgacttc | 3240 |
| ctgaagagcg atggcttcgc gaaccgcaat tcatgcagc tgattcacga tgacagcctc | 3300 |
| acattcaagg aggatatcca gaaggctcag gtgagcggcc aggggactc gctgcacgag | 3360 |
| catatcgcga acctcgctgg ctcgccagct atcaagaagg ggattctgca gaccgtgaag | 3420 |
| gttgtggacg agctggtgaa ggtcatgggc aggcacaagc tgagaacat cgtcattgag | 3480 |
| atggcccggg agaatcagac cacgcagaag ggccagaaga actcacgcga gaggatgaag | 3540 |
| aggatcgagg agggcattaa ggagctgggg tcccagatcc tcaaggagca cccggtggag | 3600 |
| aacacgcagc tgcagaatga gaagctctac ctgtactacc tccagaatgg ccgcgatatg | 3660 |
| tatgtggacc aggagctgga tattaacagg ctcagcgatt acgacgtcga tcatatcgtt | 3720 |
| ccacagtcat tcctgaagga tgactccatt gacaacaagg tcctcaccag gtcggacaag | 3780 |
| aaccggggca gtctgataa tgttccttca gaggaggtcg ttaagaagat gaagaactac | 3840 |
| tggcgccagc tcctgaatgc caagctgatc acgcagcgga agttcgataa cctcacaaag | 3900 |
| gctgagaggg gcgggctctc tgagctggac aaggcgggct tcatcaagag cagctggtc | 3960 |
| gagacacggc agatcactaa gcacgttgcg cagattctcg actcacggat gaacactaag | 4020 |
| tacgatgaga atgacaagct gatccgcgag gtgaaggtca tcaccctgaa gtcaaagctc | 4080 |
| gtctccgact tcaggaagga tttccagttc tacaaggttc gggagatcaa caattaccac | 4140 |
| catgcccatg acgcgtacct gaacgcggtg gtcggcacag ctctgatcaa gaagtaccca | 4200 |
| aagctcgaga gcgagttcgt gtacggggac tacaaggttt acgatgtgag gaagatgatc | 4260 |
| gccaagtcgg agcaggagat tggcaaggct accgccaagt acttcttcta ctctaacatt | 4320 |
| atgaatttct tcaagacaga gatcactctg gccaatggcg agatccggaa gcgcccctc | 4380 |
| atcgagacga acggcgagac gggggagatc gtgtgggaca agggcaggga tttcgcgacc | 4440 |
| gtcaggaagg ttctctccat gccacaagtg aatatcgtca agaagacaga ggtccagact | 4500 |
| ggcgggttct ctaaggagtc aattctgcct aagcggaaca gcgacaagct catcgcccgc | 4560 |
| aagaaggact gggatccgaa gaagtacggc gggttcgaca gccccactgt ggcctactcg | 4620 |
| gtcctggttg tggcgaaggt tgagaagggc aagtccaaga agctcaagag cgtgaaggag | 4680 |
| ctgctgggga tcacgattat ggagcgctcc agcttcgaga agaaccgat cgatttcctg | 4740 |
| gaggcgaagg gctacaagga ggtgaagaag gacctgatca ttaagctccc caagtactca | 4800 |
| ctcttcgagc tggagaacgg caggaagcgg atgctggctt ccgctggcga gctgcagaag | 4860 |
| gggaacgagc tggctctgcc gtccaagtat gtgaacttcc tctacctggc ctcccactac | 4920 |
| gagaagctca gggcagccc cgaggacaac gagcagaagc agctgttcgt cgagcagcac | 4980 |
| aagcattacc tcgacgagat cattgagcag atttccgagt tctccaagcg cgtgatcctg | 5040 |
| gccgacgcga atctggataa ggtcctctcc gcgtacaaca agcaccgcga caagccaatc | 5100 |
| agggagcagg ctgagaatat cattcatctc ttcacccctga cgaacctcgg cgcccctgct | 5160 |
| gctttcaagt acttcgacac aactatcgat cgcaagaggt acacaagcac taaggaggtc | 5220 |
| ctggacgcga ccctcatcca ccagtcgatt accggcctct acgagacgcg catcgacctg | 5280 |
| tctcagctcg ggggcgacaa gcggccagcg gcgacgaaga aggcggggca ggcgaagaag | 5340 | aagaagtag                                                                5349

<210> SEQ ID NO 28
<211> LENGTH: 5382
<212> TYPE: DNA
<213> ORGANISM: Artificial Sequence
<220> FEATURE:
<223> OTHER INFORMATION: Description of Artificial Sequence: Synthetic
      PABE-3 polynucleotide

<400> SEQUENCE: 28

```
atgtccgagg tggagttctc tcacgagtat tggatgaggc acgctcttac acttgctaag    60
agagcttggg acgaaagaga agtgccagtt ggcgccgttc ttgtgcataa taatagggtg   120
atcggcgagg gttggaatag accaattgga aggcatgatc caacagctca cgcagagatt   180
atggctctca gacaaggcgg cctcgttatg cagaactaca ggctcattga cgctacactc   240
tacgtgacac tcgaaccttg cgttatgtgc gccggagcta tgattcattc taggattggc   300
agggtcgtgt ttggagctag gacgctaaa acaggagccg ccggatctct tatggacgtg   360
ttgcatcatc caggcatgaa ccatagggtg gagattacag agggcatctt gcagacgag   420
tccgctgctc ttcttttccga tttcttcagg atgagaaggc aggagattaa ggcccagaag   480
aaggctcagt cttctacaga tagcggagga tcttccggag atctagcgg ctccgagaca   540
ccaggaacat ccgaaagcgc tacaccgaaa tctagcggag gctcttccgg aggatcttct   600
gaagtggagt ctcccacga gtattggatg aggcacgctc ttacacttgc taaaagggct   660
agggacgaaa cggaagttcc agttggagct gttctcgtgc tcaataacag ggtgattggc   720
gagggttgga atagagccat ggactccat gatccaacag ctcacgcaga gattatggct   780
cttagacaag gcggcctcgt tatgcagaat tacagactca tcgacgccac actctacgtt   840
accttcgaac cttgcgttat gtgcgccgga gctatgatcc attctaggat tggcagggtc   900
gtgttcggcg ttagaaacgc taagacagga gctgcaggct ctcttatgga cgttcttcat   960
tacccaggca tgaatcatag agtggagatc acagaaggca ttcttgcaga cgagtgcgca  1020
gctctccttt gctatttctt caggatgccg aggcaagttt tcaacgctca gaacaaggcc  1080
cagtcttcta cagattccgg cggatcttct ggaggatcta gcggtccga cacaccagga  1140
acatccgaat ccgctacacc agagtcttct ggaggatcta gcggaggatc tcttaagcca  1200
aaaaagaaga gaaaggtttc aggcggctcc gacaagaagt actcgatcgg cctcgccatt  1260
gggactaact ctgttggctg ggccgtgatc accgacgagt acaaggtgcc ctcaaagaag  1320
ttcaaggtcc tgggcaacac cgatcggcat tccatcaaga gaatctcat ggcgctctc  1380
ctgttcgaca cggcgagac ggctgaggct acgcggctca agcgcaccgc ccgcaggcgg  1440
tacacgcgca ggaagaatcg catctgctac ctgcaggaga tttctccaa cgagatggcg  1500
aaggttgacg attctttctt ccacaggctg gaggagtcat tcctcgtgga ggaggataag  1560
aagcacgagc ggcatccaat cttcggcaac attgtcgacg aggttgccta ccacgagaag  1620
tacccctacg atctaccatc tgcggaagaag ctcgtggact ccacagataa ggcggacctc  1680
cgcctgatct acctcgctct ggcccacatg attaagttca ggggccattt cctgatcgag  1740
ggggatctca acccggacaa tagcgatgtt gacaagctgt tcatccagct cgtgcagacg  1800
tacaaccagc tcttcgagga aaccccatt aatgcgtcag gcgtcgacgc gaaggctatc  1860
ctgtccgcta ggctctcgaa gtctcggcgc ctcgagaacc tgatcgccca gctgccgggc  1920
gagaagaaga acggcctgtt cgggaatctc attgcgctca gcctggggct cacgcccaac  1980
```

| | |
|---|---|
| ttcaagtcga atttcgatct cgctgaggac gccaagctgc agctctccaa ggacacatac | 2040 |
| gacgatgacc tggataacct cctggcccag atcggcgatc agtacgcgga cctgttcctc | 2100 |
| gctgccaaga atctgtcgga cgccatcctc ctgtctgata ttctcagggt gaacaccgag | 2160 |
| attacgaagg ctccgctctc agcctccatg atcaagcgct acgacgagca ccatcaggat | 2220 |
| ctgaccctcc tgaaggcgct ggtcaggcag cagctccccg agaagtacaa ggagatcttc | 2280 |
| ttcgatcagt cgaagaacgg ctacgctggg tacattgacg gcggggcctc tcaggaggag | 2340 |
| ttctacaagt tcatcaagcc gattctggag aagatggacg gcacggagga gctgctggtg | 2400 |
| aagctcaatc gcgaggacct cctgaggaag cagcggacat tcgataacgg cagcatccca | 2460 |
| caccagattc atctcgggga gctgcacgct atcctgagga ggcaggagga cttctaccct | 2520 |
| ttcctcaagg ataaccgcga gaagatcgag aagattctga ctttcaggat cccgtactac | 2580 |
| gtcggcccac tcgctagggg caactcccgc ttcgcttgga tgacccgcaa gtcagaggag | 2640 |
| acgatcacgc cgtggaactt cgaggaggtg gtcgacaagg gcgctagcgc tcagtcgttc | 2700 |
| atcgagagga tgacgaattt cgacaagaac ctgccaaatg agaaggtgct ccctaagcac | 2760 |
| tcgctcctgt acgagtactt cacagtctac aacgagctga ctaaggtgaa gtatgtgacc | 2820 |
| gagggcatga ggaagccggc tttcctgtct ggggagcaga agaaggccat cgtggacctc | 2880 |
| ctgttcaaga ccaaccggaa ggtcacggtt aagcagctca aggaggacta cttcaagaag | 2940 |
| attgagtgct cgattcggt cgagatctct ggcgttgagg accgcttcaa cgcctccctg | 3000 |
| gggacctacc acgatctcct gaagatcatt aaggataagg acttcctgga caacgaggag | 3060 |
| aatgaggata tcctcgagga cattgtgctg acactcactc tgttcgagga ccgggagatg | 3120 |
| atcgaggagc gcctgaagac ttacgcccat ctcttcgatg acaaggtcat gaagcagctc | 3180 |
| aagaggagga ggtacaccgg ctgggggagg ctgagcagga agctcatcaa cggcattcgg | 3240 |
| gacaagcagt ccgggaagac gatcctcgac ttcctgaaga gcgatggctt cgcgaaccgc | 3300 |
| aatttcatgc agctgattca cgatgacagc ctcacattca aggaggatat ccagaaggct | 3360 |
| caggtgagcg gccaggggga ctcgctgcac gagcatatcg cgaacctcgc tggctcgcca | 3420 |
| gctatcaaga aggggattct gcagaccgtg aaggttgtgg acgagctggt gaaggtcatg | 3480 |
| ggcaggcaca agcctgagaa catcgtcatt gagatggccc gggagaatca gaccacgcag | 3540 |
| aagggccaga agaactcacg cgagaggatg aagaggatcg aggagggcat taaggagctg | 3600 |
| gggtcccaga tcctcaagga gcacccggtg agaacacgc agctgcagaa tgagaagctc | 3660 |
| tacctgtact acctccagaa tggccgcgat atgtatgtgg accaggagct ggatattaac | 3720 |
| aggctcagcg attacgacgt cgatcatatc gttccacagt cattcctgaa ggatgactcc | 3780 |
| attgacaaca aggtcctcac caggtcggac aagaaccggg gcaagtctga taatgttcct | 3840 |
| tcagaggagg tcgttaagaa gatgaagaac tactggcgcc agctcctgaa tgccaagctg | 3900 |
| atcacgcagc ggaagttcga taacctcaca aaggctgaga ggggcgggct ctctgagctg | 3960 |
| gacaaggcgg gcttcatcaa gaggcagctg gtcgagacac ggcagatcac taagcacgtt | 4020 |
| gcgcagattc tcgactcacg gatgaacact aagtacgatg agaatgacaa gctgatccgc | 4080 |
| gaggtgaagg tcatcaccct gaagtcaaag ctcgtctccg acttcaggaa ggatttccag | 4140 |
| ttctacaagg ttcgggagat caacaattac caccatgccc atgacgcgta cctgaacgcg | 4200 |
| gtggtcggca cagctctgat caagaagtac ccaaagctcg agagcgagtt cgtgtacggg | 4260 |
| gactacaagg tttacgatgt gaggaagatg atcgccaagt cggagcagga gattggcaag | 4320 |
| gctaccgcca agtacttctt ctactctaac attatgaatt tcttcaagac agagatcact | 4380 |

-continued

```
ctggccaatg gcgagatccg gaagcgcccc ctcatcgaga cgaacggcga gacggggag    4440 atcgtgtggg acaagggcag ggatttcgcg accgtcagga aggttctctc catgccacaa    4500
gtgaatatcg tcaagaagac agaggtccag actggcgggt tctctaagga gtcaattctg    4560
cctaagcgga acagcgacaa gctcatcgcc cgcaagaagg actgggatcc gaagaagtac    4620
ggcgggttcg acagccccac tgtggcctac tcggtcctgg ttgtggcgaa ggttgagaag    4680
ggcaagtcca agaagctcaa gagcgtgaag gagctgctgg ggatcacgat tatggagcgc    4740
tccagcttcg agaagaaccc gatcgatttc ctggaggcga agggctacaa ggaggtgaag    4800
aaggacctga tcattaagct ccccaagtac tcactcttcg agctggagaa cggcaggaag    4860
cggatgctgg cttccgctgg cgagctgcag aaggggaacg agctggctct gccgtccaag    4920
tatgtgaact tcctctacct ggcctcccac tacgagaagc tcaagggcag ccccgaggac    4980
aacgagcaga agcagctgtt cgtcgagcag cacaagcatt acctcgacga gatcattgag    5040
cagatttccg agttctccaa gcgcgtgatc ctggccgacg cgaatctgga taaggtcctc    5100
tccgcgtaca acaagcaccg cgacaagcca atcagggagc aggctgagaa tatcattcat    5160
ctcttcaccc tgacgaacct cggcgcccct gctgctttca agtacttcga cacaactatc    5220
gatcgcaaga ggtacacaag cactaaggag gtcctggacg cgaccctcat ccaccagtcg    5280
attaccggcc tctacgagac gcgcatcgac ctgtctcagc tcggggggcga caagcggcca    5340 gcggcgacga agaaggcggg gcaggcgaag aagaagaagt ag                      5382
```

<210> SEQ ID NO 29
<211> LENGTH: 5382
<212> TYPE: DNA
<213> ORGANISM: Artificial Sequence
<220> FEATURE:
<223> OTHER INFORMATION: Description of Artificial Sequence: Synthetic PABE-4 polynucleotide

<400> SEQUENCE: 29

```
atgccaaaaa agaagagaaa ggtttcaggc ggctccgaca agaagtactc gatcggcctc      60
gccattggga ctaactctgt tggctgggcc gtgatcaccg acgagtacaa ggtgccctca     120
aagaagttca aggtcctggg caacaccgat cggcattcca tcaagaagaa tctcattggc     180
gctctcctgt tcgacagcgg cgagacggct gaggctacgc ggctcaagcg caccgcccgc     240
aggcggtaca cgcgcaggaa gaatcgcatc tgctacctgc aggagatttt ctccaacgag     300
atggcgaagt tgacgattc tttcttccac aggctggagg agtcattcct cgtggaggag     360
gataagaagc acgagcggca tccaatcttc ggcaacattg tcgacgaggt tgcctaccac     420
gagaagtacc ctacgatcta ccatctgcgg aagaagctcg tggactccac agataaggcg     480
gacctccgcc tgatctacct cgctctggcc cacatgatta agttcagggg ccatttcctg     540
atcgaggggg atctcaaccc ggacaatagc gatgttgaca gctgttcat ccagctcgtg     600 cagacgtaca accagctctt cgaggagaac cccattaatg cgtcaggcgt cgacgcgaag     660
gctatcctgt ccgctaggct ctcgaagtct cggcgcctcg agaacctgat cgcccagctg     720
ccgggcgaga agaagaacgg cctgttcggg aatctcattg cgctcagcct ggggctcacg     780
cccaacttca gtcgaatttt cgatctcgct gaggacgcca agctgcagct ctccaaggac     840
acatacgacg atgacctgga taaccctcctg gcccagatcg gcgatcagta cgcggacctg     900
ttcctcgctg ccaagaatct gtcggacgcc atcctcctgt ctgatattct cagggtgaac     960
accgagatta cgaaggctcc gctctcagcc tccatgatca agcgctacga cgagcaccat    1020
```

```
caggatctga ccctcctgaa ggcgctggtc aggcagcagc tccccgagaa gtacaaggag    1080
atcttcttcg atcagtcgaa gaacggctac gctgggtaca ttgacggcgg ggcctctcag    1140
gaggagttct acaagttcat caagccgatt ctggagaaga tggacggcac ggaggagctg    1200
ctggtgaagc tcaatcgcga ggacctcctg aggaagcagc ggacattcga taacggcagc    1260
atcccacacc agattcatct cggggagctg cacgctatcc tgaggaggca ggaggacttc    1320 tacccttttcc tcaaggataa ccgcgagaag atcgagaaga ttctgacttt caggatcccg    1380
tactacgtcg gcccactcgc tagggcaac tcccgcttcg cttggatgac ccgcaagtca    1440
gaggagacga tcacgccgtg gaacttcgag gaggtggtcg acaagggcgc tagcgctcag    1500
tcgttcatcg agaggatgac gaatttcgac aagaacctgc caaatgagaa ggtgctccct    1560
aagcactcgc tcctgtacga gtacttcaca gtctacaacg agctgactaa ggtgaagtat    1620
gtgaccgagg gcatgaggaa gccggctttc ctgtctgggg agcagaagaa ggccatcgtg    1680
gacctcctgt tcaagaccaa ccggaaggtc acggttaagc agctcaagga ggactacttc    1740
aagaagattg agtgcttcga ttcggtcgag atctctggcg ttgaggaccg cttcaacgcc    1800
tccctgggga cctaccacga tctcctgaag atcattaagg ataaggactt cctggacaac    1860
gaggagaatg aggatatcct cgaggacatt gtgctgacac tcactctgtt cgaggaccgg    1920
gagatgatcg aggagcgcct gaagacttac gcccatctct tcgatgacaa ggtcatgaag    1980
cagctcaaga ggaggaggta caccggctgg gggaggctga gcaggaagct catcaacggc    2040
attcgggaca gcagtccgg gaagacgatc ctcgacttcc tgaagagcga tggcttcgcg    2100
aaccgcaatt tcatgcagct gattcacgat gacagcctca cattcaagga ggatatccag    2160
aaggctcagg tgagcggcca gggggactcg ctgcacgagc atatcgcgaa cctcgctggc    2220
tcgccagcta tcaagaaggg gattctgcag accgtgaagg ttgtggacga gctggtgaag    2280
gtcatgggca ggcacaagcc tgagaacatc gtcattgaga tggcccggga gaatcagacc    2340
acgcagaagg gccagaagaa ctcacgcgag aggatgaaga ggatcgagga gggcattaag    2400
gagctggggt cccagatcct caaggagcac ccggtggaga cacgcagct gcagaatgag    2460 aagctctacc tgtactacct ccagaatggc cgcgatatgt atgtggacca ggagctggat    2520
attaacaggc tcagcgatta cgacgtcgat catatcgttc cacagtcatt cctgaaggat    2580
gactccattg acaacaaggt cctcaccagg tcggacaaga accggggcaa gtctgataat    2640
gttccttcag aggaggtcgt taagaagatg aagaactact ggcgccagct cctgaatgcc    2700
aagctgatca cgcagcggaa gttcgataac ctcacaaagg ctgagagggg cgggctctct    2760
gagctggaca aggcgggctt catcaagagg cagctggtcg agacacggca gatcactaag    2820
cacgttgcgc agattctcga ctcacggatg aacactaagt acgatgagaa tgacaagctg    2880
atccgcgagg tgaaggtcat caccctgaag tcaaagctcg tctccgactt caggaaggat    2940
ttccagttct acaaggttcg ggagatcaac aattaccacc atgcccatga cgcgtacctg    3000
aacgcggtgg tcggcacagc tctgatcaag aagtacccaa agctcgagag cgagttcgtg    3060 tacgggact acaaggttta cgatgtgagg aagatgatcg ccaagtcgga gcaggagatt    3120
ggcaaggcta ccgccaagta cttcttctac tctaacatta tgaatttctt caagacagag    3180
atcactctgg ccaatggcga gatccggaag cgccccctca tcgagacgaa cggcgagacg    3240
ggggagatcg tgtgggacaa gggcagggat ttcgcgaccg tcaggaaggt tctctccatg    3300
ccacaagtga atatcgtcaa gaagacagag gtccagactg gcgggttctc taaggagtca    3360
```

| | |
|---|---|
| attctgccta agcggaacag cgacaagctc atcgcccgca agaaggactg ggatccgaag | 3420 |
| aagtacggcg ggttcgacag ccccactgtg gcctactcgg tcctggttgt ggcgaaggtt | 3480 |
| gagaagggca agtccaagaa gctcaagagc gtgaaggagc tgctggggat cacgattatg | 3540 |
| gagcgctcca gcttcgagaa gaacccgatc gatttcctgg aggcgaaggg ctacaaggag | 3600 |
| gtgaagaagg acctgatcat taagctcccc aagtactcac tcttcgagct ggagaacggc | 3660 |
| aggaagcgga tgctggcttc cgctggcgag ctgcagaagg ggaacgagct ggctctgccg | 3720 |
| tccaagtatg tgaacttcct ctacctggcc tcccactacg agaagctcaa gggcagcccc | 3780 |
| gaggacaacg agcagaagca gctgttcgtc gagcagcaca gcattaccct cgacgagatc | 3840 |
| attgagcaga tttccgagtt ctccaagcgc gtgatcctgg ccgacgcgaa tctggataag | 3900 |
| gtcctctccg cgtacaacaa gcaccgcgac aagccaatca gggagcaggc tgagaatatc | 3960 |
| attcatctct tcaccctgac gaacctcggc gcccctgctg ctttcaagta cttcgacaca | 4020 |
| actatcgatc gcaagaggta cacaagcact aaggaggtcc tggacgcgac cctcatccac | 4080 |
| cagtcgatta ccggcctcta cgagacgcgc atcgacctgt ctcagctcgg gggcgacgaa | 4140 |
| ttctccggcg gatcttctgg aggatctagc ggctccgaga caccaggaac atccgaatcc | 4200 |
| gctacaccag agtcttctgg aggatctagc ggaggatctt ccgaggtgga gttctctcac | 4260 |
| gagtattgga tgaggcacgc tcttacactt gctaagagag cttgggacga agagaagtg | 4320 |
| ccagttggcg ccgttcttgt gcataataat agggtgatcg gcgaggggttg gaatagacca | 4380 |
| attggaaggc atgatccaac agctcacgca gagattatgg ctctcagaca aggcggcctc | 4440 |
| gttatgcaga actacaggct cattgacgct acactctacg tgacactcga accttgcgtt | 4500 |
| atgtgcgccg gagctatgat tcattctagg attggcaggg tcgtgtttgg agctagggac | 4560 |
| gctaaaacag gagccgccgg atctcttatg gacgtgttgc atcatccagg catgaaccat | 4620 |
| agggtggaga ttacagaggg cattcttgca gacgagtgcg ctgctcttct ttccgatttc | 4680 |
| ttcaggatga gaaggcagga gattaaggcc cagaagaagg ctcagtcttc tacagatagc | 4740 |
| ggaggatctt ccggaggatc tagcggctcc gagacaccag gaacatccga agcgctaca | 4800 |
| ccagaatcta gcggaggctc ttccggagga tcttctgaag tggagttctc ccacgagtat | 4860 |
| tggatgaggc acgctcttac acttgctaaa agggctaggg acgaaaggga agttccagtt | 4920 |
| ggagctgttc tcgtgctcaa taacagggtg attggcgagg gttggaatag agccattgga | 4980 |
| ctccatgatc caacagctca cgcagagatt atggctctta caaggcgg cctcgttatg | 5040 |
| cagaattaca gactcatcga cgccacactc tacgttacct tcgaaccttg cgttatgtgc | 5100 |
| gccggagcta tgatccattc taggattggc agggtcgtgt tcggcgttag aaacgctaag | 5160 |
| acaggagctg caggctctct tatggacgtt cttcattacc caggcatgaa tcatagagtg | 5220 |
| gagatcacag aaggcattct tgcagacgag tgcgcagctc tcctttgcta tttcttcagg | 5280 |
| atgccgaggc aagttttcaa cgctcagaag aaggcccagt cttctacaga taagagacca | 5340 |
| gcagctacaa agaaggccgg acaagctaag aagaagaagt ag | 5382 |

<210> SEQ ID NO 30
<211> LENGTH: 5403
<212> TYPE: DNA
<213> ORGANISM: Artificial Sequence
<220> FEATURE:
<223> OTHER INFORMATION: Description of Artificial Sequence: Synthetic
    PABE-5 polynucleotide

<400> SEQUENCE: 30

```
atgccaaaaa agaagagaaa ggtttcaggc ggctccgaca agaagtactc gatcggcctc    60
gccattggga ctaactctgt tggctgggcc gtgatcaccg acgagtacaa ggtgccctca   120
aagaagttca aggtcctggg caacaccgat cggcattcca tcaagaagaa tctcattggc   180
gctctcctgt tcgacagcgg cgagacggct gaggctacgc ggctcaagcg caccgcccgc   240
aggcggtaca cgcgcaggaa gaatcgcatc tgctacctgc aggagatttt ctccaacgag   300
atggcgaagg ttgacgattc tttcttccac aggctggagg agtcattcct cgtggaggag   360
gataagaagc acgagcggca tccaatcttc ggcaacattg tcgacgaggt tgcctaccac   420
gagaagtacc ctacgatcta ccatctgcgg aagaagctcg tggactccac agataaggcg   480
gacctccgcc tgatctacct cgctctggcc cacatgatta agttcagggg ccatttcctg   540
atcgagggg atctcaaccc ggacaatagc gatgttgaca agctgttcat ccagctcgtg   600
cagacgtaca accagctctt cgaggagaac cccattaatg cgtcaggcgt cgacgcgaag   660
gctatcctgt ccgctaggct ctcgaagtct cggcgcctcg agaacctgat cgcccagctg   720
ccgggcgaga agaagaacgg cctgttcggg aatctcattg cgctcagcct ggggctcacg   780
cccaacttca gtcgaatttt cgatctcgct gaggacgcca agctgcagct ctccaaggac   840
acatacgacg atgacctgga taacctcctg gcccagatcg gcgatcagta cgcggacctg   900
ttcctcgctg ccaagaatct gtcggacgcc atcctcctgt ctgatattct cagggtgaac   960
accgagatta cgaaggctcc gctctcagcc tccatgatca agcgctacga cgagcaccat  1020
caggatctga ccctcctgaa ggcgctggtc aggcagcagc tccccgagaa gtacaaggag  1080
atcttcttcg atcagtcgaa gaacggctac gctgggtaca ttgacggcgg ggcctctcag  1140
gaggagttct acaagttcat caagccgatt ctggagaaga tggacggcac ggaggagctg  1200
ctggtgaagc tcaatcgcga ggacctcctg aggaagcagc ggacattcga taacggcagc  1260
atcccacacc agattcatct cggggagctg cacgctatcc tgaggaggca ggaggacttc  1320
tacccttcc tcaaggataa ccgcgagaag atcgagaaga ttctgacttt caggatcccg  1380
tactacgtcg gcccactcgc taggggcaac tcccgcttcg cttggatgac ccgcaagtca  1440
gaggagacga tcacgccgtg gaacttcgag gaggtggtcg acaagggcgc tagcgctcag  1500
tcgttcatcg agaggatgac gaatttcgac aagaacctgc caaatgagaa ggtgctccct  1560
aagcactcgc tcctgtacga gtacttcaca gtctacaacg agctgactaa ggtgaagtat  1620
gtgaccgagg gcatgaggaa gccggctttc ctgtctgggg agcagaagaa ggccatcgtg  1680
gacctcctgt tcaagaccaa ccggaaggtc acggttaagc agctcaagga ggactacttc  1740
aagaagattg agtgcttcga ttcggtcgag atctctggcg ttgaggaccg cttcaacgcc  1800
tccctgggga cctaccacga tctcctgaag atcattaagg ataaggactt cctggacaac  1860
gaggagaatg aggatatcct cgaggacatt gtgctgacac tcactctgtt cgaggaccgg  1920
gagatgatcg aggagcgcct gaagacttac gcccatctct tcgatgacaa ggtcatgaag  1980
cagctcaaga ggaggaggta caccggctgg gggaggctga gcaggaagct catcaacggc  2040
attcgggaca agcagtccgg gaagacgatc ctcgacttcc tgaagagcga tggcttcgcg  2100
aaccgcaatt tcatgcagct gattcacgat gacagcctca cattcaagga ggatatccag  2160
aaggctcagg tgagcggcca gggggactcg ctgcacgagc atatcgcgaa cctcgctggc  2220
tcgccagcta tcaagaaggg gattctgcag accgtgaagg ttgtggacga gctggtgaag  2280
gtcatgggca ggcacaagcc tgagaacatc gtcattgaga tggcccggga gaatcagacc  2340
acgcagaagg gccagaagaa ctcacgcgag aggatgaaga ggatcgagga gggcattaag  2400
```

-continued

```
gagctggggt cccagatcct caaggagcac ccggtggaga acacgcagct gcagaatgag    2460
aagctctacc tgtactacct ccagaatggc cgcgatatgt atgtggacca ggagctggat    2520
attaacaggc tcagcgatta cgacgtcgat catatcgttc cacagtcatt cctgaaggat    2580
gactccattg acaacaaggt cctcaccagg tcggacaaga accggggcaa gtctgataat    2640
gttccttcag aggaggtcgt taagaagatg aagaactact ggcgccagct cctgaatgcc    2700
aagctgatca cgcagcggaa gttcgataac ctcacaaagg ctgagagggg cgggctctct    2760
gagctggaca aggcgggctt catcaagagg cagctggtcg agacacggca gatcactaag    2820
cacgttgcgc agattctcga ctcacggatg aacactaagt acgatgagaa tgacaagctg    2880
atccgcgagg tgaaggtcat caccctgaag tcaaagctcg tctccgactt caggaaggat    2940
ttccagttct acaaggttcg ggagatcaac aattaccacc atgcccatga cgcgtacctg    3000
aacgcggtgg tcggcacagc tctgatcaag aagtacccaa agctcgagag cgagttcgtg    3060
tacggggact acaaggttta cgatgtgagg aagatgatcg ccaagtcgga gcaggagatt    3120
ggcaaggcta ccgccaagta cttcttctac tctaacatta tgaatttctt caagacagag    3180
atcactctgg ccaatggcga gatccggaag cgccccctca tcgagacgaa cggcgagacg    3240
ggggagatcg tgtgggacaa gggcagggat ttcgcgaccg tcaggaaggt tctctccatg    3300
ccacaagtga atatcgtcaa gaagacagag gtccagactg gcgggttctc taaggagtca    3360
attctgccta agcggaacag cgacaagctc atcgcccgca agaaggactg ggatccgaag    3420
aagtacggcg ggttcgacag cccccactgt gcctactcgg tcctggttgt ggcgaaggtt    3480
gagaagggca gtccaagaa gctcaagagc gtgaaggagc tgctggggat cacgattatg    3540
gagcgctcca gcttcgagaa gaacccgatc gatttcctgg aggcgaaggg ctacaaggag    3600
gtgaagaagg acctgatcat taagctcccc aagtactcac tcttcgagct ggagaacggc    3660
aggaagcgga tgctggcttc cgctggcgag ctgcagaagg gaacgagct ggctctgccg    3720 tccaagtatg tgaacttcct ctacctggcc tcccactacg agaagctcaa gggcagcccc    3780
gaggacaacg agcagaagca gctgttcgtc gagcagcaca gcattacct cgacgagatc    3840 attgagcaga tttccgagtt ctccaagcgc gtgatcctgg ccgacgcgaa tctggataag    3900
gtcctctccg cgtacaacaa gcaccgcgac aagccaatca gggagcaggc tgagaatatc    3960
attcatctct tcaccctgac gaacctcggc gcccctgctg ctttcaagta cttcgacaca    4020
actatcgatc gcaagaggta cacaagcact aaggaggtcc tggacgcgac cctcatccac    4080
cagtcgatta ccgcctcta cgagacgcgc atcgacctgt ctcagctcgg gggcgacgaa    4140
ttcccaaaga gaagcgcaa ggtctccggc ggatcttctg gaggatctag cggctccgag    4200
acaccaggaa catccgaatc cgctacacca gagtcttctg gaggatctag cggaggatct    4260
tccgaggtgg agttctctca cgagtattgg atgaggcacg ctcttacact tgctaagaga    4320
gcttgggaca aaagagaagt gccagttggc gccgttcttg tgcataataa tagggtgatc    4380
ggcgagggtt ggaatagacc aattggaagg catgatccaa cagctcacgc agagattatg    4440
gctctcagac aaggcggcct cgttatgcag aactacaggc tcattgacgc tacactctac    4500
gtgacactcg aaccttgcgt tatgtgcgcc ggagctatga ttcattctag gattggcagg    4560
gtcgtgtttg gagctaggga cgctaaaaca ggagccgccg gatctcttat ggacgtgttg    4620
catcatccag gcatgaacca tagggtggag attacagagg gcattcttgc agacgagtgc    4680
gctgctcttc tttccgattt cttcaggatg agaaggcagg agattaaggc ccagaagaag    4740
```

-continued

```
gctcagtctt ctacagatag cggaggatct tccggaggat ctagcggctc cgagacacca    4800
ggaacatccg aaagcgctac accagaatct agcggaggct cttccggagg atcttctgaa    4860
gtggagttct cccacgagta ttggatgagg cacgctctta cacttgctaa aagggctagg    4920
gacgaaaggg aagttccagt tggagctgtt ctcgtgctca ataacagggt gattggcgag    4980
ggttggaata gagccattgg actccatgat ccaacagctc acgcagagat tatggctctt    5040
agacaaggcg gcctcgttat gcagaattac agactcatcg acgccacact ctacgttacc    5100
ttcgaacctt gcgttatgtg cgccggagct atgatccatt ctaggattgg cagggtcgtg    5160
ttcggcgtta gaaacgctaa gacaggagct gcaggctctc ttatggacgt tcttcattac    5220
ccaggcatga atcatagagt ggagatcaca gaaggcattc ttgcagacga gtgcgcagct    5280
ctcctttgct atttcttcag gatgccgagg caagttttca acgctcagaa gaaggcccag    5340
tcttctacag ataagagacc agcagctaca agaaggccg acaagctaa gaagaagaag    5400 tag                                                                 5403
```

<210> SEQ ID NO 31
<211> LENGTH: 5367
<212> TYPE: DNA
<213> ORGANISM: Artificial Sequence
<220> FEATURE:
<223> OTHER INFORMATION: Description of Artificial Sequence: Synthetic
      PABE-6 polynucleotide

<400> SEQUENCE: 31

```
atgtccgagg tggagttctc tcacgagtat tggatgaggc acgctcttac acttgctaag     60
agagcttggg acgaaagaga agtgccagtt ggcgccgttc ttgtgcataa aatagggtg    120 atcggcgagg gttggaatag accaattgga aggcatgatc caacagctca cgcagagatt    180
atggctctca gacaaggcgg cctcgttatg cagaactaca ggctcattga cgctacactc    240
tacgtgacac tcgaaccttg cgttatgtgc gccggagcta tgattcattc taggattggc    300
agggtcgtgt ttggagctag gacgctaaa acaggagccg ccggatctct tatggacgtg    360
ttgcatcatc caggcatgaa ccataggggtg gagattacag agggcattct tgcagacgag    420
tgcgctgctc ttctttccga tttcttcagg atgaaaggc aggagattaa ggcccagaag    480
aaggctcagt cttctacaga tagcggagga tcttccggag gatctagcgg ctccgagaca    540
ccaggaacat ccgaaagcgc tacaccagaa tctagcggag gctcttccgg aggatcttct    600
gaagtggagt ctcccacga gtattggatg aggcacgctc ttacacttgc taaaagggct    660
agggacgaaa gggaagttcc agttggagct gttctcgtgc tcaataacag ggtgattggc    720
gagggttgga atagagccat tggactccat gatccaacag ctcacgcaga gattatggct    780
cttagacaag gcggcctcgt tatgcagaat tacagactca cgacgccac actctacgtt    840 accttcgaac cttgcgttat gtgcgccgga gctatgatcc attctaggat tggcagggtc    900 gtgttcggc ttagaaacgc taagacagga gctgcaggct ctcttatgga cgttcttcat    960
tacccaggca tgaatcatag agtggagatc acagaaggca ttcttgcaga cgagtgcgca   1020 gctctcctt gctatttctt caggatgccg aggcaagttt tcaacgctca gaagaaggcc   1080
cagtcttcta cagattccgg cggatcttct ggaggatcta gcggctccca gacaccagga   1140
acatccgaat ccgctacacc agagtcttct ggaggatcta gcggaggatc tcttaaggac   1200
aagaagtact cgatcggcct cgccattggg actaactctg ttggctgggc cgtgatcacc   1260
gacgagtaca aggtgccctc aaagaagttc aaggtcctgg gcaacaccga tcggcattcc   1320
```

-continued

```
atcaagaaga atctcattgg cgctctcctg ttcgacagcg gcgagacggc tgaggctacg    1380
cggctcaagc gcaccgcccg caggcggtac acgcgcagga agaatcgcat ctgctacctg    1440
caggagattt tctccaacga gatggcgaag gttgacgatt ctttcttcca caggctggag    1500
gagtcattcc tcgtggagga ggataagaag cacgagcggc atccaatctt cggcaacatt    1560
gtcgacgagg ttgcctacca cgagaagtac cctacgatct accatctgcg gaagaagctc    1620
gtggactcca cagataaggc ggacctccgc ctgatctacc tcgctctggc ccacatgatt    1680
aagttcaggg gccatttcct gatcgagggg gatctcaacc cggacaatag cgatgttgac    1740
aagctgttca tccagctcgt gcagacgtac aaccagctct cgaggagaa ccccattaat    1800 gcgtcaggcg tcgacgcgaa ggctatcctg tccgctaggc tctcgaagtc tcggcgcctc    1860
gagaacctga tcgcccagct gccgggcgag aagaagaacg gcctgttcgg gaatctcatt    1920
gcgctcagcc tggggctcac gcccaacttc aagtcgaatt tcgatctcgc tgaggacgcc    1980
aagctgcagc tctccaagga cacatacgac gatgacctgg ataacctcct ggcccagatc    2040
ggcgatcagt acgcggacct gttcctcgct gccaagaatc tgtcggacgc catcctcctg    2100
tctgatattc tcagggtgaa caccgagatt acgaaggctc cgctctcagc ctccatgatc    2160
aagcgctacg acgagcacca tcaggatctg accctcctga aggcgctggt caggcagcag    2220
ctccccgaga agtacaagga gatcttcttc gatcagtcga agaacggcta cgctgggtac    2280
attgacggcg gggcctctca ggaggagttc tacaagttca tcaagccgat tctggagaag    2340
atggacggca cggaggagct gctggtgaag ctcaatcgcg aggacctcct gaggaagcag    2400
cggacattcg ataacggcag catcccacac cagattcatc tcggggagct gcacgctatc    2460
ctgaggaggc aggaggactt ctaccctttc ctcaaggata ccgcgagaa gatcgagaag    2520 attctgactt tcaggatccc gtactacgtc ggcccactcg ctaggggcaa ctcccgcttc    2580
gcttggatga cccgcaagtc agaggagacg atcacgccgt ggaacttcga ggaggtggtc    2640
gacaagggcg ctagcgctca gtcgttcatc gagaggatga cgaatttcga caagaacctg    2700
ccaaatgaga aggtgctccc taagcactcg ctcctgtacg agtacttcac agtctacaac    2760
gagctgacta aggtgaagta tgtgaccgag ggcatgagga agccggcttt cctgtctggg    2820
gagcagaaga aggccatcgt ggacctcctg ttcaagacca accggaaggt cacggttaag    2880
cagctcaagg aggactactt caagaagatt gagtgcttcg attcggtcga gatctctggc    2940
gttgaggacc gcttcaacgc ctccctgggg acctaccacg atctcctgaa gatcattaag    3000
gataaggact tcctggacaa cgaggagaat gaggatatcc tcgaggacat tgtgctgaca    3060
ctcactctgt tcgaggaccg ggagatgatc gaggagcgcc tgaagactta cgcccatctc    3120
ttcgatgaca aggtcatgaa gcagctcaag aggaggaggt acaccggctg ggggaggctg    3180
agcaggaagc tcatcaacgg cattcgggac aagcagtccg ggaagacgat cctcgacttc    3240
ctgaagagcg atggcttcgc gaaccgcaat ttcatgcagc tgattcacga tgacagcctc    3300
acattcaagg aggatatcca gaaggctcag gtgagcggcc aggggactc gctgcacgag    3360 catatcgcga acctcgctgg ctcgccagct atcaagaagg ggattctgca gaccgtgaag    3420
gttgtggacg agctggtgaa ggtcatgggc aggcacaagc tgagaacat cgtcattgag    3480 atggcccggg agaatcagac cacgcagaag ggccagaaga actcacgcga gaggatgaag    3540
aggatcgagg agggcattaa ggagctgggg tcccagatcc tcaaggagca cccggtggag    3600
aacacgcagc tgcagaatga gaagctctac ctgtactacc tccagaatgg ccgcgatatg    3660
tatgtggacc aggagctgga tattaacagg ctcagcgatt acgacgtcga tcatatcgtt    3720
```

| | | | |
|---|---|---|---|
| ccacagtcat | tcctgaagga | tgactccatt gacaacaagg | tcctcaccag gtcggacaag | 3780 |
| aaccggggca | agtctgataa | tgttccttca gaggaggtcg | ttaagaagat gaagaactac | 3840 |
| tggcgccagc | tcctgaatgc | caagctgatc acgcagcgga | agttcgataa cctcacaaag | 3900 |
| gctgagaggg | gcgggctctc | tgagctggac aaggcgggct | tcatcaagag gcagctggtc | 3960 |
| gagacacggc | agatcactaa | gcacgttgcg cagattctcg | actcacggat gaacactaag | 4020 |
| tacgatgaga | atgacaagct | gatccgcgag gtgaaggtca | tcaccctgaa gtcaaagctc | 4080 |
| gtctccgact | tcaggaagga | tttccagttc tacaaggttc | gggagatcaa caattaccac | 4140 |
| catgcccatg | acgcgtacct | gaacgcggtg gtcggcacag | ctctgatcaa gaagtaccca | 4200 |
| aagctcgaga | gcgagttcgt | gtacggggac tacaaggttt | acgatgtgag gaagatgatc | 4260 |
| gccaagtcgg | agcaggagat | tggcaaggct accgccaagt | acttcttcta ctctaacatt | 4320 |
| atgaatttct | tcaagacaga | gatcactctg gccaatggcg | agatccggaa gcgccccctc | 4380 |
| atcgagacga | acgcgagac | gggggagatc gtgtgggaca | agggcaggga tttcgcgacc | 4440 |
| gtcaggaagg | ttctctccat | gccacaagtg aatatcgtca | agaagacaga ggtccagact | 4500 |
| ggcgggttct | ctaaggagtc | aattctgcct aagcggaaca | gcgacaagct catcgcccgc | 4560 |
| aagaaggact | gggatccgaa | gaagtacggc gggttcgaca | gccccactgt ggcctactcg | 4620 |
| gtcctggttg | tggcgaaggt | tgagaagggc aagtccaaga | agctcaagag cgtgaaggag | 4680 |
| ctgctgggga | tcacgattat | ggagcgctcc agcttcgaga | agaacccgat cgatttcctg | 4740 |
| gaggcgaagg | gctacaagga | ggtgaagaag gacctgatca | ttaagctccc caagtactca | 4800 |
| ctcttcgagc | tggagaacgg | caggaagcgg atgctggctt | ccgctggcga gctgcagaag | 4860 |
| gggaacgagc | tggctctgcc | gtccaagtat gtgaacttcc | tctacctggc ctcccactac | 4920 |
| gagaagctca | agggcagccc | cgaggacaac gagcagaagc | agctgttcgt cgagcagcac | 4980 |
| aagcattacc | tcgacgagat | cattgagcag atttccgagt | ctccaagcg cgtgatcctg | 5040 |
| gccgacgcga | atctggataa | ggtcctctcc gcgtacaaca | agcaccgcga caagccaatc | 5100 |
| agggagcagg | ctgagaatat | cattcatctc ttcaccctga | cgaacctcgg cgcccctgct | 5160 |
| gctttcaagt | acttcgacac | aactatcgat cgcaagaggc | acacaagcac taaggaggtc | 5220 |
| ctggacgcga | ccctcatcca | ccagtcgatt accggcctct | acgagacgcg catcgacctg | 5280 |
| tctcagctcg | ggggcgactc | cggcggcagc ccaaagaaga | gcggaaggt gtctggaggt | 5340 |
| tctcctaaga | aaaagagaaa | agtgtag | | 5367 |

<210> SEQ ID NO 32
<211> LENGTH: 5400
<212> TYPE: DNA
<213> ORGANISM: Artificial Sequence
<220> FEATURE:
<223> OTHER INFORMATION: Description of Artificial Sequence: Synthetic
      PABE-7 polynucleotide

<400> SEQUENCE: 32

| | | | |
|---|---|---|---|
| atgtccgagg | tggagttctc | tcacgagtat tggatgaggc | acgctcttac acttgctaag | 60 |
| agagcttggg | acgaaagaga | agtgccagtt ggcgccgttc | ttgtgcataa taatagggtg | 120 |
| atcggcgagg | gttggaatag | accaattgga aggcatgatc | caacagctca cgcagagatt | 180 |
| atggctctca | gacaaggcgg | cctcgttatg cagaactaca | ggctcattga cgctacactc | 240 |
| tacgtgacac | tcgaaccttg | cgttatgtgc gccggagcta | tgattcattc taggattggc | 300 |
| agggtcgtgt | ttggagctag | ggacgctaaa acaggagccg | ccggatctct tatggacgtg | 360 |

```
ttgcatcatc caggcatgaa ccatagggtg gagattacag agggcattct tgcagacgag      420
tgcgctgctc ttctttccga tttcttcagg atgagaaggc aggagattaa ggcccagaag      480
aaggctcagt cttctacaga tagcggagga tcttccggag gatctagcgg ctccgagaca      540
ccaggaacat ccgaaagcgc tacaccagaa tctagcggag gctcttccgg aggatcttct      600
gaagtggagt tctcccacga gtattggatg aggcacgctc ttacacttgc taaaagggct      660
agggacgaaa gggaagttcc agttggagct gttctcgtgc tcaataacag ggtgattggc      720
gagggttgga atagagccat tggactccat gatccaacag ctcacgcaga gattatggct      780
cttagacaag gcggcctcgt tatgcagaat tacagactca tcgacgccac actctacgtt      840
accttcgaac cttgcgttat gtgcgccgga gctatgatcc attctaggat tggcagggtc      900
gtgttcggcg ttagaaacgc taagacagga gctgcaggct ctcttatgga cgttcttcat      960
tacccaggca tgaatcatag agtggagatc acagaaggca ttcttgcaga cgagtgcgca     1020
gctctccttt gctatttctt caggatgccg aggcaagttt tcaacgctca gaagaaggcc     1080
cagtcttcta cagattccgg cggatcttct ggaggatcta gcggctccga gacaccagga     1140
acatccgaat ccgctacacc agagtcttct ggaggatcta gcggaggatc tcttaaggac     1200
aagaagtact cgatcggcct cgccattggg actaactctg ttggctgggc cgtgatcacc     1260
gacgagtaca aggtgccctc aaagaagttc aaggtcctgg caacaccga tcggcattcc     1320 atcaagaaga atctcattgg cgctctcctg ttcgacagcg gcgagacggc tgaggctacg     1380
cggctcaagc gcaccgcccg caggcggtac acgcgcagga gaatcgcat ctgctacctg     1440 caggagattt tctccaacga gatggcgaag gttgacgatt ctttcttcca caggctggag     1500
gagtcattcc tcgtggagga ggataagaag cacgagcggc atccaatctt cggcaacatt     1560
gtcgacgagg ttgcctacca cgagaagtac cctacgatct accatctgcg gaagaagctc     1620
gtggactcca cagataaggc ggacctccgc ctgatctacc tcgctctggc ccacatgatt     1680
aagttcaggg gccatttcct gatcgagggg gatctcaacc cggacaatag cgatgttgac     1740
aagctgttca tccagctcgt gcagacgtac aaccagctct cgaggagaa ccccattaat     1800 gcgtcaggcg tcgacgcgaa ggctatcctg tccgctaggc tctcgaagtc tcggcgcctc     1860
gagaacctga tcgcccagct gccgggcgag aagaagaacg gcctgttcgg gaatctcatt     1920
gcgctcagcc tgggctcac gcccaacttc aagtcgaatt tcgatctcgc tgaggacgcc     1980
aagctgcagc tctccaagga cacatacgac gatgacctgg ataacctcct ggcccagatc     2040
ggcgatcagt acgcggacct gttcctcgct gccaagaatc tgtcggacgc catcctcctg     2100
tctgatattc tcagggtgaa caccgagatt acgaaggctc cgctctcagc ctccatgatc     2160
aagcgctacg acgagcacca tcaggatctg accctcctga aggcgctggt caggcagcag     2220
ctccccgaga agtacaagga gatcttcttc gatcagtcga agaacggcta cgctgggtac     2280
attgacggcg gggcctctca ggaggagttc tacaagttca tcaagccgat tctggagaag     2340
atggacggca cggaggagct gctggtgaag ctcaatcgcg aggacctcct gaggaagcag     2400
cggacattcg ataacggcag catcccacac cagattcatc tcggggagct gcacgctatc     2460
ctgaggaggc aggaggactt ctacccttc ctcaaggata ccgcgagaa gatcgagaag     2520 attctgactt tcaggatccc gtactacgtc ggcccactcg ctagggcaa ctcccgcttc     2580 gcttggatga cccgcaagtc agaggagacg atcacgccgt ggaacttcga ggaggtggtc     2640
gacaagggcg ctagcgctca gtcgttcatc gagaggatga cgaatttcga caagaacctg     2700
```

```
ccaaatgaga aggtgctccc taagcactcg ctcctgtacg agtacttcac agtctacaac   2760
gagctgacta aggtgaagta tgtgaccgag ggcatgagga agccggcttt cctgtctggg   2820
gagcagaaga aggccatcgt ggacctcctg ttcaagacca accggaaggt cacggttaag   2880
cagctcaagg aggactactt caagaagatt gagtgcttcg attcggtcga gatctctggc   2940
gttgaggacc gcttcaacgc ctccctgggg acctaccacg atctcctgaa gatcattaag   3000
gataaggact tcctggacaa cgaggagaat gaggatatcc tcgaggacat tgtgctgaca   3060
ctcactctgt tcgaggaccg ggagatgatc gaggagcgcc tgaagactta cgcccatctc   3120
ttcgatgaca aggtcatgaa gcagctcaag aggaggaggt acaccggctg ggggaggctg   3180
agcaggaagc tcatcaacgg cattcgggac aagcagtccg ggaagacgat cctcgacttc   3240
ctgaagagcg atggcttcgc gaaccgcaat ttcatgcagc tgattcacga tgacagcctc   3300
acattcaagg aggatatcca gaaggctcag gtgagcggcc aggggactc gctgcacgag   3360
catatcgcga acctcgctgg ctcgccagct atcaagaagg ggattctgca gaccgtgaag   3420
gttgtggacg agctggtgaa ggtcatgggc aggcacaagc tgagaacat cgtcattgag   3480
atggcccggg agaatcagac cacgcagaag ggccagaaga actcacgcga ggaggatgaag   3540
aggatcgagg agggcattaa ggagctgggg tcccagatcc tcaaggagca cccggtggag   3600
aacacgcagc tgcagaatga gaagctctac ctgtactacc tccagaatgg ccgcgatatg   3660
tatgtgacc aggagctgga tattaacagg ctcagcgatt acgacgtcga tcatatcgtt   3720
ccacagtcat tcctgaagga tgactccatt gacaacaagg tcctcaccag gtcggacaag   3780
aaccggggca agtctgataa tgttccttca gaggaggtcg ttaagaagat gaagaactac   3840
tggcgccagc tcctgaatgc caagctgatc acgcagcgga agttcgataa cctcacaaag   3900
gctgagaggg gcgggctctc tgagctggac aaggcgggct tcatcaagag gcagctggtc   3960
gagacacggc agatcactaa gcacgttgcg cagattctcg actcacggat gaacactaag   4020
tacgatgaga atgacaagct gatccgcgag gtgaaggtca tcaccctgaa gtcaaagctc   4080
gtctccgact tcaggaagga tttccagttc tacaaggttc gggagatcaa caattaccac   4140
catgcccatg acgcgtacct gaacgcgtg gtcggcacag ctctgatcaa gaagtaccca   4200
aagctcgaga gcgagttcgt gtacggggac tacaaggttt acgatgtgag gaagatgatc   4260
gccaagtcgg agcaggagat tggcaaggct accgccaagt acttcttcta ctctaacatt   4320
atgaatttct tcaagacaga gatcactctg gccaatggcg agatccggaa gcgcccctc   4380
atcgagacga acgcgagac ggggagatc gtgtgggaca agggcaggga tttcgcgacc   4440
gtcaggaagg ttctctccat gccacaagtg aatatcgtca agaagacaga ggtccagact   4500
ggcgggttct ctaaggagtc aattctgcct aagcggaaca gcgacaagct catcgcccgc   4560
aagaaggact gggatccgaa gaagtacggc gggttcgaca gccccactgt ggcctactcg   4620
gtcctggttg tggcgaaggt tgagaagggc aagtccaaga agctcaagag cgtgaaggag   4680
ctgctgggga tcacgattat ggagcgctcc agcttcgaga agaacccgat cgatttcctg   4740
gaggcgaagg gctacaagga ggtgaagaag acctgatca ttaagctccc caagtactca   4800
ctcttcgagc tggagaacgg caggaagcgg atgctggctt ccgctggcga gctgcagaag   4860
gggaacgagc tggctctgcc gtccaagtat gtgaacttcc tctacctggc ctcccactac   4920
gagaagctca gggcagccc cgaggacaac gagcagaagc agctgttcgt cgagcagcac   4980
aagcattacc tcgacgagat cattgagcag atttccgagt tctccaagcg cgtgatcctg   5040
gccgacgcga atctggataa ggtcctctcc gcgtacaaca agcaccgcga caagccaatc   5100
```

-continued

```
agggagcagg ctgagaatat cattcatctc ttcaccctga cgaacctcgg cgcccctgct    5160
gctttcaagt acttcgacac aactatcgat cgcaagaggt acacaagcac taaggaggtc    5220
ctggacgcga ccctcatcca ccagtcgatt accggcctct acgagacgcg catcgacctg    5280
tctcagctcg ggggcgactc cggcggcagc ccaaagaaga gcggaaggt gtctggaggt    5340 tctcctaaga aaagagaaa agtgtccggc ggctccccga agaagaagcg caaggtgtag    5400
```

<210> SEQ ID NO 33
<211> LENGTH: 1793
<212> TYPE: PRT
<213> ORGANISM: Artificial Sequence
<220> FEATURE:
<223> OTHER INFORMATION: Description of Artificial Sequence: Synthetic
      PABE-1 polypeptide

<400> SEQUENCE: 33

```
Met Pro Lys Lys Arg Lys Val Ser Gly Gly Ser Glu Val Glu
1               5                   10                  15

Phe Ser His Glu Tyr Trp Met Arg His Ala Leu Thr Leu Ala Lys Arg
                20                  25                  30

Ala Trp Asp Glu Arg Glu Val Pro Val Gly Ala Val Leu Val His Asn
            35                  40                  45

Asn Arg Val Ile Gly Glu Gly Trp Asn Arg Pro Ile Gly Arg His Asp
        50                  55                  60

Pro Thr Ala His Ala Glu Ile Met Ala Leu Arg Gln Gly Gly Leu Val
65                  70                  75                  80

Met Gln Asn Tyr Arg Leu Ile Asp Ala Thr Leu Tyr Val Thr Leu Glu
                85                  90                  95

Pro Cys Val Met Cys Ala Gly Ala Met Ile His Ser Arg Ile Gly Arg
            100                 105                 110

Val Val Phe Gly Ala Arg Asp Ala Lys Thr Gly Ala Ala Gly Ser Leu
        115                 120                 125

Met Asp Val Leu His His Pro Gly Met Asn His Arg Val Glu Ile Thr
130                 135                 140

Glu Gly Ile Leu Ala Asp Glu Cys Ala Ala Leu Leu Ser Asp Phe Phe
145                 150                 155                 160

Arg Met Arg Arg Gln Glu Ile Lys Ala Gln Lys Lys Ala Gln Ser Ser
                165                 170                 175

Thr Asp Ser Gly Gly Ser Ser Gly Gly Ser Ser Gly Ser Glu Thr Pro
            180                 185                 190

Gly Thr Ser Glu Ser Ala Thr Pro Glu Ser Ser Gly Gly Ser Ser Gly
        195                 200                 205

Gly Ser Ser Glu Val Glu Phe Ser His Glu Tyr Trp Met Arg His Ala
    210                 215                 220

Leu Thr Leu Ala Lys Arg Ala Arg Asp Glu Arg Glu Val Pro Val Gly
225                 230                 235                 240

Ala Val Leu Val Leu Asn Asn Arg Val Ile Gly Glu Gly Trp Asn Arg
                245                 250                 255

Ala Ile Gly Leu His Asp Pro Thr Ala His Ala Glu Ile Met Ala Leu
            260                 265                 270

Arg Gln Gly Gly Leu Val Met Gln Asn Tyr Arg Leu Ile Asp Ala Thr
        275                 280                 285

Leu Tyr Val Thr Phe Glu Pro Cys Val Met Cys Ala Gly Ala Met Ile
    290                 295                 300
```

-continued

His Ser Arg Ile Gly Arg Val Val Phe Gly Val Arg Asn Ala Lys Thr
305                 310                 315                 320

Gly Ala Ala Gly Ser Leu Met Asp Val Leu His Tyr Pro Gly Met Asn
            325                 330                 335

His Arg Val Glu Ile Thr Glu Gly Ile Leu Ala Asp Glu Cys Ala Ala
        340                 345                 350

Leu Leu Cys Tyr Phe Phe Arg Met Pro Arg Gln Val Phe Asn Ala Gln
    355                 360                 365

Lys Lys Ala Gln Ser Ser Thr Asp Ser Gly Ser Ser Gly Gly Ser
370                 375                 380

Ser Gly Ser Glu Thr Pro Gly Thr Ser Glu Ser Ala Thr Pro Glu Ser
385                 390                 395                 400

Ser Gly Gly Ser Ser Gly Gly Ser Leu Lys Asp Lys Lys Tyr Ser Ile
            405                 410                 415

Gly Leu Ala Ile Gly Thr Asn Ser Val Gly Trp Ala Val Ile Thr Asp
            420                 425                 430

Glu Tyr Lys Val Pro Ser Lys Lys Phe Lys Val Leu Gly Asn Thr Asp
    435                 440                 445

Arg His Ser Ile Lys Lys Asn Leu Ile Gly Ala Leu Leu Phe Asp Ser
450                 455                 460

Gly Glu Thr Ala Glu Ala Thr Arg Leu Lys Arg Thr Ala Arg Arg Arg
465                 470                 475                 480

Tyr Thr Arg Arg Lys Asn Arg Ile Cys Tyr Leu Gln Glu Ile Phe Ser
                485                 490                 495

Asn Glu Met Ala Lys Val Asp Asp Ser Phe Phe His Arg Leu Glu Glu
            500                 505                 510

Ser Phe Leu Val Glu Glu Asp Lys Lys His Glu Arg His Pro Ile Phe
    515                 520                 525

Gly Asn Ile Val Asp Glu Val Ala Tyr His Glu Lys Tyr Pro Thr Ile
530                 535                 540

Tyr His Leu Arg Lys Lys Leu Val Asp Ser Thr Asp Lys Ala Asp Leu
545                 550                 555                 560

Arg Leu Ile Tyr Leu Ala Leu Ala His Met Ile Lys Phe Arg Gly His
                565                 570                 575

Phe Leu Ile Glu Gly Asp Leu Asn Pro Asp Asn Ser Asp Val Asp Lys
            580                 585                 590

Leu Phe Ile Gln Leu Val Gln Thr Tyr Asn Gln Leu Phe Glu Glu Asn
    595                 600                 605

Pro Ile Asn Ala Ser Gly Val Asp Ala Lys Ala Ile Leu Ser Ala Arg
610                 615                 620

Leu Ser Lys Ser Arg Arg Leu Glu Asn Leu Ile Ala Gln Leu Pro Gly
625                 630                 635                 640

Glu Lys Lys Asn Gly Leu Phe Gly Asn Leu Ile Ala Leu Ser Leu Gly
                645                 650                 655

Leu Thr Pro Asn Phe Lys Ser Asn Phe Asp Leu Ala Glu Asp Ala Lys
            660                 665                 670

Leu Gln Leu Ser Lys Asp Thr Tyr Asp Asp Asp Leu Asp Asn Leu Leu
    675                 680                 685

Ala Gln Ile Gly Asp Gln Tyr Ala Asp Leu Phe Leu Ala Ala Lys Asn
690                 695                 700

Leu Ser Asp Ala Ile Leu Leu Ser Asp Ile Leu Arg Val Asn Thr Glu
705                 710                 715                 720

Ile Thr Lys Ala Pro Leu Ser Ala Ser Met Ile Lys Arg Tyr Asp Glu

```
                725                 730                 735
His His Gln Asp Leu Thr Leu Lys Ala Leu Val Arg Gln Gln Leu
            740                 745                 750
Pro Glu Lys Tyr Lys Glu Ile Phe Phe Asp Gln Ser Lys Asn Gly Tyr
            755                 760                 765
Ala Gly Tyr Ile Asp Gly Gly Ala Ser Gln Glu Glu Phe Tyr Lys Phe
            770                 775                 780
Ile Lys Pro Ile Leu Glu Lys Met Asp Gly Thr Glu Glu Leu Leu Val
785                 790                 795                 800
Lys Leu Asn Arg Glu Asp Leu Leu Arg Lys Gln Arg Thr Phe Asp Asn
                805                 810                 815
Gly Ser Ile Pro His Gln Ile His Leu Gly Glu Leu His Ala Ile Leu
                820                 825                 830
Arg Arg Gln Glu Asp Phe Tyr Pro Phe Leu Lys Asp Asn Arg Glu Lys
                835                 840                 845
Ile Glu Lys Ile Leu Thr Phe Arg Ile Pro Tyr Tyr Val Gly Pro Leu
                850                 855                 860
Ala Arg Gly Asn Ser Arg Phe Ala Trp Met Thr Arg Lys Ser Glu Glu
865                 870                 875                 880
Thr Ile Thr Pro Trp Asn Phe Glu Glu Val Val Asp Lys Gly Ala Ser
                885                 890                 895
Ala Gln Ser Phe Ile Glu Arg Met Thr Asn Phe Asp Lys Asn Leu Pro
                900                 905                 910
Asn Glu Lys Val Leu Pro Lys His Ser Leu Leu Tyr Glu Tyr Phe Thr
                915                 920                 925
Val Tyr Asn Glu Leu Thr Lys Val Lys Tyr Val Thr Glu Gly Met Arg
                930                 935                 940
Lys Pro Ala Phe Leu Ser Gly Glu Gln Lys Lys Ala Ile Val Asp Leu
945                 950                 955                 960
Leu Phe Lys Thr Asn Arg Lys Val Thr Val Lys Gln Leu Lys Glu Asp
                965                 970                 975
Tyr Phe Lys Lys Ile Glu Cys Phe Asp Ser Val Glu Ile Ser Gly Val
                980                 985                 990
Glu Asp Arg Phe Asn Ala Ser Leu Gly Thr Tyr His Asp Leu Leu Lys
            995                 1000                1005
Ile Ile Lys Asp Lys Asp Phe Leu Asp Asn Glu Glu Asn Glu Asp
            1010                1015                1020
Ile Leu Glu Asp Ile Val Leu Thr Leu Thr Leu Phe Glu Asp Arg
            1025                1030                1035
Glu Met Ile Glu Glu Arg Leu Lys Thr Tyr Ala His Leu Phe Asp
            1040                1045                1050
Asp Lys Val Met Lys Gln Leu Lys Arg Arg Arg Tyr Thr Gly Trp
            1055                1060                1065
Gly Arg Leu Ser Arg Lys Leu Ile Asn Gly Ile Arg Asp Lys Gln
            1070                1075                1080
Ser Gly Lys Thr Ile Leu Asp Phe Leu Lys Ser Asp Gly Phe Ala
            1085                1090                1095
Asn Arg Asn Phe Met Gln Leu Ile His Asp Asp Ser Leu Thr Phe
            1100                1105                1110
Lys Glu Asp Ile Gln Lys Ala Gln Val Ser Gly Gln Gly Asp Ser
            1115                1120                1125
Leu His Glu His Ile Ala Asn Leu Ala Gly Ser Pro Ala Ile Lys
            1130                1135                1140
```

```
Lys Gly Ile Leu Gln Thr Val Lys Val Asp Glu Leu Val Lys
    1145                1150            1155

Val Met Gly Arg His Lys Pro Glu Asn Ile Val Ile Glu Met Ala
    1160                1165            1170

Arg Glu Asn Gln Thr Thr Gln Lys Gly Gln Lys Asn Ser Arg Glu
    1175                1180            1185

Arg Met Lys Arg Ile Glu Glu Gly Ile Lys Glu Leu Gly Ser Gln
    1190                1195            1200

Ile Leu Lys Glu His Pro Val Glu Asn Thr Gln Leu Gln Asn Glu
    1205                1210            1215

Lys Leu Tyr Leu Tyr Tyr Leu Gln Asn Gly Arg Asp Met Tyr Val
    1220                1225            1230

Asp Gln Glu Leu Asp Ile Asn Arg Leu Ser Asp Tyr Asp Val Asp
    1235                1240            1245

His Ile Val Pro Gln Ser Phe Leu Lys Asp Asp Ser Ile Asp Asn
    1250                1255            1260

Lys Val Leu Thr Arg Ser Asp Lys Asn Arg Gly Lys Ser Asp Asn
    1265                1270            1275

Val Pro Ser Glu Glu Val Val Lys Lys Met Lys Asn Tyr Trp Arg
    1280                1285            1290

Gln Leu Leu Asn Ala Lys Leu Ile Thr Gln Arg Lys Phe Asp Asn
    1295                1300            1305

Leu Thr Lys Ala Glu Arg Gly Gly Leu Ser Glu Leu Asp Lys Ala
    1310                1315            1320

Gly Phe Ile Lys Arg Gln Leu Val Glu Thr Arg Gln Ile Thr Lys
    1325                1330            1335

His Val Ala Gln Ile Leu Asp Ser Arg Met Asn Thr Lys Tyr Asp
    1340                1345            1350

Glu Asn Asp Lys Leu Ile Arg Glu Val Lys Val Ile Thr Leu Lys
    1355                1360            1365

Ser Lys Leu Val Ser Asp Phe Arg Lys Asp Phe Gln Phe Tyr Lys
    1370                1375            1380

Val Arg Glu Ile Asn Asn Tyr His His Ala His Asp Ala Tyr Leu
    1385                1390            1395

Asn Ala Val Val Gly Thr Ala Leu Ile Lys Lys Tyr Pro Lys Leu
    1400                1405            1410

Glu Ser Glu Phe Val Tyr Gly Asp Tyr Lys Val Tyr Asp Val Arg
    1415                1420            1425

Lys Met Ile Ala Lys Ser Glu Gln Glu Ile Gly Lys Ala Thr Ala
    1430                1435            1440

Lys Tyr Phe Phe Tyr Ser Asn Ile Met Asn Phe Phe Lys Thr Glu
    1445                1450            1455

Ile Thr Leu Ala Asn Gly Glu Ile Arg Lys Arg Pro Leu Ile Glu
    1460                1465            1470

Thr Asn Gly Glu Thr Gly Glu Ile Val Trp Asp Lys Gly Arg Asp
    1475                1480            1485

Phe Ala Thr Val Arg Lys Val Leu Ser Met Pro Gln Val Asn Ile
    1490                1495            1500

Val Lys Lys Thr Glu Val Gln Thr Gly Gly Phe Ser Lys Glu Ser
    1505                1510            1515

Ile Leu Pro Lys Arg Asn Ser Asp Lys Leu Ile Ala Arg Lys Lys
    1520                1525            1530
```

```
Asp Trp Asp Pro Lys Lys Tyr Gly Gly Phe Asp Ser Pro Thr Val
    1535            1540                1545

Ala Tyr Ser Val Leu Val Ala Lys Val Glu Lys Gly Lys Ser
    1550            1555                1560

Lys Lys Leu Lys Ser Val Lys Glu Leu Leu Gly Ile Thr Ile Met
    1565            1570                1575

Glu Arg Ser Ser Phe Glu Lys Asn Pro Ile Asp Phe Leu Glu Ala
    1580            1585                1590

Lys Gly Tyr Lys Glu Val Lys Lys Asp Leu Ile Ile Lys Leu Pro
    1595            1600                1605

Lys Tyr Ser Leu Phe Glu Leu Glu Asn Gly Arg Lys Arg Met Leu
    1610            1615                1620

Ala Ser Ala Gly Glu Leu Gln Lys Gly Asn Glu Leu Ala Leu Pro
    1625            1630                1635

Ser Lys Tyr Val Asn Phe Leu Tyr Leu Ala Ser His Tyr Glu Lys
    1640            1645                1650

Leu Lys Gly Ser Pro Glu Asp Asn Glu Gln Lys Gln Leu Phe Val
    1655            1660                1665

Glu Gln His Lys His Tyr Leu Asp Glu Ile Ile Glu Gln Ile Ser
    1670            1675                1680

Glu Phe Ser Lys Arg Val Ile Leu Ala Asp Ala Asn Leu Asp Lys
    1685            1690                1695

Val Leu Ser Ala Tyr Asn Lys His Arg Asp Lys Pro Ile Arg Glu
    1700            1705                1710

Gln Ala Glu Asn Ile Ile His Leu Phe Thr Leu Thr Asn Leu Gly
    1715            1720                1725

Ala Pro Ala Ala Phe Lys Tyr Phe Asp Thr Thr Ile Asp Arg Lys
    1730            1735                1740

Arg Tyr Thr Ser Thr Lys Glu Val Leu Asp Ala Thr Leu Ile His
    1745            1750                1755

Gln Ser Ile Thr Gly Leu Tyr Glu Thr Arg Ile Asp Leu Ser Gln
    1760            1765                1770

Leu Gly Gly Asp Lys Arg Pro Ala Ala Thr Lys Lys Ala Gly Gln
    1775            1780                1785

Ala Lys Lys Lys Lys
    1790

<210> SEQ ID NO 34
<211> LENGTH: 1777
<212> TYPE: PRT
<213> ORGANISM: Artificial Sequence
<220> FEATURE:
<223> OTHER INFORMATION: Description of Artificial Sequence: Synthetic
      PABE-2 polypeptide

<400> SEQUENCE: 34

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
                20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Met Gln Asn Tyr Arg Leu Ile Asp Ala Thr Leu
65                  70                  75                  80
```

```
Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
               100                 105                 110

Ala Ala Gly Ser Leu Met Asp Val Leu His His Pro Gly Met Asn His
               115                 120                 125

Arg Val Glu Ile Thr Glu Gly Ile Leu Ala Asp Glu Cys Ala Ala Leu
               130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Gly Gly Ser Ser
               165                 170                 175

Gly Ser Glu Thr Pro Gly Thr Ser Glu Ser Ala Thr Pro Glu Ser Ser
               180                 185                 190

Gly Gly Ser Ser Gly Gly Ser Ser Glu Val Glu Phe Ser His Glu Tyr
               195                 200                 205

Trp Met Arg His Ala Leu Thr Leu Ala Lys Arg Ala Arg Asp Glu Arg
               210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
               245                 250                 255

Glu Ile Met Ala Leu Arg Gln Gly Gly Leu Val Met Gln Asn Tyr Arg
               260                 265                 270

Leu Ile Asp Ala Thr Leu Tyr Val Thr Phe Glu Pro Cys Val Met Cys
               275                 280                 285

Ala Gly Ala Met Ile His Ser Arg Ile Gly Arg Val Val Phe Gly Val
               290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
               325                 330                 335

Asp Glu Cys Ala Ala Leu Leu Cys Tyr Phe Phe Arg Met Pro Arg Gln
               340                 345                 350

Val Phe Asn Ala Gln Lys Lys Ala Gln Ser Ser Thr Asp Ser Gly Gly
               355                 360                 365

Ser Ser Gly Gly Ser Ser Gly Ser Glu Thr Pro Gly Thr Ser Glu Ser
370                 375                 380

Ala Thr Pro Glu Ser Ser Gly Gly Ser Ser Gly Gly Ser Leu Lys Asp
385                 390                 395                 400

Lys Lys Tyr Ser Ile Gly Leu Ala Ile Gly Thr Asn Ser Val Gly Trp
               405                 410                 415

Ala Val Ile Thr Asp Glu Tyr Lys Val Pro Ser Lys Lys Phe Lys Val
               420                 425                 430

Leu Gly Asn Thr Asp Arg His Ser Ile Lys Lys Asn Leu Ile Gly Ala
               435                 440                 445

Leu Leu Phe Asp Ser Gly Glu Thr Ala Glu Ala Thr Arg Leu Lys Arg
               450                 455                 460

Thr Ala Arg Arg Arg Tyr Thr Arg Arg Lys Asn Arg Ile Cys Tyr Leu
465                 470                 475                 480

Gln Glu Ile Phe Ser Asn Glu Met Ala Lys Val Asp Asp Ser Phe Phe
               485                 490                 495
```

-continued

His Arg Leu Glu Glu Ser Phe Leu Val Glu Asp Lys Lys His Glu
            500                 505                 510

Arg His Pro Ile Phe Gly Asn Ile Val Asp Glu Val Ala Tyr His Glu
            515                 520                 525

Lys Tyr Pro Thr Ile Tyr His Leu Arg Lys Lys Leu Val Asp Ser Thr
            530                 535                 540

Asp Lys Ala Asp Leu Arg Leu Ile Tyr Leu Ala Leu Ala His Met Ile
545                 550                 555                 560

Lys Phe Arg Gly His Phe Leu Ile Glu Gly Asp Leu Asn Pro Asp Asn
                565                 570                 575

Ser Asp Val Asp Lys Leu Phe Ile Gln Leu Val Gln Thr Tyr Asn Gln
            580                 585                 590

Leu Phe Glu Glu Asn Pro Ile Asn Ala Ser Gly Val Asp Ala Lys Ala
            595                 600                 605

Ile Leu Ser Ala Arg Leu Ser Lys Ser Arg Arg Leu Glu Asn Leu Ile
610                 615                 620

Ala Gln Leu Pro Gly Glu Lys Lys Asn Gly Leu Phe Gly Asn Leu Ile
625                 630                 635                 640

Ala Leu Ser Leu Gly Leu Thr Pro Asn Phe Lys Ser Asn Phe Asp Leu
            645                 650                 655

Ala Glu Asp Ala Lys Leu Gln Leu Ser Lys Asp Thr Tyr Asp Asp Asp
            660                 665                 670

Leu Asp Asn Leu Leu Ala Gln Ile Gly Asp Gln Tyr Ala Asp Leu Phe
            675                 680                 685

Leu Ala Ala Lys Asn Leu Ser Asp Ala Ile Leu Leu Ser Asp Ile Leu
            690                 695                 700

Arg Val Asn Thr Glu Ile Thr Lys Ala Pro Leu Ser Ala Ser Met Ile
705                 710                 715                 720

Lys Arg Tyr Asp Glu His His Gln Asp Leu Thr Leu Leu Lys Ala Leu
            725                 730                 735

Val Arg Gln Gln Leu Pro Glu Lys Tyr Lys Glu Ile Phe Phe Asp Gln
            740                 745                 750

Ser Lys Asn Gly Tyr Ala Gly Tyr Ile Asp Gly Gly Ala Ser Gln Glu
            755                 760                 765

Glu Phe Tyr Lys Phe Ile Lys Pro Ile Leu Glu Lys Met Asp Gly Thr
            770                 775                 780

Glu Glu Leu Leu Val Lys Leu Asn Arg Glu Asp Leu Leu Arg Lys Gln
785                 790                 795                 800

Arg Thr Phe Asp Asn Gly Ser Ile Pro His Gln Ile His Leu Gly Glu
            805                 810                 815

Leu His Ala Ile Leu Arg Arg Gln Glu Asp Phe Tyr Pro Phe Leu Lys
            820                 825                 830

Asp Asn Arg Glu Lys Ile Glu Lys Ile Leu Thr Phe Arg Ile Pro Tyr
            835                 840                 845

Tyr Val Gly Pro Leu Ala Arg Gly Asn Ser Arg Phe Ala Trp Met Thr
850                 855                 860

Arg Lys Ser Glu Glu Thr Ile Thr Pro Trp Asn Phe Glu Glu Val Val
865                 870                 875                 880

Asp Lys Gly Ala Ser Ala Gln Ser Phe Ile Glu Arg Met Thr Asn Phe
            885                 890                 895

Asp Lys Asn Leu Pro Asn Glu Lys Val Leu Pro Lys His Ser Leu Leu
            900                 905                 910

Tyr Glu Tyr Phe Thr Val Tyr Asn Glu Leu Thr Lys Val Lys Tyr Val

-continued

```
            915                 920                 925
Thr Glu Gly Met Arg Lys Pro Ala Phe Leu Ser Gly Glu Gln Lys Lys
            930                 935                 940

Ala Ile Val Asp Leu Leu Phe Lys Thr Asn Arg Lys Val Thr Val Lys
945                 950                 955                 960

Gln Leu Lys Glu Asp Tyr Phe Lys Lys Ile Glu Cys Phe Asp Ser Val
                965                 970                 975

Glu Ile Ser Gly Val Glu Asp Arg Phe Asn Ala Ser Leu Gly Thr Tyr
            980                 985                 990

His Asp Leu Leu Lys Ile Ile Lys Asp Lys Asp Phe Leu Asp Asn Glu
                995                1000                1005

Glu Asn Glu Asp Ile Leu Glu Asp Ile Val Leu Thr Leu Thr Leu
        1010                1015                1020

Phe Glu Asp Arg Glu Met Ile Glu Glu Arg Leu Lys Thr Tyr Ala
        1025                1030                1035

His Leu Phe Asp Asp Lys Val Met Lys Gln Leu Lys Arg Arg Arg
        1040                1045                1050

Tyr Thr Gly Trp Gly Arg Leu Ser Arg Lys Leu Ile Asn Gly Ile
        1055                1060                1065

Arg Asp Lys Gln Ser Gly Lys Thr Ile Leu Asp Phe Leu Lys Ser
        1070                1075                1080

Asp Gly Phe Ala Asn Arg Asn Phe Met Gln Leu Ile His Asp Asp
        1085                1090                1095

Ser Leu Thr Phe Lys Glu Asp Ile Gln Lys Ala Gln Val Ser Gly
        1100                1105                1110

Gln Gly Asp Ser Leu His Glu His Ile Ala Asn Leu Ala Gly Ser
        1115                1120                1125

Pro Ala Ile Lys Lys Gly Ile Leu Gln Thr Val Lys Val Val Asp
        1130                1135                1140

Glu Leu Val Lys Val Met Gly Arg His Lys Pro Glu Asn Ile Val
        1145                1150                1155

Ile Glu Met Ala Arg Glu Asn Gln Thr Thr Gln Lys Gly Gln Lys
        1160                1165                1170

Asn Ser Arg Glu Arg Met Lys Arg Ile Glu Glu Gly Ile Lys Glu
        1175                1180                1185

Leu Gly Ser Gln Ile Leu Lys Glu His Pro Val Glu Asn Thr Gln
        1190                1195                1200

Leu Gln Asn Glu Lys Leu Tyr Leu Tyr Tyr Leu Gln Asn Gly Arg
        1205                1210                1215

Asp Met Tyr Val Asp Gln Glu Leu Asp Ile Asn Arg Leu Ser Asp
        1220                1225                1230

Tyr Asp Val Asp His Ile Val Pro Gln Ser Phe Leu Lys Asp Asp
        1235                1240                1245

Ser Ile Asp Asn Lys Val Leu Thr Arg Ser Asp Lys Asn Arg Gly
        1250                1255                1260

Lys Ser Asp Asn Val Pro Ser Glu Glu Val Val Lys Lys Met Lys
        1265                1270                1275

Asn Tyr Trp Arg Gln Leu Leu Asn Ala Lys Leu Ile Thr Gln Arg
        1280                1285                1290

Lys Phe Asp Asn Leu Thr Lys Ala Glu Arg Gly Gly Leu Ser Glu
        1295                1300                1305

Leu Asp Lys Ala Gly Phe Ile Lys Arg Gln Leu Val Glu Thr Arg
        1310                1315                1320
```

```
Gln Ile Thr Lys His Val Ala Gln Ile Leu Asp Ser Arg Met Asn
1325                1330                1335

Thr Lys Tyr Asp Glu Asn Asp Lys Leu Ile Arg Glu Val Lys Val
1340                1345                1350

Ile Thr Leu Lys Ser Lys Leu Val Ser Asp Phe Arg Lys Asp Phe
1355                1360                1365

Gln Phe Tyr Lys Val Arg Glu Ile Asn Asn Tyr His His Ala His
1370                1375                1380

Asp Ala Tyr Leu Asn Ala Val Val Gly Thr Ala Leu Ile Lys Lys
1385                1390                1395

Tyr Pro Lys Leu Glu Ser Glu Phe Val Tyr Gly Asp Tyr Lys Val
1400                1405                1410

Tyr Asp Val Arg Lys Met Ile Ala Lys Ser Glu Gln Glu Ile Gly
1415                1420                1425

Lys Ala Thr Ala Lys Tyr Phe Phe Tyr Ser Asn Ile Met Asn Phe
1430                1435                1440

Phe Lys Thr Glu Ile Thr Leu Ala Asn Gly Glu Ile Arg Lys Arg
1445                1450                1455

Pro Leu Ile Glu Thr Asn Gly Glu Thr Gly Glu Ile Val Trp Asp
1460                1465                1470

Lys Gly Arg Asp Phe Ala Thr Val Arg Lys Val Leu Ser Met Pro
1475                1480                1485

Gln Val Asn Ile Val Lys Lys Thr Glu Val Gln Thr Gly Gly Phe
1490                1495                1500

Ser Lys Glu Ser Ile Leu Pro Lys Arg Asn Ser Asp Lys Leu Ile
1505                1510                1515

Ala Arg Lys Lys Asp Trp Asp Pro Lys Lys Tyr Gly Gly Phe Asp
1520                1525                1530

Ser Pro Thr Val Ala Tyr Ser Val Leu Val Val Ala Lys Val Glu
1535                1540                1545

Lys Gly Lys Ser Lys Lys Leu Lys Ser Val Lys Glu Leu Leu Gly
1550                1555                1560

Ile Thr Ile Met Glu Arg Ser Ser Phe Glu Lys Asn Pro Ile Asp
1565                1570                1575

Phe Leu Glu Ala Lys Gly Tyr Lys Glu Val Lys Lys Asp Leu Ile
1580                1585                1590

Ile Lys Leu Pro Lys Tyr Ser Leu Phe Glu Leu Glu Asn Gly Arg
1595                1600                1605

Lys Arg Met Leu Ala Ser Ala Gly Glu Leu Gln Lys Gly Asn Glu
1610                1615                1620

Leu Ala Leu Pro Ser Lys Tyr Val Asn Phe Leu Tyr Leu Ala Ser
1625                1630                1635

His Tyr Glu Lys Leu Lys Gly Ser Pro Glu Asp Asn Glu Gln Lys
1640                1645                1650

Gln Leu Phe Val Glu Gln His Lys His Tyr Leu Asp Glu Ile Ile
1655                1660                1665

Glu Gln Ile Ser Glu Phe Ser Lys Arg Val Ile Leu Ala Asp Ala
1670                1675                1680

Asn Leu Asp Lys Val Leu Ser Ala Tyr Asn Lys His Arg Asp Lys
1685                1690                1695

Pro Ile Arg Glu Gln Ala Glu Asn Ile Ile His Leu Phe Thr Leu
1700                1705                1710
```

-continued

```
Thr Asn Leu Gly Ala Pro Ala Ala Phe Lys Tyr Phe Asp Thr Thr
    1715                1720                1725

Ile Asp Arg Lys Arg Tyr Ser Thr Lys Glu Val Leu Asp Ala
    1730                1735                1740

Thr Leu Ile His Gln Ser Ile Thr Gly Leu Tyr Glu Thr Arg Ile
    1745                1750                1755

Asp Leu Ser Gln Leu Gly Gly Asp Ser Gly Gly Ser Pro Lys Lys
    1760                1765                1770

Lys Arg Lys Val
    1775

<210> SEQ ID NO 35
<211> LENGTH: 1793
<212> TYPE: PRT
<213> ORGANISM: Artificial Sequence
<220> FEATURE:
<223> OTHER INFORMATION: Description of Artificial Sequence: Synthetic
      PABE-3 polypeptide

<400> SEQUENCE: 35

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
                20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
        195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
        275                 280                 285
```

```
Ala Gly Ala Met Ile His Ser Arg Ile Gly Arg Val Val Phe Gly Val
        290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                    325                 330                 335

Asp Glu Cys Ala Ala Leu Leu Cys Tyr Phe Phe Arg Met Pro Arg Gln
                340                 345                 350

Val Phe Asn Ala Gln Lys Lys Ala Gln Ser Ser Thr Asp Ser Gly Gly
            355                 360                 365

Ser Ser Gly Gly Ser Ser Gly Ser Glu Thr Pro Gly Thr Ser Glu Ser
        370                 375                 380

Ala Thr Pro Glu Ser Ser Gly Gly Ser Ser Gly Gly Ser Leu Lys Pro
385                 390                 395                 400

Lys Lys Lys Arg Lys Val Ser Gly Gly Ser Asp Lys Lys Tyr Ser Ile
                405                 410                 415

Gly Leu Ala Ile Gly Thr Asn Ser Val Gly Trp Ala Val Ile Thr Asp
                420                 425                 430

Glu Tyr Lys Val Pro Ser Lys Lys Phe Lys Val Leu Gly Asn Thr Asp
            435                 440                 445

Arg His Ser Ile Lys Lys Asn Leu Ile Gly Ala Leu Leu Phe Asp Ser
        450                 455                 460

Gly Glu Thr Ala Glu Ala Thr Arg Leu Lys Arg Thr Ala Arg Arg Arg
465                 470                 475                 480

Tyr Thr Arg Arg Lys Asn Arg Ile Cys Tyr Leu Gln Glu Ile Phe Ser
                485                 490                 495

Asn Glu Met Ala Lys Val Asp Asp Ser Phe Phe His Arg Leu Glu Glu
                500                 505                 510

Ser Phe Leu Val Glu Glu Asp Lys Lys His Glu Arg His Pro Ile Phe
            515                 520                 525

Gly Asn Ile Val Asp Glu Val Ala Tyr His Glu Lys Tyr Pro Thr Ile
        530                 535                 540

Tyr His Leu Arg Lys Lys Leu Val Asp Ser Thr Asp Lys Ala Asp Leu
545                 550                 555                 560

Arg Leu Ile Tyr Leu Ala Leu Ala His Met Ile Lys Phe Arg Gly His
                565                 570                 575

Phe Leu Ile Glu Gly Asp Leu Asn Pro Asp Asn Ser Asp Val Asp Lys
                580                 585                 590

Leu Phe Ile Gln Leu Val Gln Thr Tyr Asn Gln Leu Phe Glu Glu Asn
            595                 600                 605

Pro Ile Asn Ala Ser Gly Val Asp Ala Lys Ala Ile Leu Ser Ala Arg
        610                 615                 620

Leu Ser Lys Ser Arg Arg Leu Glu Asn Leu Ile Ala Gln Leu Pro Gly
625                 630                 635                 640

Glu Lys Lys Asn Gly Leu Phe Gly Asn Leu Ile Ala Leu Ser Leu Gly
                645                 650                 655

Leu Thr Pro Asn Phe Lys Ser Asn Phe Asp Leu Ala Glu Asp Ala Lys
                660                 665                 670

Leu Gln Leu Ser Lys Asp Thr Tyr Asp Asp Asp Leu Asp Asn Leu Leu
            675                 680                 685

Ala Gln Ile Gly Asp Gln Tyr Ala Asp Leu Phe Leu Ala Ala Lys Asn
        690                 695                 700
```

```
Leu Ser Asp Ala Ile Leu Leu Ser Asp Ile Leu Arg Val Asn Thr Glu
705                 710                 715                 720

Ile Thr Lys Ala Pro Leu Ser Ala Ser Met Ile Lys Arg Tyr Asp Glu
                725                 730                 735

His His Gln Asp Leu Thr Leu Leu Lys Ala Leu Val Arg Gln Gln Leu
            740                 745                 750

Pro Glu Lys Tyr Lys Glu Ile Phe Phe Asp Gln Ser Lys Asn Gly Tyr
        755                 760                 765

Ala Gly Tyr Ile Asp Gly Gly Ala Ser Gln Glu Glu Phe Tyr Lys Phe
770                 775                 780

Ile Lys Pro Ile Leu Glu Lys Met Asp Gly Thr Glu Glu Leu Leu Val
785                 790                 795                 800

Lys Leu Asn Arg Glu Asp Leu Leu Arg Lys Gln Arg Thr Phe Asp Asn
                805                 810                 815

Gly Ser Ile Pro His Gln Ile His Leu Gly Glu Leu His Ala Ile Leu
                820                 825                 830

Arg Arg Gln Glu Asp Phe Tyr Pro Phe Leu Lys Asp Asn Arg Glu Lys
                835                 840                 845

Ile Glu Lys Ile Leu Thr Phe Arg Ile Pro Tyr Tyr Val Gly Pro Leu
850                 855                 860

Ala Arg Gly Asn Ser Arg Phe Ala Trp Met Thr Arg Lys Ser Glu Glu
865                 870                 875                 880

Thr Ile Thr Pro Trp Asn Phe Glu Glu Val Val Asp Lys Gly Ala Ser
                885                 890                 895

Ala Gln Ser Phe Ile Glu Arg Met Thr Asn Phe Asp Lys Asn Leu Pro
                900                 905                 910

Asn Glu Lys Val Leu Pro Lys His Ser Leu Leu Tyr Glu Tyr Phe Thr
                915                 920                 925

Val Tyr Asn Glu Leu Thr Lys Val Lys Tyr Val Thr Glu Gly Met Arg
930                 935                 940

Lys Pro Ala Phe Leu Ser Gly Glu Gln Lys Lys Ala Ile Val Asp Leu
945                 950                 955                 960

Leu Phe Lys Thr Asn Arg Lys Val Thr Val Lys Gln Leu Lys Glu Asp
                965                 970                 975

Tyr Phe Lys Lys Ile Glu Cys Phe Asp Ser Val Glu Ile Ser Gly Val
                980                 985                 990

Glu Asp Arg Phe Asn Ala Ser Leu Gly Thr Tyr His Asp Leu Leu Lys
            995                 1000                1005

Ile Ile Lys Asp Lys Asp Phe Leu Asp Asn Glu Glu Asn Glu Asp
    1010                1015                1020

Ile Leu Glu Asp Ile Val Leu Thr Leu Thr Leu Phe Glu Asp Arg
    1025                1030                1035

Glu Met Ile Glu Glu Arg Leu Lys Thr Tyr Ala His Leu Phe Asp
    1040                1045                1050

Asp Lys Val Met Lys Gln Leu Lys Arg Arg Arg Tyr Thr Gly Trp
    1055                1060                1065

Gly Arg Leu Ser Arg Lys Leu Ile Asn Gly Ile Arg Asp Lys Gln
    1070                1075                1080

Ser Gly Lys Thr Ile Leu Asp Phe Leu Lys Ser Asp Gly Phe Ala
    1085                1090                1095

Asn Arg Asn Phe Met Gln Leu Ile His Asp Asp Ser Leu Thr Phe
    1100                1105                1110

Lys Glu Asp Ile Gln Lys Ala Gln Val Ser Gly Gln Gly Asp Ser
```

```
              1115                1120                 1125

Leu His Glu His Ile Ala Asn Leu Ala Gly Ser Pro Ala Ile Lys
         1130                1135                 1140

Lys Gly Ile Leu Gln Thr Val Lys Val Val Asp Glu Leu Val Lys
         1145                1150                 1155

Val Met Gly Arg His Lys Pro Glu Asn Ile Val Ile Glu Met Ala
         1160                1165                 1170

Arg Glu Asn Gln Thr Thr Gln Lys Gly Gln Lys Asn Ser Arg Glu
         1175                1180                 1185

Arg Met Lys Arg Ile Glu Glu Gly Ile Lys Glu Leu Gly Ser Gln
         1190                1195                 1200

Ile Leu Lys Glu His Pro Val Glu Asn Thr Gln Leu Gln Asn Glu
         1205                1210                 1215

Lys Leu Tyr Leu Tyr Tyr Leu Gln Asn Gly Arg Asp Met Tyr Val
         1220                1225                 1230

Asp Gln Glu Leu Asp Ile Asn Arg Leu Ser Asp Tyr Asp Val Asp
         1235                1240                 1245

His Ile Val Pro Gln Ser Phe Leu Lys Asp Asp Ser Ile Asp Asn
         1250                1255                 1260

Lys Val Leu Thr Arg Ser Asp Lys Asn Arg Gly Lys Ser Asp Asn
         1265                1270                 1275

Val Pro Ser Glu Glu Val Val Lys Lys Met Lys Asn Tyr Trp Arg
         1280                1285                 1290

Gln Leu Leu Asn Ala Lys Leu Ile Thr Gln Arg Lys Phe Asp Asn
         1295                1300                 1305

Leu Thr Lys Ala Glu Arg Gly Gly Leu Ser Glu Leu Asp Lys Ala
         1310                1315                 1320

Gly Phe Ile Lys Arg Gln Leu Val Glu Thr Arg Gln Ile Thr Lys
         1325                1330                 1335

His Val Ala Gln Ile Leu Asp Ser Arg Met Asn Thr Lys Tyr Asp
         1340                1345                 1350

Glu Asn Asp Lys Leu Ile Arg Glu Val Lys Val Ile Thr Leu Lys
         1355                1360                 1365

Ser Lys Leu Val Ser Asp Phe Arg Lys Asp Phe Gln Phe Tyr Lys
         1370                1375                 1380

Val Arg Glu Ile Asn Asn Tyr His His Ala His Asp Ala Tyr Leu
         1385                1390                 1395

Asn Ala Val Val Gly Thr Ala Leu Ile Lys Lys Tyr Pro Lys Leu
         1400                1405                 1410

Glu Ser Glu Phe Val Tyr Gly Asp Tyr Lys Val Tyr Asp Val Arg
         1415                1420                 1425

Lys Met Ile Ala Lys Ser Glu Gln Glu Ile Gly Lys Ala Thr Ala
         1430                1435                 1440

Lys Tyr Phe Phe Tyr Ser Asn Ile Met Asn Phe Phe Lys Thr Glu
         1445                1450                 1455

Ile Thr Leu Ala Asn Gly Glu Ile Arg Lys Arg Pro Leu Ile Glu
         1460                1465                 1470

Thr Asn Gly Glu Thr Gly Glu Ile Val Trp Asp Lys Gly Arg Asp
         1475                1480                 1485

Phe Ala Thr Val Arg Lys Val Leu Ser Met Pro Gln Val Asn Ile
         1490                1495                 1500

Val Lys Lys Thr Glu Val Gln Thr Gly Gly Phe Ser Lys Glu Ser
         1505                1510                 1515
```

-continued

```
Ile Leu Pro Lys Arg Asn Ser Asp Lys Leu Ile Ala Arg Lys Lys
    1520                1525                1530

Asp Trp Asp Pro Lys Lys Tyr Gly Gly Phe Asp Ser Pro Thr Val
    1535                1540                1545

Ala Tyr Ser Val Leu Val Val Ala Lys Val Glu Lys Gly Lys Ser
    1550                1555                1560

Lys Lys Leu Lys Ser Val Lys Glu Leu Leu Gly Ile Thr Ile Met
    1565                1570                1575

Glu Arg Ser Ser Phe Glu Lys Asn Pro Ile Asp Phe Leu Glu Ala
    1580                1585                1590

Lys Gly Tyr Lys Glu Val Lys Lys Asp Leu Ile Ile Lys Leu Pro
    1595                1600                1605

Lys Tyr Ser Leu Phe Glu Leu Glu Asn Gly Arg Lys Arg Met Leu
    1610                1615                1620

Ala Ser Ala Gly Glu Leu Gln Lys Gly Asn Glu Leu Ala Leu Pro
    1625                1630                1635

Ser Lys Tyr Val Asn Phe Leu Tyr Leu Ala Ser His Tyr Glu Lys
    1640                1645                1650

Leu Lys Gly Ser Pro Glu Asp Asn Glu Gln Lys Gln Leu Phe Val
    1655                1660                1665

Glu Gln His Lys His Tyr Leu Asp Glu Ile Ile Glu Gln Ile Ser
    1670                1675                1680

Glu Phe Ser Lys Arg Val Ile Leu Ala Asp Ala Asn Leu Asp Lys
    1685                1690                1695

Val Leu Ser Ala Tyr Asn Lys His Arg Asp Lys Pro Ile Arg Glu
    1700                1705                1710

Gln Ala Glu Asn Ile Ile His Leu Phe Thr Leu Thr Asn Leu Gly
    1715                1720                1725

Ala Pro Ala Ala Phe Lys Tyr Phe Asp Thr Thr Ile Asp Arg Lys
    1730                1735                1740

Arg Tyr Thr Ser Thr Lys Glu Val Leu Asp Ala Thr Leu Ile His
    1745                1750                1755

Gln Ser Ile Thr Gly Leu Tyr Glu Thr Arg Ile Asp Leu Ser Gln
    1760                1765                1770

Leu Gly Gly Asp Lys Arg Pro Ala Ala Thr Lys Lys Ala Gly Gln
    1775                1780                1785

Ala Lys Lys Lys Lys
    1790

<210> SEQ ID NO 36
<211> LENGTH: 1793
<212> TYPE: PRT
<213> ORGANISM: Artificial Sequence
<220> FEATURE:
<223> OTHER INFORMATION: Description of Artificial Sequence: Synthetic
      PABE-4 polypeptide

<400> SEQUENCE: 36

Met Pro Lys Lys Lys Arg Lys Val Ser Gly Gly Ser Asp Lys Lys Tyr
1               5                   10                  15

Ser Ile Gly Leu Ala Ile Gly Thr Asn Ser Val Gly Trp Ala Val Ile
                20                  25                  30

Thr Asp Glu Tyr Lys Val Pro Ser Lys Lys Phe Lys Val Leu Gly Asn
            35                  40                  45

Thr Asp Arg His Ser Ile Lys Lys Asn Leu Ile Gly Ala Leu Leu Phe
```

```
                50                  55                  60
Asp Ser Gly Glu Thr Ala Glu Ala Thr Arg Leu Lys Arg Thr Ala Arg
65                  70                  75                  80

Arg Arg Tyr Thr Arg Arg Lys Asn Arg Ile Cys Tyr Leu Gln Glu Ile
                85                  90                  95

Phe Ser Asn Glu Met Ala Lys Val Asp Asp Ser Phe Phe His Arg Leu
                100                 105                 110

Glu Glu Ser Phe Leu Val Glu Glu Asp Lys Lys His Glu Arg His Pro
                115                 120                 125

Ile Phe Gly Asn Ile Val Asp Glu Val Ala Tyr His Glu Lys Tyr Pro
                130                 135                 140

Thr Ile Tyr His Leu Arg Lys Lys Leu Val Asp Ser Thr Asp Lys Ala
145                 150                 155                 160

Asp Leu Arg Leu Ile Tyr Leu Ala Leu Ala His Met Ile Lys Phe Arg
                165                 170                 175

Gly His Phe Leu Ile Glu Gly Asp Leu Asn Pro Asp Asn Ser Asp Val
                180                 185                 190

Asp Lys Leu Phe Ile Gln Leu Val Gln Thr Tyr Asn Gln Leu Phe Glu
                195                 200                 205

Glu Asn Pro Ile Asn Ala Ser Gly Val Asp Ala Lys Ala Ile Leu Ser
                210                 215                 220

Ala Arg Leu Ser Lys Ser Arg Arg Leu Glu Asn Leu Ile Ala Gln Leu
225                 230                 235                 240

Pro Gly Glu Lys Lys Asn Gly Leu Phe Gly Asn Leu Ile Ala Leu Ser
                245                 250                 255

Leu Gly Leu Thr Pro Asn Phe Lys Ser Asn Phe Asp Leu Ala Glu Asp
                260                 265                 270

Ala Lys Leu Gln Leu Ser Lys Asp Thr Tyr Asp Asp Leu Asp Asn
                275                 280                 285

Leu Leu Ala Gln Ile Gly Asp Gln Tyr Ala Asp Leu Phe Leu Ala Ala
                290                 295                 300

Lys Asn Leu Ser Asp Ala Ile Leu Leu Ser Asp Ile Leu Arg Val Asn
305                 310                 315                 320

Thr Glu Ile Thr Lys Ala Pro Leu Ser Ala Ser Met Ile Lys Arg Tyr
                325                 330                 335

Asp Glu His His Gln Asp Leu Thr Leu Leu Lys Ala Leu Val Arg Gln
                340                 345                 350

Gln Leu Pro Glu Lys Tyr Lys Glu Ile Phe Phe Asp Gln Ser Lys Asn
                355                 360                 365

Gly Tyr Ala Gly Tyr Ile Asp Gly Gly Ala Ser Gln Glu Glu Phe Tyr
                370                 375                 380

Lys Phe Ile Lys Pro Ile Leu Glu Lys Met Asp Gly Thr Glu Glu Leu
385                 390                 395                 400

Leu Val Lys Leu Asn Arg Glu Asp Leu Leu Arg Lys Gln Arg Thr Phe
                405                 410                 415

Asp Asn Gly Ser Ile Pro His Gln Ile His Leu Gly Glu Leu His Ala
                420                 425                 430

Ile Leu Arg Arg Gln Glu Asp Phe Tyr Pro Phe Leu Lys Asp Asn Arg
                435                 440                 445

Glu Lys Ile Glu Lys Ile Leu Thr Phe Arg Ile Pro Tyr Tyr Val Gly
                450                 455                 460

Pro Leu Ala Arg Gly Asn Ser Arg Phe Ala Trp Met Thr Arg Lys Ser
465                 470                 475                 480
```

```
Glu Glu Thr Ile Thr Pro Trp Asn Phe Glu Glu Val Val Asp Lys Gly
            485                 490                 495

Ala Ser Ala Gln Ser Phe Ile Glu Arg Met Thr Asn Phe Asp Lys Asn
            500                 505                 510

Leu Pro Asn Glu Lys Val Leu Pro Lys His Ser Leu Leu Tyr Glu Tyr
            515                 520                 525

Phe Thr Val Tyr Asn Glu Leu Thr Lys Val Lys Tyr Val Thr Glu Gly
            530                 535                 540

Met Arg Lys Pro Ala Phe Leu Ser Gly Glu Gln Lys Lys Ala Ile Val
545                 550                 555                 560

Asp Leu Leu Phe Lys Thr Asn Arg Lys Val Thr Val Lys Gln Leu Lys
            565                 570                 575

Glu Asp Tyr Phe Lys Lys Ile Glu Cys Phe Asp Ser Val Glu Ile Ser
            580                 585                 590

Gly Val Glu Asp Arg Phe Asn Ala Ser Leu Gly Thr Tyr His Asp Leu
            595                 600                 605

Leu Lys Ile Ile Lys Asp Lys Asp Phe Leu Asp Asn Glu Glu Asn Glu
            610                 615                 620

Asp Ile Leu Glu Asp Ile Val Leu Thr Leu Thr Leu Phe Glu Asp Arg
625                 630                 635                 640

Glu Met Ile Glu Glu Arg Leu Lys Thr Tyr Ala His Leu Phe Asp Asp
            645                 650                 655

Lys Val Met Lys Gln Leu Lys Arg Arg Arg Tyr Thr Gly Trp Gly Arg
            660                 665                 670

Leu Ser Arg Lys Leu Ile Asn Gly Ile Arg Asp Lys Gln Ser Gly Lys
            675                 680                 685

Thr Ile Leu Asp Phe Leu Lys Ser Asp Gly Phe Ala Asn Arg Asn Phe
            690                 695                 700

Met Gln Leu Ile His Asp Asp Ser Leu Thr Phe Lys Glu Asp Ile Gln
705                 710                 715                 720

Lys Ala Gln Val Ser Gly Gln Gly Asp Ser Leu His Glu His Ile Ala
            725                 730                 735

Asn Leu Ala Gly Ser Pro Ala Ile Lys Lys Gly Ile Leu Gln Thr Val
            740                 745                 750

Lys Val Val Asp Glu Leu Val Lys Val Met Gly Arg His Lys Pro Glu
            755                 760                 765

Asn Ile Val Ile Glu Met Ala Arg Glu Asn Gln Thr Thr Gln Lys Gly
            770                 775                 780

Gln Lys Asn Ser Arg Glu Arg Met Lys Arg Ile Glu Glu Gly Ile Lys
785                 790                 795                 800

Glu Leu Gly Ser Gln Ile Leu Lys Glu His Pro Val Glu Asn Thr Gln
            805                 810                 815

Leu Gln Asn Glu Lys Leu Tyr Leu Tyr Tyr Leu Gln Asn Gly Arg Asp
            820                 825                 830

Met Tyr Val Asp Gln Glu Leu Asp Ile Asn Arg Leu Ser Asp Tyr Asp
            835                 840                 845

Val Asp His Ile Val Pro Gln Ser Phe Leu Lys Asp Asp Ser Ile Asp
            850                 855                 860

Asn Lys Val Leu Thr Arg Ser Asp Lys Asn Arg Gly Lys Ser Asp Asn
865                 870                 875                 880

Val Pro Ser Glu Glu Val Val Lys Lys Met Lys Asn Tyr Trp Arg Gln
            885                 890                 895
```

```
Leu Leu Asn Ala Lys Leu Ile Thr Gln Arg Lys Phe Asp Asn Leu Thr
                900                 905                 910

Lys Ala Glu Arg Gly Gly Leu Ser Glu Leu Asp Lys Ala Gly Phe Ile
            915                 920                 925

Lys Arg Gln Leu Val Glu Thr Arg Gln Ile Thr Lys His Val Ala Gln
        930                 935                 940

Ile Leu Asp Ser Arg Met Asn Thr Lys Tyr Asp Glu Asn Asp Lys Leu
945                 950                 955                 960

Ile Arg Glu Val Lys Val Ile Thr Leu Lys Ser Lys Leu Val Ser Asp
                965                 970                 975

Phe Arg Lys Asp Phe Gln Phe Tyr Lys Val Arg Glu Ile Asn Asn Tyr
            980                 985                 990

His His Ala His Asp Ala Tyr Leu Asn Ala Val Val Gly Thr Ala Leu
        995                 1000                1005

Ile Lys Lys Tyr Pro Lys Leu Glu Ser Glu Phe Val Tyr Gly Asp
        1010                1015                1020

Tyr Lys Val Tyr Asp Val Arg Lys Met Ile Ala Lys Ser Glu Gln
        1025                1030                1035

Glu Ile Gly Lys Ala Thr Ala Lys Tyr Phe Phe Tyr Ser Asn Ile
        1040                1045                1050

Met Asn Phe Phe Lys Thr Glu Ile Thr Leu Ala Asn Gly Glu Ile
        1055                1060                1065

Arg Lys Arg Pro Leu Ile Glu Thr Asn Gly Glu Thr Gly Glu Ile
        1070                1075                1080

Val Trp Asp Lys Gly Arg Asp Phe Ala Thr Val Arg Lys Val Leu
        1085                1090                1095

Ser Met Pro Gln Val Asn Ile Val Lys Lys Thr Glu Val Gln Thr
        1100                1105                1110

Gly Gly Phe Ser Lys Glu Ser Ile Leu Pro Lys Arg Asn Ser Asp
        1115                1120                1125

Lys Leu Ile Ala Arg Lys Lys Asp Trp Asp Pro Lys Lys Tyr Gly
        1130                1135                1140

Gly Phe Asp Ser Pro Thr Val Ala Tyr Ser Val Leu Val Val Ala
        1145                1150                1155

Lys Val Glu Lys Gly Lys Ser Lys Lys Leu Lys Ser Val Lys Glu
        1160                1165                1170

Leu Leu Gly Ile Thr Ile Met Glu Arg Ser Ser Phe Glu Lys Asn
        1175                1180                1185

Pro Ile Asp Phe Leu Glu Ala Lys Gly Tyr Lys Glu Val Lys Lys
        1190                1195                1200

Asp Leu Ile Ile Lys Leu Pro Lys Tyr Ser Leu Phe Glu Leu Glu
        1205                1210                1215

Asn Gly Arg Lys Arg Met Leu Ala Ser Ala Gly Glu Leu Gln Lys
        1220                1225                1230

Gly Asn Glu Leu Ala Leu Pro Ser Lys Tyr Val Asn Phe Leu Tyr
        1235                1240                1245

Leu Ala Ser His Tyr Glu Lys Leu Lys Gly Ser Pro Glu Asp Asn
        1250                1255                1260

Glu Gln Lys Gln Leu Phe Val Glu Gln His Lys His Tyr Leu Asp
        1265                1270                1275

Glu Ile Ile Glu Gln Ile Ser Glu Phe Ser Lys Arg Val Ile Leu
        1280                1285                1290

Ala Asp Ala Asn Leu Asp Lys Val Leu Ser Ala Tyr Asn Lys His
```

```
            1295                1300                1305
Arg Asp Lys Pro Ile Arg Glu Gln Ala Glu Asn Ile Ile His Leu
    1310                1315                1320
Phe Thr Leu Thr Asn Leu Gly Ala Pro Ala Ala Phe Lys Tyr Phe
    1325                1330                1335
Asp Thr Thr Ile Asp Arg Lys Arg Tyr Thr Ser Thr Lys Glu Val
    1340                1345                1350
Leu Asp Ala Thr Leu Ile His Gln Ser Ile Thr Gly Leu Tyr Glu
    1355                1360                1365
Thr Arg Ile Asp Leu Ser Gln Leu Gly Gly Asp Glu Phe Ser Gly
    1370                1375                1380
Gly Ser Ser Gly Gly Ser Ser Gly Ser Glu Thr Pro Gly Thr Ser
    1385                1390                1395
Glu Ser Ala Thr Pro Glu Ser Ser Gly Gly Ser Ser Gly Gly Ser
    1400                1405                1410
Ser Glu Val Glu Phe Ser His Glu Tyr Trp Met Arg His Ala Leu
    1415                1420                1425
Thr Leu Ala Lys Arg Ala Trp Asp Glu Arg Glu Val Pro Val Gly
    1430                1435                1440
Ala Val Leu Val His Asn Asn Arg Val Ile Gly Glu Gly Trp Asn
    1445                1450                1455
Arg Pro Ile Gly Arg His Asp Pro Thr Ala His Ala Glu Ile Met
    1460                1465                1470
Ala Leu Arg Gln Gly Gly Leu Val Met Gln Asn Tyr Arg Leu Ile
    1475                1480                1485
Asp Ala Thr Leu Tyr Val Thr Leu Glu Pro Cys Val Met Cys Ala
    1490                1495                1500
Gly Ala Met Ile His Ser Arg Ile Gly Arg Val Val Phe Gly Ala
    1505                1510                1515
Arg Asp Ala Lys Thr Gly Ala Ala Gly Ser Leu Met Asp Val Leu
    1520                1525                1530
His His Pro Gly Met Asn His Arg Val Glu Ile Thr Glu Gly Ile
    1535                1540                1545
Leu Ala Asp Glu Cys Ala Ala Leu Leu Ser Asp Phe Phe Arg Met
    1550                1555                1560
Arg Arg Gln Glu Ile Lys Ala Gln Lys Lys Ala Gln Ser Ser Thr
    1565                1570                1575
Asp Ser Gly Gly Ser Ser Gly Gly Ser Ser Gly Ser Glu Thr Pro
    1580                1585                1590
Gly Thr Ser Glu Ser Ala Thr Pro Glu Ser Ser Gly Gly Ser Ser
    1595                1600                1605
Gly Gly Ser Ser Glu Val Glu Phe Ser His Glu Tyr Trp Met Arg
    1610                1615                1620
His Ala Leu Thr Leu Ala Lys Arg Ala Arg Asp Glu Arg Glu Val
    1625                1630                1635
Pro Val Gly Ala Val Leu Val Leu Asn Asn Arg Val Ile Gly Glu
    1640                1645                1650
Gly Trp Asn Arg Ala Ile Gly Leu His Asp Pro Thr Ala His Ala
    1655                1660                1665
Glu Ile Met Ala Leu Arg Gln Gly Gly Leu Val Met Gln Asn Tyr
    1670                1675                1680
Arg Leu Ile Asp Ala Thr Leu Tyr Val Thr Phe Glu Pro Cys Val
    1685                1690                1695
```

```
Met Cys Ala Gly Ala Met Ile His Ser Arg Ile Gly Arg Val Val
        1700                1705                1710

Phe Gly Val Arg Asn Ala Lys Thr Gly Ala Ala Gly Ser Leu Met
        1715                1720                1725

Asp Val Leu His Tyr Pro Gly Met Asn His Arg Val Glu Ile Thr
        1730                1735                1740

Glu Gly Ile Leu Ala Asp Glu Cys Ala Ala Leu Leu Cys Tyr Phe
        1745                1750                1755

Phe Arg Met Pro Arg Gln Val Phe Asn Ala Gln Lys Lys Ala Gln
        1760                1765                1770

Ser Ser Thr Asp Lys Arg Pro Ala Ala Thr Lys Lys Ala Gly Gln
        1775                1780                1785

Ala Lys Lys Lys Lys
        1790

<210> SEQ ID NO 37
<211> LENGTH: 1802
<212> TYPE: PRT
<213> ORGANISM: Artificial Sequence
<220> FEATURE:
<223> OTHER INFORMATION: Description of Artificial Sequence: Synthetic
      PABE-5 polypeptide

<400> SEQUENCE: 37

Met Pro Lys Lys Lys Arg Lys Val Ser Gly Gly Ser Asp Lys Lys Tyr
1               5                   10                  15

Ser Ile Gly Leu Ala Ile Gly Thr Asn Ser Val Gly Trp Ala Val Ile
            20                  25                  30

Thr Asp Glu Tyr Lys Val Pro Ser Lys Lys Phe Lys Val Leu Gly Asn
        35                  40                  45

Thr Asp Arg His Ser Ile Lys Lys Asn Leu Ile Gly Ala Leu Leu Phe
    50                  55                  60

Asp Ser Gly Glu Thr Ala Glu Ala Thr Arg Leu Lys Arg Thr Ala Arg
65                  70                  75                  80

Arg Arg Tyr Thr Arg Arg Lys Asn Arg Ile Cys Tyr Leu Gln Glu Ile
                85                  90                  95

Phe Ser Asn Glu Met Ala Lys Val Asp Asp Ser Phe Phe His Arg Leu
            100                 105                 110

Glu Glu Ser Phe Leu Val Glu Glu Asp Lys Lys His Glu Arg His Pro
        115                 120                 125

Ile Phe Gly Asn Ile Val Asp Glu Val Ala Tyr His Glu Lys Tyr Pro
    130                 135                 140

Thr Ile Tyr His Leu Arg Lys Lys Leu Val Asp Ser Thr Asp Lys Ala
145                 150                 155                 160

Asp Leu Arg Leu Ile Tyr Leu Ala Leu Ala His Met Ile Lys Phe Arg
                165                 170                 175

Gly His Phe Leu Ile Glu Gly Asp Leu Asn Pro Asp Asn Ser Asp Val
            180                 185                 190

Asp Lys Leu Phe Ile Gln Leu Val Gln Thr Tyr Asn Gln Leu Phe Glu
        195                 200                 205

Glu Asn Pro Ile Asn Ala Ser Gly Val Asp Ala Lys Ala Ile Leu Ser
    210                 215                 220

Ala Arg Leu Ser Lys Ser Arg Arg Leu Glu Asn Leu Ile Ala Gln Leu
225                 230                 235                 240

Pro Gly Glu Lys Lys Asn Gly Leu Phe Gly Asn Leu Ile Ala Leu Ser
```

```
              245                 250                 255
Leu Gly Leu Thr Pro Asn Phe Lys Ser Asn Phe Asp Leu Ala Glu Asp
            260                 265                 270
Ala Lys Leu Gln Leu Ser Lys Asp Thr Tyr Asp Asp Leu Asp Asn
        275                 280                 285
Leu Leu Ala Gln Ile Gly Asp Gln Tyr Ala Asp Leu Phe Leu Ala Ala
        290                 295                 300
Lys Asn Leu Ser Asp Ala Ile Leu Leu Ser Asp Ile Leu Arg Val Asn
305                 310                 315                 320
Thr Glu Ile Thr Lys Ala Pro Leu Ser Ala Ser Met Ile Lys Arg Tyr
                325                 330                 335
Asp Glu His His Gln Asp Leu Thr Leu Leu Lys Ala Leu Val Arg Gln
            340                 345                 350
Gln Leu Pro Glu Lys Tyr Lys Glu Ile Phe Phe Asp Gln Ser Lys Asn
            355                 360                 365
Gly Tyr Ala Gly Tyr Ile Asp Gly Gly Ala Ser Gln Glu Glu Phe Tyr
        370                 375                 380
Lys Phe Ile Lys Pro Ile Leu Glu Lys Met Asp Gly Thr Glu Glu Leu
385                 390                 395                 400
Leu Val Lys Leu Asn Arg Glu Asp Leu Leu Arg Lys Gln Arg Thr Phe
                405                 410                 415
Asp Asn Gly Ser Ile Pro His Gln Ile His Leu Gly Glu Leu His Ala
                420                 425                 430
Ile Leu Arg Arg Gln Glu Asp Phe Tyr Pro Phe Leu Lys Asp Asn Arg
            435                 440                 445
Glu Lys Ile Glu Lys Ile Leu Thr Phe Arg Ile Pro Tyr Tyr Val Gly
        450                 455                 460
Pro Leu Ala Arg Gly Asn Ser Arg Phe Ala Trp Met Thr Arg Lys Ser
465                 470                 475                 480
Glu Glu Thr Ile Thr Pro Trp Asn Phe Glu Glu Val Val Asp Lys Gly
                485                 490                 495
Ala Ser Ala Gln Ser Phe Ile Glu Arg Met Thr Asn Phe Asp Lys Asn
            500                 505                 510
Leu Pro Asn Glu Lys Val Leu Pro Lys His Ser Leu Leu Tyr Glu Tyr
        515                 520                 525
Phe Thr Val Tyr Asn Glu Leu Thr Lys Val Lys Tyr Val Thr Glu Gly
        530                 535                 540
Met Arg Lys Pro Ala Phe Leu Ser Gly Glu Gln Lys Lys Ala Ile Val
545                 550                 555                 560
Asp Leu Leu Phe Lys Thr Asn Arg Lys Val Thr Val Lys Gln Leu Lys
                565                 570                 575
Glu Asp Tyr Phe Lys Lys Ile Glu Cys Phe Asp Ser Val Glu Ile Ser
            580                 585                 590
Gly Val Glu Asp Arg Phe Asn Ala Ser Leu Gly Thr Tyr His Asp Leu
        595                 600                 605
Leu Lys Ile Ile Lys Asp Lys Asp Phe Leu Asp Asn Glu Glu Asn Glu
        610                 615                 620
Asp Ile Leu Glu Asp Ile Val Leu Thr Leu Thr Leu Phe Glu Asp Arg
625                 630                 635                 640
Glu Met Ile Glu Glu Arg Leu Lys Thr Tyr Ala His Leu Phe Asp Asp
                645                 650                 655
Lys Val Met Lys Gln Leu Lys Arg Arg Arg Tyr Thr Gly Trp Gly Arg
            660                 665                 670
```

```
Leu Ser Arg Lys Leu Ile Asn Gly Ile Arg Asp Lys Gln Ser Gly Lys
            675                 680                 685

Thr Ile Leu Asp Phe Leu Lys Ser Asp Gly Phe Ala Asn Arg Asn Phe
690                 695                 700

Met Gln Leu Ile His Asp Asp Ser Leu Thr Phe Lys Glu Asp Ile Gln
705                 710                 715                 720

Lys Ala Gln Val Ser Gly Gln Gly Asp Ser Leu His Glu His Ile Ala
                725                 730                 735

Asn Leu Ala Gly Ser Pro Ala Ile Lys Lys Gly Ile Leu Gln Thr Val
            740                 745                 750

Lys Val Val Asp Glu Leu Val Lys Val Met Gly Arg His Lys Pro Glu
            755                 760                 765

Asn Ile Val Ile Glu Met Ala Arg Glu Asn Gln Thr Thr Gln Lys Gly
770                 775                 780

Gln Lys Asn Ser Arg Glu Arg Met Lys Arg Ile Glu Glu Gly Ile Lys
785                 790                 795                 800

Glu Leu Gly Ser Gln Ile Leu Lys Glu His Pro Val Glu Asn Thr Gln
                805                 810                 815

Leu Gln Asn Glu Lys Leu Tyr Leu Tyr Tyr Leu Gln Asn Gly Arg Asp
            820                 825                 830

Met Tyr Val Asp Gln Glu Leu Asp Ile Asn Arg Leu Ser Asp Tyr Asp
            835                 840                 845

Val Asp His Ile Val Pro Gln Ser Phe Leu Lys Asp Asp Ser Ile Asp
850                 855                 860

Asn Lys Val Leu Thr Arg Ser Asp Lys Asn Arg Gly Lys Ser Asp Asn
865                 870                 875                 880

Val Pro Ser Glu Glu Val Val Lys Lys Met Lys Asn Tyr Trp Arg Gln
                885                 890                 895

Leu Leu Asn Ala Lys Leu Ile Thr Gln Arg Lys Phe Asp Asn Leu Thr
            900                 905                 910

Lys Ala Glu Arg Gly Gly Leu Ser Glu Leu Asp Lys Ala Gly Phe Ile
            915                 920                 925

Lys Arg Gln Leu Val Glu Thr Arg Gln Ile Thr Lys His Val Ala Gln
930                 935                 940

Ile Leu Asp Ser Arg Met Asn Thr Lys Tyr Asp Glu Asn Asp Lys Leu
945                 950                 955                 960

Ile Arg Glu Val Lys Val Ile Thr Leu Lys Ser Lys Leu Val Ser Asp
                965                 970                 975

Phe Arg Lys Asp Phe Gln Phe Tyr Lys Val Arg Glu Ile Asn Asn Tyr
            980                 985                 990

His His Ala His Asp Ala Tyr Leu Asn Ala Val Val Gly Thr Ala Leu
            995                 1000                1005

Ile Lys Lys Tyr Pro Lys Leu Glu Ser Glu Phe Val Tyr Gly Asp
    1010                1015                1020

Tyr Lys Val Tyr Asp Val Arg Lys Met Ile Ala Lys Ser Glu Gln
    1025                1030                1035

Glu Ile Gly Lys Ala Thr Ala Lys Tyr Phe Phe Tyr Ser Asn Ile
    1040                1045                1050

Met Asn Phe Phe Lys Thr Glu Ile Thr Leu Ala Asn Gly Glu Ile
    1055                1060                1065

Arg Lys Arg Pro Leu Ile Glu Thr Asn Gly Glu Thr Gly Glu Ile
    1070                1075                1080
```

```
Val Trp Asp Lys Gly Arg Asp Phe Ala Thr Val Arg Lys Val Leu
1085                1090                1095

Ser Met Pro Gln Val Asn Ile Val Lys Lys Thr Glu Val Gln Thr
1100                1105                1110

Gly Gly Phe Ser Lys Glu Ser Ile Leu Pro Lys Arg Asn Ser Asp
1115                1120                1125

Lys Leu Ile Ala Arg Lys Lys Asp Trp Asp Pro Lys Lys Tyr Gly
1130                1135                1140

Gly Phe Asp Ser Pro Thr Val Ala Tyr Ser Val Leu Val Val Ala
1145                1150                1155

Lys Val Glu Lys Gly Lys Ser Lys Lys Leu Lys Ser Val Lys Glu
1160                1165                1170

Leu Leu Gly Ile Thr Ile Met Glu Arg Ser Ser Phe Glu Lys Asn
1175                1180                1185

Pro Ile Asp Phe Leu Glu Ala Lys Gly Tyr Lys Glu Val Lys Lys
1190                1195                1200

Asp Leu Ile Ile Lys Leu Pro Lys Tyr Ser Leu Phe Glu Leu Glu
1205                1210                1215

Asn Gly Arg Lys Arg Met Leu Ala Ser Ala Gly Glu Leu Gln Lys
1220                1225                1230

Gly Asn Glu Leu Ala Leu Pro Ser Lys Tyr Val Asn Phe Leu Tyr
1235                1240                1245

Leu Ala Ser His Tyr Glu Lys Leu Lys Gly Ser Pro Glu Asp Asn
1250                1255                1260

Glu Gln Lys Gln Leu Phe Val Glu Gln His Lys His Tyr Leu Asp
1265                1270                1275

Glu Ile Ile Glu Gln Ile Ser Glu Phe Ser Lys Arg Val Ile Leu
1280                1285                1290

Ala Asp Ala Asn Leu Asp Lys Val Leu Ser Ala Tyr Asn Lys His
1295                1300                1305

Arg Asp Lys Pro Ile Arg Glu Gln Ala Glu Asn Ile Ile His Leu
1310                1315                1320

Phe Thr Leu Thr Asn Leu Gly Ala Pro Ala Ala Phe Lys Tyr Phe
1325                1330                1335

Asp Thr Thr Ile Asp Arg Lys Arg Tyr Thr Ser Thr Lys Glu Val
1340                1345                1350

Leu Asp Ala Thr Leu Ile His Gln Ser Ile Thr Gly Leu Tyr Glu
1355                1360                1365

Thr Arg Ile Asp Leu Ser Gln Leu Gly Gly Asp Glu Phe Pro Lys
1370                1375                1380

Lys Lys Arg Lys Val Glu Phe Ser Gly Gly Ser Gly Gly Ser
1385                1390                1395

Ser Gly Ser Glu Thr Pro Gly Thr Ser Glu Ser Ala Thr Pro Glu
1400                1405                1410

Ser Ser Gly Gly Ser Ser Gly Gly Ser Ser Glu Val Glu Phe Ser
1415                1420                1425

His Glu Tyr Trp Met Arg His Ala Leu Thr Leu Ala Lys Arg Ala
1430                1435                1440

Trp Asp Glu Arg Glu Val Pro Val Gly Ala Val Leu Val His Asn
1445                1450                1455

Asn Arg Val Ile Gly Glu Gly Trp Asn Arg Pro Ile Gly Arg His
1460                1465                1470

Asp Pro Thr Ala His Ala Glu Ile Met Ala Leu Arg Gln Gly Gly
```

```
            1475                1480                1485

Leu Val Met Gln Asn Tyr Arg Leu Ile Asp Ala Thr Leu Tyr Val
        1490                1495                1500

Thr Leu Glu Pro Cys Val Met Cys Ala Gly Ala Met Ile His Ser
        1505                1510                1515

Arg Ile Gly Arg Val Val Phe Gly Ala Arg Asp Ala Lys Thr Gly
        1520                1525                1530

Ala Ala Gly Ser Leu Met Asp Val Leu His His Pro Gly Met Asn
        1535                1540                1545

His Arg Val Glu Ile Thr Glu Gly Ile Leu Ala Asp Glu Cys Ala
        1550                1555                1560

Ala Leu Leu Ser Asp Phe Phe Arg Met Arg Arg Gln Glu Ile Lys
        1565                1570                1575

Ala Gln Lys Lys Ala Gln Ser Ser Thr Asp Ser Gly Gly Ser Ser
        1580                1585                1590

Gly Gly Ser Ser Gly Ser Glu Thr Pro Gly Thr Ser Glu Ser Ala
        1595                1600                1605

Thr Pro Glu Ser Ser Gly Gly Ser Ser Gly Gly Ser Ser Glu Val
        1610                1615                1620

Glu Phe Ser His Glu Tyr Trp Met Arg His Ala Leu Thr Leu Ala
        1625                1630                1635

Lys Arg Ala Arg Asp Glu Arg Glu Val Pro Val Gly Ala Val Leu
        1640                1645                1650

Val Leu Asn Asn Arg Val Ile Gly Glu Gly Trp Asn Arg Ala Ile
        1655                1660                1665

Gly Leu His Asp Pro Thr Ala His Ala Glu Ile Met Ala Leu Arg
        1670                1675                1680

Gln Gly Gly Leu Val Met Gln Asn Tyr Arg Leu Ile Asp Ala Thr
        1685                1690                1695

Leu Tyr Val Thr Phe Glu Pro Cys Val Met Cys Ala Gly Ala Met
        1700                1705                1710

Ile His Ser Arg Ile Gly Arg Val Val Phe Gly Val Arg Asn Ala
        1715                1720                1725

Lys Thr Gly Ala Ala Gly Ser Leu Met Asp Val Leu His Tyr Pro
        1730                1735                1740

Gly Met Asn His Arg Val Glu Ile Thr Glu Gly Ile Leu Ala Asp
        1745                1750                1755

Glu Cys Ala Ala Leu Leu Cys Tyr Phe Phe Arg Met Pro Arg Gln
        1760                1765                1770

Val Phe Asn Ala Gln Lys Lys Ala Gln Ser Ser Thr Asp Lys Arg
        1775                1780                1785

Pro Ala Ala Thr Lys Lys Ala Gly Gln Ala Lys Lys Lys Lys
        1790                1795                1800

<210> SEQ ID NO 38
<211> LENGTH: 1788
<212> TYPE: PRT
<213> ORGANISM: Artificial Sequence
<220> FEATURE:
<223> OTHER INFORMATION: Description of Artificial Sequence: Synthetic
      PABE-6 polypeptide

<400> SEQUENCE: 38

Met Ser Glu Val Glu Phe Ser His Glu Tyr Trp Met Arg His Ala Leu
1               5                   10                  15
```

```
Thr Leu Ala Lys Arg Ala Trp Asp Glu Arg Glu Val Pro Val Gly Ala
                20                  25                  30
Val Leu Val His Asn Asn Arg Val Ile Gly Glu Gly Trp Asn Arg Pro
            35                  40                  45
Ile Gly Arg His Asp Pro Thr Ala His Ala Glu Ile Met Ala Leu Arg
 50                  55                  60
Gln Gly Gly Leu Val Met Gln Asn Tyr Arg Leu Ile Asp Ala Thr Leu
 65                  70                  75                  80
Tyr Val Thr Leu Glu Pro Cys Val Met Cys Ala Gly Ala Met Ile His
                85                  90                  95
Ser Arg Ile Gly Arg Val Val Phe Gly Ala Arg Asp Ala Lys Thr Gly
            100                 105                 110
Ala Ala Gly Ser Leu Met Asp Val Leu His His Pro Gly Met Asn His
            115                 120                 125
Arg Val Glu Ile Thr Glu Gly Ile Leu Ala Asp Glu Cys Ala Ala Leu
            130                 135                 140
Leu Ser Asp Phe Phe Arg Met Arg Arg Gln Glu Ile Lys Ala Gln Lys
145                 150                 155                 160
Lys Ala Gln Ser Ser Thr Asp Ser Gly Gly Ser Ser Gly Gly Ser Ser
                165                 170                 175
Gly Ser Glu Thr Pro Gly Thr Ser Glu Ser Ala Thr Pro Glu Ser Ser
            180                 185                 190
Gly Gly Ser Ser Gly Gly Ser Ser Glu Val Glu Phe Ser His Glu Tyr
            195                 200                 205
Trp Met Arg His Ala Leu Thr Leu Ala Lys Arg Ala Arg Asp Glu Arg
            210                 215                 220
Glu Val Pro Val Gly Ala Val Leu Val Leu Asn Asn Arg Val Ile Gly
225                 230                 235                 240
Glu Gly Trp Asn Arg Ala Ile Gly Leu His Asp Pro Thr Ala His Ala
                245                 250                 255
Glu Ile Met Ala Leu Arg Gln Gly Gly Leu Val Met Gln Asn Tyr Arg
            260                 265                 270
Leu Ile Asp Ala Thr Leu Tyr Val Thr Phe Glu Pro Cys Val Met Cys
            275                 280                 285
Ala Gly Ala Met Ile His Ser Arg Ile Gly Arg Val Val Phe Gly Val
            290                 295                 300
Arg Asn Ala Lys Thr Gly Ala Ala Gly Ser Leu Met Asp Val Leu His
305                 310                 315                 320
Tyr Pro Gly Met Asn His Arg Val Glu Ile Thr Glu Gly Ile Leu Ala
                325                 330                 335
Asp Glu Cys Ala Ala Leu Leu Cys Tyr Phe Phe Arg Met Pro Arg Gln
            340                 345                 350
Val Phe Asn Ala Gln Lys Lys Ala Gln Ser Ser Thr Asp Ser Gly Gly
            355                 360                 365
Ser Ser Gly Gly Ser Ser Gly Ser Glu Thr Pro Gly Thr Ser Glu Ser
            370                 375                 380
Ala Thr Pro Glu Ser Ser Gly Gly Ser Ser Gly Gly Ser Leu Lys Asp
385                 390                 395                 400
Lys Lys Tyr Ser Ile Gly Leu Ala Ile Gly Thr Asn Ser Val Gly Trp
                405                 410                 415
Ala Val Ile Thr Asp Glu Tyr Lys Val Pro Ser Lys Lys Phe Lys Val
            420                 425                 430
Leu Gly Asn Thr Asp Arg His Ser Ile Lys Lys Asn Leu Ile Gly Ala
```

```
            435                 440                 445
Leu Leu Phe Asp Ser Gly Glu Thr Ala Glu Ala Thr Arg Leu Lys Arg
    450                 455                 460

Thr Ala Arg Arg Arg Tyr Thr Arg Arg Lys Asn Arg Ile Cys Tyr Leu
465                 470                 475                 480

Gln Glu Ile Phe Ser Asn Glu Met Ala Lys Val Asp Asp Ser Phe Phe
                    485                 490                 495

His Arg Leu Glu Glu Ser Phe Leu Val Glu Glu Asp Lys Lys His Glu
                500                 505                 510

Arg His Pro Ile Phe Gly Asn Ile Val Asp Glu Val Ala Tyr His Glu
            515                 520                 525

Lys Tyr Pro Thr Ile Tyr His Leu Arg Lys Lys Leu Val Asp Ser Thr
        530                 535                 540

Asp Lys Ala Asp Leu Arg Leu Ile Tyr Leu Ala Leu Ala His Met Ile
545                 550                 555                 560

Lys Phe Arg Gly His Phe Leu Ile Glu Gly Asp Leu Asn Pro Asp Asn
                    565                 570                 575

Ser Asp Val Asp Lys Leu Phe Ile Gln Leu Val Gln Thr Tyr Asn Gln
                580                 585                 590

Leu Phe Glu Glu Asn Pro Ile Asn Ala Ser Gly Val Asp Ala Lys Ala
            595                 600                 605

Ile Leu Ser Ala Arg Leu Ser Lys Ser Arg Arg Leu Glu Asn Leu Ile
        610                 615                 620

Ala Gln Leu Pro Gly Glu Lys Lys Asn Gly Leu Phe Gly Asn Leu Ile
625                 630                 635                 640

Ala Leu Ser Leu Gly Leu Thr Pro Asn Phe Lys Ser Asn Phe Asp Leu
                    645                 650                 655

Ala Glu Asp Ala Lys Leu Gln Leu Ser Lys Asp Thr Tyr Asp Asp Asp
                660                 665                 670

Leu Asp Asn Leu Leu Ala Gln Ile Gly Asp Gln Tyr Ala Asp Leu Phe
            675                 680                 685

Leu Ala Ala Lys Asn Leu Ser Asp Ala Ile Leu Leu Ser Asp Ile Leu
        690                 695                 700

Arg Val Asn Thr Glu Ile Thr Lys Ala Pro Leu Ser Ala Ser Met Ile
705                 710                 715                 720

Lys Arg Tyr Asp Glu His His Gln Asp Leu Thr Leu Leu Lys Ala Leu
                    725                 730                 735

Val Arg Gln Gln Leu Pro Glu Lys Tyr Lys Glu Ile Phe Phe Asp Gln
                740                 745                 750

Ser Lys Asn Gly Tyr Ala Gly Tyr Ile Asp Gly Gly Ala Ser Gln Glu
            755                 760                 765

Glu Phe Tyr Lys Phe Ile Lys Pro Ile Leu Glu Lys Met Asp Gly Thr
        770                 775                 780

Glu Glu Leu Leu Val Lys Leu Asn Arg Glu Asp Leu Leu Arg Lys Gln
785                 790                 795                 800

Arg Thr Phe Asp Asn Gly Ser Ile Pro His Gln Ile His Leu Gly Glu
                    805                 810                 815

Leu His Ala Ile Leu Arg Arg Gln Glu Asp Phe Tyr Pro Phe Leu Lys
                820                 825                 830

Asp Asn Arg Glu Lys Ile Glu Lys Ile Leu Thr Phe Arg Ile Pro Tyr
            835                 840                 845

Tyr Val Gly Pro Leu Ala Arg Gly Asn Ser Arg Phe Ala Trp Met Thr
        850                 855                 860
```

```
Arg Lys Ser Glu Glu Thr Ile Thr Pro Trp Asn Phe Glu Glu Val Val
865                 870                 875                 880

Asp Lys Gly Ala Ser Ala Gln Ser Phe Ile Glu Arg Met Thr Asn Phe
                885                 890                 895

Asp Lys Asn Leu Pro Asn Glu Lys Val Leu Pro Lys His Ser Leu Leu
        900                 905                 910

Tyr Glu Tyr Phe Thr Val Tyr Asn Glu Leu Thr Lys Val Lys Tyr Val
            915                 920                 925

Thr Glu Gly Met Arg Lys Pro Ala Phe Leu Ser Gly Glu Gln Lys Lys
930                 935                 940

Ala Ile Val Asp Leu Leu Phe Lys Thr Asn Arg Lys Val Thr Val Lys
945                 950                 955                 960

Gln Leu Lys Glu Asp Tyr Phe Lys Lys Ile Glu Cys Phe Asp Ser Val
                965                 970                 975

Glu Ile Ser Gly Val Glu Asp Arg Phe Asn Ala Ser Leu Gly Thr Tyr
            980                 985                 990

His Asp Leu Leu Lys Ile Ile Lys Asp Lys Asp Phe Leu Asp Asn Glu
        995                 1000                1005

Glu Asn Glu Asp Ile Leu Glu Asp Ile Val Leu Thr Leu Thr Leu
    1010                1015                1020

Phe Glu Asp Arg Glu Met Ile Glu Glu Arg Leu Lys Thr Tyr Ala
    1025                1030                1035

His Leu Phe Asp Asp Lys Val Met Lys Gln Leu Lys Arg Arg Arg
    1040                1045                1050

Tyr Thr Gly Trp Gly Arg Leu Ser Arg Lys Leu Ile Asn Gly Ile
    1055                1060                1065

Arg Asp Lys Gln Ser Gly Lys Thr Ile Leu Asp Phe Leu Lys Ser
    1070                1075                1080

Asp Gly Phe Ala Asn Arg Asn Phe Met Gln Leu Ile His Asp Asp
    1085                1090                1095

Ser Leu Thr Phe Lys Glu Asp Ile Gln Lys Ala Gln Val Ser Gly
    1100                1105                1110

Gln Gly Asp Ser Leu His Glu His Ile Ala Asn Leu Ala Gly Ser
    1115                1120                1125

Pro Ala Ile Lys Lys Gly Ile Leu Gln Thr Val Lys Val Val Asp
    1130                1135                1140

Glu Leu Val Lys Val Met Gly Arg His Lys Pro Glu Asn Ile Val
    1145                1150                1155

Ile Glu Met Ala Arg Glu Asn Gln Thr Thr Gln Lys Gly Gln Lys
    1160                1165                1170

Asn Ser Arg Glu Arg Met Lys Arg Ile Glu Glu Gly Ile Lys Glu
    1175                1180                1185

Leu Gly Ser Gln Ile Leu Lys Glu His Pro Val Glu Asn Thr Gln
    1190                1195                1200

Leu Gln Asn Glu Lys Leu Tyr Leu Tyr Tyr Leu Gln Asn Gly Arg
    1205                1210                1215

Asp Met Tyr Val Asp Gln Glu Leu Asp Ile Asn Arg Leu Ser Asp
    1220                1225                1230

Tyr Asp Val Asp His Ile Val Pro Gln Ser Phe Leu Lys Asp Asp
    1235                1240                1245

Ser Ile Asp Asn Lys Val Leu Thr Arg Ser Asp Lys Asn Arg Gly
    1250                1255                1260
```

```
Lys Ser Asp Asn Val Pro Ser Glu Glu Val Val Lys Lys Met Lys
1265                1270                1275

Asn Tyr Trp Arg Gln Leu Leu Asn Ala Lys Leu Ile Thr Gln Arg
1280                1285                1290

Lys Phe Asp Asn Leu Thr Lys Ala Glu Arg Gly Gly Leu Ser Glu
1295                1300                1305

Leu Asp Lys Ala Gly Phe Ile Lys Arg Gln Leu Val Glu Thr Arg
1310                1315                1320

Gln Ile Thr Lys His Val Ala Gln Ile Leu Asp Ser Arg Met Asn
1325                1330                1335

Thr Lys Tyr Asp Glu Asn Asp Lys Leu Ile Arg Glu Val Lys Val
1340                1345                1350

Ile Thr Leu Lys Ser Lys Leu Val Ser Asp Phe Arg Lys Asp Phe
1355                1360                1365

Gln Phe Tyr Lys Val Arg Glu Ile Asn Asn Tyr His His Ala His
1370                1375                1380

Asp Ala Tyr Leu Asn Ala Val Val Gly Thr Ala Leu Ile Lys Lys
1385                1390                1395

Tyr Pro Lys Leu Glu Ser Glu Phe Val Tyr Gly Asp Tyr Lys Val
1400                1405                1410

Tyr Asp Val Arg Lys Met Ile Ala Lys Ser Glu Gln Glu Ile Gly
1415                1420                1425

Lys Ala Thr Ala Lys Tyr Phe Phe Tyr Ser Asn Ile Met Asn Phe
1430                1435                1440

Phe Lys Thr Glu Ile Thr Leu Ala Asn Gly Glu Ile Arg Lys Arg
1445                1450                1455

Pro Leu Ile Glu Thr Asn Gly Glu Thr Gly Glu Ile Val Trp Asp
1460                1465                1470

Lys Gly Arg Asp Phe Ala Thr Val Arg Lys Val Leu Ser Met Pro
1475                1480                1485

Gln Val Asn Ile Val Lys Lys Thr Glu Val Gln Thr Gly Gly Phe
1490                1495                1500

Ser Lys Glu Ser Ile Leu Pro Lys Arg Asn Ser Asp Lys Leu Ile
1505                1510                1515

Ala Arg Lys Lys Asp Trp Asp Pro Lys Lys Tyr Gly Gly Phe Asp
1520                1525                1530

Ser Pro Thr Val Ala Tyr Ser Val Leu Val Val Ala Lys Val Glu
1535                1540                1545

Lys Gly Lys Ser Lys Lys Leu Lys Ser Val Lys Glu Leu Leu Gly
1550                1555                1560

Ile Thr Ile Met Glu Arg Ser Ser Phe Glu Lys Asn Pro Ile Asp
1565                1570                1575

Phe Leu Glu Ala Lys Gly Tyr Lys Glu Val Lys Lys Asp Leu Ile
1580                1585                1590

Ile Lys Leu Pro Lys Tyr Ser Leu Phe Glu Leu Glu Asn Gly Arg
1595                1600                1605

Lys Arg Met Leu Ala Ser Ala Gly Glu Leu Gln Lys Gly Asn Glu
1610                1615                1620

Leu Ala Leu Pro Ser Lys Tyr Val Asn Phe Leu Tyr Leu Ala Ser
1625                1630                1635

His Tyr Glu Lys Leu Lys Gly Ser Pro Glu Asp Asn Glu Gln Lys
1640                1645                1650

Gln Leu Phe Val Glu Gln His Lys His Tyr Leu Asp Glu Ile Ile
```

-continued

```
                1655                1660                1665

Glu Gln Ile Ser Glu Phe Ser Lys Arg Val Ile Leu Ala Asp Ala
            1670                1675                1680

Asn Leu Asp Lys Val Leu Ser Ala Tyr Asn Lys His Arg Asp Lys
            1685                1690                1695

Pro Ile Arg Glu Gln Ala Glu Asn Ile Ile His Leu Phe Thr Leu
            1700                1705                1710

Thr Asn Leu Gly Ala Pro Ala Phe Lys Tyr Phe Asp Thr Thr
            1715                1720                1725

Ile Asp Arg Lys Arg Tyr Thr Ser Thr Lys Glu Val Leu Asp Ala
            1730                1735                1740

Thr Leu Ile His Gln Ser Ile Thr Gly Leu Tyr Glu Thr Arg Ile
            1745                1750                1755

Asp Leu Ser Gln Leu Gly Gly Asp Ser Gly Gly Ser Pro Lys Lys
            1760                1765                1770

Lys Arg Lys Val Ser Gly Gly Ser Pro Lys Lys Lys Arg Lys Val
            1775                1780                1785

<210> SEQ ID NO 39
<211> LENGTH: 1799
<212> TYPE: PRT
<213> ORGANISM: Artificial Sequence
<220> FEATURE:
<223> OTHER INFORMATION: Description of Artificial Sequence: Synthetic
      PABE-7 polypeptide

<400> SEQUENCE: 39

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
                20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
                100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
        130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Gly Gly Ser Ser
                165                 170                 175

Gly Ser Glu Thr Pro Gly Thr Ser Glu Ser Ala Thr Pro Glu Ser Ser
                180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
        210                 215                 220
```

```
Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
        260                 265                 270

Leu Ile Asp Ala Thr Leu Tyr Val Thr Phe Glu Pro Cys Val Met Cys
    275                 280                 285

Ala Gly Ala Met Ile His Ser Arg Ile Gly Arg Val Val Phe Gly Val
290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
        340                 345                 350

Val Phe Asn Ala Gln Lys Lys Ala Gln Ser Ser Thr Asp Ser Gly Gly
    355                 360                 365

Ser Ser Gly Gly Ser Ser Gly Ser Glu Thr Pro Gly Thr Ser Glu Ser
370                 375                 380

Ala Thr Pro Glu Ser Ser Gly Gly Ser Ser Gly Gly Ser Leu Lys Asp
385                 390                 395                 400

Lys Lys Tyr Ser Ile Gly Leu Ala Ile Gly Thr Asn Ser Val Gly Trp
            405                 410                 415

Ala Val Ile Thr Asp Glu Tyr Lys Val Pro Ser Lys Lys Phe Lys Val
        420                 425                 430

Leu Gly Asn Thr Asp Arg His Ser Ile Lys Lys Asn Leu Ile Gly Ala
    435                 440                 445

Leu Leu Phe Asp Ser Gly Glu Thr Ala Glu Ala Thr Arg Leu Lys Arg
450                 455                 460

Thr Ala Arg Arg Arg Tyr Thr Arg Arg Lys Asn Arg Ile Cys Tyr Leu
465                 470                 475                 480

Gln Glu Ile Phe Ser Asn Glu Met Ala Lys Val Asp Asp Ser Phe Phe
            485                 490                 495

His Arg Leu Glu Glu Ser Phe Leu Val Glu Glu Asp Lys Lys His Glu
        500                 505                 510

Arg His Pro Ile Phe Gly Asn Ile Val Asp Glu Val Ala Tyr His Glu
    515                 520                 525

Lys Tyr Pro Thr Ile Tyr His Leu Arg Lys Lys Leu Val Asp Ser Thr
530                 535                 540

Asp Lys Ala Asp Leu Arg Leu Ile Tyr Leu Ala Leu Ala His Met Ile
545                 550                 555                 560

Lys Phe Arg Gly His Phe Leu Ile Glu Gly Asp Leu Asn Pro Asp Asn
            565                 570                 575

Ser Asp Val Asp Lys Leu Phe Ile Gln Leu Val Gln Thr Tyr Asn Gln
        580                 585                 590

Leu Phe Glu Glu Asn Pro Ile Asn Ala Ser Gly Val Asp Ala Lys Ala
    595                 600                 605

Ile Leu Ser Ala Arg Leu Ser Lys Ser Arg Arg Leu Glu Asn Leu Ile
610                 615                 620

Ala Gln Leu Pro Gly Glu Lys Lys Asn Gly Leu Phe Gly Asn Leu Ile
625                 630                 635                 640

Ala Leu Ser Leu Gly Leu Thr Pro Asn Phe Lys Ser Asn Phe Asp Leu
```

```
                645                 650                 655
Ala Glu Asp Ala Lys Leu Gln Leu Ser Lys Asp Thr Tyr Asp Asp Asp
                660                 665                 670

Leu Asp Asn Leu Leu Ala Gln Ile Gly Asp Gln Tyr Ala Asp Leu Phe
                675                 680                 685

Leu Ala Ala Lys Asn Leu Ser Asp Ala Ile Leu Leu Ser Asp Ile Leu
            690                 695                 700

Arg Val Asn Thr Glu Ile Thr Lys Ala Pro Leu Ser Ala Ser Met Ile
705                 710                 715                 720

Lys Arg Tyr Asp Glu His His Gln Asp Leu Thr Leu Leu Lys Ala Leu
                725                 730                 735

Val Arg Gln Gln Leu Pro Glu Lys Tyr Lys Glu Ile Phe Phe Asp Gln
                740                 745                 750

Ser Lys Asn Gly Tyr Ala Gly Tyr Ile Asp Gly Gly Ala Ser Gln Glu
                755                 760                 765

Glu Phe Tyr Lys Phe Ile Lys Pro Ile Leu Glu Lys Met Asp Gly Thr
770                 775                 780

Glu Glu Leu Leu Val Lys Leu Asn Arg Glu Asp Leu Leu Arg Lys Gln
785                 790                 795                 800

Arg Thr Phe Asp Asn Gly Ser Ile Pro His Gln Ile His Leu Gly Glu
                805                 810                 815

Leu His Ala Ile Leu Arg Arg Gln Glu Asp Phe Tyr Pro Phe Leu Lys
                820                 825                 830

Asp Asn Arg Glu Lys Ile Glu Lys Ile Leu Thr Phe Arg Ile Pro Tyr
                835                 840                 845

Tyr Val Gly Pro Leu Ala Arg Gly Asn Ser Arg Phe Ala Trp Met Thr
850                 855                 860

Arg Lys Ser Glu Glu Thr Ile Thr Pro Trp Asn Phe Glu Glu Val Val
865                 870                 875                 880

Asp Lys Gly Ala Ser Ala Gln Ser Phe Ile Glu Arg Met Thr Asn Phe
                885                 890                 895

Asp Lys Asn Leu Pro Asn Glu Lys Val Leu Pro Lys His Ser Leu Leu
                900                 905                 910

Tyr Glu Tyr Phe Thr Val Tyr Asn Glu Leu Thr Lys Val Lys Tyr Val
                915                 920                 925

Thr Glu Gly Met Arg Lys Pro Ala Phe Leu Ser Gly Glu Gln Lys Lys
                930                 935                 940

Ala Ile Val Asp Leu Leu Phe Lys Thr Asn Arg Lys Val Thr Val Lys
945                 950                 955                 960

Gln Leu Lys Glu Asp Tyr Phe Lys Lys Ile Glu Cys Phe Asp Ser Val
                965                 970                 975

Glu Ile Ser Gly Val Glu Asp Arg Phe Asn Ala Ser Leu Gly Thr Tyr
                980                 985                 990

His Asp Leu Leu Lys Ile Ile Lys Asp Lys Asp Phe Leu Asp Asn Glu
                995                 1000                1005

Glu Asn Glu Asp Ile Leu Glu Asp Ile Val Leu Thr Leu Thr Leu
                1010                1015                1020

Phe Glu Asp Arg Glu Met Ile Glu Glu Arg Leu Lys Thr Tyr Ala
                1025                1030                1035

His Leu Phe Asp Asp Lys Val Met Lys Gln Leu Lys Arg Arg Arg
                1040                1045                1050

Tyr Thr Gly Trp Gly Arg Leu Ser Arg Lys Leu Ile Asn Gly Ile
                1055                1060                1065
```

-continued

```
Arg Asp Lys Gln Ser Gly Lys Thr Ile Leu Asp Phe Leu Lys Ser
    1070            1075            1080

Asp Gly Phe Ala Asn Arg Asn Phe Met Gln Leu Ile His Asp Asp
    1085            1090            1095

Ser Leu Thr Phe Lys Glu Asp Ile Gln Lys Ala Gln Val Ser Gly
    1100            1105            1110

Gln Gly Asp Ser Leu His Glu His Ile Ala Asn Leu Ala Gly Ser
    1115            1120            1125

Pro Ala Ile Lys Lys Gly Ile Leu Gln Thr Val Lys Val Val Asp
    1130            1135            1140

Glu Leu Val Lys Val Met Gly Arg His Lys Pro Glu Asn Ile Val
    1145            1150            1155

Ile Glu Met Ala Arg Glu Asn Gln Thr Thr Gln Lys Gly Gln Lys
    1160            1165            1170

Asn Ser Arg Glu Arg Met Lys Arg Ile Glu Glu Gly Ile Lys Glu
    1175            1180            1185

Leu Gly Ser Gln Ile Leu Lys Glu His Pro Val Glu Asn Thr Gln
    1190            1195            1200

Leu Gln Asn Glu Lys Leu Tyr Leu Tyr Tyr Leu Gln Asn Gly Arg
    1205            1210            1215

Asp Met Tyr Val Asp Gln Glu Leu Asp Ile Asn Arg Leu Ser Asp
    1220            1225            1230

Tyr Asp Val Asp His Ile Val Pro Gln Ser Phe Leu Lys Asp Asp
    1235            1240            1245

Ser Ile Asp Asn Lys Val Leu Thr Arg Ser Asp Lys Asn Arg Gly
    1250            1255            1260

Lys Ser Asp Asn Val Pro Ser Glu Glu Val Val Lys Lys Met Lys
    1265            1270            1275

Asn Tyr Trp Arg Gln Leu Leu Asn Ala Lys Leu Ile Thr Gln Arg
    1280            1285            1290

Lys Phe Asp Asn Leu Thr Lys Ala Glu Arg Gly Gly Leu Ser Glu
    1295            1300            1305

Leu Asp Lys Ala Gly Phe Ile Lys Arg Gln Leu Val Glu Thr Arg
    1310            1315            1320

Gln Ile Thr Lys His Val Ala Gln Ile Leu Asp Ser Arg Met Asn
    1325            1330            1335

Thr Lys Tyr Asp Glu Asn Asp Lys Leu Ile Arg Glu Val Lys Val
    1340            1345            1350

Ile Thr Leu Lys Ser Lys Leu Val Ser Asp Phe Arg Lys Asp Phe
    1355            1360            1365

Gln Phe Tyr Lys Val Arg Glu Ile Asn Asn Tyr His His Ala His
    1370            1375            1380

Asp Ala Tyr Leu Asn Ala Val Val Gly Thr Ala Leu Ile Lys Lys
    1385            1390            1395

Tyr Pro Lys Leu Glu Ser Glu Phe Val Tyr Gly Asp Tyr Lys Val
    1400            1405            1410

Tyr Asp Val Arg Lys Met Ile Ala Lys Ser Glu Gln Glu Ile Gly
    1415            1420            1425

Lys Ala Thr Ala Lys Tyr Phe Phe Tyr Ser Asn Ile Met Asn Phe
    1430            1435            1440

Phe Lys Thr Glu Ile Thr Leu Ala Asn Gly Glu Ile Arg Lys Arg
    1445            1450            1455
```

```
Pro Leu Ile Glu Thr Asn Gly Glu Thr Gly Glu Ile Val Trp Asp
    1460                1465                1470

Lys Gly Arg Asp Phe Ala Thr Val Arg Lys Val Leu Ser Met Pro
    1475                1480                1485

Gln Val Asn Ile Val Lys Lys Thr Glu Val Gln Thr Gly Gly Phe
    1490                1495                1500

Ser Lys Glu Ser Ile Leu Pro Lys Arg Asn Ser Asp Lys Leu Ile
    1505                1510                1515

Ala Arg Lys Lys Asp Trp Asp Pro Lys Lys Tyr Gly Gly Phe Asp
    1520                1525                1530

Ser Pro Thr Val Ala Tyr Ser Val Leu Val Val Ala Lys Val Glu
    1535                1540                1545

Lys Gly Lys Ser Lys Lys Leu Lys Ser Val Lys Glu Leu Leu Gly
    1550                1555                1560

Ile Thr Ile Met Glu Arg Ser Ser Phe Glu Lys Asn Pro Ile Asp
    1565                1570                1575

Phe Leu Glu Ala Lys Gly Tyr Lys Glu Val Lys Lys Asp Leu Ile
    1580                1585                1590

Ile Lys Leu Pro Lys Tyr Ser Leu Phe Glu Leu Glu Asn Gly Arg
    1595                1600                1605

Lys Arg Met Leu Ala Ser Ala Gly Glu Leu Gln Lys Gly Asn Glu
    1610                1615                1620

Leu Ala Leu Pro Ser Lys Tyr Val Asn Phe Leu Tyr Leu Ala Ser
    1625                1630                1635

His Tyr Glu Lys Leu Lys Gly Ser Pro Glu Asp Asn Glu Gln Lys
    1640                1645                1650

Gln Leu Phe Val Glu Gln His Lys His Tyr Leu Asp Glu Ile Ile
    1655                1660                1665

Glu Gln Ile Ser Glu Phe Ser Lys Arg Val Ile Leu Ala Asp Ala
    1670                1675                1680

Asn Leu Asp Lys Val Leu Ser Ala Tyr Asn Lys His Arg Asp Lys
    1685                1690                1695

Pro Ile Arg Glu Gln Ala Glu Asn Ile Ile His Leu Phe Thr Leu
    1700                1705                1710

Thr Asn Leu Gly Ala Pro Ala Ala Phe Lys Tyr Phe Asp Thr Thr
    1715                1720                1725

Ile Asp Arg Lys Arg Tyr Thr Ser Thr Lys Glu Val Leu Asp Ala
    1730                1735                1740

Thr Leu Ile His Gln Ser Ile Thr Gly Leu Tyr Glu Thr Arg Ile
    1745                1750                1755

Asp Leu Ser Gln Leu Gly Gly Asp Ser Gly Gly Ser Pro Lys Lys
    1760                1765                1770

Lys Arg Lys Val Ser Gly Gly Ser Pro Lys Lys Lys Arg Lys Val
    1775                1780                1785

Ser Gly Gly Ser Pro Lys Lys Lys Arg Lys Val
    1790                1795

<210> SEQ ID NO 40
<211> LENGTH: 23
<212> TYPE: DNA
<213> ORGANISM: Unknown
<220> FEATURE:
<223> OTHER INFORMATION: Description of Unknown:
      mGFP target sequence

<400> SEQUENCE: 40
```
ccttcaccta cggcgtgtag tgc                                           23

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcggcacta cacgccgtag gtga                                          24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaactcacct acggcgtgta gtgc                                          24

<210> SEQ ID NO 43
<211> LENGTH: 23
<212> TYPE: DNA
<213> ORGANISM: Oryza sativa
<220> FEATURE:
<223> OTHER INFORMATION: OsALS-T1 target sequence

<400> SEQUENCE: 43
cccaagtggg ggcgcattca agg                                           23

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggcgcccaag tgggggcgca ttca                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aaactgaatg cgcccccact tggg                                          24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgcacccaag tgggggcgca ttca                                          24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaactgaatg cgcccccact tggg                                            24

<210> SEQ ID NO 48
<211> LENGTH: 23
<212> TYPE: DNA
<213> ORGANISM: Oryza sativa
<220> FEATURE:
<223> OTHER INFORMATION: OsALS-T2 target sequence

<400> SEQUENCE: 48
cctcatgaac attcaggagc tgg                                             23

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggcgcctcat gaacattcag gagc                                            24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aaacgctcct gaatgttcat gagg                                            24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tgcacctcat gaacattcag gagc                                            24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aaacgctcct gaatgttcat gagg                                            24

```
<210> SEQ ID NO 53
<211> LENGTH: 23
<212> TYPE: DNA
<213> ORGANISM: Oryza sativa
<220> FEATURE:
<223> OTHER INFORMATION: OsCDC48-T1 target sequence

<400> SEQUENCE: 53
gctagctttg acataatctc cgg                                             23

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggcggctagc tttgacataa tctc                                            24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aaacgagatt atgtcaaagc tagc                                            24

<210> SEQ ID NO 56
<211> LENGTH: 23
<212> TYPE: DNA
<213> ORGANISM: Oryza sativa
<220> FEATURE:
<223> OTHER INFORMATION: OsCDC48-T2 target sequence

<400> SEQUENCE: 56
ccaatgcatc cgtgagaaga tgg                                             23

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggcgccaatg catccgtgag aaga                                            24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aaactcttct cacggatgca ttgg                                            24

<210> SEQ ID NO 59
<211> LENGTH: 23
<212> TYPE: DNA
```

```
<213> ORGANISM: Oryza sativa
<220> FEATURE:
<223> OTHER INFORMATION: OsCDC48-T3 target sequence

<400> SEQUENCE: 59
tagcacccat gacaatgaca tgg                                               23

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggcgtagcac ccatgacaat gaca                                              24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aaactgtcat tgtcatgggt gcta                                              24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tgcatagcac ccatgacaat gaca                                              24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aaactgtcat tgtcatgggt gcta                                              24

<210> SEQ ID NO 64
<211> LENGTH: 23
<212> TYPE: DNA
<213> ORGANISM: Oryza sativa
<220> FEATURE:
<223> OTHER INFORMATION: OsAAT target sequence

<400> SEQUENCE: 64
caaggatccc agccccgtga agg                                               23

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 65
ggcgcaagga tcccagcccc gtga                                           24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aaactcacgg ggctgggatc cttg                                           24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tgcacaagga tcccagcccc gtga                                           24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aaactcacgg ggctgggatc cttg                                           24

<210> SEQ ID NO 69
<211> LENGTH: 23
<212> TYPE: DNA
<213> ORGANISM: Oryza sativa
<220> FEATURE:
<223> OTHER INFORMATION: OsDEP1-T1 target sequence

<400> SEQUENCE: 69
agcacatgag agaacaatat tgg                                            23

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ggcgagcaca tgagagaaca atat                                           24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aaacatattg ttctctcatg tgct                                               24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgcaagcaca tgagagaaca atat                                               24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aaacatattg ttctctcatg tgct                                               24

<210> SEQ ID NO 74
<211> LENGTH: 23
<212> TYPE: DNA
<213> ORGANISM: Oryza sativa
<220> FEATURE:
<223> OTHER INFORMATION: OsDEP1-T2 target sequence

<400> SEQUENCE: 74
agacaagctt ggccctcttt ggg                                                23

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggcgagacaa gcttggccct cttt                                               24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aaacaaagag ggccaagctt gtct                                               24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgcaagacaa gcttggccct cttt                                              24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaacaaagag ggccaagctt gtct                                              24

<210> SEQ ID NO 79
<211> LENGTH: 23
<212> TYPE: DNA
<213> ORGANISM: Oryza sativa
<220> FEATURE:
<223> OTHER INFORMATION: OsDEP1-T3 target sequence

<400> SEQUENCE: 79
atttcaaatg gatctaaaca ggg                                               23

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ggcgatttca aatggatcta aaca                                              24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aaactgttta gatccatttg aaat                                              24

<210> SEQ ID NO 82
<211> LENGTH: 23
<212> TYPE: DNA
<213> ORGANISM: Oryza sativa
<220> FEATURE:
<223> OTHER INFORMATION: OsDEP1-T4 target sequence

<400> SEQUENCE: 82
acagatcttg ccgtcttttt cgg                                               23

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggcgacagat cttgccgtct tttt                                              24

```
<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
aaacaaaaag acggcaagat ctgt                                          24

<210> SEQ ID NO 85
<211> LENGTH: 23
<212> TYPE: DNA
<213> ORGANISM: Oryza sativa
<220> FEATURE:
<223> OTHER INFORMATION: OsACC-T1 target sequence

<400> SEQUENCE: 85
cccagaccgc attgagtgct atg                                           23

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggcgcatagc actcaatgcg gtct                                          24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aaacagaccg cattgagtgc tatg                                          24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tgcacatagc actcaatgcg gtct                                          24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aaacagaccg cattgagtgc tatg                                          24

<210> SEQ ID NO 90
<211> LENGTH: 23
```

```
<212> TYPE: DNA
<213> ORGANISM: Oryza sativa
<220> FEATURE:
<223> OTHER INFORMATION: OsACC-T2 target sequence

<400> SEQUENCE: 90
tactagtcac acttgcactg tgg                                            23

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggcgtactag tcacacttgc actg                                           24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aaaccagtgc aagtgtgact agta                                           24

<210> SEQ ID NO 93
<211> LENGTH: 23
<212> TYPE: DNA
<213> ORGANISM: Oryza sativa
<220> FEATURE:
<223> OTHER INFORMATION: OsNRT1.1B-T1 target sequence

<400> SEQUENCE: 93
actagatatc taaaccatta agg                                            23

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ggcgactaga tatctaaacc atta                                           24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aaactaatgg tttagatatc tagt                                           24

<210> SEQ ID NO 96
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 96
tgcaactaga tatctaaacc atta                                            24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
aaactaatgg tttagatatc tagt                                            24

<210> SEQ ID NO 98
<211> LENGTH: 23
<212> TYPE: DNA
<213> ORGANISM: Oryza sativa
<220> FEATURE:
<223> OTHER INFORMATION: OsNRT1.1B-T2 target sequence

<400> SEQUENCE: 98
ggccatggcg cccgcggcgg cgg                                             23

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggcgggccat ggcgcccgcg gcgg                                            24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aaacccgccg cgggcgccat ggcc                                            24

<210> SEQ ID NO 101
<211> LENGTH: 23
<212> TYPE: DNA
<213> ORGANISM: Oryza sativa
<220> FEATURE:
<223> OTHER INFORMATION: OsEV target sequence

<400> SEQUENCE: 101
cacacacaca ctagtacctc tgg                                             23

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggcgcacaca cacactagta cctc                                          24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaacgaggta ctagtgtgtg tgtg                                          24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tgcacacaca cacactagta cctc                                          24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaacgaggta ctagtgtgtg tgtg                                          24

<210> SEQ ID NO 106
<211> LENGTH: 23
<212> TYPE: DNA
<213> ORGANISM: Oryza sativa
<220> FEATURE:
<223> OTHER INFORMATION: OsOD target sequence

<400> SEQUENCE: 106
acacacacac tagtacctct ggg                                           23

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggcgacacac acactagtac ctct                                          24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

```
aaacagaggt actagtgtgt gtgt                                           24
```

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109

```
tgcaacacac acactagtac ctct                                           24
```

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110

```
aaacagaggt actagtgtgt gtgt                                           24
```

<210> SEQ ID NO 111
<211> LENGTH: 23
<212> TYPE: DNA
<213> ORGANISM: Triticum aestivum
<220> FEATURE:
<223> OTHER INFORMATION: TaDEP1 target sequence

<400> SEQUENCE: 111

```
acgagctaca tttacttgaa ggg                                            23
```

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112

```
cttgacgagc tacatttact tgaa                                           24
```

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

```
aaacttcaag taaatgtagc tcgt                                           24
```

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114

```
tgcaacgagc tacatttact tgaa                                           24
```

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
aaacttcaag taaatgtagc tcgt                                          24

<210> SEQ ID NO 116
<211> LENGTH: 23
<212> TYPE: DNA
<213> ORGANISM: Triticum aestivum
<220> FEATURE:
<223> OTHER INFORMATION: TaEPSPS target sequence

<400> SEQUENCE: 116
gaggaagtaa agctcttctt ggg                                           23

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
cttggaggaa gtaaagctct tctt                                          24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
aaacaagaag agctttactt cctc                                          24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
tgcagaggaa gtaaagctct tctt                                          24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
aaacaagaag agctttactt cctc                                          24

<210> SEQ ID NO 121

```
<211> LENGTH: 23
<212> TYPE: DNA
<213> ORGANISM: Triticum aestivum
<220> FEATURE:
<223> OTHER INFORMATION: TaGW2 target sequence

<400> SEQUENCE: 121
cacaagaaaa tccaccagga tgg                                            23

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cttgcacaag aaaatccacc agga                                           24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
aaactcctgg tggattttct tgtg                                           24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tgcacacaag aaaatccacc agga                                           24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
aaactcctgg tggattttct tgtg                                           24

<210> SEQ ID NO 126
<211> LENGTH: 29
<212> TYPE: DNA
<213> ORGANISM: Artificial Sequence
<220> FEATURE:
<223> OTHER INFORMATION: Description of Artificial Sequence: Synthetic
      F1 primer

<400> SEQUENCE: 126
atgctcaccc tgttgtttgg tgttacttc                                      29

<210> SEQ ID NO 127
<211> LENGTH: 27
<212> TYPE: DNA
```

<213> ORGANISM: Artificial Sequence
<220> FEATURE:
<223> OTHER INFORMATION: Description of Artificial Sequence: Synthetic
      R1 primer

<400> SEQUENCE: 127
cttctgggcc ttaatctcct gccttct                                           27

<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Synthetic
      F2 primer

<400> SEQUENCE: 128
tccgctacac cagagtcttc tggaggatct ag                                     32

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: Synthetic
      R2 primer

<400> SEQUENCE: 129
gcagatggta gatcgtaggg tacttctcgt gg                                     32

<210> SEQ ID NO 130
<211> LENGTH: 29
<212> TYPE: DNA
<213> ORGANISM: Artificial Sequence
<220> FEATURE:
<223> OTHER INFORMATION: Description of Artificial Sequence: Synthetic
      F3 primer

<400> SEQUENCE: 130
gaagaactac tggcgccagc tcctgaatg                                         29

<210> SEQ ID NO 131
<211> LENGTH: 28
<212> TYPE: DNA
<213> ORGANISM: Artificial Sequence
<220> FEATURE:
<223> OTHER INFORMATION: Description of Artificial Sequence: Synthetic
      R3 primer

<400> SEQUENCE: 131
ggcgatcatc ttcctcacat cgtaaacc                                          28

<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Synthetic
      F4 primer

<400> SEQUENCE: 132
tcgacagccc cactgtggcc tactc                                             25

<210> SEQ ID NO 133
<211> LENGTH: 28
<212> TYPE: DNA
<213> ORGANISM: Artificial Sequence

```
<220> FEATURE:
<223> OTHER INFORMATION: Description of Artificial Sequence: Synthetic
      R4 primer

<400> SEQUENCE: 133
ttatatgctc aacacatgag cgaaaccc                                       28

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      F5 primer

<400> SEQUENCE: 134
gaccaagccc gttattctga c                                              21

<210> SEQ ID NO 135
<211> LENGTH: 26
<212> TYPE: DNA
<213> ORGANISM: Artificial Sequence
<220> FEATURE:
<223> OTHER INFORMATION: Description of Artificial Sequence: Synthetic
      R5 primer

<400> SEQUENCE: 135
tgaccatgat tacgccaagc ttagac                                         26

<210> SEQ ID NO 136
<211> LENGTH: 25
<212> TYPE: DNA
<213> ORGANISM: Artificial Sequence
<220> FEATURE:
<223> OTHER INFORMATION: Description of Artificial Sequence: Synthetic
      F6 primer

<400> SEQUENCE: 136
tgaaaaagtg gcaccgagtc ggtgc                                          25

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      R6 primer

<400> SEQUENCE: 137
ggcgcagcgg tcgggctg                                                  18

<210> SEQ ID NO 138
<211> LENGTH: 76
<212> TYPE: DNA
<213> ORGANISM: Artificial Sequence
<220> FEATURE:
<223> OTHER INFORMATION: Description of Artificial Sequence: Synthetic
      sgRNA oligonucleotide

<400> SEQUENCE: 138
gttttagagc tagaaatagc aagttaaaat aaggctagtc cgttatcaac ttgaaaaagt    60
ggcaccgagt cggtgc                                                    76

<210> SEQ ID NO 139
<211> LENGTH: 86
<212> TYPE: DNA
```

```
<213> ORGANISM: Artificial Sequence
<220> FEATURE:
<223> OTHER INFORMATION: Description of Artificial Sequence: Synthetic
      esgRNA oligonucleotide

<400> SEQUENCE: 139
gtttaagagc tatgctggaa acagcatagc aagtttaaat aaggctagtc cgttatcaac    60
ttgaaaaagt ggcaccgagt cggtgc                                        86

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Lys Lys Arg Lys Val
1               5

<210> SEQ ID NO 141
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
aagaagagaa aggtc                                                    15

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Pro Lys Lys Lys Arg Lys Val
1               5

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cccaagaaga agaggaaggt g                                             21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ccaaagaaga agaggaaggt t                                             21
```

```
<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Gly Gly Ser Pro Lys Lys Lys Arg Lys Val
1               5                   10

<210> SEQ ID NO 146
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146 tcgggggggga gcccaaagaa gaagcggaag gtg                                33

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Lys Arg Pro Ala Ala Thr Lys Lys Ala Gly Gln Ala Lys Lys Lys Lys
1               5                   10                  15

<210> SEQ ID NO 148
<211> LENGTH: 23
<212> TYPE: DNA
<213> ORGANISM: Oryza sativa

<400> SEQUENCE: 148
catagcactc aactcagttt ggg                                            23

<210> SEQ ID NO 149
<211> LENGTH: 23
<212> TYPE: DNA
<213> ORGANISM: Oryza sativa

<400> SEQUENCE: 149
aatagcactc attgagatct tgg                                            23

<210> SEQ ID NO 150
<211> LENGTH: 23
<212> TYPE: DNA
<213> ORGANISM: Oryza sativa

<400> SEQUENCE: 150
catagcactt aatgtgggcg gag                                            23

<210> SEQ ID NO 151
<211> LENGTH: 58
<212> TYPE: DNA
<213> ORGANISM: Oryza sativa

<400> SEQUENCE: 151
catcaatccg aggctggcga gacaagcttg gccctctttg ggcgtggcgc catggctg      58
```

<210> SEQ ID NO 152
<211> LENGTH: 58
<212> TYPE: DNA
<213> ORGANISM: Oryza sativa

<400> SEQUENCE: 152
catcaatccg aggctggcga gacgagcttg gccctctttg ggcgtggcgc catggctg    58

<210> SEQ ID NO 153
<211> LENGTH: 58
<212> TYPE: DNA
<213> ORGANISM: Oryza sativa

<400> SEQUENCE: 153
catcaatccg aggctggcga ggcgggcttg gccctctttg ggcgtggcgc catggctg    58

<210> SEQ ID NO 154
<211> LENGTH: 58
<212> TYPE: DNA
<213> ORGANISM: Oryza sativa

<400> SEQUENCE: 154
catcaatccg aggctggcga gacaggcttg gccctctttg ggcgtggcgc catggctg    58

<210> SEQ ID NO 155
<211> LENGTH: 58
<212> TYPE: DNA
<213> ORGANISM: Oryza sativa

<400> SEQUENCE: 155
acagaaagag aaggaggcac agatcttgcc gtcttttcg gtggatcggg tatgtttt    58

<210> SEQ ID NO 156
<211> LENGTH: 58
<212> TYPE: DNA
<213> ORGANISM: Oryza sativa

<400> SEQUENCE: 156
acagaaagag aaggaggcac ggatcttgcc gtcttttcg gtggatcggg tatgtttt    58

<210> SEQ ID NO 157
<211> LENGTH: 58
<212> TYPE: DNA
<213> ORGANISM: Oryza sativa

<400> SEQUENCE: 157
ttactctcac tttctcctgc tagctttgac ataatctccg ggccattaat cagaaaga    58

<210> SEQ ID NO 158
<211> LENGTH: 58
<212> TYPE: DNA
<213> ORGANISM: Oryza sativa

<400> SEQUENCE: 158
ttactctcac tttctcctgc tggctttgac ataatctccg ggccattaat cagaaaga    58

<210> SEQ ID NO 159
<211> LENGTH: 554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159

```
agtaattcat ccaggtcacc aagttctagg attttcagaa ctgcaactta ttttatcaag      60
gaatctttaa acatacgaac agatcactta aagttcttct gaagcaactt aaagttatca     120
ggcatgcatg gatcttggag gaatcagatg tgcagtcagg gaccatagca caagacaggc    180
gtcttctact ggtgctacca gcaaatgctg gaagccggga acactgggta cgttggaaac    240
cacgtgatgt gaagaagtaa gataaactgt aggagaaaag catttcgtag tgggccatga    300
agcctttcag gacatgtatt gcagtatggg ccggcccatt acgcaattgg acgacaacaa    360
agactagtat tagtaccacc tcggctatcc acatagatca aagctgattt aaaagagttg    420
tgcagatgat ccgtggcgtg agaccctgca gggtctctgt tttagagcta gaaatagcaa    480
gttaaaataa ggctagtccg ttatcaactt gaaaaagtgg caccgagtcg gtgcttttt    540
tgttttttat gtct                                                     554
```

<210> SEQ ID NO 160
<211> LENGTH: 564
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 160

```
agtaattcat ccaggtcacc aagttctagg attttcagaa ctgcaactta ttttatcaag      60
gaatctttaa acatacgaac agatcactta aagttcttct gaagcaactt aaagttatca     120
ggcatgcatg gatcttggag gaatcagatg tgcagtcagg gaccatagca caagacaggc    180
gtcttctact ggtgctacca gcaaatgctg gaagccggga acactgggta cgttggaaac    240
cacgtgatgt gaagaagtaa gataaactgt aggagaaaag catttcgtag tgggccatga    300
agcctttcag gacatgtatt gcagtatggg ccggcccatt acgcaattgg acgacaacaa    360
agactagtat tagtaccacc tcggctatcc acatagatca aagctgattt aaaagagttg    420
tgcagatgat ccgtggcgtg agaccctgca gggtctctgt ttagagcta tgctggaaac     480
agcatagcaa gtttaaataa ggctagtccg ttatcaactt gaaaaagtgg caccgagtcg    540
gtgcttttt tgttttttat gtct                                           564
```

<210> SEQ ID NO 161
<211> LENGTH: 572
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161

```
aaggaatctt taaacatacg aacagatcac ttaaagttct tctgaagcaa cttaaagtta      60
tcaggcatgc atggatcttg gaggaatcag atgtgcagtc agggaccata gcacaagaca    120
ggcgtcttct actggtgcta ccagcaaatg ctggaagccg ggaacactgg gtacgtcgga    180
aaccacgtga tgtgaagaag taagataaac tgtaggagaa aagcatttcg tagtgggcca    240
tgaagccttt caggacatgt attgcagtat gggccggccc attacgcaat tggacgacaa    300
caaagactag tattagtacc acctcggcta tccacataga tcaaagctga tttaaaagag    360
ttgtgcagat gatccgtggc aacaaagcac cagtggtcta gtggtagaat agtaccctgc    420
```

```
cacggtacag acccgggttc gattcccggc tggtgcaaga gaccgatatc ccatggctcg      480
agggtctcgg ttttagagct agaaatagca agttaaaata aggctagtcc gttatcaact      540
tgaaaaagtg gcaccgagtc ggtgcttttt tt                                   572
```

<210> SEQ ID NO 162
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162

```
gaccaagccc gttattctga cagttctggt gctcaacaca tttatattta tcaaggagca       60
cattgttact cactgctagg agggaatcga actaggaata ttgatcagag gaactacgag      120
agagctgaag ataactgccc tctagctctc actgatctgg gcgcatagtg agatgcagcc      180
cacgtgagtt cagcaacggt ctagcgctgg gcttttaggc ccgcatgatc gggctttgtc      240
gggtggtcga cgtgttcacg attggggaga gcaacgcagc agttcctctt agtttagtcc      300
cacctcgcct gtccagcaga gttctgaccg gtttataaac tcgcttgctg catcagactt      360
gtgagaccct gcagggtctc tgttttagag ctagaaatag caagttaaaa taaggctagt      420
ccgttatcaa cttgaaaaag tggcaccgag tcggtgcttt ttttgttttt tatgtct         477
```

<210> SEQ ID NO 163
<211> LENGTH: 487
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163

```
gaccaagccc gttattctga cagttctggt gctcaacaca tttatattta tcaaggagca       60
cattgttact cactgctagg agggaatcga actaggaata ttgatcagag gaactacgag      120
agagctgaag ataactgccc tctagctctc actgatctgg gcgcatagtg agatgcagcc      180
cacgtgagtt cagcaacggt ctagcgctgg gcttttaggc ccgcatgatc gggctttgtc      240
gggtggtcga cgtgttcacg attggggaga gcaacgcagc agttcctctt agtttagtcc      300
cacctcgcct gtccagcaga gttctgaccg gtttataaac tcgcttgctg catcagactt      360
gtgagaccct gcagggtctc tgtttaagag ctatgctgga aacagcatag caagtttaaa      420
taaggctagt ccgttatcaa cttgaaaaag tggcaccgag tcggtgcttt ttttgttttt      480
tatgtct                                                               487
```

<210> SEQ ID NO 164
<211> LENGTH: 553
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164

```
gaccaagccc gttattctga cagttctggt gctcaacaca tttatattta tcaaggagca       60
cattgttact cactgctagg agggaatcga actaggaata ttgatcagag gaactacgag      120
agagctgaag ataactgccc tctagctctc actgatctgg gcgcatagtg agatgcagcc      180
```

```
cacgtgagtt cagcaacggt ctagcgctgg gcttttaggc ccgcatgatc gggctttgtc      240
gggtggtcga cgtgttcacg attggggaga gcaacgcagc agttcctctt agtttagtcc      300
cacctcgcct gtccagcaga gttctgaccg gtttataaac tcgcttgctg catcagactt      360
gaacaaagca ccagtggtct agtggtagaa tagtaccctg ccacggtaca gacccgggtt      420
cgattcccgg ctggtgcaag agaccgatat cccatggctc gagggtctcg gttttagagc      480
tagaaatagc aagttaaaat aaggctagtc cgttatcaac ttgaaaaagt ggcaccgagt      540
cggtgctttt ttt                                                         553

<210> SEQ ID NO 165
<211> LENGTH: 20
<212> TYPE: DNA
<213> ORGANISM: Oryza sativa

<400> SEQUENCE: 165
cccaagtggg ggcgcattca                                                   20

<210> SEQ ID NO 166
<211> LENGTH: 20
<212> TYPE: DNA
<213> ORGANISM: Oryza sativa

<400> SEQUENCE: 166
cctcatgaac attcaggagc                                                   20

<210> SEQ ID NO 167
<211> LENGTH: 20
<212> TYPE: DNA
<213> ORGANISM: Oryza sativa

<400> SEQUENCE: 167
tagcacccat gacaatgaca                                                   20

<210> SEQ ID NO 168
<211> LENGTH: 20
<212> TYPE: DNA
<213> ORGANISM: Oryza sativa

<400> SEQUENCE: 168
caaggatccc agccccgtga                                                   20

<210> SEQ ID NO 169
<211> LENGTH: 20
<212> TYPE: DNA
<213> ORGANISM: Oryza sativa

<400> SEQUENCE: 169
agcacatgag agaacaatat                                                   20

<210> SEQ ID NO 170
<211> LENGTH: 20
<212> TYPE: DNA
<213> ORGANISM: Oryza sativa

<400> SEQUENCE: 170
agacaagctt ggccctgttt                                                   20

<210> SEQ ID NO 171
<211> LENGTH: 20
<212> TYPE: DNA
<213> ORGANISM: Oryza sativa
```

```
<400> SEQUENCE: 171
catagcactc aatgcggtct                                              20

<210> SEQ ID NO 172
<211> LENGTH: 20
<212> TYPE: DNA
<213> ORGANISM: Oryza sativa

<400> SEQUENCE: 172
actagatatc taaaccatta                                              20

<210> SEQ ID NO 173
<211> LENGTH: 20
<212> TYPE: DNA
<213> ORGANISM: Oryza sativa

<400> SEQUENCE: 173
cacacacaca cacacacaca                                              20

<210> SEQ ID NO 174
<211> LENGTH: 20
<212> TYPE: DNA
<213> ORGANISM: Oryza sativa

<400> SEQUENCE: 174
acacacacac acacacacac                                              20

<210> SEQ ID NO 175
<211> LENGTH: 20
<212> TYPE: DNA
<213> ORGANISM: Triticum aestivum

<400> SEQUENCE: 175
acgagctaca tttacttgaa                                              20

<210> SEQ ID NO 176
<211> LENGTH: 20
<212> TYPE: DNA
<213> ORGANISM: Triticum aestivum

<400> SEQUENCE: 176
gaggaagtaa agctcttctt                                              20

<210> SEQ ID NO 177
<211> LENGTH: 37
<212> TYPE: DNA
<213> ORGANISM: Oryza sativa

<400> SEQUENCE: 177
agataaaccc agaccgcatt gagtgctatg ctgagag                           37

<210> SEQ ID NO 178
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
agataaaccc agaccgcatt gagtgccatg ctgagag                           37
```

```
<210> SEQ ID NO 179
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
agataaaccc agaccgcatt gagcgctatg ctgagag                             37

<210> SEQ ID NO 180
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
agataaaccc agaccgcatt gagcgccatg ctgagag                             37

<210> SEQ ID NO 181
<211> LENGTH: 35
<212> TYPE: DNA
<213> ORGANISM: Oryza sativa

<400> SEQUENCE: 181
atgatcccaa gtgggggcgc attcaaggac atgat                               35

<210> SEQ ID NO 182
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atgatcccag gtgggggcgc attcaaggac atgat                               35

<210> SEQ ID NO 183
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
atgatcccga gtgggggcgc attcaaggac atgat                               35

<210> SEQ ID NO 184
<211> LENGTH: 38
<212> TYPE: DNA
<213> ORGANISM: Oryza sativa

<400> SEQUENCE: 184
cggtttgtag cacccatgac aatgacatgg gaacgagc                            38

<210> SEQ ID NO 185
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 185
cggtttgtag cgcccatgac aatgacatgg gaacgagc                                          38

<210> SEQ ID NO 186
<211> LENGTH: 34
<212> TYPE: DNA
<213> ORGANISM: Oryza sativa

<400> SEQUENCE: 186
catctagcac atgagagaac aatattggtc taac                                              34

<210> SEQ ID NO 187
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
catctagcac gtgagagaac aatattggtc taac                                              34

<210> SEQ ID NO 188
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
catctagcgc atgagagaac aatattggtc taac                                              34

<210> SEQ ID NO 189
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
catctagcgc gtgagagaac aatattggtc taac                                              34

<210> SEQ ID NO 190
<211> LENGTH: 38
<212> TYPE: DNA
<213> ORGANISM: Oryza sativa

<400> SEQUENCE: 190
ggctggcgag acaagcttgg ccctctttgg gcgtggcg                                          38

<210> SEQ ID NO 191
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ggctggcgag acgagcttgg ccctctttgg gcgtggcg                                          38

<210> SEQ ID NO 192

```
<210> SEQ ID NO 192
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ggctggcgag acaggcttgg ccctctttgg gcgtggcg                              38

<210> SEQ ID NO 193
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ggctggcgag gcaggcttgg ccctctttgg gcgtggcg                              38

<210> SEQ ID NO 194
<211> LENGTH: 37
<212> TYPE: DNA
<213> ORGANISM: Oryza sativa

<400> SEQUENCE: 194
ccagcactac tagatatcta aaccattaag gtaggtc                               37

<210> SEQ ID NO 195
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ccagcactac taggtatcta aaccattaag gtaggtc                               37

<210> SEQ ID NO 196
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ccagcactac tagatgtcta aaccattaag gtaggtc                               37

<210> SEQ ID NO 197
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ccagcactac taggtgtcta aaccattaag gtaggtc                               37

<210> SEQ ID NO 198
<211> LENGTH: 37
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 198
ccagcactac tggatgtcta aaccattaag gtaggtc                              37

<210> SEQ ID NO 199
<211> LENGTH: 37
<212> TYPE: DNA
<213> ORGANISM: Triticum aestivum

<400> SEQUENCE: 199
cgcaggacga gctacattta cttgaagggg ctcaacc                              37

<210> SEQ ID NO 200
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cgcaggacga gctgcattta cttgaagggg ctcaacc                              37

<210> SEQ ID NO 201
<211> LENGTH: 37
<212> TYPE: DNA
<213> ORGANISM: Triticum aestivum

<400> SEQUENCE: 201
tagcagcaac agcacaagaa aatccaccag gatgggg                              37

<210> SEQ ID NO 202
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tagcagcaac agcacaggaa aatccaccag gatgggg                              37

<210> SEQ ID NO 203
<211> LENGTH: 27
<212> TYPE: DNA
<213> ORGANISM: Oryza sativa

<400> SEQUENCE: 203
aacccagacc gcattgagtg ctatgct                                         27

<210> SEQ ID NO 204
<211> LENGTH: 9
<212> TYPE: PRT
<213> ORGANISM: Oryza sativa

<400> SEQUENCE: 204

Asn Pro Asp Arg Ile Glu Cys Tyr Ala
1               5

<210> SEQ ID NO 205
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 205
aacccagacc gcattgagcg ctatgct                                            27

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asn Pro Asp Arg Ile Glu Arg Tyr Ala
1               5

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Gly Gly Gly Ser
1               5

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Gly Gly Gly Ser Gly Gly Gly Gly Ser Gly Gly Gly Gly Ser
1               5                   10                  15

<210> SEQ ID NO 209
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 210
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 210

Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
                20                  25                  30

<210> SEQ ID NO 211
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
cgcaggacga gctacattta cttgaagggg ctcaacc                              37

<210> SEQ ID NO 212
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tagcagcaac agcacaagaa aatccaccag gatgggg                              37
```

METHOD FOR BASE EDITING IN PLANTS

CROSS-REFERENCE TO RELATED APPLICATIONS

This application is a U.S. National Phase of International Patent Application No. PCT/CN2018/122640, filed on Dec. 21, 2018, which claims priority to Chinese Application No. 201711393160.7, filed Dec. 21, 2017, and Chinese Application No. 201810402244.0, filed Apr. 28, 2018. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 30, 2020, is named 245761_000108_SL.txt and is 430,605 bytes in size.

TECHNICAL FIELD

The invention relates to the field of genetic engineering. In particular, the invention relates to a method for base editing in plants. More specifically, the present invention relates to a highly efficient A to G base editing method for a target sequence in a genome of a plant (e.g., a crop plant) by a guide RNA-directed CRISPR-adenine deaminase fusion protein, and the plant and their progeny produced by the method.

TECHNICAL BACKGROUND

The prerequisite for efficient crop improvement is the capacity to obtain new genetic mutations that can be easily introduced into modern cultivars. Genetic studies, especially those studies based on whole-genome, have shown that changes in single nucleotides are the main reasons for differences in crop traits. Single base variations result in amino acid substitutions leading to the evolution of superior alleles and superior traits. Before the emergence of genome editing, targeting induced local lesions in genomes (TILLING) can be used as a method for generating mutations that are urgently needed in crop improvement. However, TILLING screening is time consuming and laborious, and the identified point mutations are often limited both for the number and types thereof. Genome editing techniques, particularly those based on the CRISPR/Cas9 system, enable the introduction of specific base substitutions in genomic loci by homologous recombination (HR)-mediated DNA repair pathways. However, the successful use of this method is currently limited, mainly due to the low frequency of HR-mediated double-strand broken chain repair in plants. In addition, effectively providing a sufficient amount of DNA repair templates is also a major difficulty. These problems make it a challenge to efficiently and simply achieve site-directed mutagenesis in plants through HR.

Currently, C to T base editing has been achieved in plants by using a fusion protein of Cas9 and cytosine deaminase. However, there is still a pressing need in the art for methods for A to G point mutations in plant genomes.

BRIEF DESCRIPTION OF THE INVENTION

In the first aspect, the present invention provides a system for base editing of a target sequence in plant genome, comprising at least one of the following i) to v):

i) a base-editing fusion protein, and a guide RNA;
ii) an expression construct comprising a nucleotide sequence encoding a base-editing fusion protein, and a guide RNA;
iii) a base-editing fusion protein, and an expression construct comprising a nucleotide sequence encoding a guide RNA;
iv) an expression construct comprising a nucleotide sequence encoding a base-editing fusion protein, and an expression construct comprising a nucleotide sequence encoding a guide RNA;
v) an expression construct comprising a nucleotide sequence encoding a base-editing fusion protein and a nucleotide sequence encoding a guide RNA;
wherein the base-editing fusion protein comprises a nuclease-inactivated CRISPR effector protein (such as Cas9, Cpf1 and the like) and DNA-dependent adenine deaminase, the guide RNA being capable of targeting the base-editing fusion protein to a target sequence in the plant genome, thereby the base-editing fusion protein results in one or more A in the target sequence being replaced by G.

In the second aspect, the invention provides a method of producing a genetically modified plant, comprising introducing a system of the invention for base editing of a target sequence in a plant genome into the plant, whereby the guide RNA targets the base-editing fusion protein to a target sequence in the plant genome, resulting one or more A in the target sequence being replaced with G.

In the third aspect, the present invention provides a genetically modified plant or a progeny thereof, wherein the plant is obtained by the method of the invention.

In the fourth aspect, the present invention provides a method of plant breeding comprising crossing a first plant containing a genetic modification obtained by the above method of the present invention with a second plant not containing the genetic modification, thereby the genetic modification is introduced into the second plant.

DESCRIPTION OF THE DRAWINGS

FIG. 3. Base editing of plant endogenous genes by the adenine base editing system. Figure discloses SEQ ID NOS 151-153, 153 and 154-158, respectively, in order of appearance.

FIG. 5. PABE-1 to PABE-7 constructs and their gene editing results.

FIG. 7. Schematic diagram of three sgRNA formats in which the rice U3 promoter, wheat U6 promoter, sgRNA scaffold, esgRNA scaffold, and tRNA sequences are represented by blue, purple, red, green, and brown, respectively; transcription initiation site is represented by yellow highlighting; arrows indicate the RNase Z cleavage site of the tRNA; underline represents BsaI restriction sites, the annealed oligonucleotide can be used to insert the leader sequence between the two BsaI sites. Figure discloses SEQ ID NOS 159-164, respectively, in order of appearance.

DETAILED DESCRIPTION OF THE INVENTION

1. Definition

Figure 1:
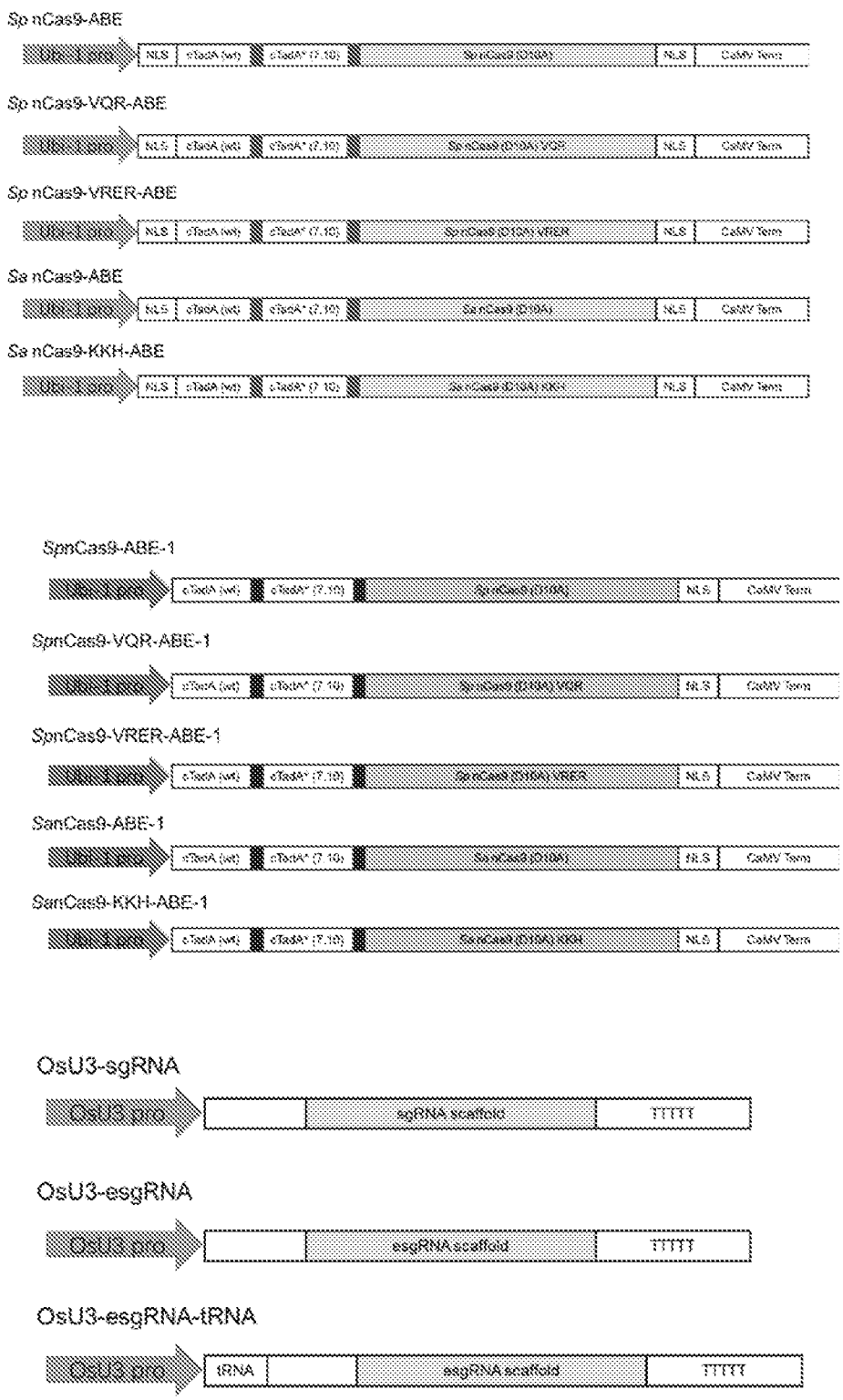
FIG. 1. Adenine base editing construct suitable for editing in plant cells.

In the present invention, the scientific and technical terms used herein have the meaning as commonly understood by a person skilled in the art unless otherwise specified. Also, the protein and nucleic acid chemistry, molecular biology, cell and tissue culture, microbiology, immunology related terms, and laboratory procedures used herein are terms and routine steps that are widely used in the corresponding field. For example, standard recombinant DNA and molecular cloning techniques used in the present invention are well known to those skilled in the art and are more fully described in the following document: Sambrook, J., Fritsch, E. F. and Maniatis, T., Molecular Cloning: A Laboratory Manual; Cold Spring Harbor Laboratory Press: Cold Spring Harbor, 1989 (hereinafter referred to as "Sambrook"). In the meantime, in order to better understand the present invention, definitions and explanations of related terms are provided below.

As used herein, the term "CRISPR effector protein" generally refers to a nuclease present in a naturally occurring CRISPR system, as well as modified forms thereof, variants thereof, catalytically active fragments thereof, and the like. The term encompasses any effector protein based on the CRISPR system that enables gene targeting (e.g., gene editing, gene targeting regulation, etc.) within a cell.

Examples of "CRISPR effector proteins" include Cas9 nucleases or variants thereof. The Cas9 nuclease may be a Cas9 nuclease from different species, such as spCas9 from *S. pyogenes* or SaCas9 derived from *S. aureus*. "Cas9 Nuclease" and "Cas9" are used interchangeably herein and refer to RNA-directed nuclease comprising a Cas9 protein or a fragment thereof (eg, a protein comprising an active DNA cleavage domain of Cas9 and/or a gRNA binding domain of Cas9). Cas9 is a component of the CRISPR/Cas (clustered regularly interspaced short palindromic repeats and related systems) genome editing system that targets and cleaves DNA target sequences under the guidance of a guide RNA to form DNA double-strand breaks (DSB).

Examples of "CRISPR effector proteins" may also include Cpf1 nucleases or variants thereof such as highly specific variants. The Cpf1 nuclease may be a Cpf1 nuclease from a different species, such as a Cpf1 nuclease from *Francisella novicida* U112, Acidaminococcus sp. BV3L6, and Lachnospiraceae bacterium ND2006.

As used herein, "gRNA" and "guide RNA" can be used interchangeably, which refers to an RNA molecule capable of forming a complex with a CRISPR effector protein and capable of targeting the complex to a target sequence due to certain complementarity to the target sequence. For example, in a Cas9-based gene editing system, gRNAs are typically are composed of crRNA and tracrRNA molecules forming complexes through partial complement, wherein crRNA comprises a sequence that is sufficiently complementary to a target sequence for hybridization and directs the CRISPR complex (Cas9+crRNA+tracrRNA) to specifically bind to the target sequence. However, it is known in the art that single guide RNA (sgRNA) can be designed, which comprises the characteristics of both crRNA and tracrRNA. The guide RNA of the Cpf1-mediated genome editing system is typically composed only of mature crRNA molecules, wherein the crRNA comprises a sequence that is sufficiently identical to the target sequence to hybridize to the complement of the target sequence and direct the complex (Cpf1+crRNA) to sequence specifically bind to the target sequence. It is within the ability of those skilled in the art to design suitable gRNA sequences based on the CRISPR effector proteins used and the target sequences to be edited.

"Adenine deaminase" refers to adenine deaminase which is capable of catalyzing the formation of inosine (I) from adenosine or deoxyadenosine (A).

"Genome" as used herein encompasses not only chromosomal DNA present in the nucleus, but also organellar DNA present in the subcellular components (e.g., mitochondria, plastids) of the cell.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, and includes protoplast cells without a cell wall and plant cells with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant part" in embodiments herein.

The term "protoplast", as used herein, refers to a plant cell that had its cell wall completely or partially removed, with the lipid bilayer membrane thereof naked. Typically, a protoplast is an isolated plant cell without cell walls which has the potency for regeneration into cell culture or a whole plant.

"Progeny" of a plant comprises any subsequent generation of the plant.

A "genetically modified plant" includes a plant which comprises within its genome an exogenous polynucleotide. For example, the exogenous polynucleotide is stably integrated within the genome such that the polynucleotide is passed on to successive generations. The exogenous polynucleotide may be integrated into the genome alone or as part of a recombinant DNA construct. The modified gene or expression regulatory sequence means that, in the plant genome, said sequence comprises one or more nucleotide substitution, deletion, or addition. For example, a genetically modified plant obtained by the present invention may comprise one or more substitutions of A to G relative to a wild type (corresponding plant without such genetic modification).

"Exogenous" in reference to a sequence means a sequence from a foreign species, or refers to a sequence in which significant changes in composition and/or locus occur from its native form through deliberate human intervention if from the same species.

"Polynucleotide", "nucleic acid sequence", "nucleotide sequence" or "nucleic acid fragment" are used interchangeably and are single-stranded or double-stranded RNA or DNA polymers, optionally containing synthetic, non-natural or altered nucleotide bases. Nucleotides are referred to by their single letter names as follows: "A" is adenosine or deoxyadenosine (corresponding to RNA or DNA, respectively), "C" means cytidine or deoxycytidine, "G" means guanosine or deoxyguanosine, "U" represents uridine, "T" means deoxythymidine, "R" means purine (A or G), "Y" means pyrimidine (C or T), "K" means G or T, "H" means A or C or T, "I" means inosine, and "N" means any nucleotide.

"Polypeptide," "peptide," and "protein" are used interchangeably in the present invention to refer to a polymer of amino acid residues. The terms apply to an amino acid polymer in which one or more amino acid residues is artificial chemical analogue of corresponding naturally occurring amino acid(s), as well as to a naturally occurring amino acid polymer. The terms "polypeptide," "peptide," "amino acid sequence," and "protein" may also include modified forms including, but not limited to, glycosylation, lipid ligation, sulfation, y carboxylation of glutamic acid residues, and ADP-ribosylation.

As used in the present invention, "expression construct" refers to a vector such as a recombinant vector that is suitable for expression of a nucleotide sequence of interest in a plant. "Expression" refers to the production of a functional product. For example, expression of a nucleotide sequence may refer to the transcription of a nucleotide sequence (eg, transcription to produce mRNA or functional RNA) and/or the translation of an RNA into a precursor or mature protein.

The "expression construct" of the present invention may be a linear nucleic acid fragment, a circular plasmid, a viral vector or, in some embodiments, an RNA that is capable of translation (such as mRNA).

The "expression construct" of the present invention may comprise regulatory sequences and nucleotide sequences of interest from different origins, or regulatory sequences and nucleotide sequences of interest from the same source but arranged in a manner different from that normally occurring in nature.

"Regulatory sequence" and "regulatory element" are used interchangeably to refer to a nucleotide sequence that is located upstream (5 'non-coding sequence), middle or downstream (3' non-coding sequence) of a coding sequence and affects the transcription, RNA processing or stability or translation of the relevant coding sequence. Plant expression regulatory elements refer to nucleotide sequences that are capable of controlling transcription, RNA processing or stability or translation of a nucleotide sequence of interest in a plant.

Regulatory sequences may include, but are not limited to, promoters, translation leaders, introns and polyadenylation recognition sequences.

"Promoter" refers to a nucleic acid fragment capable of controlling the transcription of another nucleic acid fragment. In some embodiments of the present invention, the promoter is a promoter capable of controlling the transcription of a gene in a plant cell, whether or not it is derived from the plant cell. The promoter may be a constitutive promoter or tissue-specific promoter or developmentally-regulated promoter or inducible promoter.

"Constitutive promoter" refers to a promoter that may in general cause the gene to be expressed in most cases in most cell types. "Tissue-specific promoter" and "tissue-preferred promoter" are used interchangeably and mean that they are expressed primarily but not necessarily exclusively in one tissue or organ, but also in a specific cell or cell type. "Developmentally-regulated promoter" refers to a promoter whose activity is dictated by developmental events. "Inducible promoter" selectively express operably linked DNA sequences in response to an endogenous or exogenous stimulus (environment, hormones, chemical signals, etc.).

As used herein, the term "operably linked" refers to the linkage of a regulatory element (e.g., but not limited to, a promoter sequence, a transcription termination sequence, etc.) to a nucleic acid sequence (e.g., a coding sequence or an open reading frame) such that transcription of the nucleotide sequence is controlled and regulated by the transcriptional regulatory element. Techniques for operably linking regulatory element regions to nucleic acid molecules are known in the art.

"Introduction" of a nucleic acid molecule (e.g., plasmid, linear nucleic acid fragment, RNA, etc.) or protein into a plant means that the nucleic acid or protein is used to transform a plant cell such that the nucleic acid or protein is capable of functioning in the plant cell. As used in the present invention, "transformation" includes both stable and transient transformations.

"Stable transformation" refers to the introduction of exogenous nucleotide sequences into the plant genome, resulting in the stable inheritance of foreign genes. Once stably transformed, the exogenous nucleic acid sequence is stably integrated into the genome of the plant and any of its successive generations.

"Transient transformation" refers to the introduction of a nucleic acid molecule or protein into a plant cell, performing a function without the stable inheritance of an exogenous gene. In transient transformation, the exogenous nucleic acid sequences are not integrated into the plant genome.

"Trait" refers to the physiological, morphological, biochemical, or physical characteristics of a plant or a particular plant material or cell. In some embodiments, the characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield. In some embodiments, trait also includes resistance of a plant to herbicides.

"Agronomic trait" is a measurable parameter including but not limited to, leaf greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, disease resistance, cold resistance, salt tolerance, and tiller number and so on.

2. Adenine Base Editing System for Plants

The present invention provides a system for base editing of a target sequence in plant genome, comprising at least one of the following i) to v):
i) a base-editing fusion protein, and a guide RNA;
ii) an expression construct comprising a nucleotide sequence encoding a base-editing fusion protein, and a guide RNA;
iii) a base-editing fusion protein, and an expression construct comprising a nucleotide sequence encoding a guide RNA;
iv) an expression construct comprising a nucleotide sequence encoding a base-editing fusion protein, and an expression construct comprising a nucleotide sequence encoding a guide RNA;
v) an expression construct comprising a nucleotide sequence encoding a base-editing fusion protein and a nucleotide sequence encoding a guide RNA;
wherein the base-editing fusion protein comprises a nuclease-inactivated CRISPR effector protein (such as Cas9, Cpf1 and the like) and DNA-dependent adenine deaminase, the guide RNA being capable of targeting the base-editing fusion protein to a target sequence in the plant genome, thereby the base-editing fusion protein results in one or more A in the target sequence being replaced by G.

As used herein, a "nuclease-inactivated CRISPR effector protein" refers to a CRISPR effector protein that lacks the double-stranded nucleic acid cleavage activity, but retains gRNA-directed DNA targeting ability. A CRISPR effector protein lacking double-stranded nucleic acid cleavage activity also encompasses a nickase that only forms a nick in a double-stranded nucleic acid molecule but does not completely cleave double-stranded nucleic acid.

In some embodiments, the nuclease inactivated CRISPR effector protein is a nuclease inactivated Cas9. The DNA cleavage domain of Cas9 nuclease is known to comprise two subdomains: the HNH nuclease subdomain and the RuvC subdomain. The HNH subdomain cleaves a strand complementary to the gRNA, while the RuvC subdomain cleaves the non-complementary strand. Mutations in these subdomains can inactivate the nuclease activity of Cas9, forming a "nuclease inactivated Cas9." The nuclease-inactivated Cas9 still retains gRNA-directed DNA binding ability. Thus, in principle, when fused to another protein, nuclease-inactivated Cas9 can target the additional protein to almost any DNA sequence simply by co-expression with a suitable guide RNA.

The naturally occurring adenine deaminase converts adenosine on a single-stranded RNA into inosine (I) by deamination using RNA as a substrate. Recently, DNA-dependent adenine deaminase that convert deoxyguanosine on a single-stranded DNA to inosine (I) using single-stranded DNA as a substrate has been obtained based on tRNA adenine deaminase TadA of *E. coli* by means of directed evolution. See Nicloe M. Gaudelli et al., doi: 10.1038/nature 24644, 2017. However, whether such a DNA-dependent adenine deaminase can function in plants is unknown and difficult to predict.

The present inventors have surprisingly found that nuclease-inactivated CRISPR effector proteins (such as nuclease-inactivated Cas9) is fused to a DNA-dependent adenine deaminase, and under the guidance of a guide RNA, the fusion protein can target a target sequence in the plant genome. Due to the deficient activity of the nuclease in CRISPR effector proteins, the DNA double strands are not cleaved, and the DNA-dependent adenine deaminase in the fusion protein is capable of deaminating the adenosine(s) in the single-stranded DNA produced during the formation of the CRISPR effector proteins-guide RNA-DNA complex into a inosine (I). Since DNA polymerase treats inosine (I) as guanine (G), substitution of A to G can be achieved by base mismatch repair.

In some embodiments of the present invention, the DNA-dependent adenine deaminase is a variant of the *E. coli* tRNA adenine deaminase TadA (ecTadA), in particular a variant which can accept single-stranded DNA as a substrate, the variant comprises, relative to wild-type ecTadA, one or more sets of mutations selected from the group consisting of:
1) A106V and D108N;
2) D147Y and E155V;
3) L84F, H123Y and I156F;
4) A142N;
5) H36L, R51L, S146C and K157N;
6) P48S/T/A;
7) A142N;
8) W23L/R;
9) R152H/P.

In a preferred embodiment of the present invention, the DNA-dependent adenine deaminase comprises the following mutations relative to wild-type ecTadA: W23R, H36L, R51L, S146C, K157N, A106V, D108N, P48A, L84F, H123Y, I156F, D147Y, E155V, R152P.

Amino acid sequence of wild-type EcTadA is shown as SEQ ID NO:1.

The amino acid sequence of a preferred ecTadA-derived DNA-dependent adenine deaminase is set forth in SEQ ID NO: 2.

The nuclease-inactivated Cas9 of the present invention may be derived from Cas9 of different species, for example, from *S. pyogenes* Cas9 (SpCas9), or from *S. aureus* Cas9 (SaCas9). Mutation of both the HNH nuclease subdomain and the RuvC subdomain of Cas9 (for example, including the mutations D10A and H840A) will inactivate Cas9 nuclease into nuclease death Cas9 (dCas9). The mutation inactivation in one of the subdomains allows Cas9 to have nickase activity, i.e., obtain Cas9 nickase (nCas9), for example, nCas9 with only the mutation D10A.

Thus, in some embodiments of the invention, the nuclease-inactivated Cas9 of the invention comprises an amino acid substitution D10A and/or H840A relative to wild-type Cas9.

In some preferred embodiments of the invention, the nuclease inactivated Cas9 of the invention has nickase activity. Without being bound by any theory, it is believed that the mismatch repair of eukaryotes directs the removal and repair of mismatched bases by the nicks on the DNA strand. The I:T mismatch formed by DNA-dependent adenine deaminase may be repaired to A:T. By introducing a nick on a chain containing unedited T, it will be possible to preferentially repair the I:T mismatch to the desired C:G. Thus, preferably, the nuclease-inactivated Cas9 is a Cas9 nickase that retains the cleavage activity of the HNH subdomain of Cas9, while the cleavage activity of the RuvC subdomain is inactivated. For example, the nuclease inactivated Cas9 comprises an amino acid substitution D10A relative to wild type Cas9.

In some embodiments of the invention, the nuclease inactivated Cas9 may also comprise additional mutations. For example, nuclease-inactivated SpCas9 may also comprise a VQR or VRER mutation and SaCas9 may also comprise a KKH mutation (Kim et al. Nat. Biotechnol. 35, 371-376.).

In embodiments of the invention, the nuclease inactivated SpnCas9 comprises the amino acid sequence set forth in SEQ ID NO:3.

In some embodiments of the present invention, the deaminase is fused to the N-terminus of nuclease-inactivated CRISPR effector proteins (e.g., nuclease-inactivated Cas9).

In some preferred embodiments, the N-terminus of the DNA-dependent adenine deaminase is fused with a corresponding wild-type adenine deaminase. It is expected that the formation of heterodimers between DNA-dependent adenine deaminase and wild-type adenine deaminase can significantly increase the A to G editing activity of the fusion protein.

In some embodiments of the present invention, the DNA-dependent adenine deaminase and the nuclease-inactivated CRISPR effector proteins are fused via a linker. The linker may be 1-50 (for example, 1, 2, 3, 4, 5, 6, 7, 8, 9, 10, 11, 12, 13, 14, 15, 16, 17, 18, 19, 20 or 20-25, 25-50) amino acids in length, or non-functional amino acid sequences with more amino acids and without secondary or higher structures. For example, the linker can be a flexible linker such as GGGGS (SEQ ID NO: 207), GS, GAP, (GGGGS)×3 (SEQ ID NO: 208), GGS and (GGS)×7 (SEQ ID NO: 209), and the like. Preferably, the linker is 32 amino acids in length. In some preferred embodiments, the amino acid sequence of the linker is: SGGSSGGSSGSETPGTSESATPESSGGSSGGS (SEQ ID NO: 210).

In some embodiments of the present invention, the base-editing fusion proteins of the present invention further comprise a nuclear localization sequence (NLS). In general, one or more NLSs in the base-editing fusion protein should be of sufficient strength to drive the base-editing fusion protein in the nucleus of a plant cell to achieve an amount accumulation of base editing function. In general, the intensity of nuclear localization activity is determined by the number, location, one or more specific NLSs used of the NLS in the base-editing fusion protein, or a combination of these factors.

In some embodiments of the present invention, the NLS of the base-editing fusion protein of the present invention may be located at the N-terminus and/or C-terminus. In some embodiments of the invention, the NLS of the base-editing fusion protein of the invention may be between the adenine deaminase and the nuclease-inactivated CRISPR effector protein. In some embodiments of the invention, the NLS of the base-editing fusion protein of the invention may be between the DNA-dependent adenine deaminase and the nuclease-inactivated CRISPR effector protein. In some embodiments, the base-editing fusion protein comprises about 1, 2, 3, 4, 5, 6, 7, 8, 9, 10 or more NLSs. In some embodiments, the base-editing fusion protein comprises about 1, 2, 3, 4, 5, 6, 7, 8, 9, 10 or more NLS at or near the N-terminus. In some embodiments, the base-editing fusion protein comprises about 1, 2, 3, 4, 5, 6, 7, 8, 9, 10 or more NLSs at or near the C-terminus. In some embodiments, the base-editing fusion protein comprises a combination of these, such as comprises one or more NLSs at the N-terminus and one or more NLSs at the C-terminus. When there is more than one NLS, each can be selected to be independent of other NLSs. In some preferred embodiments of the present invention, the base-editing fusion protein comprises at least 2 NLSs, for example, the at least 2 NLSs are located at the C-terminus. In some preferred embodiments, the NLS is at the C-terminus of the base-editing fusion protein. In some preferred embodiments of the present invention, the base-editing fusion protein comprises at least 3 NLSs. In more preferred embodiments of the present invention, the base-editing fusion protein comprises at least 3 NLSs at the C-terminus. In some preferred embodiments, the base-editing fusion protein does not comprise NLS at the N-terminus and/or between the adenine deaminase and the nuclease-inactivated CRISPR effector protein.

In general, NLS consists of one or more short sequences of positively charged lysine or arginine exposed on the surface of the protein, but other types of NLS are also known. Non-limiting examples of NLS include: KKRKV (SEQ ID NO: 140) (nucleotide sequence 5'-AAGAAGAGAAAGGTC-3' (SEQ ID NO: 141)), PKKKRKV (SEQ ID NO: 142) (nucleotide sequence 5'-CCCAAGAAGAAGAGGAAGGTG-3' (SEQ ID NO: 143) or CCAAAGAAGAAGAGGAAGGTT (SEQ ID NO: 144)), or SGGSPKKKRKV (SEQ ID NO: 145) (nucleotide sequence 5'-TCGGGGGGGAGCCCAAAGAAGAAGCG-GAAGGTG-3' (SEQ ID NO: 146)).

In some embodiments of the present invention, the N-terminus of the base-editing fusion protein comprises the NLS with the amino acid sequence set forth in PKKKRKV (SEQ ID NO: 142). In some embodiments of the present invention, the C-terminus of the base-editing fusion protein comprises the NLS with the amino acid sequence set forth by KRPAATKKAGQAKKKK (SEQ ID NO: 147). In some embodiments of the invention, the C-terminus of the base-editing fusion protein comprises a higher efficient NLS with the amino acid sequence represented by PKKKRKV (SEQ ID NO: 142).

Furthermore, depending on the location of the DNA to be edited, the base-editing fusion proteins of the present invention may also include other localization sequences, such as cytoplasmic localization sequences, chloroplast localization sequences, mitochondrial localization sequences, and the like.

In other specific embodiments of the invention, the base-editing fusion protein comprises the amino acid sequence set forth in SEQ ID NO:4.

In other specific embodiments of the invention, the base-editing fusion protein comprises the amino acid sequence set forth in SEQ ID NO:5.

In other specific embodiments of the invention, the base-editing fusion protein comprises the amino acid sequence set forth in one of SEQ ID NOs: 18-25. In other specific embodiments of the invention, the base-editing fusion protein comprises the amino acid sequence set forth in one of SEQ ID NOs: 33-39. In other preferred embodiments of the invention, the base-editing fusion protein comprises the amino acid sequence set forth in one of SEQ ID NOs: 33-35, 38 and 39. In a preferred embodiment, the base-editing fusion protein comprises the amino acid sequence set forth in SEQ ID NO:39.

To obtain efficient expression in plant, in some embodiments of the present invention, the nucleotide sequence encoding the base-editing fusion protein is codon optimized for the plant to be base edited.

Codon optimization refers to the replacement of at least one codon (eg, about or more than about 1, 2, 3, 4, 5, 10, 15, 20, 25, 50 or more codons) of a native sequence by a codon that is used more frequently or most frequently in the gene of the host cell, modifying the nucleic acid sequence while maintaining the native amino acid sequence to enhance expression in the host cell of interest. Different species show specific preferences for certain codons of a particular amino acid. Codon preference (difference in codon usage between organisms) is often associated with the efficiency of translation of messenger RNA (mRNA), which is believed to depend on the nature of the translated codon and the availability of specific transfer RNA (tRNA) molecules. The advantages of selected tRNAs within cells generally reflect the most frequently used codons for peptide synthesis. Therefore, genes can be customized to be best gene expressed in a given organism based on codon optimization. The codon usage table can be easily obtained, for example, in the Codon Usage Database available at www.kazusa.orjp/codon/, and these tables can be adjusted in different ways. See, Nakamura Y. et. al "Codon usage tabulated from the international DNA sequence databases: status for the year2000 Nucl. Acids Res, 28: 292 (2000).

In some embodiments of the invention, the nucleotide sequence encoding the base-editing fusion protein with codon optimization is shown in SEQ ID NO: 6.

In other specific embodiments of the invention, the nucleotide sequence encoding the base-editing fusion protein with codon optimization is shown in SEQ ID NO:7.

In other specific embodiments of the invention, the nucleotide sequence encoding the base-editing fusion protein with codon optimization is shown in one of SEQ ID NOs: 10-17.

In other specific embodiments of the invention, the nucleotide sequence encoding the base-editing fusion protein with codon optimization is shown in one of SEQ ID NOs: 26-32. In other preferred embodiments of the invention, the nucleotide sequence encoding the base-editing fusion protein with codon optimization is shown in one of SEQ ID NOs: 26-28, 31 and 32. Preferably, the nucleotide sequence encoding the base-editing fusion protein with codon optimization is shown in SEQ ID NO:32.

In some embodiments of the invention, the guide RNA is a single guide RNA (sgRNA). Methods for constructing suitable sgRNAs from a given target sequence are known in the art. See, for example, Wang, Y. et al. Simultaneous editing of three homoeoalleles in hexaploid bread wheat confers heritable resistance to powdery mildew. Nat. Biotechnol. 32, 947-951 (2014); Shan, Q. et al. Targeted Nat. Biotechnol. 31, 686-688 (2013); Liang, Z. et al. Targeted mutagenesis in *Zea mays* using TALENs and the CRISPR/Cas system. J Genet Genomics. 41, 63-68 (2014).

In some embodiments of the invention, the sequence of the sgRNA comprises the following scaffold sequence:
gffitagagctagaaatagcaagttaaaataaggctagtccgttatcaactt-gaaaaagtggcaccgagtcg gtgc (SEQ ID NO: 138, corresponding to the sgRNA in Example) or
gtttaagagctatgctggaaacagcatagcaagtttaaataaggtagtccgttat-caacttgaaaaagtggca ccgagtcggtgc (SEQ ID NO: 139, corresponding to the esgRNA in Example) wherein the target sequence (or spacer sequence) in the sgRNA is at the 5' end of the above scaffold sequence.

In a preferred embodiment, the base-editing fusion protein comprises the amino acid sequence set forth in SEQ ID NO: 39, and the guide RNA is a single guide RNA comprising the scaffold sequence set forth in SEQ ID NO:139.

In some embodiments of the invention, the nucleotide sequence encoding the base-editing fusion protein and/or the nucleotide sequence encoding the guide RNA is operably linked to a plant expression regulatory element such as a promoter.

Examples of promoters that can be used in the present invention include, but are not limited to, cauliflower mosaic virus 35S promoter (Odell et al. (1985) Nature 313: 810-812), maize Ubi-1 promoter, wheat U6 promoter, rice U3 promoter, maize U3 promoter, rice actin promoter, TrpPro5 promoter (U.S. patent application Ser. No. 10/377,318; Mar. 16, 2005), pEMU promoter (Last et al. (1991) Theor Appl. Genet. 81: 581-588), MAS promoter (Velten et al. (1984) EMBO J. 3: 2723-2730), maize H3 histone promoter (Lepetit et al. (1992) Mol. Gen. Genet. 231:276-285 and Atanassova et al. (1992) Plant J. 2(3): 291-300) and *Brassica napus* ALS3 (PCT application WO 97/41228) promoter. Promoters useful in the present invention also include the commonly used tissue-specific promoters reviewed in Moore et al. (2006) Plant 45(4): 651-683.

The precise RNA of the sgRNA which can be used in the present invention can be produced by self-cleavage of tRNA (Zhang et al. (2017) Genome Biology, 2017, 18: 191).

3. The Method of Producing Genetically Modified Plant

In another aspect, the invention provides a method of producing a genetically modified plant, comprising introducing a system of the invention for base editing of a target sequence in a plant genome into the plant, whereby the guide RNA targets the base-editing fusion protein to a target sequence in the plant genome, resulting in one or more A in the target sequence being replaced with G.

The design of target sequences that can be recognized and targeted by Cas9 and the guide RNA complex is within the skill of those skilled in the art. In general, the target sequence is a sequence complementary to a guide sequence of about 20 nucleotides contained in the guide RNA, and the 3' end is immediately adjacent to the protospacer adjacent motif (PAM) NGG.

For example, in some embodiments of the present invention, the target sequence has the following structure: 5'-Nx-NGG-3', wherein N is independently selected from A, G, C and T; X is an integer of 14≤X≤35; Nx represents X consecutive nucleotides, NGG is a PAM sequence. In some preferred embodiments of the invention, X is 20. In some embodiments, the base editing window is located at positions 4-8 of the target sequence. That is, the system of the present invention can cause one or more A to G substitution in the range of position 4 to 8 from the 5' end of the target sequence.

In some embodiments of the methods of the present invention, further comprising screening for a plant having the desired nucleotide substitution. Nucleotide substitution in plants can be detected by T7EI, PCR/RE or sequencing methods, see, for example, Shan, Q., Wang, Y, Li, J. & Gao, C. Genome editing in rice and wheat using the CRISPR/Cas system. Nat. Protoc. 9, 2395-2410 (2014).

In the methods of the present invention, the base editing system can be introduced into the plant by a variety of methods well known to those skilled in the art. Methods that can be used to introduce a genome editing system of the present invention into the plant include, but are not limited to, gene gun method, PEG-mediated protoplast transformation, *Agrobacterium*-mediated transformation, plant virus-mediated transformation, pollen tube pathway and ovary injection method. Preferably, the base editing system is introduced into the plant by transient transformation.

In the method of the present invention, the modification of the target sequence can be achieved only by introducing or producing the base-editing fusion protein and the guide RNA in the plant cell, and the modification can be stably inherited, without any need to stably transform the base editing system into plants. This avoids the potential off-target effect of the stable transformed base editing system and also avoids the integration of the exogenous nucleotide sequence in the plant genome, thereby providing greater biosafety.

In some preferred embodiments, the introduction is carried out in the absence of selection pressure to avoid integration of the exogenous nucleotide sequence into the plant genome.

In some embodiments, the introducing comprises transforming the base editing system of the present invention into an isolated plant cell or tissue and then regenerating the transformed plant cell or tissue into an intact plant. Preferably, the regeneration is carried out in the absence of selection pressure, i.e., no selection agent for the selection gene on the expression vector is used during tissue culture. Avoiding the use of a selection agent can increase the regeneration efficiency of the plant, obtaining a modified plant free of exogenous nucleotide sequences.

In other embodiments, the base editing system of the present invention can be transformed into specific parts of an intact plant, such as leaves, shoot tips, pollen tubes, young ears or hypocotyls. This is particularly suitable for the transformation of plants that are difficult to regenerate in tissue culture.

In some embodiments of the invention, the in vitro expressed protein and/or the in vitro transcribed RNA molecule are directly transformed into the plant. The protein and/or RNA molecule is capable of base editing in plant cells and subsequent degradation by the cell, avoiding integration of the exogenous nucleotide sequence in the plant genome.

Thus, in some embodiments, plants can be genetically modified and bred using the methods of the invention to obtain plants that are free of exogenous DNA integration, i.e., transgene-free modified plants. Furthermore, the base editing system of the present invention has high specificity (low off-target rate) and improved biosafety when performing base editing in plants.

Plants that can be base-edited by the methods of the invention include monocots and dicots. For example, the plant may be a crop plant such as wheat, rice, corn, soybean, sunflower, sorghum, canola, alfalfa, cotton, barley, millet, sugar cane, tomato, tobacco, tapioca or potato.

In some embodiments of the present invention, wherein the target sequence is associated with a plant trait, such as an agronomic trait, whereby the base editing results in the plant having altered traits relative to a wild type plant. In the present invention, the target sequence to be modified may be located at any position in the genome, for example, in a functional gene such as a protein-encoding gene, or may be, for example, located in a gene expression regulatory region such as a promoter region or an enhancer region, thereby gene functional modification or gene expression modification can be achieved. Accordingly, in some embodiments of the present invention, the substitution of A to G results in an amino acid substitution in the target protein. In other embodiments of the present invention, the substitution of A to G results in a change in expression of the target gene.

In some embodiments, the gene modified by the methods of the invention may be an herbicide resistant gene acetolactate synthase (ALS) and an acetyl CoA carboxylase (ACC) gene. A-to-G mutations in key amino acid sites of the herbicide genes ALS and ACC can confer herbicide resistance to plants. In some embodiments, the ACC gene is modified. In some embodiments, the rice ACC gene is modified and the ACC protein encoded by the modified ACC gene has a C2186R mutation.

In some embodiments of the present invention, the method further comprises obtaining progeny of the genetically modified plant.

In another aspect, the present invention provides a genetically modified plant or a progeny thereof, or a part thereof, wherein the plant is obtained by the method of the invention described above. In some embodiments, the genetically modified plant or a progeny thereof or a part thereof is transgene-free.

In another aspect, the present invention provides a method of plant breeding comprising crossing a genetically modified first plant obtained by the above method of the present invention with a second plant not containing the genetic modification, thereby the genetic modification is introduced into the second plant.

EXAMPLE

Construction of nCas9-ABE Expression Vector

The ABE, XTEN, nCas9(D10A) sequences were codon optimized for plants and ordered from GenScript (Nanjing). The full-length nCas9-ABE fragment was amplified using primer pairs HindIII-F (with HindIII restriction site) and EcoRI (with EcoRI restriction site). The PCR product was digested with HindIII and EcoRI, and then inserted into the two enzyme-digested pJIT163-GFP vectors (sequence of this vector is shown in SEQ ID NO: 8) to generate the fusion expression vector pn/dCas9-PBE.

Construction of sgRNA Expression Vector

According to the previous description (Wang, Y. et al. Simultaneous editing of three homoeoalleles in hexaploid bread wheat confers heritable resistance to powdery mildew. Nat. Biotechnol. 32, 947-951, 2014; Shan, Q. et al. Targeted genome modification of Crops using a CRISPR-Cas system. Nat. Biotechnol. 31, 686-688, 2013; and Liang, Z. et al. Targeted mutagenesis in Zea mays using TALENs and the CRISPR/Cas system. J Genet Genomics. 41, 63-68, 2014), an sgRNA expression vector was constructed based on pTaU6-sgRNA (Addgene ID53062) or pOsU3-sgRNA (Addgene ID53063) or pZmU3-sgRNA (Addgene ID5306) or OsU3/TaU6-tRNA-sgRNA (Zhang et al. 2017. Genome Biology. DOI:10.1186/s13059-017-1325-9):

pTaU3-mGFPP-sgRNA, pOsU3-mGFP-sgRNA, pZmU3-mGFP-sgRNA, pOsU3-DEP1-T6-sgRNA, pOsU3-DEP1-T7-sgRNA, pOsU3-ACC-T3-sgRNA, pOsU3-NRT1.1-T1-sgRNA.

GFP Expression Vector pUbi-mGFP, sequence of the vector is shown in SEQ ID NO: 9.

Protoplast Assays

Wheat Bobwhite and rice Nipponbare were used in this study. Protoplast transformation was performed as described below. The average transformation efficiency is 55-70%. Protoplasts transformation is performed as described below. Transformation is carried out with 10 μg of each plasmid by PEG-mediated method. Protoplasts were collected after 48 h and DNA was extracted for T7EI and PCR-RE assay.

Preparation and Transformation of Wheat Protoplasts

1) The middle parts of wheat tender leaves were cut into strips of 0.5-1 mm in width. The strips were placed into 0.6M Mannitol solution for 10 minutes, filtered, and then placed in 50 ml enzyme solution 20-25° C. in darkness, with gently shaking (10 rmp) for 5 hours.
2) 10 ml W5 was added to dilute the enzymolysis products and the products were filtered with a 75 μm nylon filter in a round bottom centrifuge tube (50 ml).
3) 23° C. 100 g centrifugation for 3 min, and the supernatant was discarded. 4) The products were gently suspended with 10 ml W5, placed on the ice for 30 min to allow the protoplasts gradually settling, and the supernatant was discarded.
5) Protoplasts were suspended by adding an appropriate amount of MMG, placed on ice until transformation.
6) 10-20 μg plasmid, 200 μl protoplasts (about 4×105 cells), 220 μl fresh PEG solution were added into a 2 ml centrifuge tube, mixed up, and placed under room temperature in darkness for 10-20 minutes to induce transformation.
7) After the induction of transformation, 880 μl W5 solution was slowly added, and the tubes were gently turned upside down for mixing, then 100 g horizontal centrifuged for 3 min, and the supernatant was discarded.
8) The products were resuspended in 2 ml W5 solution, transferred to a six-well plate, cultivated under room temperature (or 25° C.) in darkness. For protoplast genomic DNA extraction, the products need to be cultivated for 48 h.

Preparation and Transformation of Rice Protoplast

1) Leaf sheath of the seedlings were used for protoplasts isolation, and cut into about 0.5 mm wide with a sharp blade.
2) Immediately after incision, transferred into 0.6M Mannitol solution, and placed in the dark for 10 min.
3) Mannitol solution was removed by filtration, and the products were transferred into enzymolysis solution, and evacuated for 30 min.
4) Enzymolysis was performed for 5-6 h in darkness with gently shaking (decolorization shaker, speed 10).
5) After enzymolysis completion, an equal volume of W5 was added, horizontal shake for 10 s to release protoplasts.
6) Protoplasts were filtered into a 50 ml round bottom centrifuge tube with a 40 μm nylon membrane and washed with W5 solution.
7) 250 g horizontal centrifugation for 3 min to precipitate the protoplasts, the supernatant was discarded.
8) Protoplasts were resuspended by adding 10 ml W5, and then centrifuged at 250 g for 3 min, and the supernatant was discarded.
9) An appropriate amount of MMG solution was added to resuspend the protoplasts to a concentration of $2 \times 10^6$/ml.

Note: All the above steps were carried out at room temperature.

10) 10-20 μg plasmid, 200 μl protoplasts (about $4 \times 10^5$ cells), and 220 μl fresh PEG solution were added into a 2 ml centrifugal tube, mixed, and placed at room temperature in darkness for 10-20 minutes to induce transformation.
11) After the completion of the transformation, 880 μl W5 solution was slowly added, and the tubes were gently turned upside down for mixing, 250 g horizontal centrifuged for 3 min, and the supernatant was discarded.
12) The products were resuspended in 2 ml WI solution, transferred to a six-well plate, cultivated in room temperature (or 25° C.) in darkness. For protoplast genomic DNA extraction, the products need to be cultivated for 48 h.

PCR/RE:

1) Plant genomic DNA was extracted.
2) Fragments containing the target sites, the length of which is between 350-1000 bp, were amplified with synthetic ene-specific primers:

| | |
|---|---|
| 10 × EasyTaq Buffer | 5 μl |
| dNTP (2.5 mM) | 4 μl |
| Forward primer (10 μM) | 2 μl |
| Forward primer (10 μM) | 2 μl |
| Easy Taq | 0.5 μl |
| DNA | 2 μl |
| ddH$_2$O | To 50 μl |

3) The general reaction conditions are: denaturation at 94° C. for 5 min; denaturation at 94° C. for 30 s; anneal at 58° C. for 30 s, extension at 72° C. for 30 s, amplification for 30 to 35 cycles; incubation at 72° C. for 5 min; incubation at 12° C. 5 μl PCR products were subjected to electrophoresis.
4) PCR products were digested with restriction endonuclease as follows:

| | |
|---|---|
| 10 × Fastdigest Buffer | 2 μl |
| Restriction enzymes | 1 μl |
| PCR product | 3-5 μl |
| ddH$_2$O | To 20 μl |

5) Digestion at 37° C. for 2-3 h. Products were analyzed by 1.2% agarose gel electrophoresis.
6) The uncut mutant bands in the PCR products were recovered and purified, and subjected to TA cloning as follows:

| pEasy-T Vector | 1 μl |
|---|---|
| Recovered uncleaved PCR product | 4 μl |

7) The ligation was performed at 22° C. for 12 min. And the products were transformed into *E. coli* competent cells, which were then plated on LB plates (Amp100, IPTG, and X-gal), incubated at 22° C. for 12-16 h. White colonies were picked for identifying positive clones and sequencing.

Agrobacterium-Mediated Transformation of Rice Callus

*Agrobacterium tumefaciens* strain AGL1 was transformed by electroporation using pH-PABE-7-esgRNA or pH-PABE-7-sgRNA binary vector. *Agrobacterium*-mediated transformation of rice (Zhonghua 11) callus was processed according to the method described by Shan Q et al. (Shan Q et al., Rapid and efficient gene modification in rice and Brachypodium using TALENs. Mol Plant 2013, 6:1365-1368), and transgenic plants was selected using hygromycin.

Introduction of DNA Constructs into Wheat Immature Embryo Cells by Gene Gun

PABE-7 and pTaU6-esgRNA plasmid DNA were simultaneously introduced into immature wheat embryos by gene gun, and the plant was regenerated without selection agents according to the previous description (Zhang Y, Liang Z, Zong Y, Wang Y, Liu J, Chen K, Qiu J L, Gao C: Efficient and transgene-free genome editing in wheat through transient expression of CRISPR/Cas9 DNA or RNA. Nat Commun 2016, 7:12617).

Sequencing

Different sgRNA expression vectors were transformed into wheat and rice protoplast with ABE and pwCas9 for 48 hours-60 hours, and protoplasts were collected and DNA was extracted for sequencing. In the first round of PCR, the target region was amplified using site-specific primers. In second round of PCR, forward and reverse tags were added to the end of the PCR product for library construction. Equal amounts of different PCR products were pooled. Samples were then sequenced using the Illumina High-Seq 4000 at the Beijing Genomics Institute or using the Illumina Next-Seq 500 platform at the Mega Genomics (Beijing, China).

Example 1. Base Editing of GFP by ABE System in Plant Protoplasts

The inventors first constructed an ABE (adenine base editing) system suitable for plant cell editing, including SpnCas9-ABE (SEQ ID NO: 4, SEQ ID NO: 6), and SpnCas9-VQR-ABE (SEQ ID NO: 10, SEQ ID NO: 18), SpnCas9-VRER-ABE (SEQ ID NO: 11, SEQ ID NO: 19), SanCas9-ABE (SEQ ID NO: 12, SEQ ID NO: 20), SanCas9-KKH-ABE (SEQ ID NO: 13, SEQ ID NO: 21), SpnCas9-ABE-1 (SEQ ID NO: 5, SEQ ID NO: 7), SpnCas9-VQR-ABE-1 (SEQ ID NO: 14, 22), SpnCas9-VRER-ABE-1 (SEQ ID NO: 15, SEQ ID NO: 23), SanCas9-ABE-1 (SEQ ID NO: 16, SEQ ID NO: 24), SanCas9-KKH-ABE-1 (SEQ ID NO: 17. SEQ ID NO: 25), each system was codon optimized for expression in plants. The amino acid sequence and nucleotide sequence of each base-editing fusion protein are shown in the attached sequence listing. The structure of each construct is shown in FIG. 1.

The inventors then used the protoplast transient expression system and the GFP reporter system to detect the function of the ABE system in plant cells.

First, an Ubi promoter-driven inactivated GFP expression vector (Ubi-mGFP) was constructed in which the amino acid codon (CAG) at position 70 of GFP was mutated to a stop codon (tAG) to inactivate GFP. The vector is co-transformed with the above ABE system into plant protoplasts. If the ABE system mutates the stop codon (tAG) to (CAG), it will restore mGFP to the wild type, causing it to produce green fluorescence. The experimental principle is shown in FIG. 2A.

Figure 2:
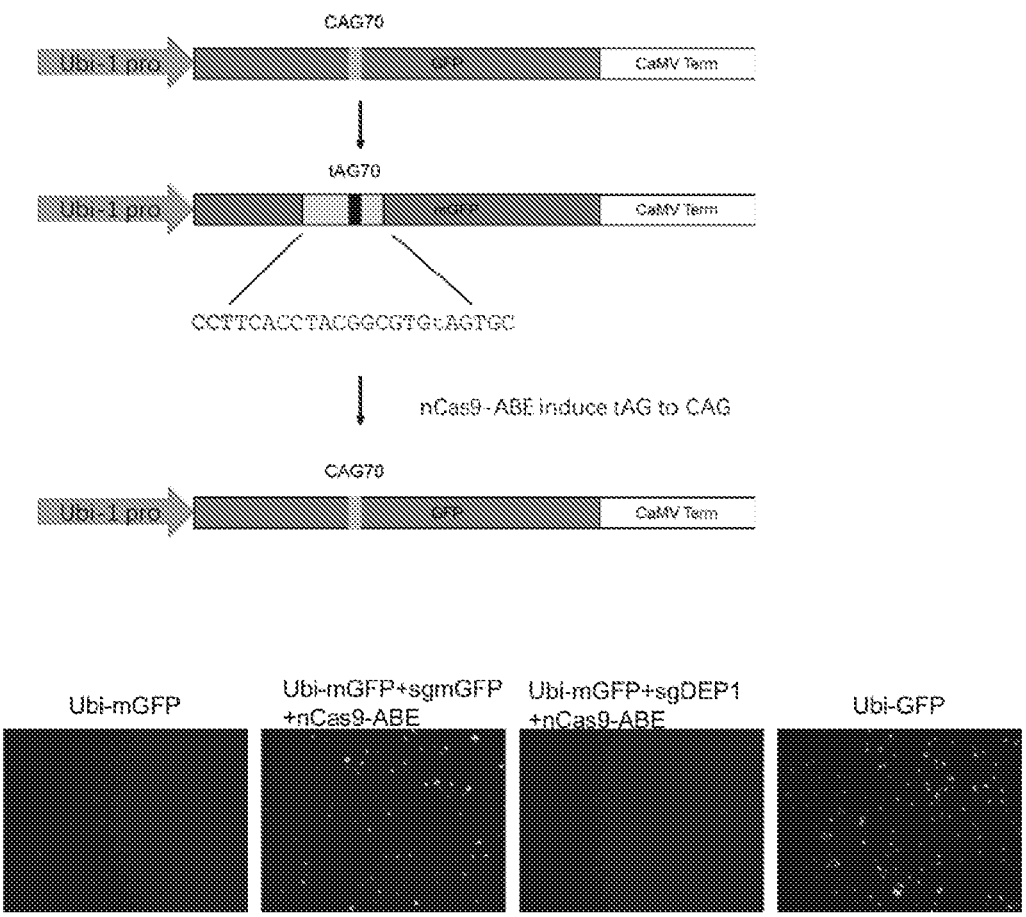
FIG. 2. Adenine base editing system enables base editing of exogenous GFP genes in plant protoplasts. Figure discloses SEQ ID NO: 40.

The experimental results are shown in FIG. 2B. The protoplast cells transformed with the negative control Ubi-mGFP vector alone had no green fluorescence produced, and the protoplast cells transformed with the positive control Ubi-GFP alone had green fluorescence produced. When the Ubi-mGFP vector was co-transformed with the ABE system against mGFP, green fluorescence was produced. When the Ubi-mGFP vector was co-transformed with the ABE system for the unrelated gene DEP1, no green fluorescence was produced. It can be seen that the ABE system can achieve base editing of A to G in plant protoplasts.

Example 2. Editing of Plant Endogenous Genes by ABE

The rice OsDEP1, OsCDC48, OsACC and OsNRT1.1b genes were selected as the research objects, and the target sequence is shown in the underlined part of FIG. 3B.

Figure 4:
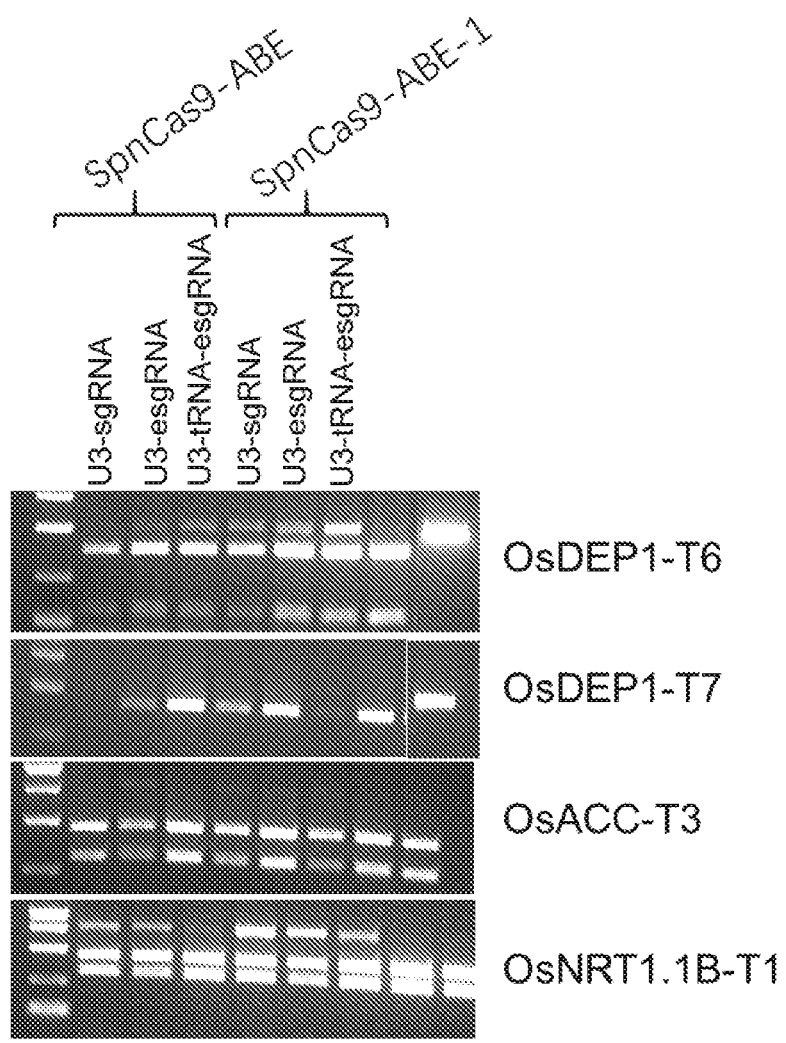
FIG. 4. Base editing of plant endogenous genes by different adenine base editing constructs.

A cleavage site was selected at the mutation site for PCR/RE detection. The digestion and sequencing results showed a mutation of A to G at the target site (FIG. 3 and FIG. 4).

Example 3. Effect of ABE Structure on Gene Editing

In this example, seven ABE fusion proteins were constructed. The seven fusion proteins were named PABE-1 to PABE-7, differing in the location of adenine deaminase and the number and location of NLS. The structures of the 7 fusion proteins are shown in FIG. 5A, the sequences of which are shown in SEQ ID NOs: 33-39, and the coding sequences for codon-optimization based on the grains are shown in SEQ ID NOs: 26-32.

First, the editing efficiency of the above PABE fusion proteins was tested by the experiment of restoring mutant GFP to wild type GFP as described in Example 1. The results showed that cells treated with five of these seven fusion proteins (PABE-1, PABE-2, PABE-3, PABE-6, and PABE-7) showed stable GFP fluorescence (FIG. 5B).

Flow cytometry analysis showed that the percentage of cells that showed fluorescence was between 0.1% and 32.8% (FIG. 5C). Treatment with nCas9 with 3 copies of NLS (PABE-7) at the C-terminus produced the highest ratio of cells expressing GFP, significantly higher than that with PABE-2 and other PABE constructs (FIG. 5B, C). The efficiency of PABE with NLS only at the C-terminus was higher than that of PABE with NLS at the N-terminus.

Example 4. Editing of Plant Endogenous Genes by PABE-2 and PABE-7

To further compare the editing efficiencies of PABE-2 and PABE-7, in this example, 16 rice endogenous genomic loci were tested. Specific target sites and sequences are shown in Table 1.

TABLE 1

Target sites and sequences of sgRNA.

| Gene | Target Sequence | Oligonucleotides (5'-3') | Application |
|---|---|---|---|
| mGFP | CCTTCACCTACGGCGTG<u>T</u>AGTGC (SEQ ID NO: 40) | F: GGCGGCACTACACGCCGTAGGTGA (SEQ ID NO: 41)<br>R: AAACTCACCTACGGCGTGTAGTGC (SEQ ID NO: 42) | pOsU3-sgRNA Construction |
| OsALS-T1 | CCC<u>A</u>AGTGGGGCGCATTCAAGG (SEQ ID NO: 43) | F: GGCGCCCAAGTGGGGCGCATTCA (SEQ ID NO: 44)<br>R: AAACTGAATGCGCCCCCACTTGGG (SEQ ID NO: 45) | pOsU3-sgRNA/esgRNA Construction |
| | | F: TGCACCCAAGTGGGGCGCATTCA (SEQ ID NO: 46)<br>R: AAACTGAATGCGCCCCCACTTGGG (SEQ ID NO: 47) | pOsU3-tRNA-sgRNA Construction |
| OsALS-T2 | CCTC<u>A</u>TG<u>AA</u>CATTCAGGAGCTGG (SEQ ID NO: 48) | F: GGCGCCTCATGAACATTCAGGAGC (SEQ ID NO: 49)<br>R: AAACGCTCCTGAATGTTCATGAGG (SEQ ID NO: 50) | pOsU3-sgRNA/esgRNA Construction |
| | | F: TGCACCTCATGAACATTCAGGAGC (SEQ ID NO: 51)<br>R: AAACGCTCCTGAATGTTCATGAGG (SEQ ID NO: 52) | pOsU3-tRNA-sgRNA Construction |
| OsCDC48-T1 | GCT<u>A</u>GCTTTGACATAATCTCCGG (SEQ ID NO: 53) | F: GGCGGCTAGCTTTGACATAATCTC (SEQ ID NO: 54)<br>R: AAACGAGATTATGTCAAAGCTAGC (SEQ ID NO: 55) | pOsU3-sgRNA Construction |
| OsCDC48-T2 | CC<u>A</u>ATGC<u>A</u>TCCGTGAGAAGATGG (SEQ ID NO: 56) | F: GGCGCCAATGCATCCGTGAGAAGA (SEQ ID NO: 57)<br>R: AAACTCTTCTCACGGATGCATTGG (SEQ ID NO: 58) | pOsU3-sgRNA Construction |
| OsCDC48-T3 | TAGC<u>A</u>CCC<u>A</u>TGACAATGACATGG (SEQ ID NO: 59) | F: GGCGTAGCACCCATGACAATGACA (SEQ ID NO: 60)<br>R: AAACTGTCATTGTCATGGGTGCTA (SEQ ID NO: 61) | pOsU3-sgRNA/esgRNA Construction |
| | | F: TGCATAGCACCCATGACAATGACA (SEQ ID NO: 62)<br>R: AAACTGTCATTGTCATGGGTGCTA (SEQ ID NO: 63) | pOsU3-tRNA-sgRNA Construction |
| OsAAT | C<u>A</u>AGG<u>A</u>TCCCAGCCCCGTGAAGG (SEQ ID NO: 64) | F: GGCGCAAGGATCCCAGCCCCGTGA (SEQ ID NO: 65)<br>R: AAACTCACGGGGCTGGGATCCTTG (SEQ ID NO: 66) | pOsU3-sgRNA/sgRNA Construction |
| | | F: TGCACAAGGATCCCAGCCCCGTGA (SEQ ID NO: 67)<br>R: AAACTCACGGGGCTGGGATCCTTG (SEQ ID NO: 68) | pOsU3-tRNA-sgRNA Construction |
| OsDEP1-T1 | AGC<u>A</u>CATGAGAGAACAATATTGG (SEQ ID NO: 69) | F: GGCGAGCACATGAGAGAACAATAT (SEQ ID NO: 70)<br>R: AAACATATTGTTCTCTCATGTGCT (SEQ ID NO: 71) | pOsU3-sgRNA/esgRNA Construction |
| | | F: TGCAAGCACATGAGAGAACAATAT (SEQ ID NO: 72)<br>R: AAACATATTGTTCTCTCATGTGCT (SEQ ID NO: 73) | pOsU3-tRNA-sgRNA Construction |
| OsDEP1-T2 | AG<u>A</u>C<u>AA</u>GCTTGGCCCTCTTTGGG (SEQ ID NO: 74) | F: GGCGAGACAAGCTTGGCCCTCTTT (SEQ ID NO: 75)<br>R: AAACAAAGAGGGCCAAGCTTGTCT (SEQ ID NO: 76) | pOsU3-sgRNA/esgRNA Construction |
| | | F: TGCAAGACAAGCTTGGCCCTCTTT (SEQ ID NO: 77)<br>R: AAACAAAGAGGGCCAAGCTTGTCT (SEQ ID NO: 78) | pOsU3-tRNA-sgRNA Construction |
| OsDEP1-T3 | ATTTC<u>AA</u>ATGGATCTAAACAGGG (SEQ ID NO: 79) | F: GGCGATTTCAAATGGATCTAAACA (SEQ ID NO: 80)<br>R: AAACTGTTTAGATCCATTTGAAAT (SEQ ID NO: 81) | pOsU3-sgRNA Construction |

TABLE 1-continued

Target sites and sequences of sgRNA.

| Gene | Target Sequence | Oligonucleotides (5'-3') | Application |
|---|---|---|---|
| OsDEP1-T4 | ACAGATCTTGCCGTCTTTTTCGG (SEQ ID NO: 82) | F: GGCGACAGATCTTGCCGTCTTTTT (SEQ ID NO: 83)<br>R: AAACAAAAAGACGGCAAGATCTGT (SEQ ID NO: 84) | pOsU3-sgRNA Construction |
| OsACC-T1 | CCCAGACCGCATTGAGTGCTATG (SEQ ID NO: 85) | F: GGCGCATAGCACTCAATGCGGTCT (SEQ ID NO: 86)<br>R: AAACAGACCGCATTGAGTGCTATG (SEQ ID NO: 87) | pOsU3-sgRNA/esgRNA Construction |
| | | F: TGCACATAGCACTCAATGCGGTCT (SEQ ID NO: 88)<br>R: AAACAGACCGCATTGAGTGCTATG (SEQ ID NO: 89) | pOsU3-tRNA-sgRNA Construction |
| OsACC-T2 | TACTAGTCACACTTGCACTGTGG (SEQ ID NO: 90) | F: GGCGTACTAGTCACACTTGCACTG (SEQ ID NO: 91)<br>R: AAACCAGTGCAAGTGTGACTAGTA (SEQ ID NO: 92) | pOsU3-sgRNA Construction |
| OsNRT1.1B-T1 | ACTAGATATCTAAACCATTAAGG (SEQ ID NO: 93) | F: GGCGACTAGATATCTAAACCATTA (SEQ ID NO: 94)<br>R: AAACTAATGGTTTAGATATCTAGT (SEQ ID NO: 95) | pOsU3-sgRNA/esgRNA Construction |
| | | F: TGCAACTAGATATCTAAACCATTA (SEQ ID NO: 96)<br>R: AAACTAATGGTTTAGATATCTAGT (SEQ ID NO: 97) | pOsU3-tRNA-sgRNA Construction |
| OsNRT1.1B-T2 | GGCCATGGCGCCCGCGGCGGCGG (SEQ ID NO: 98) | F: GGCGGGCCATGGCGCCCGCGGCGG (SEQ ID NO: 99)<br>R: AAACCCGCCGCGGGCGCCATGGCC (SEQ ID NO: 100) | pOsU3-sgRNA Construction |
| OsEV | CACACACACACTAGTACCTCTGG (SEQ ID NO: 101) | F: GGCGCACACACACACTAGTACCTC (SEQ ID NO: 102)<br>R: AAACGAGGTACTAGTGTGTGTGTG (SEQ ID NO: 103) | pOsU3-sgRNA/esgRNA Construction |
| | | F: TGCACACACACACACTAGTACCTC (SEQ ID NO: 104)<br>R: AAACGAGGTACTAGTGTGTGTGTG (SEQ ID NO: 105) | pOsU3-tRNA-sgRNA Construction |
| OsOD | ACACACACACTAGTACCTCTGGG (SEQ ID NO: 106) | F: GGCGACACACACACTAGTACCTCT (SEQ ID NO: 107)<br>R: AAACAGAGGTACTAGTGTGTGTGT (SEQ ID NO: 108) | pOsU3-sgRNA/esgRNA Construction |
| | | F: TGCAACACACACACTAGTACCTCT (SEQ ID NO: 109)<br>R: AAACAGAGGTACTAGTGTGTGTGT (SEQ ID NO: 110) | pOsU3-tRNA-sgRNA Construction |
| TaDEP1 | ACGAGCTACATTTACTTGAAGGG (SEQ ID NO: 111) | F: CTTGACGAGCTACATTTACTTGAA (SEQ ID NO: 112)<br>R: AAACTTCAAGTAAATGTAGCTCGT (SEQ ID NO: 113) | pTaU6-sgRNA/esgRNA Construction |
| | | F: TGCAACGAGCTACATTTACTTGAA (SEQ ID NO: 114)<br>R: AAACTTCAAGTAAATGTAGCTCGT (SEQ ID NO: 115) | pTaU6-tRNA-sgRNA Construction |
| TaEPSPS | GAGGAAGTAAAGCTCTTCTTGGG (SEQ ID NO: 116) | F: CTTGGAGGAAGTAAAGCTCTTCTT (SEQ ID NO: 117)<br>R: AAACAAGAAGAGCTTTACTTCCTC (SEQ ID NO: 118) | pTaU6-sgRNA/esgRNA Construction |
| | | F: TGCAGAGGAAGTAAAGCTCTTCTT (SEQ ID NO: 119)<br>R: AAACAAGAAGAGCTTTACTTCCTC (SEQ ID NO: 120) | pTaU6-tRNA-sgRNA Construction |

TABLE 1-continued

Target sites and sequences of sgRNA.

| Gene | Target Sequence | Oligonucleotides (5'-3') | Application |
| --- | --- | --- | --- |
| TaGW2 | CAC<u>AAGAA</u>AATCCACCAGGATGG (SEQ ID NO: 121) | F: CTTGCACAAGAAAATCCACCAGGA (SEQ ID NO: 122) R: AAACTCCTGGTGGATTTTCTTGTG (SEQ ID NO: 123) | pTaU6-sgRNA/esgRNA Construction |
| | | F: TGCACACAAGAAAATCCACCAGGA (SEQ ID NO: 124) R: AAACTCCTGGTGGATTTTCTTGTG (SEQ ID NO: 125) | pTaU6-tRNA-sgRNA Construction |

It was found that plant ABE modified the underlined A/T base. PAM domains in each target sequence are shown in bold type.

Figure 6:
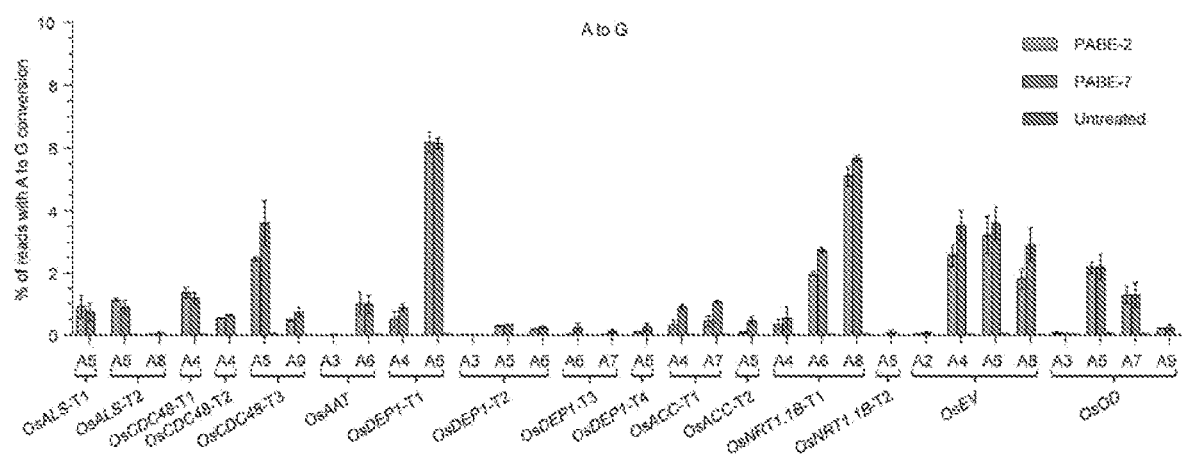
FIG. 6. Editing of endogenous genes in rice by PABE-2 and PABE-7.

A to G base editing of each gene in protoplasts was assessed by sequencing (100,000-220,000 reads per locus). As shown in FIG. 6, the base editing efficiency of PABE-7 was higher, and the A/T to C/G conversion at each point increased by an average of about 1.1 times compared to PABE-2. Collectively, these results demonstrate that the plant ABE system is capable of inducing A to G conversion in rice and that the editing efficiency was maximized when there are three NLSs at the C-terminus of nCas9.

Example 5. Effect of sgRNA on Editing Efficiency

To identify the optimal sgRNA format for PABE-7 activity, this example tested a variety of sgRNA modifications in a wide range of endogenous loci. The inventors compared the base editing activities of three sgRNA formats (native sgRNA, esgRNA and tRNA-sgRNA) in the 10 rice endogenous genomic target sites and 3 wheat endogenous genomic target sites in Table 1, respectively.

Figure 8:
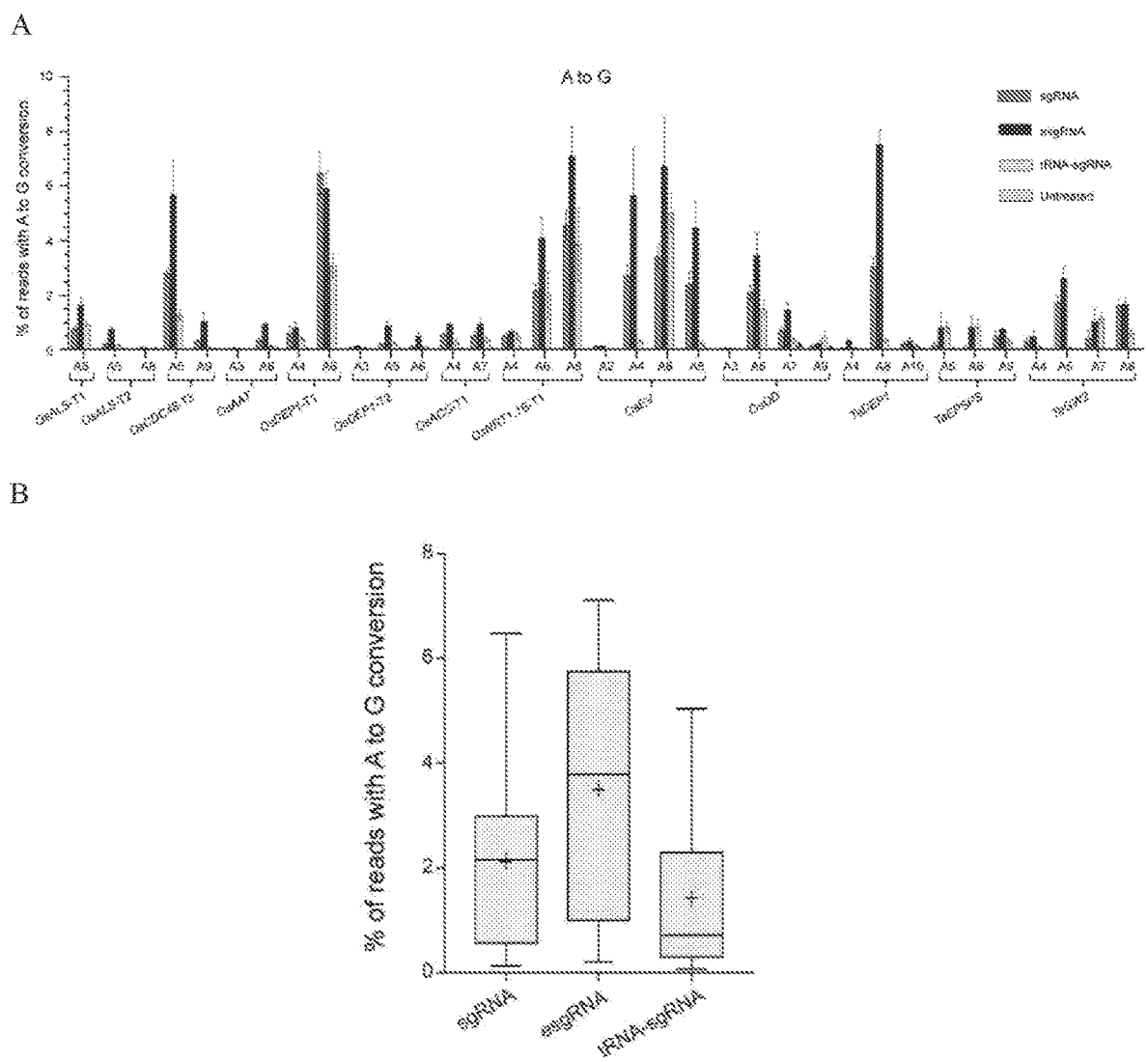
FIG. 8. Effect of different sgRNA formats on gene editing.
Figure 9:
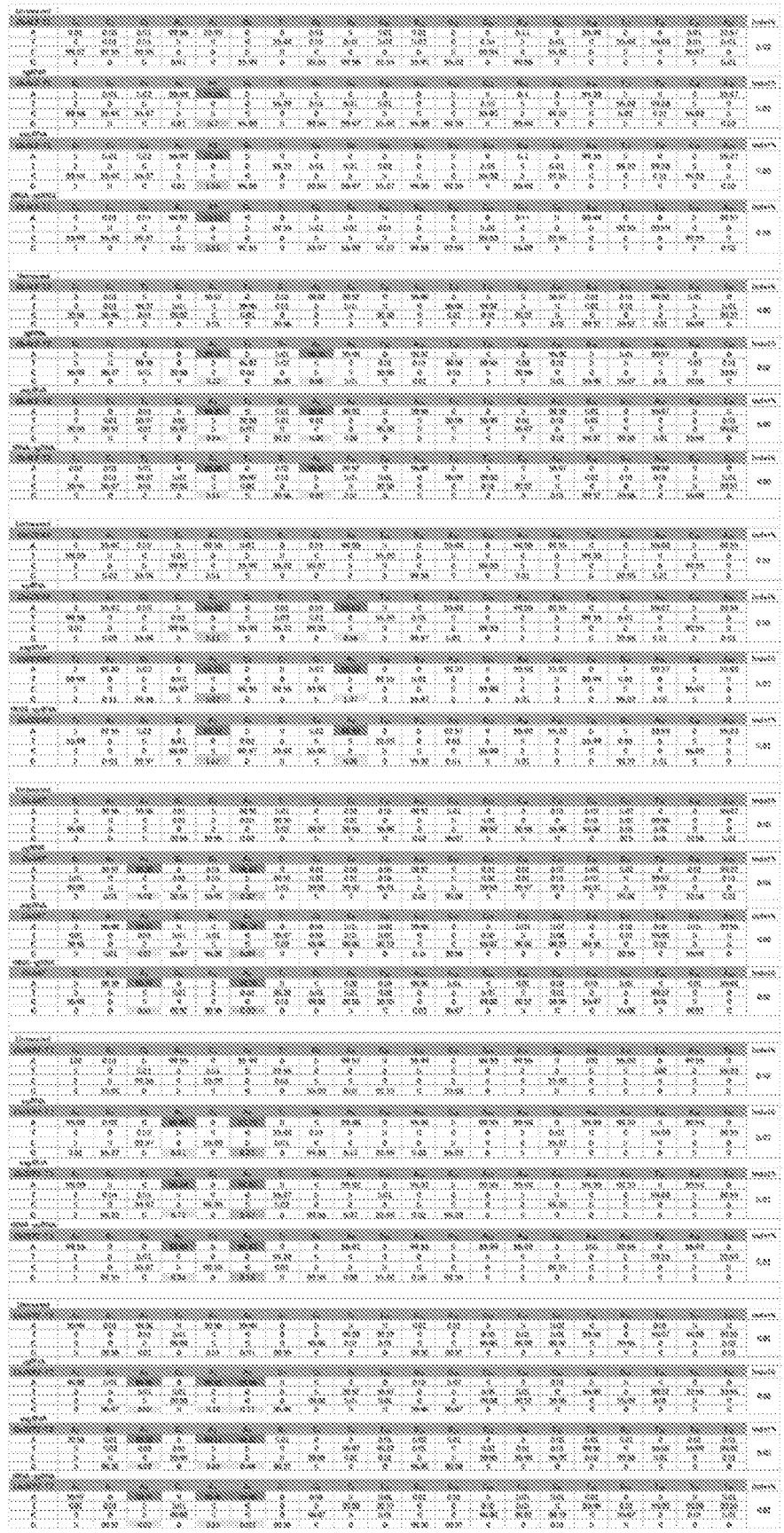
FIG. 9. Product purity of the editing of rice genomic locus by plant ABE, where product distribution and indel mutation frequency were detected at 10 representative rice genomic DNA sites, the samples were rice protoplasts treated by PABE-7 and corresponding native sgRNA, esgRNA and tRNA-sgRNA; a total of 48,616-111,697 sequencing reads were used at each position. Figure discloses SEQ ID NOS 165, 165, 165, 165, 166, 166, 166, 166, 167, 167, 167, 167, 168, 168, 168, 168, 169, 169, 169, 169, 170, 170, 170, 170, 171, 171, 171, 171, 172, 172, 172, 172, 173, 173, 173, 173, 174, 174, 174 and 174, respectively, in order of appearance.
Figure 9:
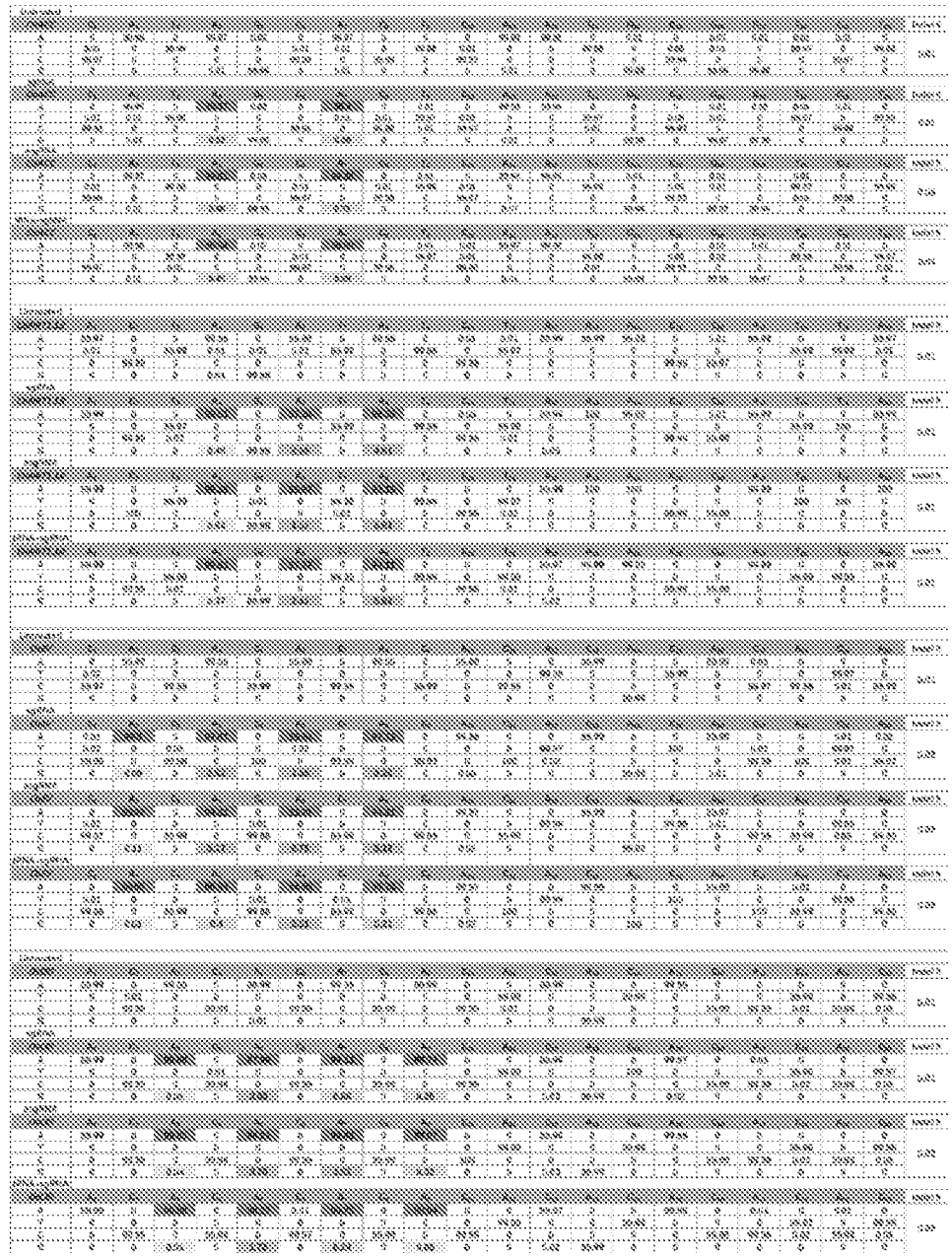
Figure 10:
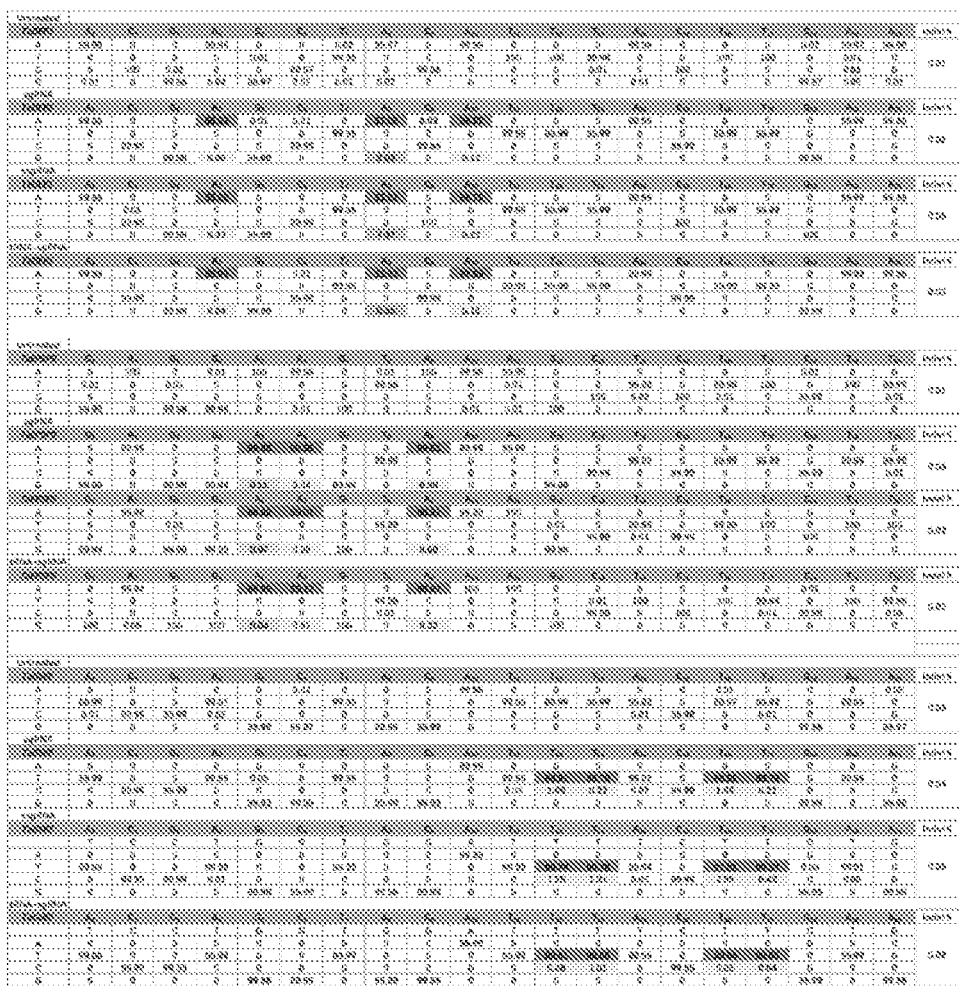
FIG. 10. Product purity the editing of wheat genomic locus by plant ABE, where product distribution and indel mutation frequency were detected at 3 representative wheat genomic DNA sites, the samples were rice protoplasts treated by PABE-7 and corresponding native sgRNA, esgRNA and tRNA-sgRNA; a total of 28,110-28,4527 sequencing reads were used at each position. Figure discloses SEQ ID NOS 175, 175, 175, 175, 176, 176, 176, 176, 175, 175, 175 and 175, respectively, in order of appearance.
Figure 11:
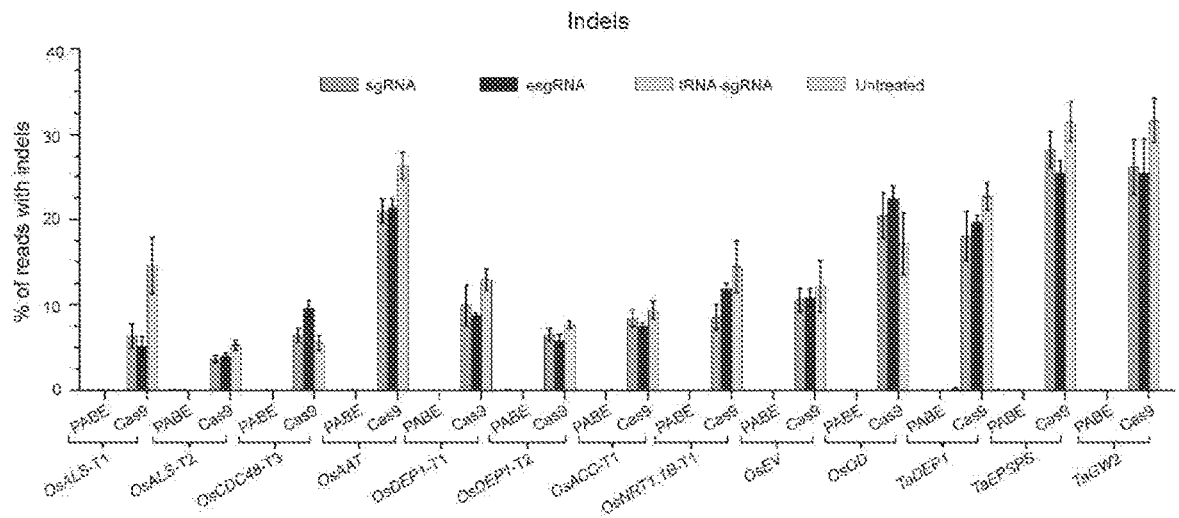
FIG. 11. Effect of sgRNA formats on indel mutations.

The protospacer sequences targeting these endogenous genes were cloned into three sgRNA structures, respectively (as shown in FIG. 7), and co-transformed with PABE-7. Wild type Cas9 (WT Cas9) was used as a control to generate deletions and/or indels. The combination of each PABE-7 and sgRNA expression system observed A to G conversion at all 13 target sites, with positions 4-8 within the protospacer sequence having an effective editing frequency (FIG. 8A). FIG. 8A also shows that esgRNA showed the highest base editing efficiency in most of the tests in the three sgRNA constructs, ranging from 0.1 to 7.5% in both rice and wheat. The average efficiency of esgRNA at 13 sites was approximately 2-fold higher than that of native sgRNA and approximately 3-fold higher than that of tRNA-sgRNA (FIG. 8B). In the above study, only A to G conversion was observed, and there is no evidence of undesired editing (<0.02%) in any genomic target locus of rice and wheat (FIGS. 9, 10), and the frequency of indel mutations (<0.1%) is much lower than that of WT Cas9 (3.3-31.6%) (FIG. 11).

Taken together, the PABE-7 base editing construct, together with esgRNA, efficiently induces A to G substitutions and has high precision in multiple loci in rice and wheat.

Example 6. Effect of Spacer Sequence on Editing

Figure 12:
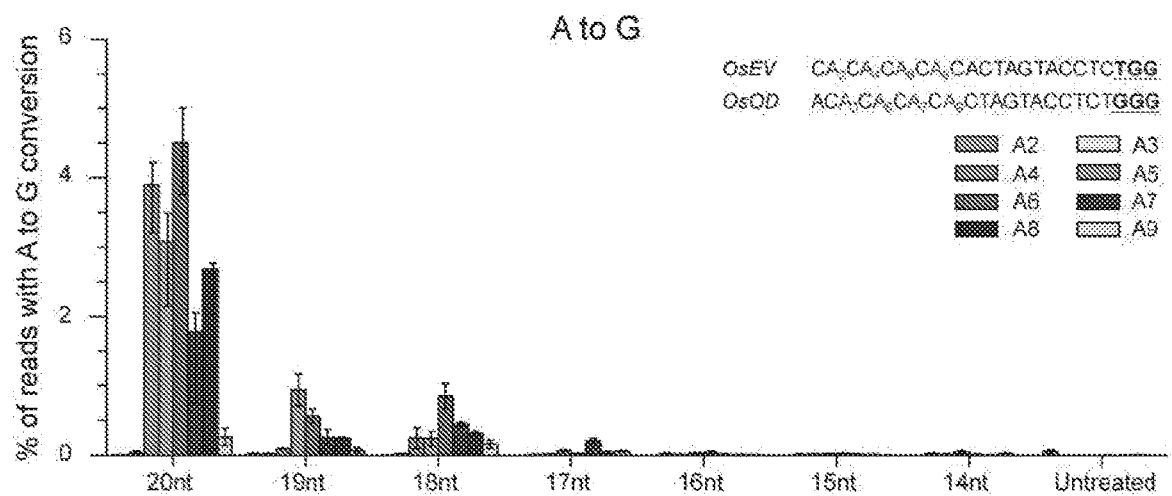
FIG. 12. Effect of the length of spacer sequence on A to G base editing. Figure discloses SEQ ID NOS 101 and 106, respectively, in order of appearance.

This example tested the effect of spacer sequence length of esgRNA on base editing efficiency by targeting OsEV and OsOD (as shown in Table 1). As a result, as shown in FIG. 12, the conventional 20-nt spacer sequence showed the highest A to G conversion efficiency. At these two sites, esgRNAs with a spacer sequence in length of 14-nt to 19-nt showed substantially decreased or undetectable A to G base editing activity (<0.9%), compared to esgRNA with a conventional 20-nt spacer sequence (<4.5%).

Figure 13:
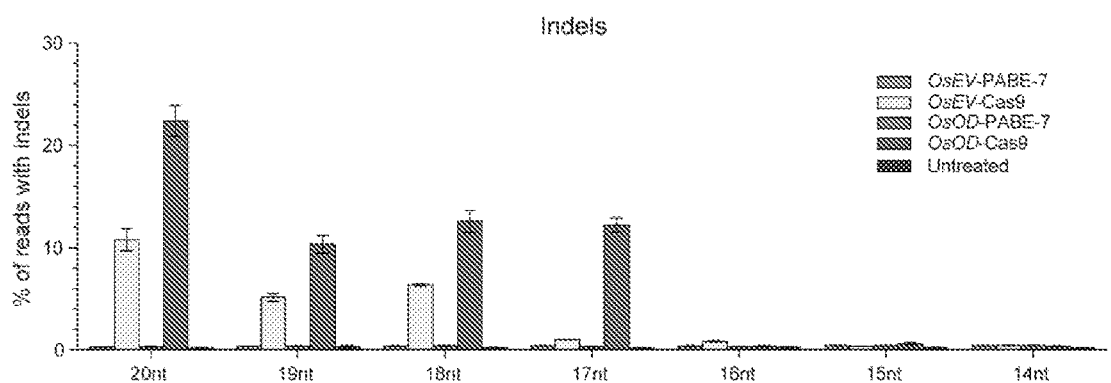
FIG. 13. Effect of the length of spacer sequence on indel mutations.

In addition, at these two sites, in the control WT Cas9, the indel mutation frequency (0.3-12.6%) of the esgRNA with a spacer sequence length of 14-nt to 19-nt was much lower than that of esgRNA with 20-nt spacer sequence (FIG. 13).

These results suggest that esgRNA with a 20-nt spacer sequence is critical for the plant ABE system and is not tolerant to shortened length.

Example 7. Production of Rice and Wheat with A to G Substitution

Figure 14:
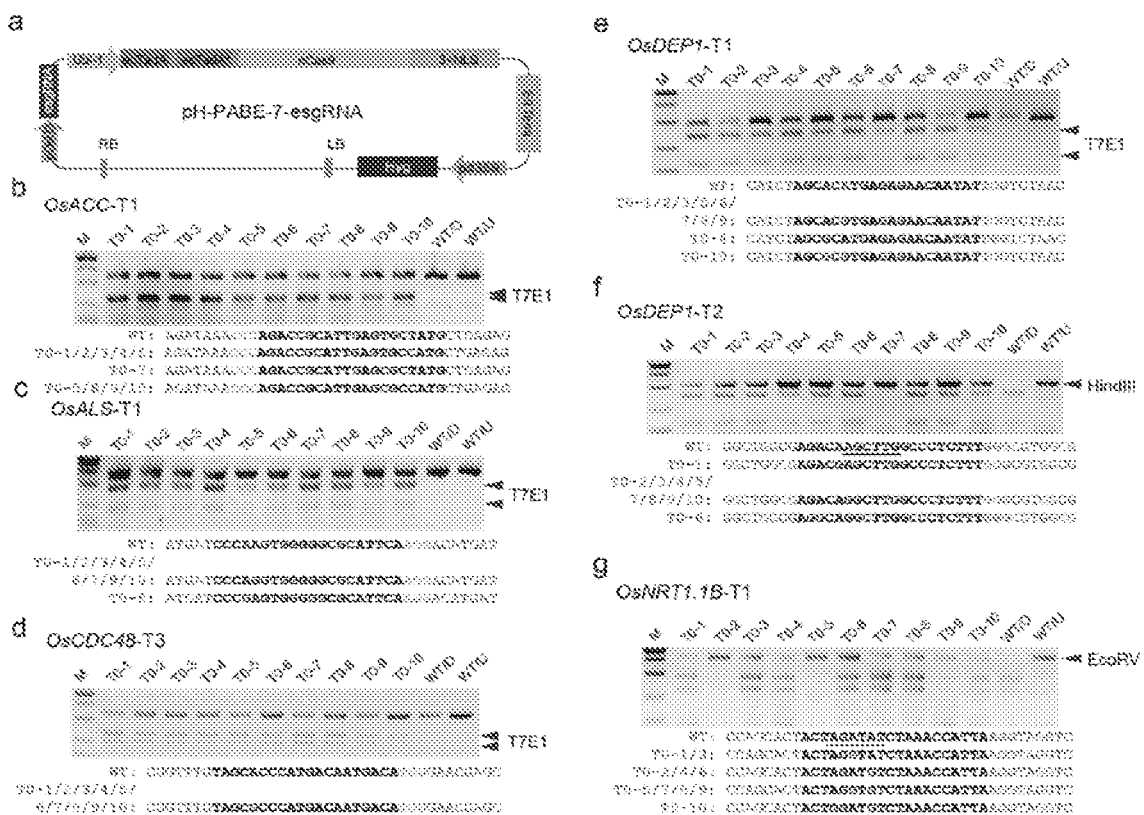
FIG. 14. Production of rice plants with A to G substitutions using PABE-7. Figure discloses SEQ ID NOS 177-198, respectively, in order of appearance by column.

In this example, 6 rice genome loci (OsACC-T1, OsALS-T1, OsCDC48-T3, OsDEP1-T1, OsDEP1-T2, and OsNRT1.1B-T1) were targeted by PABE-7 by *Agrobacterium*-mediated transgene, as shown in Tables 1 and 2), and the rice mutant plants was regenerated. The vector structure is shown in FIG. 14A. The substitution efficiency of A to G is 15.8%-59.1%. 1, 6, 1, and 13 mutant homozygous lines were identified for OsACC-T1, OsDEP1-T1, OsDEP1-T2, and OsNRT1.1B-T1, respectively.

Importantly, comparative experiments showed that the conversion frequency of PABE-7 when using esgRNA was on average 1.7-fold higher than that of native sgRNA (as shown in Table 2). This is consistent with the results observed with protoplasts (FIG. 8A, B). At all six target sites, the effective deamination window (positions 4 to 8) was consistent with the results in protoplast. In addition, transgenic rice plants did not contain any indel mutations or undesired editing at the target site (FIG. 14B-G).

TABLE 2

Mutation frequency of PABE-7 induced in T0 rice and wheat plants

| Species | Target site | sgRNA format | Number of mutant lines/plants [a] | Transgenic rice lines or bombarded wheat embryos | A•T to G•C frequency(%) [b] | Mutant genotype | Heterozygous/homozygous |
|---|---|---|---|---|---|---|---|
| Rice | OsACC-T1 | sgRNA | 9 | 130 | 6.9 | $T_4 > C_4$ (2); $T_4C_7 > T_4C_7$ (7) | 9/0 |
|  |  | esgRNA | 33 | 160 | 20.6 | $T_4 > C_4$ (10); $T_7 > C_7$ (2); $A_4A_7 > G_4G_7$ (21) | 32/1 |
|  | OsALS-T1 | sgRNA | 16 | 184 | 8.7 | $A_5 > G_5$ (16) | 16/0 |
|  |  | esgRNA | 42 | 196 | 21.4 | $A_4 > G_4$ (1); $A_5 > G_5$ (41) | 42/0 |
|  | OsCDC48-T3 | sgRNA | 19 | 210 | 9.0 | $A_5 > G_5$ (19) | 19/0 |
|  |  | esgRNA | 60 | 180 | 33.3 | $A_5 > G_5$ (60) | 60/0 |
|  | OsDEP1-T1 | sgRNA | 101 | 217 | 46.5 | $A_4 > G_4$ (2); $A_6 > G_6$ (90); $A_4A_6 > G_4G_6$ (9) | 88/13 |
|  |  | esgRNA | 83 | 211 | 39.3 | $A_4 > G_4$ (4); $A_6 > G_6$ (73); $A_4A_6 > G_4G_6$ (6) | 77/6 |
|  | OsDEP1-T2 | sgRNA | 5 | 154 | 3.2 | $A_6 > G_6$ (5); | 5/0 |
|  |  | esgRNA | 34 | 215 | 15.8 | $A_5 > G_5$ (1); $A_6 > G_6$ (32); $A_3A_6 > G_3G_6$ (1) | 33/1 |
|  | OsNRT1.1B-T1 | sgRNA | 116 | 303 | 38.3 | $A_6 > G_6$ (8); $A_8 > G_8$ (30); $A_4A_8 > G_4G_8$ (3); $A_6A_8 > G_6G_8$ (75) | 111/5 |
|  |  | esgRNA | 149 | 252 | 59.1 | $A_6G_6$ (6); $A_8 > G_8$ (46); $A_4A_8 > G_4G_8$ (2); $A_6A_8 > G_6G_8$ (95) | 136/13 |
| Wheat | TaDEP1 | esgRNA | 5 | 460 | 1.1 | $A_8 > G_8$ (4, AaBBDD; 1, AABbDD) | 5/0 |
|  | TaGW2 | esgRNA | 2 | 480 | 0.4 | $A_5 > G_5$ (2, AABbDD) | 2/0 |

[a] The number of rice mutant lines and the number of wheat mutant plants.

[b] Based on the ratio of the number of T0 lines (rice) or plants (wheat) with observed mutations to the total number of T0 transgenic rice lines analyzed and the number of immature embryos of bombarded wheat.

Figure 15:
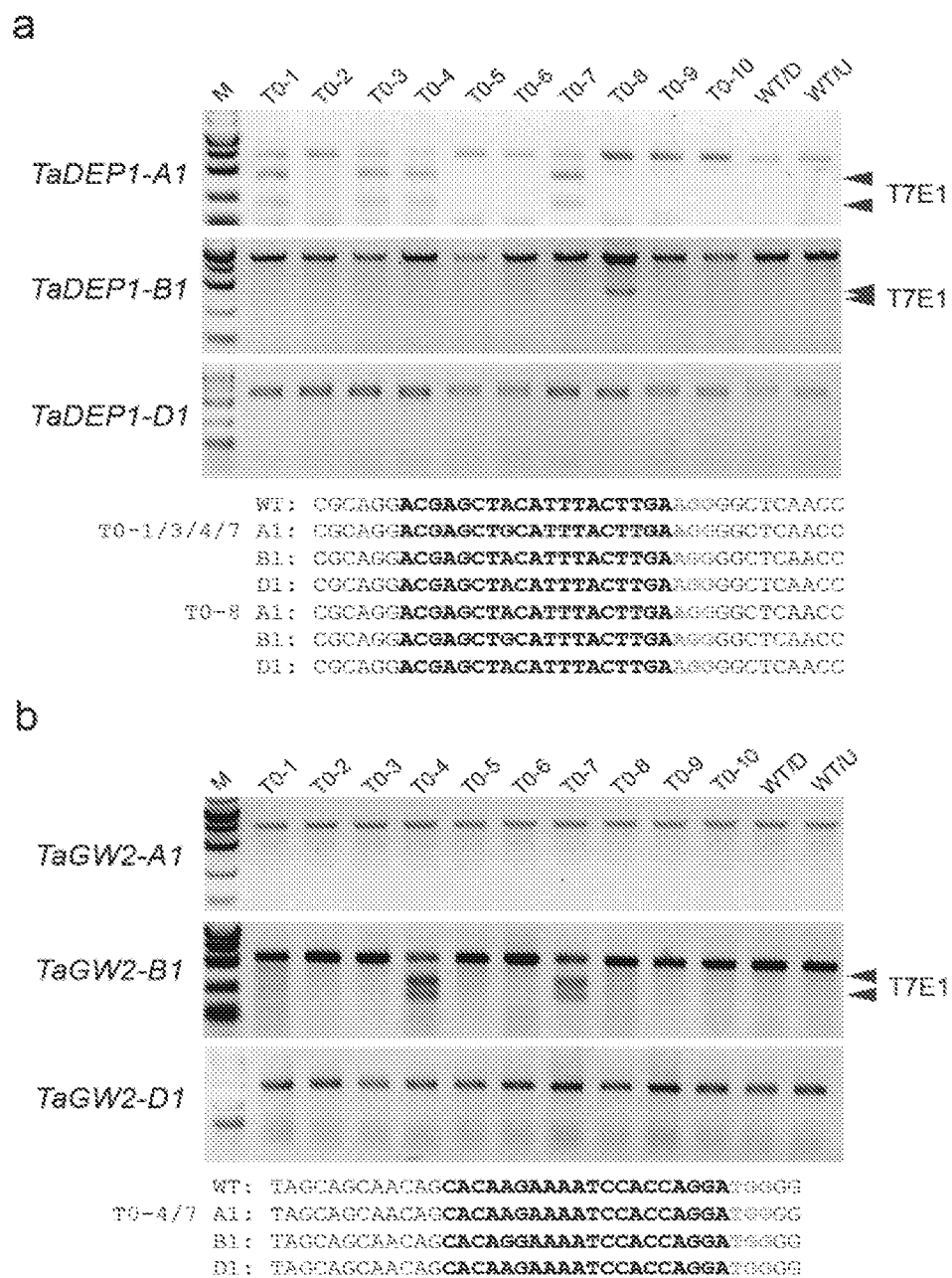
FIG. 15. Production of wheat plants with A to G substitutions using PABE-7. Figure discloses SEQ ID NOS 199, 200, 211, 211, 211, 200, 211, 201, 212, 202 and 212, respectively, in order of appearance.
Figure 16:
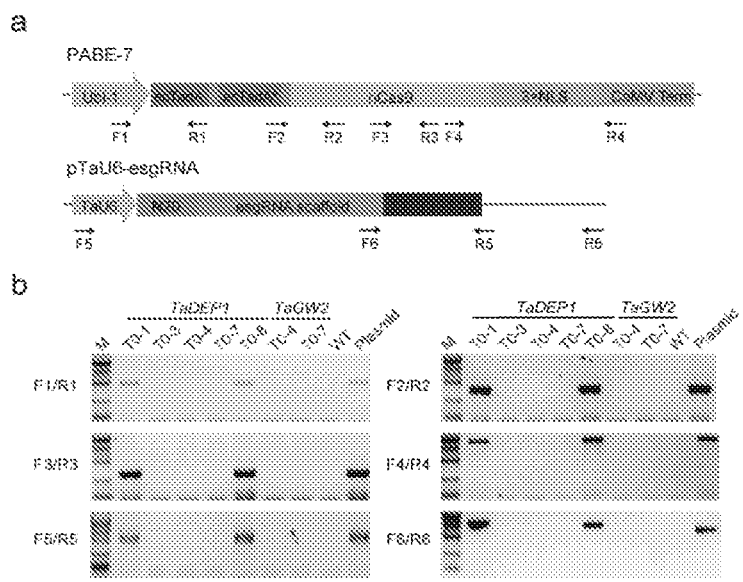
FIG. 16. Detection of transgenic vectors in wheat plants.

In this example, a base-edited wheat plant was also generated using the plant ABE system targeting the TaDEP1 and TaGW2 genes by gene gun transformation. Five A8 to G8 heterozygous TaDEP1 mutant plants (shown in Table 2 and FIG. 15A) were regenerated from 460 bombarded immature embryos by T7E1 and Sanger sequencing, four of which were TaDEP1-A heterozygous mutants (tadep1-AaBBDD), one line is a heterozygous mutant of TaDEP1-B (tadep1-AABbDD). For the TaGW2 target site, two heterozygous mutants were identified, both having A to G substitutions at position 5 of TaGW2-B (tagw2-AABbDD) (as shown in Table 2 and FIG. 15B). No indel mutations were observed in the target regions of all mutant plants. In addition, PCR screening was performed using 6 sets of primers specific for PABE-7 and pTaU6-esgRNA (as shown in Table 3), and 3 of the 5 TaDEP1 mutants and 2 TaGW2 mutants did not carry the transgenic vector (FIG. 16).

TABLE 3

PCR primers

| Primer | Primer sequence (5'-3') | SEQ ID NO: |
|---|---|---|
| F1 | ATGCTCACCCTGTTGTTTGGTGTTACTTC | 126 |
| R1 | CTTCTGGGCCTTAATCTCCTGCCTTCT | 127 |
| F2 | TCCGCTACACCAGAGTCTTCTGGAGGATCTAG | 128 |
| R2 | GCAGATGGTAGATCGTAGGGTACTTCTCGTGG | 129 |
| F3 | GAAGAACTACTGGCGCCAGCTCCTGAATG | 130 |
| R3 | GGCGATCATCTTCCTCACATCGTAAACC | 131 |
| P4 | TCGACAGCCCCACTGTGGCCTACTC | 132 |
| R4 | TTATATGCTCAACACATGAGCGAAACCC | 133 |
| F5 | GACCAAGCCCGTTATTCTGAC | 134 |
| R5 | TGACCATGATTACGCCAAGCTTAGAC | 135 |

TABLE 3-continued

PCR primers

| Primer | Primer sequence (5'-3') | SEQ ID NO: |
|---|---|---|
| F6 | TGAAAAAGTGGCACCGAGTCGGTGC | 136 |
| R6 | GGCGCAGCGGTCGGGCTG | 137 |

Taken together, these results indicate that the plant ABE system effectively induces specific site mutations in rice and wheat in a highly deliberate and precise manner without causing other genome modifications. Moreover, the plant ABE system of the present invention does not integrate a foreign DNA sequence (such as a transgenic vector) into the plant genome when performing genome modification.

Example 8. Induction of Herbicide Resistance in Rice

In this example, the herbicide resistance of rice modified at the target site OsACC-T1 was analyzed. This modification targets the ACC gene in rice, and the modified rice ACC carries the mutation C2186R, which corresponds to the mutation C2088R of the black grass ACC.

Figure 17:
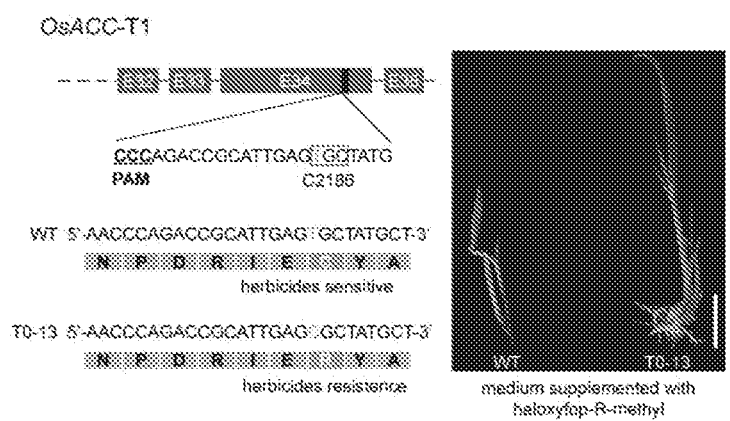
FIG. 17. Rice with herbicide resistance produced by base editing. Figure discloses SEQ ID NOS 85 and 203-206, respectively, in order of appearance.

Detection of 160 pH-PABE-7-esgRNA transformed lines showed that 33 of the lines had at least one T to C substitution in the target region (mutation efficiency 20.6, as shown in Table 2). One of these mutant lines contained homozygous substitutions (T4T7 to C4C7), while the other 32 contained heterozygous substitutions, of which 20 had a double base substitution (T4T7 to C4C7) and 10 had a T4 to C4 single base substitutions, as well as 2 had single base substitutions (T7 to C7; TO-7 and TO-13) providing the desired C2186R amino acid substitution at one of the alleles. The results are shown in FIGS. 14B, 17 and Table 2.

In addition, no mutations were detected in potential off-target areas in all of the mutant lines (as shown in Table 4).

TABLE 4

Potential off-target analysis of the OsACC-T1 endogenous genomic locus

| Potential off-target sites | Sequence[a] | Mismatch No. | Target loci | Mutant genotype | Detection method |
|---|---|---|---|---|---|
| Correct site | CCCAGACCGCATTGAGTGCTATG | 0 | LOC_Os05g22940 | A to G | T7E1/Sanger Sequencing |
| Off-target site-1 | CATAGCACTCAActCaGTtTGG | 4 | LOC_Os08g35020 | No A-G conversion and indel mutations were found | T7E1/Sanger Sequencing |
| Off-target site-2 | aATAGCACTCAtTGaGaTCTTGG | 4 | LOC_Os05g30010 | | T7E1/Sanger Sequencing |
| Off-target site-3 | CATAGCACTtAATGtGGgCgGAG | 4 | LOC_Os03g45820 | | T7E1/Sanger Sequencing |

[a] mismatch base in a potential off-target site (14) is indicated in lowercase letters. PAM continues to be represented in bold font.

Further, the inventors tested the herbicide resistance of the TO-13 lines. After one week of growth on regeneration medium supplemented with 0.086 ppm of haloxyfop-R-methyl ester, the mutant plants had a normal phenotype with no signs of damage, whereas wild-type (WT) plants showed severe atrophy and withering leaf (as shown in FIG. 17). The above results indicate that herbicide resistant rice carrying C2186R substitution of ACC was produced using a genome editing tool. The above results also indicate that the genome editing system of the present invention has a low off-target rate in plants and can perform accurate base editing.

The invention claimed is:

1. A method of producing a genetically modified plant, comprises introducing a system for base editing of a target sequence in the plant genome into the plant, whereby the guide RNA targets the base-editing fusion protein to a target sequence in the plant genome, resulting in one or more A in the target sequence being replaced with G, and wherein the system comprises at least one of the following i) to v):
  i) a base-editing fusion protein, and a guide RNA;
  ii) an expression construct comprising a nucleotide sequence encoding a base-editing fusion protein, and a guide RNA;
  iii) a base-editing fusion protein, and an expression construct comprising a nucleotide sequence encoding a guide RNA;
  iv) an expression construct comprising a nucleotide sequence encoding a base-editing fusion protein, and an expression construct comprising a nucleotide sequence encoding a guide RNA;
  v) an expression construct comprising a nucleotide sequence encoding a base-editing fusion protein and a nucleotide sequence encoding a guide RNA;
  wherein the base-editing fusion protein comprises the amino acid sequence set forth in SEQ ID NO: 39,
  wherein the guide RNA is an enhanced single guide RNA (esgRNA) comprising the scaffold sequence set forth in SEQ ID NO:139, and
  wherein the introduction is carried out in the absence of selection pressure.

2. The method of claim 1, wherein the nucleotide sequence encoding the base-editing fusion protein comprises the nucleic acid sequence of SEQ ID NO: 32.

3. The method of claim 1, wherein the nucleotide sequence encoding the base-editing fusion protein and/or the nucleotide sequence encoding the guide RNA is operably linked to a plant expression regulatory element.

4. The method of claim 3, wherein the regulatory element is a 35S promoter, a maize Ubi-1 promoter, a wheat U6 promoter, a rice U3 promoter or a maize U3 promoter.

5. The method of claim 1, wherein the guide RNA comprises a region that is 20 nucleotides in length corresponding to the target sequence.

6. The method of claim 1, further comprising screening for a plant having a desired nucleotide substitution.

7. The method of claim 1, wherein the plant is selected from monocots and dicots.

8. The method of claim 7, wherein the plant is wheat, rice, corn, soybean, sunflower, sorghum, canola, alfalfa, cotton, barley, millet, sugar cane, tomato, tobacco, tapioca or potato.

9. The method of claim 1, wherein the target sequence is associated with a plant trait, whereby the base editing results in the plant having an altered trait relative to a wild type plant.

10. The method of claim 1, wherein the system is introduced by transient transformation.

11. The method of claim 1, wherein the method that can be used to introduce the system into the plant is selected from: gene gun method, PEG-mediated protoplast transformation, *Agrobacterium*-mediated transformation, plant virus-mediated transformation, pollen tube pathway and ovary injection method.

12. The method of claim 1, further comprises obtaining progeny of the genetically modified plant.

13. The method of claim 1, wherein no exogenous DNA is integrated into the genome of the modified plant.

14. The method of claim 1, further comprising crossing a first plant containing a genetic modification obtained by the method of claim 1 with a second plant not containing the genetic modification, thereby the genetic modification is introduced into the second plant.

\* \* \* \* \*